US006979559B2

(12) United States Patent
Harris, Jr. et al.

(10) Patent No.: US 6,979,559 B2
(45) Date of Patent: Dec. 27, 2005

(54) POLYVALENT CATION-SENSING RECEPTOR IN ATLANTIC SALMON

(75) Inventors: H. William Harris, Jr., Portland, ME (US); Jacqueline Nearing, N. Yarmouth, ME (US); Marlies Betka, Portland, ME (US)

(73) Assignee: MariCal, Inc., Portland, ME (US)

( * ) Notice: Subject to any disclaimer, the term of this patent is extended or adjusted under 35 U.S.C. 154(b) by 118 days.

(21) Appl. No.: 10/125,792

(22) Filed: Apr. 18, 2002

(65) Prior Publication Data

US 2003/0051269 A1 Mar. 13, 2003

Related U.S. Application Data

(63) Continuation-in-part of application No. 10/121,441, filed on Apr. 11, 2002, now abandoned, which is a continuation-in-part of application No. PCT/US01/31704, filed on Oct. 11, 2001.

(60) Provisional application No. 60/240,392, filed on Oct. 12, 2000, and provisional application No. 60/240,003, filed on Oct. 12, 2000.

(51) Int. Cl.[7] .......................... C12N 15/63; C12N 15/85; C12N 15/86; C07H 21/04; C07K 14/00

(52) U.S. Cl. .............. 435/69.1; 435/253.3; 435/254.11; 435/320.1; 435/325; 530/300; 530/350; 536/23.1; 536/23.5

(58) Field of Search ............................ 435/69.1, 252.3, 435/254.11, 320.1, 325; 530/300, 350; 536/23.1, 23.5

(56) References Cited

U.S. PATENT DOCUMENTS

| | | | | |
|---|---|---|---|---|
| 4,683,202 A | | 7/1987 | Mullis | |
| 5,545,808 A | | 8/1996 | Hew et al. | |
| 5,763,569 A | | 6/1998 | Brown et al. | |
| 5,858,684 A | | 1/1999 | Nemeth et al. | |
| 5,962,314 A | | 10/1999 | Brown et al. | |
| 5,981,599 A | | 11/1999 | Moe et al. | |
| 6,001,884 A | | 12/1999 | Nemeth et al. | |
| 6,337,391 B1 | | 1/2002 | Harris et al. | |
| 6,463,882 B1 | | 10/2002 | Harris, Jr. et al. | |
| 6,463,883 B1 | | 10/2002 | Harris, Jr. et al. | |
| 6,475,792 B1 | | 11/2002 | Harris, Jr. et al. | |
| 6,481,379 B1 | | 11/2002 | Harris, Jr. et al. | |
| 6,564,747 B2 | | 5/2003 | Harris, Jr. et al. | |
| 2003/0082574 A1 | | 5/2003 | Harris, Jr. et al. | |
| 2003/0124657 A1 | * | 7/2003 | Harris et al. | 435/69.1 |
| 2003/0232366 A1 | * | 12/2003 | Harris et al. | 435/6 |

FOREIGN PATENT DOCUMENTS

| | | |
|---|---|---|
| SU | 1784152 A1 | 12/1992 |
| WO | WO 9735977 | 10/1997 |
| WO | WO 02/30182 | 4/2002 |
| WO | WO 02/031149 | 4/2002 |
| WO | WO 03/030639 | 4/2003 |

OTHER PUBLICATIONS

Doerks et al., (Jun. 1998) "Protein annotation: detective work for function prediction." Trends in Genetics 14(6): 248–250.*

(Continued)

*Primary Examiner*—Elizabeth C. Kemmerer
*Assistant Examiner*—Christopher James Nichols
(74) *Attorney, Agent, or Firm*—Hamilton, Brook, Smith & Reynolds, P.C.

(57) ABSTRACT

The present invention encompasses three full length nucleic acid and amino acid sequences for PolyValent Cation-Sensing Receptors (PVCR) in Atlantic Salmon. These PVCR have been named SalmoKCaR#1, SalmoKCaR#2, and SalmoKCaR#3. The present invention includes homologs thereof, antibodies thereto, and methods for assessing SalmoKCaR nucleic acid molecules and polypeptides. The present invention further includes plasmids, vectors, host cells containing the nucleic acid sequences of SalmoKCaR #1,2 and/or 3.

22 Claims, 91 Drawing Sheets

OTHER PUBLICATIONS

Smith and Zhang (Nov. 1997) "The challenges of genome sequence annotation or 'The devil is in the details'." Nature Biotechnology 15:1222–1223.*

Brenner (Apr. 1999) "Errors in genome annotation." Trends in Genetics 15(4): 132–133.*

Bork and Bairoch (Oct. 1996) "Go hunting in sequence databases but watch out for the traps." Trends in Genetics 12(10): 425–427.*

Wells (Sep. 18, 1990) "Additivity of Mutational Effects in Proteins." Biochemistry 29(37): 8509–8517.*

Ngo et al. (Mar. 2, 1995) "The Protein Folding Problem and Tertiary Structure Prediction, Chapter 14: Computational Complexity Protein Structure Prediction, and the Levinthal Paradox" pp. 433–506.*

Bork (2000) "Powers and Pitfalls in Sequence Analysis: The 70% Hurdle." Genome Research 10:398–400.*

Skolnick and Fetrow (2000) "From gene to protein structure and function: novel applications of computational approaches in th genomic era." Trends in Biotech. 18(1): 34–39.*

Naito, T., et al., "Putative pheromone receptors . . . ," *Proc. Natl. Acad. Science*, 95: 5178–5181 (1998).

Clark, M.S., et al., "Sparus aurata mRNA . . . ," *EMBL Databse Accession No.: AJ289717* (Jun. 9, 2001).

Nearing, J., "Polyvalent cation receptor . . . ," *PNAS*, 99(14): 9231–9236 (2002).

Nearing, J. et al., "Cloning and Expression of a homologue . . . ," *Journal of The American Society of Nephrology*, 8: 40A. (From ASN Program and Abstracts, 1997, Abstract No. A0194) (1997).

Baum, M.S., et al., "An apical extracellular Calcium/Polyvalent cation sensing receptor (CaR)present in the osmoregulatory organs of salt water (SW) and fresh water (FW) fish likely plays a role in salinity adaptation," *Journal of Am. Society of Nephrology* 7(9): p. 1276 (1996).

Riccardi, D., et al., "Cloning and Functional Expression of a Rat Kidney Extracellular Calcium/Polyvalent cation–Sensing Receptor," *Proc. Nat. Acad. Sci.USA*, 92: 131–135 (1995).

Brown, E.M., et al., "Calcium–Ion–Sensing Cell–Surface Receptors," *The New England Journal of Medicine*, 333(4): 234–240 (1995).

Brown, E.M., et al., "Cloning and Characterization of an Extracellular $Ca^{2+}$–Sensing Receptor from Bovine Parathyroid," *Nature*, 366:575–580 (1993).

Brown, E.M., et al., "Neomycin mimics the Effects of HighExtracellular Calcium Concentration on Parathyroid Function in Dispersed Bovine Parathyroid Cells," *Endocrinology*, 128(6): 3047–3054 (1991).

Sands, J.M., et al., "Apical Extracellular Calcium/Polyvalent Cation–sensing Receptor Requlates Vasopressin–elicited Water Permeability in Rat Kidney Inner Medullary Collecting Duct," *J. Clinical Investigation*, 99(6): 1399–1405 (1997).

Garrett, J.E.,et al., "Molecular Cloning and Functional Expression of Human Parathyroid Calcium Receptor cDNAs," *Journal of Biological Chemistry*, 270(21): 12919–12925 (1995).

Sands, A.T., et al., "High Susceptibility to Ultraviolet–Induced Arcinogenesis in Mice Lacking XPC," *Nature*, 377: 162–165 (1995).

Aida, K., "Molecular Cloning of a Putative $^{Ca2+}$ Sensing Receptor cDNA from Human Kidney," *Biochemical & Biophysical Research Communications*, 214(2): 524–529(1995).

Ward, D.T., et al., "Disulfide–bonds in the extracellular calcium–polyvalent cation sensing receptor mediate dimer formation and its response to divalent cations in vitro," *J. Bio. Chemistry*, 273: 14476–14483 (1998).

Radman, DP, et al., "Evidence for calcium Receptor mediated stanniocalcin secretion in fish," *Molecular and Cellulare Endocrinology*, 186: 111–119 (2002).

Abnet, C.C., et al., "Two forms of aryl hydrocarbon receptor type 2 in rainbow trout (Oncorhynchus mykiss)," *J. of Biological Chemistry*, 274: 15159–15166 (1999).

Usher, M. L., et al., Effects of transfer to seawater on growth and feeding in Atlantic salmon smolts (*Salmo salar* L.), *Aquaculture*, 94: 309–326 (1991).

Morkore, T., and Rorvik, K., "Seasonal variations in growth, feed utilisation and product quality of farmed Atlantic salmon (*Sakni sakar*) transferred to seawater as 0+ smolts or 1 + smolts," *Aquaculture*, 199: 145–157 (2001).

Johnston, I. A., et al., "Muscle fibre density in relation to the colour and texture of smoked Atlantic salmon (*Salmo salar* L.)," *Aquaculture*, 189: 335–349 (2000).

Pace, A.J.,et al., "Dimerization of the calcium–sensing receptor occurs within the extracellular domain and is eliminated by cys to Ser mutations at Cys101 and Cys236," *J. Biol. Chemistry*, 274: 11629–11634 (1999).

Bai, M., et al., "Expression and characterization of inactivating and activating mutations in the human $Ca^{2+}{}_{0}$–sensing receptor," *J. Biol. Chemistry*, 271(32): 19537–19545 (1996).

Pearce, S.H.S., et al., "Functional characterization of calcium–sensing receptor mutations expressed in human embryonic kidney cells," *J. Clin. Invest.*, 98: 860–1866 (1996).

Ray, K., et al., "The carboxyl terminus of the human calcium receptor. Requirements for cell surface expression and signal transduction," *J. Biol. Chem.*, 272: 31355–31361 (1997).

Gama, L. and Breitwieser, "A carboxyl–terminal domain controls the cooperativity for extracellular $Ca^{2+}$ activation of the human calcium sensing receptor. A study with receptor–green fluorescent protein fusions," *J. Biol. Chemistry*, 273: 29712–29718 (1998).

Ho, C., et al., "A mouse model of human familial hypocalciuric hypercalcemia and neonatal severe hyperparathyroidism," *Nature* (*Genetics*), 11: 389–394 (1995).

Pollak, M.R., et al., "Mutations in the Human $Ca^{2+}$ –Sensing Receptor Gene Cause Familial Hypocalciuric Hypercalcemia and Neonatal Severe Hyperparathryoidism", *Cell*, 75: 1297–1303 (1993).

Malaga–Trillo, E. and A. Meyer, "Genome duplicatins and acceleratied evolution of Hox gene and cluster architecture in teleost fishes," American Zoology , 41: 676–686 (2001).

Lopreato, G.F., et al., "Evolution and divergence of sodim channel genes in verterbrates," *Proc. Nat. Acad. Sci.*, 98: 7588–7592 (2001).

Chen, TT, et al., "Transgenic Fish," *Trends in Biotechnology*, 8: 209–215 (1990).

Takeo, J. and S. Yamashita, "Two distinct isoforms of cDNA encoding rainbow trout androgen receptors," *J. Biol. Chem*, 274 5674–5680 (1999).

Robinson–Rechavi, M., et al., "An Ancestral whole–genome duplication may not have been responsible for the abundance of duplicated fish genes," *Current Biology*, 26: R458–R459 (2001).

Mattila, et al., "Fidelity of DNA synthesis by the *Thermococcus litoralis* DNA polymerase—an extremely heat stable enzzyme with proofreading activity," *Nucleic Acid Research*, 19(18): 4967–1973 (1991).

Nowak, MA, et al., "Evolution of genetic redundancy," *Nature*, 388: 167–170 (1997).

Force. A., et al., Preservation of duplicate genes by complementary, degenerative mutations, *Genetics*, 151: 1531–1545 (1999).

Lynch, M. and Force, A., "Probability of duplicate gene preservation by subfunctionalization," *Genetics*, 154: 459–473 (2000).

Nemeth, E.F., et al., "Calcimimetics with potent and selective activity on the parathryoid calcium receptor," *Proc Nat. Acad. Sci.*, 95: 4040–4045 (1998).

Quinn, S.J., et al., "The $Ca^{2+}$ –sensing receptor: a target for polyamines," *American Journal of Physiology*, 273(4): C1315–1323 (1997).

Conigrave, A.D., et al., "L–Amino acid sensing by the extracellular $Ca^{2+}$ –sensing receptor," *Proc. Nat. Acad. Sci.*, 97(9): 4419–4819 (2000).

Siner, J., et al., "Cloning of an aquaporin homologue present in water channel containing endosomes of toad urinary bladder," *Am. J. Physiol.*, 270: C372–C381 (1996).

Bodznick, D. J., "Calcium ion: an odorant for natural water discriminations and the migratory behavior of sockeye salmon," *J. Comp. Physiol A* 127: 157–166 (1975).

Hubbard, PC, et al., "Olfactory sensitivity to changes in environmental Ca2+ in the marine teleost Sparus Aurata," *J. Exp. Biol*: 203: 3821–3829 (2000).

Royce–Malmgren and Watson, "Modificaion of Olfactory–related Behavior in Juvenile Atlantic Salmon by Changes in pH," *J. of Chemical Ecology*, 13(3): 533–546 (1987).

Clark, M.S. et al., "Calcitonin: characterisation and expression in a teleost fish, *Fugu rubripes,*" *J. Mol. Endocrin* 28(2):111–123 (Apr. 2002).

Lo, Y.H. et al., "High–affinity $Ca^{2+}$, $Mg^{2+}$ –ATPase in plasma membrane–rich preparations from olfactory epithelium of Atlantic salmon," Biochimica et Biophysica Acta 1192(2):153–158 (1994).

* cited by examiner

```
aattccgttg ctgtcggttc agtccaagtc tcctccagtg caaaatgaga aatggtggtc 60
gccattacag gaacatgcac tacatctgtg ttaatgaaat attgtcagtt atctgaaggt 120
tattaaaatg tttctgcaag gatggcttca cgagaaatca attctgcacg ttttcccatt 180
gtcattgtat gaataactga ccaaagggat gtaacaaaat ggaacaaagc tgaggaccac 240
gttcaccctt tcttggagca tacgatcaac cctgaaggag atggaagact tgaggaggaa 300
atggggattg atcttccagg agttctgctg taaagcgatc cctcaccatt acaaagataa 360
gcagaaatcc tccaggcatc ctctgtaaac gggctggcgt agtgtggctt ggtcaaggaa 420
cagagacagg gctgcaca atg gct cag ctt cac tgc caa ctc tta ttc ttg   471
                   Met Ala Gln Leu His Cys Gln Leu Leu Phe Leu
                    1               5                  10

gga ttt aca ctc cta cag tcg tac aat gtc tca ggg tat ggt cca aac   519
Gly Phe Thr Leu Leu Gln Ser Tyr Asn Val Ser Gly Tyr Gly Pro Asn
            15                  20                  25

caa agg gcc cag aag aaa gga gac atc ata ctg gga ggt ctc ttc cca   567
Gln Arg Ala Gln Lys Lys Gly Asp Ile Ile Leu Gly Gly Leu Phe Pro
        30                  35                  40

ata cac ttt gga gta gcc gcc aag gat cag gac tta aaa tcg aga ccg   615
Ile His Phe Gly Val Ala Ala Lys Asp Gln Asp Leu Lys Ser Arg Pro
    45                  50                  55

gag gcg aca aaa tgt att cgg tac aat ttt cga ggc ttc cga tgg ctc   663
Glu Ala Thr Lys Cys Ile Arg Tyr Asn Phe Arg Gly Phe Arg Trp Leu
60                  65                  70                  75

cag gcg atg ata ttc gca att gaa gag att aac aac agt atg act ttc   711
Gln Ala Met Ile Phe Ala Ile Glu Glu Ile Asn Asn Ser Met Thr Phe
                80                  85                  90

ctg ccc aat atc acc ctg gga tat cgc ata ttt gac acg tgt aac acc   759
Leu Pro Asn Ile Thr Leu Gly Tyr Arg Ile Phe Asp Thr Cys Asn Thr
            95                  100                 105

gtg tcc aag gcg cta gag gca aca ctc agc ttt gtg gcc cag aac aaa   807
Val Ser Lys Ala Leu Glu Ala Thr Leu Ser Phe Val Ala Gln Asn Lys
        110                 115                 120

atc gac tcg ctg aac tta gat gag ttc tgt aac tgc tct gac cat atc   855
Ile Asp Ser Leu Asn Leu Asp Glu Phe Cys Asn Cys Ser Asp His Ile
    125                 130                 135

cca tcc aca ata gca gtg gtc ggg gca acc ggg tca gga atc tcc acg   903
Pro Ser Thr Ile Ala Val Val Gly Ala Thr Gly Ser Gly Ile Ser Thr
140                 145                 150                 155

gct gtg gcc aat cta ttg gga tta ttt tac att cca cag gtc agc tat   951
Ala Val Ala Asn Leu Leu Gly Leu Phe Tyr Ile Pro Gln Val Ser Tyr
                160                 165                 170

gcc tcc tcg agc agg ctg ctc agc aac aag aat gag tac aag gcc ttc   999
Ala Ser Ser Ser Arg Leu Leu Ser Asn Lys Asn Glu Tyr Lys Ala Phe
            175                 180                 185

ctg agg acc atc ccc aat gat gag caa cag gcc acg gcc atg gcc gag   1047
Leu Arg Thr Ile Pro Asn Asp Glu Gln Gln Ala Thr Ala Met Ala Glu
        190                 195                 200
```

FIG. 1A

```
atc atc gag cac ttc cag tgg aac tgg gtg gga acc ctg gca gcc gac      1095
Ile Ile Glu His Phe Gln Trp Asn Trp Val Gly Thr Leu Ala Ala Asp
    205                 210                 215

gat gac tat ggc cgc cca ggc att gac aag ttc cgg gag gag gcc gtt      1143
Asp Asp Tyr Gly Arg Pro Gly Ile Asp Lys Phe Arg Glu Glu Ala Val
220                 225                 230                 235

aag agg gac atc tgt att gac ttc agt gag atg atc tct cag tac tac      1191
Lys Arg Asp Ile Cys Ile Asp Phe Ser Glu Met Ile Ser Gln Tyr Tyr
                240                 245                 250

acc cag aag cag ttg gag ttc atc gcc gac gtc atc cag aac tcc tcg      1239
Thr Gln Lys Gln Leu Glu Phe Ile Ala Asp Val Ile Gln Asn Ser Ser
            255                 260                 265

gcc aag gtc atc gtg gtc ttc tcc aat ggc ccc gac ctg gag ccg ctc      1287
Ala Lys Val Ile Val Val Phe Ser Asn Gly Pro Asp Leu Glu Pro Leu
        270                 275                 280

atc cag gag ata gtt cgg aga aac atc acc gat cgg atc tgg ctg gcc      1335
Ile Gln Glu Ile Val Arg Arg Asn Ile Thr Asp Arg Ile Trp Leu Ala
    285                 290                 295

agc gag gct tgg gcc agc tct tcg ctc att gcc aag cca gag tac ttc      1383
Ser Glu Ala Trp Ala Ser Ser Ser Leu Ile Ala Lys Pro Glu Tyr Phe
300                 305                 310                 315

cac gtg gtc ggc ggc acc atc ggc ttc gct ctc agg gcg ggg cgt atc      1431
His Val Val Gly Gly Thr Ile Gly Phe Ala Leu Arg Ala Gly Arg Ile
                320                 325                 330

cca ggg ttc aac aag ttc ctg aag gag gtc cac ccc agc agg tcc tcg      1479
Pro Gly Phe Asn Lys Phe Leu Lys Glu Val His Pro Ser Arg Ser Ser
            335                 340                 345

gac aat ggg ttt gtc aag gag ttc tgg gag gag acc ttc aac tgc tac      1527
Asp Asn Gly Phe Val Lys Glu Phe Trp Glu Glu Thr Phe Asn Cys Tyr
        350                 355                 360

ttc acc gag aag acc ctg acg cag ctg aag aat tcc aag gtg ccc tcg      1575
Phe Thr Glu Lys Thr Leu Thr Gln Leu Lys Asn Ser Lys Val Pro Ser
    365                 370                 375

cac gga ccg gcg gct caa ggg gac ggc tcc aag gcg ggg aac tcc aga      1623
His Gly Pro Ala Ala Gln Gly Asp Gly Ser Lys Ala Gly Asn Ser Arg
380                 385                 390                 395

cgg aca gcc cta cgc cac ccc tgc act ggg gag gag aac atc acc agc      1671
Arg Thr Ala Leu Arg His Pro Cys Thr Gly Glu Glu Asn Ile Thr Ser
                400                 405                 410

gtg gag acc ccc tac ctg gat tat aca cac ctg agg atc tcc tac aat      1719
Val Glu Thr Pro Tyr Leu Asp Tyr Thr His Leu Arg Ile Ser Tyr Asn
            415                 420                 425

gta tac gtg gcc gtc tac tcc att gct cac gcc ctg caa gac atc cac      1767
Val Tyr Val Ala Val Tyr Ser Ile Ala His Ala Leu Gln Asp Ile His
        430                 435                 440
```

FIG. 1B tct tgc aaa ccc ggc acg ggc atc ttt gca aac gga tct tgt gca gat 1815
Ser Cys Lys Pro Gly Thr Gly Ile Phe Ala Asn Gly Ser Cys Ala Asp
445 450 455 att aaa aaa gtt gag gcc tgg cag gtc ctc aac cat ctg ctg cat ctg 1863
Ile Lys Lys Val Glu Ala Trp Gln Val Leu Asn His Leu Leu His Leu
460 465 470 475 aag ttt acc aac agc atg ggt gag cag gtt gac ttt gac gat caa ggt 1911
Lys Phe Thr Asn Ser Met Gly Glu Gln Val Asp Phe Asp Asp Gln Gly
480 485 490 gac ctc aag ggg aac tac acc att atc aac tgg cag ctc tcc gca gag 1959
Asp Leu Lys Gly Asn Tyr Thr Ile Ile Asn Trp Gln Leu Ser Ala Glu
495 500 505 gat gaa tcg gtg ttg ttc cat gag gtg ggc aac tac aac gcc tac gct 2007
Asp Glu Ser Val Leu Phe His Glu Val Gly Asn Tyr Asn Ala Tyr Ala
510 515 520 aag ccc agt gac cga ctc aac atc aac gaa aag aaa atc ctc tgg agt 2055
Lys Pro Ser Asp Arg Leu Asn Ile Asn Glu Lys Lys Ile Leu Trp Ser
525 530 535 ggc ttc tcc aaa gtg gtt cct ttc tcc aac tgc agt cga gac tgt gtg 2103
Gly Phe Ser Lys Val Val Pro Phe Ser Asn Cys Ser Arg Asp Cys Val
540 545 550 555 ccg ggc acc agg aag ggg atc atc gag ggg gag ccc acc tgc tgc ttt 2151
Pro Gly Thr Arg Lys Gly Ile Ile Glu Gly Glu Pro Thr Cys Cys Phe
560 565 570 gaa tgc atg gca tgt gca gag gga gag ttc agt gat gaa aac gat gca 2199
Glu Cys Met Ala Cys Ala Glu Gly Glu Phe Ser Asp Glu Asn Asp Ala
575 580 585 agt gcg tgt aca aag tgc ccg aat gat ttc tgg tcg aat gag aac cac 2247
Ser Ala Cys Thr Lys Cys Pro Asn Asp Phe Trp Ser Asn Glu Asn His
590 595 600 acg tcg tgc atc gcc aag gag atc gag tac ctg tcg tgg acg gag ccc 2295
Thr Ser Cys Ile Ala Lys Glu Ile Glu Tyr Leu Ser Trp Thr Glu Pro
605 610 615 ttc ggg atc gct ctg acc atc ttc gcc gta ctg ggc atc ctg atc acc 2343
Phe Gly Ile Ala Leu Thr Ile Phe Ala Val Leu Gly Ile Leu Ile Thr
620 625 630 635 tcc ttc gtg ctg ggg gtc ttc atc aag ttc agg aac act ccc atc gtg 2391
Ser Phe Val Leu Gly Val Phe Ile Lys Phe Arg Asn Thr Pro Ile Val
640 645 650 aag gcc acc aac cgg gag ttg tcc tac ctg ctg ctc ttc tcc ctc atc 2439
Lys Ala Thr Asn Arg Glu Leu Ser Tyr Leu Leu Leu Phe Ser Leu Ile
655 660 665 tgc tgc ttc tcc agc tcg ctc atc ttc atc ggc gag ccc agg gac tgg 2487
Cys Cys Phe Ser Ser Ser Leu Ile Phe Ile Gly Glu Pro Arg Asp Trp
670 675 680

FIG. 1C acc tgt cgg ctc cgc caa ccg gcc ttt ggc atc agc ttc gtc ctg tgc 2535
Thr Cys Arg Leu Arg Gln Pro Ala Phe Gly Ile Ser Phe Val Leu Cys
685 690 695 atc tcc tgc atc ctg gtg aag acc aac cgg gtg ctg ctg gtc ttc gag 2583
Ile Ser Cys Ile Leu Val Lys Thr Asn Arg Val Leu Leu Val Phe Glu
700 705 710 715 gcc aag atc ccc acc agc ctc cac cgc aag tgg gtg ggc ctc aac ctg 2631
Ala Lys Ile Pro Thr Ser Leu His Arg Lys Trp Val Gly Leu Asn Leu
720 725 730 cag ttc ctc ctg gtc ttc ctc tgc atc ctg gtg caa atc gtc acc tgc 2679
Gln Phe Leu Leu Val Phe Leu Cys Ile Leu Val Gln Ile Val Thr Cys
735 740 745 atc atc tgg ctc tac acc gcg cct ccc tcc agc tac agg aac cat gag 2727
Ile Ile Trp Leu Tyr Thr Ala Pro Pro Ser Ser Tyr Arg Asn His Glu
750 755 760 ctg gag gac gag gtc atc ttc atc acc tgc gac gag ggc tcg ctc atg 2775
Leu Glu Asp Glu Val Ile Phe Ile Thr Cys Asp Glu Gly Ser Leu Met
765 770 775 gcg ctg ggc ttc ctc atc ggc tac acc tgc ctc ctc gcc gcc atc tgc 2823
Ala Leu Gly Phe Leu Ile Gly Tyr Thr Cys Leu Leu Ala Ala Ile Cys
780 785 790 795 ttc ttc ttc gcc ttc aag tcc cgt aag ctg ccg gag aac ttc aac gag 2871
Phe Phe Phe Ala Phe Lys Ser Arg Lys Leu Pro Glu Asn Phe Asn Glu
800 805 810 gct aag ttc atc acc ttc agc atg ttg atc ttc ttc atc gtc tgg atc 2919
Ala Lys Phe Ile Thr Phe Ser Met Leu Ile Phe Phe Ile Val Trp Ile
815 820 825 tcc ttc atc ccc gcc tat gtc agc acc tac ggc aag ttt gtg tcg gcc 2967
Ser Phe Ile Pro Ala Tyr Val Ser Thr Tyr Gly Lys Phe Val Ser Ala
830 835 840 gtg gag gtg att gcc atc ctg gcc tcc agc ttc ggg ctg ctg ggc tgc 3015
Val Glu Val Ile Ala Ile Leu Ala Ser Ser Phe Gly Leu Leu Gly Cys
845 850 855 att tac ttc aac aag tgt tac atc atc ctg ttc aag ccg tgc cgt aac 3063
Ile Tyr Phe Asn Lys Cys Tyr Ile Ile Leu Phe Lys Pro Cys Arg Asn
860 865 870 875 acc atc gag gag gtg cgc tgc agc acg gcg gcc cac gcc ttc aag gtg 3111
Thr Ile Glu Glu Val Arg Cys Ser Thr Ala Ala His Ala Phe Lys Val
880 885 890 gcg gcc cgg gcc acc ctc cgg cgc agc gcc gcg tct cgc aag cgc tcc 3159
Ala Ala Arg Ala Thr Leu Arg Arg Ser Ala Ala Ser Arg Lys Arg Ser
895 900 905 agc agc ctg tgc ggc tcc acc atc tcc tcg ccc gcc tcg tcc acc tgc 3207
Ser Ser Leu Cys Gly Ser Thr Ile Ser Ser Pro Ala Ser Ser Thr Cys
910 915 920

FIG. 1D

```
ggg ccg ggc ctc acc atg gag atg cag cgc tgc agc acg cag aag gtc     3255
Gly Pro Gly Leu Thr Met Glu Met Gln Arg Cys Ser Thr Gln Lys Val
    925                 930                 935

agc ttc ggc agc ggc acc gtc acc ctg tcg ctc agc ttc gag gag aca     3303
Ser Phe Gly Ser Gly Thr Val Thr Leu Ser Leu Ser Phe Glu Glu Thr
940                 945                 950                 955

ggc cga tac gcc acc ctc agc cgc acg gcc cgc agc agg aac tcg gcg     3351
Gly Arg Tyr Ala Thr Leu Ser Arg Thr Ala Arg Ser Arg Asn Ser Ala
                960                 965                 970

gat ggc cgc agc ggc gac gac ctg cca tct aga cac cac gac cag ggc     3399
Asp Gly Arg Ser Gly Asp Asp Leu Pro Ser Arg His His Asp Gln Gly
            975                 980                 985

ccg cct cag aaa tgc gag ccc cag ccc gcc aac gat gcc cga tac aag     3447
Pro Pro Gln Lys Cys Glu Pro Gln Pro Ala Asn Asp Ala Arg Tyr Lys
        990                 995                 1000

gcg gcg ccg acc aag ggc acc cta gag tcg ccg ggc ggc agc aag gag     3495
Ala Ala Pro Thr Lys Gly Thr Leu Glu Ser Pro Gly Gly Ser Lys Glu
    1005                1010                1015

cgc ccc aca act atg gag gaa acc taa tccaactcct ccatcaaccc          3542
Arg Pro Thr Thr Met Glu Glu Thr  *
1020                1025

caagaacatc ctccacggca gcaccgtcga caactgacat caactcctaa ccggtggctg 3602
cccaacctct cccctctccg gcactttgcg ttttgctgaa gattgcagca tctgcagttc 3662
cttttatccc tgattttctg acttggatat ttactagtgt gcgatggaat atcacaacat 3722
aatgagttgc acaattaggt gagcagagtt gtgtcaaagt atctgaacta tctgaagtat 3782
ctgaactact ttatttctct gaattgtatt acaaacattt gaagtatttt tagtgacatt 3842
atgttctaac attgtcaaga taatttgtta caacatataa ggtaccacct gaagcagtga 3902
ctgagattgc cactgtgatg acagaactgt tttataacat ttatcattga aacctggatt 3962
gcaacaggaa tataatgact gtaacaaaaa aattgttgat tatcttaaaa atgcaaattg 4022
taatcagatg tgtaaaattg gtaattactt ctgtacatta aatgcatatt tcttgataaa 4082
aaaaaaaaaa aaaaaaaaaa aaaaaaaaaa aaaagcggcc cgacagcaac gg         4134
```

FIG. 1E

```
Atlantic Salmon

Sequence Range: 1 to 594

                 10         20         30         40         50
                  *          *          *          *          *
C TTG GCA TTA TGC TCT GTG CTG GGG GTA TTC TTG ACA GCA TTC GTG ATG GGA
  Leu Ala Leu Cys Ser Val Leu Gly Val Phe Leu Thr Ala Phe Val Met Gly>
  ___a___a___a___TRANSLATION OF ATLANTIC SALMON NA.MV____a___a___a___>

       60         70         80         90        100
        *          *          *          *          *
GTG TTT ATC AAA TTT CGC AAC ACC CCA ATT GTT AAG GCC ACA AAC AGA GAG CTA
Val Phe Ile Lys Phe Arg Asn Thr Pro Ile Val Lys Ala Thr Asn Arg Glu Leu>
___a___a___a___a_TRANSLATION OF ATLANTIC SALMON NA.MV__a___a___a___a___>

  110        120        130        140        150        160
    *          *          *          *          *          *
TCC TAC CTC CTC CTG TTC TCA CTC ATC TGC TGT TTC TCC AGT TCC CTC ATC TTC
Ser Tyr Leu Leu Leu Phe Ser Leu Ile Cys Cys Phe Ser Ser Ser Leu Ile Phe>
___a___a___a___a_TRANSLATION OF ATLANTIC SALMON NA.MV__a___a___a___a___>

         170        180        190        200        210
           *          *          *          *          *
ATT GGT GAA CCC CAG GAC TGG ACA TGC CGT CTA CGC CAG CCT GCA TTC GGG ATA
Ile Gly Glu Pro Gln Asp Trp Thr Cys Arg Leu Arg Gln Pro Ala Phe Gly Ile>
___a___a___a___a_TRANSLATION OF ATLANTIC SALMON NA.MV__a___a___a___a___>

    220        230        240        250        260
      *          *          *          *          *
AGT TTT GTT CTC TGC ATC TCC TGC ATC CTG GTA AAA ACT AAC CGA GTA CTT CTA
Ser Phe Val Leu Cys Ile Ser Cys Ile Leu Val Lys Thr Asn Arg Val Leu Leu>
___a___a___a___a_TRANSLATION OF ATLANTIC SALMON NA.MV__a___a___a___a___>

270        280        290        300        310        320
  *          *          *          *          *          *
GTG TTC GAA GCC AAG ATC CCC ACC AGT CTC CAT CGT AAG TGG TGG GGG CTA AAC
Val Phe Glu Ala Lys Ile Pro Thr Ser Leu His Arg Lys Trp Trp Gly Leu Asn>
___a___a___a___a_TRANSLATION OF ATLANTIC SALMON NA.MV__a___a___a___a___>

      330        340        350        360        370
        *          *          *          *          *
TTC CAG TTC CTG TTA GTG TTC CTC TTC ACA TTT GTG CAA GTG ATG ATA TGT GTG
Leu Gln Phe Leu Leu Val Phe Leu Phe Thr Phe Val Gln Val Met Ile Cys Val>
___a___a___a___a_TRANSLATION OF ATLANTIC SALMON NA.MV__a___a___a___a___>

  380        390        400        410        420        430
    *          *          *          *          *          *
GTC TGG CTT TAC AAT GCT CCT CCG GCG AGC TAC AGG AAC CAT GAC ATT GAT GAG
Val Trp Leu Tyr Asn Ala Pro Pro Ala Ser Tyr Arg Asn His Asp Ile Asp Glu>
___a___a___a___a_TRANSLATION OF ATLANTIC SALMON NA.MV__a___a___a___a___>

        440        450        460        470        480
          *          *          *          *          *
ATA ATT TTC ATT ACA TGC AAT GAG GGC TCT ATG ATG GCG CTT GGC TTC CTA ATT
Ile Ile Phe Ile Thr Cys Asn Glu Gly Ser Met Met Ala Leu Gly Phe Leu Ile>
___a___a___a___a_TRANSLATION OF ATLANTIC SALMON NA.MV__a___a___a___a___>

    490        500        510        520        530
      *          *          *          *          *
GGG TAC ACA TGC CTG CTG GCA GCC ATA TRC TTC TTC TTT GCA TTT AAA TCA CGA
Gly Tyr Thr Cys Leu Leu Ala Ala Ile Xxx Phe Phe Phe Ala Phe Lys Ser Arg>
___a___a___a___a_TRANSLATION OF ATLANTIC SALMON NA.MV__a___a___a___a___>

540        550        560        570        580        590
  *          *          *          *          *          *
```

Atlantic Salmon

```
AAA CTG CCA GAG AAC TTT ACT GAG GCT AAG TTC ATC ACC TTC AGC ATG CTC ATC
Lys Leu Pro Glu Asn Phe Thr Glu Ala Lys Phe Ile Thr Phe Ser Met Leu Ile>
___a___a___a___a_TRANSLATION OF ATLANTIC SALMON NA.MV__a___a___a___a___>

TT
Xxx>
__>
```

FIG. 7B

```
        10        20        30        40        50        60        70
GTGATCACAAAGGTAAGAAAGACAGTGAAAAATCTGAACTACCCCATTATATAATCTGTTGCTATTTCAT 70
ATGTTTCTATCAATAATACAAACACTACTTCTCTATTCCTGCAGATGCCAGTGTTTGTACCAAGTGTCCC 140
AATGACTCATGGTCTAATGAGAACCACACATCTTGTTTCCTGAAGGAGATAGAGTTTCTGTCTTGGACAG 210
AGCCCTTTGGGATCGCCTTGGCATTATGCTCTGTGCTGGGGGTATTCTTGACAGCATTCGTGATGGGAGT 280
GTTTATCAAATTTCGCAACACCCCAATTGTTAAGGCCACAAACAGAGAGCTATCCTACCTCCTCCTGTTC 350
       360       370       380       390       400       410       420
TCACTCATCTGCTGTTTCTCCAGTTCCCTCATCTTCATTGGTGAACCCCAGGACTGGACATGCCGTCTAC 420
GCCAGCCTGCATTCGGGATAAGTTTTGTTCTCTGCATCTCCTGCATCCTGGTAAAAACTAACCGAGTACT 490
TCTAGTGTTCGAAGCCAAGATCCCCACCAGTCTCCATCGTAAGTGGTGGGGGCTAAACTTGCAGTTCCTG 560
TTAGTGTTCCTGTTCACATTTGTGCAAGTGATGATATGTGTGGTCTGGCTTTACAATGCTCCTCCGGCGA 630
GCTACAGGAACCATGACATTGATGAGATAATTTTCATTACATGCAATGAGGGCTCTATGATGGCGCTTGG 700
       710       720       730       740       750       760       770
CTTCCTAATTGGGTACACATGCCTGCTGGCAGCCATATGCTTCTTCTTTGCATTTAAATCACGAAAACTG 770
CCAGAGAACTTTACTGAGGCTAAGTTCATCACCTTCAGCATGCTCATCTTCTTCATCGTCTGGATCTCTT 840
TCATCCCTGCCTACTTCAGCACTTACGGAAAGTTTGTGTCGGCTGTGGAGGTCATCGCCATACTAGCCTC 910
CAGCTTTGGCCTGCTGGCCTGTATTTTCTTCAATAAAGTCTACATCATCCTCTTCAAACCGTCCAGGAAC 980
ACTATAGAGGAGGTTCGCTGTAGCACTGCGGCCCATTCTTTCAAAGTGGCAGCCAAGGCCACTCTGAGAC 1050
      1060      1070      1080      1090      1100      1110      1120
ACAGCTCAGCCTCCAGGAAGAGGTCCAGCAGTGTGGGGGATCCTGTGCCTCAACTCCCTCCTCATCCAT 1120
CAGCCTCAAGACCAATGACAATGACTCCCCATCAGGTCAGCAGAGAATCCATAAGCCAAGAGTAAGCTTT 1190
GGAAGTGGAACAGTTACTCTGTCCTTGAGCTTTGAGGAGTCCAGAAAGAATTCTATGAAGTAGGGAAGTG 1260
TCTTTTGGTGGGCCGAGAGCCTTGTCAAAACCTGAGTTGGTGTTGCATTCTTTGTTGGCTGGGTAGTTGG 1330
AGCAGAAATTATGATATTAAAAGCTTTGATGTATTCAGAATGGTGACACAGCATAGGTGGCCAAGATTCC 1400
```

FIG. 8A

```
     1410      1420      1430      1440      1450      1460      1470
ATTATATTACAATAATCTGTGTTGTTCATTATGAGGACATTTCAAAATGCTGAAAATCATCAAATACATA 1470
ATTTACTGAGTTTTCTTGATAATCTTGAGAATAGAATAGCCTATTCAAGTCATCGTTGAGCAGACATTAA 1540
TTAACAATGATGTAATACTTTCCATACCTATTTTCTTTAACAATAGATTCACATTGTTAAAGTTCAACTA 1610
TGACCTGTAAAATACATGAGGTATAACAGGAGACAATAAAACTATGCATATCCTAGCTTCTGGGCCTGAG 1680
TAGCAGGCAGTTTACTCTGGGCACGCTTTTCATCCAAACTTCCGAATGCTGCCCCCAATCCTAGTGAGGT 1750
     1760      1770      1780      1790      1800      1810      1820
TAAAGGCCCAGTGCAGTCATATCTTTTCTCTAGGCACGCTTTTCATCCAAACTTCCGAATGCGGCTATAT 1820
CAGTCTCTTTCCTACTGTCTTTTTCATTAGGCCAGTGTTTAACAACCCTGGTCCTTAAGTACACACAACA 1890
GAACACATTTTTGTTGTAGCCCTGGACAATCACTCCTCACTCAGCTCATTGAGGGCCTGATGATTAGTTG 1960
ACAAGTTGAATCAGGTGTGCTTGTCCAGGGTTACAATACAAATGTGTACTGTTGGGGGTAC 2021
```

FIG. 8B

```
        10         20         30         40
YKHYFSIPADASVCTKCPNDSWSNENHTSCFLKEIEFLSW  40
TEPFGIALALCSVLGVFLTAFVMGVFIKFRNTPIVKATNR  80
ELSYLLLFSLICCFSSSLIFIGEPQDWTCRLRQPAFGISF  120
VLCISCILVKTNRVLLVFEAKIPTSLHRKWWGLNLQFLLV  160
FLFTFVQVMICVVWLYNAPPASYRNHDIDEIIFITCNEGS  200
        210        220        230        240
MMALGFLIGYTCLLAAICFFFAFKSRKLPENFTEAKFITF  240
SMLIFFIVWISFIPAYFSTYGKFVSAVEVIAILASSFGLL  280
ACIFFNKVYIILFKPSRNTIEEVRCSTAAHSFKVAAKATL  320
RHSSASRKRSSSVGGSCASTPSSSISLKTNDNDSPSGQQR  360
IHKPRVSFGSGTVTLSLSFEESRKNSMK  388
```

FIG. 8C

```
Sequence Range: 1 to 3941
        10        20        30        40        50        60        70        80
TTCCAACAGCATATTTTTGTTGTATTTGCTTTGGTTTGTCTGAAATCAAGCATTATCAAGATCAAGAACAGCATGAGTCA

        90       100       110       120       130       140       150       160
GAAACAAGGCGACAGCCAGAGTCACTGGAGGGGACAAGACTGAGGTTAACTCTGAAGTCTAATGTGCTGAGAGGACAAGG

       170       180         190         200         210         220
CCCTCCTGAGAGCTGAACG ATG AGA TTT TAC CTG TAT TAC CTG GTG CTT TTG GGC TTC AGT TCT
                    Met Arg Phe Tyr Leu Tyr Tyr Leu Val Leu Leu Gly Phe Ser Ser>

    230         240         250         260         270         280
GTC ATC TCC ACC TAT GGG CCT CAT CAG AGA GCA CAG AAG ACT GGG GAT ATT CTG CTG GGC
Val Ile Ser Thr Tyr Gly Pro His Gln Arg Ala Gln Lys Thr Gly Asp Ile Leu Leu Gly>

    290         300         310         320         330         340
GGG CTG TTT CCA ATG CAC TTT GGT GTT ACC TCC AAA GAC CAA GAC CTG GCA GCG CGG CCA
Gly Leu Phe Pro Met His Phe Gly Val Thr Ser Lys Asp Gln Asp Leu Ala Ala Arg Pro>

    350         360         370         380         390         400
GAA TCC ACA GAG TGT GTT AGG TAC AAT TTC CGG GGA TTC CGT TGG CTT CAG GCC ATG ATT
Glu Ser Thr Glu Cys Val Arg Tyr Asn Phe Arg Gly Phe Arg Trp Leu Gln Ala Met Ile>

    410         420         430         440         450         460
TTT GCA ATA GAG GAG ATC AAC AAC AGC AGT ACT CTC CTG CCC AAC ATC ACA CTG GGC TAC
Phe Ala Ile Glu Glu Ile Asn Asn Ser Ser Thr Leu Leu Pro Asn Ile Thr Leu Gly Tyr>

    470         480         490         500         510         520
AGG ATC TTT GAC ACC TGC AAC ACC GTG TCC AAG GCC CTG GAG GCT ACC CTC AGT TTC GTA
Arg Ile Phe Asp Thr Cys Asn Thr Val Ser Lys Ala Leu Glu Ala Thr Leu Ser Phe Val>

    530         540         550         560         570         580
GCA CAG AAT AAG ATT GAC TCT CTG AAC TTG GAT GAA TTC TGT AAC TGC ACT GAT CAC ATC
Ala Gln Asn Lys Ile Asp Ser Leu Asn Leu Asp Glu Phe Cys Asn Cys Thr Asp His Ile>

    590         600         610         620         630         640
CCA TCG ACT ATA GCA GTG GTG GGG GCT TCT GGG TCA GCG GTC TCC ACT GCT GTT GCC AAT
Pro Ser Thr Ile Ala Val Val Gly Ala Ser Gly Ser Ala Val Ser Thr Ala Val Ala Asn>

    650         660         670         680         690         700
CTG TTG GGC CTT TTC TAC ATC CCA CAG ATC AGC TAT GCC TCT TCC AGT CGC CTA CTA AGC
Leu Leu Gly Leu Phe Tyr Ile Pro Gln Ile Ser Tyr Ala Ser Ser Ser Arg Leu Leu Ser>

    710         720         730         740         750         760
AAC AAG AAC CAG TTC AAA TCC TTC ATG AGG ACC ATT CCC ACA GAT GAG CAC CAG GCC ACT
Asn Lys Asn Gln Phe Lys Ser Phe Met Arg Thr Ile Pro Thr Asp Glu His Gln Ala Thr>

    770         780         790         800         810         820
GCC ATG GCA GAT ATC ATC GAC TAC TTC CAA TGG AAT TGG GTC ATT GCA GTT GCG TCT GAT
Ala Met Ala Asp Ile Ile Asp Tyr Phe Gln Trp Asn Trp Val Ile Ala Val Ala Ser Asp>

    830         840         850         860         870         880
GAT GAG TAT GGA CGT CCG GGG ATT GAA AAA TTT GAG AAA GAG ATG GAA GAA CGA GAC ATT
Asp Glu Tyr Gly Arg Pro Gly Ile Glu Lys Phe Glu Lys Glu Met Glu Glu Arg Asp Ile>
```

FIG. 9A

```
     890              900             910             920             930             940
TGT ATC CAT CTG AGT GAG CTG ATC TCT CAG TAC TTT GAG GAG TGG CAG ATC CAA GGA TTG
Cys Ile His Leu Ser Glu Leu Ile Ser Gln Tyr Phe Glu Glu Trp Gln Ile Gln Gly Leu>

     950              960             970             980             990            1000
GTT GAC CGT ATT GAG AAC TCC TCA GCT AAA GTT ATA GTC GTT TTC GCC AGT GGG CCT GAC
Val Asp Arg Ile Glu Asn Ser Ser Ala Lys Val Ile Val Val Phe Ala Ser Gly Pro Asp>

    1010             1020            1030            1040            1050            1060
ATT GAG CCT CTT ATT AAA GAG ATG GTC AGA CGG AAC ATC ACC GAC CGC ATC TGG TTG GCC
Ile Glu Pro Leu Ile Lys Glu Met Val Arg Arg Asn Ile Thr Asp Arg Ile Trp Leu Ala>

    1070             1080            1090            1100            1110            1120
AGC GAG GCT TGG GCA ACC ACC TCC CTC ATC GCC AAA CCA GAG TAC CTT GAT GTT GTA GTT
Ser Glu Ala Trp Ala Thr Thr Ser Leu Ile Ala Lys Pro Glu Tyr Leu Asp Val Val Val>

    1130             1140            1150            1160            1170            1180
GGG ACC ATT GGC TTT GCT CTC AGA GCA GGC GAA ATA CCT GGC TTC AAG GAC TTC TTA CAA
Gly Thr Ile Gly Phe Ala Leu Arg Ala Gly Glu Ile Pro Gly Phe Lys Asp Phe Leu Gln>

    1190             1200            1210            1220            1230            1240
GAG GTC ACA CCA AAG AAA TCC AGC CAC AAT GAA TTT GTC AGG GAG TTT TGG GAG GAG ACT
Glu Val Thr Pro Lys Lys Ser Ser His Asn Glu Phe Val Arg Glu Phe Trp Glu Glu Thr>

    1250             1260            1270            1280            1290            1300
TTT AAC TGC TAT CTG GAA GAC AGC CAG AGA CTG AGA GAC AGT GAG AAT GGG AGC ACC AGT
Phe Asn Cys Tyr Leu Glu Asp Ser Gln Arg Leu Arg Asp Ser Glu Asn Gly Ser Thr Ser>

    1310             1320            1330            1340            1350            1360
TTC AGA CCA TTG TGT ACT GGC GAG GAG GAC ATT ATG GGT GCA GAG ACC CCA TAT CTG GAT
Phe Arg Pro Leu Cys Thr Gly Glu Glu Asp Ile Met Gly Ala Glu Thr Pro Tyr Leu Asp>

    1370             1380            1390            1400            1410            1420
TAC ACT CAT CTT CGT ATT TCC TAT AAT GTG TAT GTT GCA GTT CAC TCC ATT GCA CAG GCC
Tyr Thr His Leu Arg Ile Ser Tyr Asn Val Tyr Val Ala Val His Ser Ile Ala Gln Ala>

    1430             1440            1450            1460            1470            1480
CTA CAG GAC ATT CTC ACC TGC ATT CCT GGA CGG GGT CTT TTT TCC AAC AAC TCA TGT GCA
Leu Gln Asp Ile Leu Thr Cys Ile Pro Gly Arg Gly Leu Phe Ser Asn Asn Ser Cys Ala>

    1490             1500            1510            1520            1530            1540
GAT ATA AAG AAA ATA GAA GCA TGG CAG GTT CTC AAG CAG CTC AGA CAT TTA AAC TTC TCA
Asp Ile Lys Lys Ile Glu Ala Trp Gln Val Leu Lys Gln Leu Arg His Leu Asn Phe Ser>

    1550             1560            1570            1580            1590            1600
AAC AGT ATG GGA GAA AAG GTA CAT TTT GAT GAG AAT GCT GAT CCG TCA GGA AAC TAC ACC
Asn Ser Met Gly Glu Lys Val His Phe Asp Glu Asn Ala Asp Pro Ser Gly Asn Tyr Thr>

    1610             1620            1630            1640            1650            1660
ATT ATC AAT TGG CAC CGG TCT CCT GAG GAT GGT TCT GTT GTG TTT GAA GAG GTC GGT TTC
Ile Ile Asn Trp His Arg Ser Pro Glu Asp Gly Ser Val Val Phe Glu Glu Val Gly Phe>

    1670             1680            1690            1700            1710            1720
TAC AAC ATG CGA GCT AAG AGA GGA GTA CAA CTT TTC ATT GAT AAC ACA AAG ATT CTA TGG
Tyr Asn Met Arg Ala Lys Arg Gly Val Gln Leu Phe Ile Asp Asn Thr Lys Ile Leu Trp>
```

FIG. 9B

```
   1730           1740           1750           1760           1770           1780
AAT GGA TAT AAT ACT GAG GTT CCA TTC TCT AAC TGT AGT GAA GAT TGT GAA CCA GGC ACC
Asn Gly Tyr Asn Thr Glu Val Pro Phe Ser Asn Cys Ser Glu Asp Cys Glu Pro Gly Thr>

   1790           1800           1810           1820           1830           1840
AGA AAG GGG ATC ATA GAA AGC ATG CCA ACG TGT TGC TTT GAA TGT ACA GAA TGC TCA GAA
Arg Lys Gly Ile Ile Glu Ser Met Pro Thr Cys Cys Phe Glu Cys Thr Glu Cys Ser Glu>

   1850           1860           1870           1880           1890           1900
GGA GAG TAT AGT GAT CAC AAA GAT GCC AGT GTT TGT ACC AAG TGT CCC AAT GAC TCA TGG
Gly Glu Tyr Ser Asp His Lys Asp Ala Ser Val Cys Thr Lys Cys Pro Asn Asp Ser Trp>

   1910           1920           1930           1940           1950           1960
TCT AAT GAG AAC CAC ACA TCT TGT TTC CTG AAG GAG ATA GAG TTT CTG TCT TGG ACA GAG
Ser Asn Glu Asn His Thr Ser Cys Phe Leu Lys Glu Ile Glu Phe Leu Ser Trp Thr Glu>

   1970           1980           1990           2000           2010           2020
CCC TTT GGG ATC GCC TTG GCA TTA TGC TCT GTG CTG GGG GTA TTC TTG ACA GCA TTC GTG
Pro Phe Gly Ile Ala Leu Ala Leu Cys Ser Val Leu Gly Val Phe Leu Thr Ala Phe Val>

   2030           2040           2050           2060           2070           2080
ATG GGA GTG TTT ATC AAA TTT CGC AAC ACC CCA ATT GTT AAG GCC ACA AAC AGA GAG CTA
Met Gly Val Phe Ile Lys Phe Arg Asn Thr Pro Ile Val Lys Ala Thr Asn Arg Glu Leu>

   2090           2100           2110           2120           2130           2140
TCC TAC CTC CTC CTG TTC TCA CTC ATC TGC TGT TTC TCC AGT TCC CTC ATC TTC ATT GGT
Ser Tyr Leu Leu Leu Phe Ser Leu Ile Cys Cys Phe Ser Ser Ser Leu Ile Phe Ile Gly>

   2150           2160           2170           2180           2190           2200
GAA CCC CAG GAC TGG ACA TGC CGT CTA CGC CAG CCT GCA TTC GGG ATA AGT TTT GTT CTC
Glu Pro Gln Asp Trp Thr Cys Arg Leu Arg Gln Pro Ala Phe Gly Ile Ser Phe Val Leu>

   2210           2220           2230           2240           2250           2260
TGC ATC TCC TGC ATC CTG GTA AAA ACT AAC CGA GTA CTT CTA GTG TTC GAA GCC AAG ATC
Cys Ile Ser Cys Ile Leu Val Lys Thr Asn Arg Val Leu Leu Val Phe Glu Ala Lys Ile>

   2270           2280           2290           2300           2310           2320
CCC ACC AGT CTC CAT CGT AAG TGG TGG GGG CTA AAC TTG CAG TTC CTG TTA GTG TTC CTG
Pro Thr Ser Leu His Arg Lys Trp Trp Gly Leu Asn Leu Gln Phe Leu Leu Val Phe Leu>

   2330           2340           2350           2360           2370           2380
TTC ACA TTT GTG CAA GTG ATG ATA TGT GTG GTC TGG CTT TAC AAT GCT CCT CCG GCG AGC
Phe Thr Phe Val Gln Val Met Ile Cys Val Val Trp Leu Tyr Asn Ala Pro Pro Ala Ser>

   2390           2400           2410           2420           2430           2440
TAC AGG AAC CAT GAC ATT GAT GAG ATA ATT TTC ATT ACA TGC AAT GAG GGC TCT ATG ATG
Tyr Arg Asn His Asp Ile Asp Glu Ile Ile Phe Ile Thr Cys Asn Glu Gly Ser Met Met>

   2450           2460           2470           2480           2490           2500
GCG CTT GGC TTC CTA ATT GGG TAC ACA TGC CTG CTG GCA GCC ATA TGC TTC TTC TTT GCA
Ala Leu Gly Phe Leu Ile Gly Tyr Thr Cys Leu Leu Ala Ala Ile Cys Phe Phe Phe Ala>

   2510           2520           2530           2540           2550           2560
TTT AAA TCA CGA AAA CTG CCA GAG AAC TTT ACT GAG GCT AAG TTC ATC ACC TTC AGC ATG
Phe Lys Ser Arg Lys Leu Pro Glu Asn Phe Thr Glu Ala Lys Phe Ile Thr Phe Ser Met>
```

FIG. 9C

```
   2570            2580          2590          2600           2610          2620
CTC ATC TTC TTC ATC GTC TGG ATC TCT TTC ATC CCT GCC TAC TTC AGC ACT TAC GGA AAG
Leu Ile Phe Phe Ile Val Trp Ile Ser Phe Ile Pro Ala Tyr Phe Ser Thr Tyr Gly Lys>

   2630            2640          2650          2660           2670          2680
TTT GTG TCG GCT GTG GAG GTC ATC GCC ATA CTA GCC TCC AGC TTT GGC CTG CTG GCC TGT
Phe Val Ser Ala Val Glu Val Ile Ala Ile Leu Ala Ser Ser Phe Gly Leu Leu Ala Cys>

   2690            2700          2710          2720           2730          2740
ATT TTC TTC AAT AAA GTC TAC ATC ATC CTC TTC AAA CCG TCC AGG AAC ACT ATA GAG GAG
Ile Phe Phe Asn Lys Val Tyr Ile Ile Leu Phe Lys Pro Ser Arg Asn Thr Ile Glu Glu>

   2750            2760          2770          2780           2790          2800
GTT CGC TGT AGC ACT GCG GCC CAT TCT TTC AAA GTG GCA GCC AAG GCC ACT CTG AGA CAC
Val Arg Cys Ser Thr Ala Ala His Ser Phe Lys Val Ala Ala Lys Ala Thr Leu Arg His>

   2810            2820          2830          2840           2850          2860
AGC TCA GCC TCC AGG AAG AGG TCC AGC AGT GTG GGG GGA TCC TGT GCC TCA ACT CCC TCC
Ser Ser Ala Ser Arg Lys Arg Ser Ser Ser Val Gly Gly Ser Cys Ala Ser Thr Pro Ser>

   2870            2880          2890          2900           2910          2920
TCA TCC ATC AGC CTC AAG ACC AAT GAC AAT GAC TCC CCA TCA GGT CAG CAG AGA ATC CAT
Ser Ser Ile Ser Leu Lys Thr Asn Asp Asn Asp Ser Pro Ser Gly Gln Gln Arg Ile His>

   2930            2940          2950          2960           2970          2980
AAG CCA AGA GTA AGC TTT GGA AGT GGA ACA GTT ACT CTG TCC TTG AGC TTT GAG GAG TCC
Lys Pro Arg Val Ser Phe Gly Ser Gly Thr Val Thr Leu Ser Leu Ser Phe Glu Glu Ser>

   2990            3000          3010       3020       3030       3040
AGA AAG AAT TCT ATG AAG TAG GGAAGTGTCTTTTGGTGGGCCGAGAGCCTTGTCAA
Arg Lys Asn Ser Met Lys ***> (SEQ ID NO: 8)

      3050       3060       3070       3080       3090       3100       3110       3120
AACCTGAGTTGGTGTTGCATTCTTTGTTGGCTGGGTAGTTGGAGCAGAAATTATGATATTAAAAGCTTTGATGTATTCAG

      3130       3140       3150       3160       3170       3180       3190       3200
AATGGTGACACAGCATAGGTGGCCAAGATTCCATTATATTACAATAATCTGTGTTGTTCATTATGAGGACATTTCAAAAT

      3210       3220       3230       3240       3250       3260       3270       3280
GCTGAAAATCATCAAATACATAATTTACTGAGTTTTCTTGATAATCTTGAGAATAGAATAGCCTATTCAAGTCATCGTTG

      3290       3300       3310       3320       3330       3340       3350       3360
AGCAGACATTAATTAACAATGATGTAATACTTTCCATACCTATTTTCTTTAACAATAGATTCACATTGTTAAAGTTCAAC

      3370       3380       3390       3400       3410       3420       3430       3440
TATGACCTGTAAAATACATGAGGTATAACAGGAGACAATAAAACTATGCATATCCTAGCTTCTGGGCCTGAGTAGCAGGC

      3450       3460       3470       3480       3490       3500       3510       3520
AGTTTACTCTGGGCACGCTTTTCATCCAAACTTCCGAATGCTGCCCCCAATCCTAGTGAGGTTAAAGGCCCAGTGCAGTC

      3530       3540       3550       3560       3570       3580       3590       3600
ATATCTTTTCTCTAGGCACGCTTTTCATCCAAACTTCCGAATGCGGCTATATCAGTCTCTTTCCTACTGTCTTTTTCATT

      3610       3620       3630       3640       3650       3660       3670       3680
AGGCCAGTGTTTAACAACCCTGGTCCTTAAGTACACACAACAGAGCACATTTTTGTTGTGGCCCTGGACAATCACTCCTC
```

FIG. 9D

```
      3690      3700      3710      3720      3730      3740      3750      3760
ACTCAGCTCATTGAGGGCCTGATGATTAGTTGACAAGTTGAGTCGGGTGTGCTTGTCCGGGGTTGCAATACAGATGTGTA

      3770      3780      3790      3800      3810      3820      3830      3840
CTGTTGGGGGTACTCGAGGACCAGGATTGGGAAACATTACATTAGGACTACTGTAGGTTCTTCAATATGGTGTCATACGG

      3850      3860      3870      3880      3890      3900      3910      3920
TCATATGGTGTCATATGGTGTCTGGTTGTTTTCTGCATATGTGTATTTCACCAAGTTACTGCACATGTTAGACCTATACA

      3930      3940
CTGGAATAAACATTTTTTTTC (SEQ ID NO: 7)
```

FIG. 9E

Sequence Range: 1 to 4031

```
        10         20         30         40         50         60         70         80
GTTCCAACAGCATATTTTTGTTGTATTTGCTTTGGTTTGTCTGAAATCAAGCATTATCAAGGATTGAGCAAGACAACTGA

        90        100        110        120        130        140        150        160
GTTGTCAGACTAAGAATATACACATTTCCAGTTCTCTCTTTAATGGACTTCTCACACTGATGTTCTTCAGATCAAGAACA

       170        180        190        200        210        220        230        240
GCATGAGTCAGAAACAAGGCGACAGCCAGAGTCACTGGAGGGGACAAGACTGAGGTTAACTCTGAAGTCTAATGTGCTGA

       250        260        270            280            290            300
GAGGACAAGGCCCTCCTGAGAGCTGAACG ATG AGA TTT TAC CTG TAT TAC CTG GTG CTT TTG GGC TTC
                              Met Arg Phe Tyr Leu Tyr Tyr Leu Val Leu Leu Gly Phe>

310          320          330          340          350          360
 AGT TCT GTC ATC TCC ACC TAT GGG CCT CAT CAG AGA GCA CAG AAG ACT GGG GAT ATT CTG
 Ser Ser Val Ile Ser Thr Tyr Gly Pro His Gln Arg Ala Gln Lys Thr Gly Asp Ile Leu>

370          380          390          400          410          420
 CTG GGC GGG CTG TTT CCA ATG CAC TTT GGT GTT ACC TCC AAA GAC CAA GAC CTG GCA GCG
 Leu Gly Gly Leu Phe Pro Met His Phe Gly Val Thr Ser Lys Asp Gln Asp Leu Ala Ala>

430          440          450          460          470          480
 CGG CCA GAA TCC ACA GAG TGT GTT AGG TAC AAT TTC CGG GGA TTC CGT TGG CTT CAG GCC
 Arg Pro Glu Ser Thr Glu Cys Val Arg Tyr Asn Phe Arg Gly Phe Arg Trp Leu Gln Ala>

490          500          510          520          530          540
 ATG ATT TTT GCA ATA GAG GAG ATC AAC AAC AGC AGT ACT CTC CTG CCC AAC ATC ACA CTG
 Met Ile Phe Ala Ile Glu Glu Ile Asn Asn Ser Ser Thr Leu Leu Pro Asn Ile Thr Leu>

550          560          570          580          590          600
 GGC TAC AGG ATC TTT GAC ACC TGC AAC ACC GTG TCC AAG GCC CTG GAG GCT ACC CTC AGT
 Gly Tyr Arg Ile Phe Asp Thr Cys Asn Thr Val Ser Lys Ala Leu Glu Ala Thr Leu Ser>

610          620          630          640          650          660
 TTC GTA GCA CAG AAT AAG ATT GAC TCT CTG AAC TTG GAT GAA TTC TGT AAC TGC ACT GAT
 Phe Val Ala Gln Asn Lys Ile Asp Ser Leu Asn Leu Asp Glu Phe Cys Asn Cys Thr Asp>

670          680          690          700          710          720
 CAC ATC CCA TCG ACT ATA GCA GTG GTG GGG GCT TCT GGG TCA GCG GTC TCC ACT GCT GTT
 His Ile Pro Ser Thr Ile Ala Val Val Gly Ala Ser Gly Ser Ala Val Ser Thr Ala Val>

730          740          750          760          770          780
 GCC AAT CTG TTG GGC CTT TTC TAC ATC CCA CAG ATC AGC TAT GCC TCT TCC AGT CGC CTA
 Ala Asn Leu Leu Gly Leu Phe Tyr Ile Pro Gln Ile Ser Tyr Ala Ser Ser Ser Arg Leu>

790          800          810          820          830          840
 CTA AGC AAC AAG AAC CAG TTC AAA TCC TTC ATG AGG ACC ATT CCC ACA GAT GAG CAC CAG
 Leu Ser Asn Lys Asn Gln Phe Lys Ser Phe Met Arg Thr Ile Pro Thr Asp Glu His Gln>

850          860          870          880          890          900
 GCC ACT GCC ATG GCA GAT ATC ATC GAC TAC TTC CAA TGG AAT TGG GTC ATT GCA GTT GCG
 Ala Thr Ala Met Ala Asp Ile Ile Asp Tyr Phe Gln Trp Asn Trp Val Ile Ala Val Ala>

910          920          930          940          950          960
 TCT GAT GAT GAG TAT GGA CGT CCG GGG ATT GAA AAA TTT GAG AAA GAG ATG GAA GAA CGA
 Ser Asp Asp Glu Tyr Gly Arg Pro Gly Ile Glu Lys Phe Glu Lys Glu Met Glu Glu Arg>
```

FIG. 10A

```
970         980         990         1000        1010        1020
GAC ATT TGT ATC CAT CTG AGT GAG CTG ATC TCT CAG TAC TTT GAG GAG TGG CAG ATC CAA
Asp Ile Cys Ile His Leu Ser Glu Leu Ile Ser Gln Tyr Phe Glu Glu Trp Gln Ile Gln>

1030        1040        1050        1060        1070        1080
GGA TTG GTT GGC CGT ATT GAG AAC TCC TCA GCT AAA GTT ATA GTC GTT TTC GCC AGT GGG
Gly Leu Val Gly Arg Ile Glu Asn Ser Ser Ala Lys Val Ile Val Val Phe Ala Ser Gly>

1090        1100        1110        1120        1130        1140
CCT GAC ATT GAG CCT CTT ATT AAA GAG ATG GTC AGA CGG AAC ATC ACC GAC CGC ATC TGG
Pro Asp Ile Glu Pro Leu Ile Lys Glu Met Val Arg Arg Asn Ile Thr Asp Arg Ile Trp>

1150        1160        1170        1180        1190        1200
TTG GCC AGC GAG GCT TGG GCA ACC ACC TCC CTC ATC GCC AAA CCA GAG TAC CTT GAT GTT
Leu Ala Ser Glu Ala Trp Ala Thr Thr Ser Leu Ile Ala Lys Pro Glu Tyr Leu Asp Val>

1210        1220        1230        1240        1250        1260
GTA GTT GGG ACC ATT GGC TTT GCT CTC AGA GCA GGC GAA ATA CCT GGC TTC AAG GAC TTC
Val Val Gly Thr Ile Gly Phe Ala Leu Arg Ala Gly Glu Ile Pro Gly Phe Lys Asp Phe>

1270        1280        1290        1300        1310        1320
TTA CAA GAG GTC ACA CCA AAG AAA TCC AGC CAC AAT GAA TTT GTC AGG GAG TTT TGG GAG
Leu Gln Glu Val Thr Pro Lys Lys Ser Ser His Asn Glu Phe Val Arg Glu Phe Trp Glu>

1330        1340        1350        1360        1370        1380
GAG ACT TTT AAC TGC TAT CTG GAA GAC AGC CAG AGA CTG AGA GAC AGT GAG AAT GGG AGC
Glu Thr Phe Asn Cys Tyr Leu Glu Asp Ser Gln Arg Leu Arg Asp Ser Glu Asn Gly Ser>

1390        1400        1410        1420        1430        1440
ACC AGT TTC AGA CCA TTG TGT ACT GGC GAG GAG GAC ATT ATG GGT GCA GAG ACC CCA TAT
Thr Ser Phe Arg Pro Leu Cys Thr Gly Glu Glu Asp Ile Met Gly Ala Glu Thr Pro Tyr>

1450        1460        1470        1480        1490        1500
CTG GAT TAC ACT CAT CTT CGT ATT TCC TAT AAT GTG TAT GTT GCA GTT CAC TCC ATT GCA
Leu Asp Tyr Thr His Leu Arg Ile Ser Tyr Asn Val Tyr Val Ala Val His Ser Ile Ala>

1510        1520        1530        1540        1550        1560
CAG GCC CTA CAG GAC ATT CTC ACC TGC ATT CCT GGA CGG GGT CTT TTT TCC AAC AAC TCA
Gln Ala Leu Gln Asp Ile Leu Thr Cys Ile Pro Gly Arg Gly Leu Phe Ser Asn Asn Ser>

1570        1580        1590        1600        1610        1620
TGT GCA GAT ATA AAG AAA ATA GAA GCA TGG CAG GTT CTC AAG CAG CTC AGA CAT TTA AAC
Cys Ala Asp Ile Lys Lys Ile Glu Ala Trp Gln Val Leu Lys Gln Leu Arg His Leu Asn>

1630        1640        1650        1660        1670        1680
TTC TCA AAC AGT ATG GGA GAA AAG GTA CAT TTT GAT GAG AAT GCT GAT CCG TCA GGA AAC
Phe Ser Asn Ser Met Gly Glu Lys Val His Phe Asp Glu Asn Ala Asp Pro Ser Gly Asn>

1690        1700        1710        1720        1730        1740
TAC ACC ATT ATC AAT TGG CAC CGG TCT CCT GAG GAT GGT TCT GTT GTG TTT GAA GAG GTC
Tyr Thr Ile Ile Asn Trp His Arg Ser Pro Glu Asp Gly Ser Val Val Phe Glu Glu Val>

1750        1760        1770        1780        1790        1800
GGT TTC TAC AAC ATG CGA GCT AAG AGA GGA GTA CAA CTT TTC ATT GAT AAC ACA AAG ATT
Gly Phe Tyr Asn Met Arg Ala Lys Arg Gly Val Gln Leu Phe Ile Asp Asn Thr Lys Ile>

1810        1820        1830        1840        1850        1860
```

```
      CTA TGG AAT GGA TAT AAT ACT GAG GTT CCA TTC TCT AAC TGT AGT GAA GAT TGT GAA CCA
      Leu Trp Asn Gly Tyr Asn Thr Glu Val Pro Phe Ser Asn Cys Ser Glu Asp Cys Glu Pro>

   1870      1880      1890      1900      1910      1920
      GGC ACC AGA AAG GGG ATC ATA GAA AGC ATG CCA ACG TGT TGC TTT GAA TGT ACA GAA TGC
      Gly Thr Arg Lys Gly Ile Ile Glu Ser Met Pro Thr Cys Cys Phe Glu Cys Thr Glu Cys>

   1930      1940      1950      1960      1970      1980
      TCA GAA GGA GAG TAT AGT GAT CAC AAA GAT GCC AGT GTT TGT ACC AAG TGT CCC AAT GAC
      Ser Glu Gly Glu Tyr Ser Asp His Lys Asp Ala Ser Val Cys Thr Lys Cys Pro Asn Asp>

   1990      2000      2010      2020      2030      2040
      TCA TGG TCT AAT GAG AAC CAC ACA TCT TGT TTC CTG AAG GAG ATA GAG TTT CTG TCT TGG
      Ser Trp Ser Asn Glu Asn His Thr Ser Cys Phe Leu Lys Glu Ile Glu Phe Leu Ser Trp>

   2050      2060      2070      2080      2090      2100
      ACA GAG CCC TTT GGG ATC GCC TTG GCA TTA TGC TCT GTG CTG GGG GTA TTC TTG ACA GCA
      Thr Glu Pro Phe Gly Ile Ala Leu Ala Leu Cys Ser Val Leu Gly Val Phe Leu Thr Ala>

   2110      2120      2130      2140      2150      2160
      TTC GTG ATG GGA GTG TTT ATC AAA TTT CGC AAC ACC CCA ATT GTT AAG GCC ACA AAC AGA
      Phe Val Met Gly Val Phe Ile Lys Phe Arg Asn Thr Pro Ile Val Lys Ala Thr Asn Arg>

   2170      2180      2190      2200      2210      2220
      GAG CTA TCC TAC CTC CTC CTG TTC TCA CTC ATC TGC TGT TTC TCC AGT TCC CTC ATC TTC
      Glu Leu Ser Tyr Leu Leu Leu Phe Ser Leu Ile Cys Cys Phe Ser Ser Ser Leu Ile Phe>

   2230      2240      2250      2260      2270      2280
      ATT GGT GAA CCC CAG GAC TGG ACA TGC CGT CTA CGC CAG CCT GCA TTC GGG ATA AGT TTT
      Ile Gly Glu Pro Gln Asp Trp Thr Cys Arg Leu Arg Gln Pro Ala Phe Gly Ile Ser Phe>

   2290      2300      2310      2320      2330      2340
      GTT CTC TGC ATC TCC TGC ATC CTG GTA AAA ACT AAC CGA GTA CTT CTA GTG TTC GAA GCC
      Val Leu Cys Ile Ser Cys Ile Leu Val Lys Thr Asn Arg Val Leu Leu Val Phe Glu Ala>

   2350      2360      2370      2380      2390      2400
      AAG ATC CCC ACC AGT CTC CAT CGT AAG TGG TGG GGG CTA AAC TTG CAG TTC CTG TTA GTG
      Lys Ile Pro Thr Ser Leu His Arg Lys Trp Trp Gly Leu Asn Leu Gln Phe Leu Leu Val>

   2410      2420      2430      2440      2450      2460
      TTC CTG TTC ACA TTT GTG CAA GTG ATG ATA TGT GTG GTC TGG CTT TAC AAT GCT CCT CCG
      Phe Leu Phe Thr Phe Val Gln Val Met Ile Cys Val Val Trp Leu Tyr Asn Ala Pro Pro>

   2470      2480      2490      2500      2510      2520
      GCG AGC TAC AGG AAC CAT GAC ATT GAT GAG ATA ATT TTC ATT ACA TGC AAT GAG GGC TCT
      Ala Ser Tyr Arg Asn His Asp Ile Asp Glu Ile Ile Phe Ile Thr Cys Asn Glu Gly Ser>

   2530      2540      2550      2560      2570      2580
      ATG ATG GCG CTT GGC TTC CTA ATT GGG TAC ACA TGC CTG CTG GCA GCC ATA TGC TTC TTC
      Met Met Ala Leu Gly Phe Leu Ile Gly Tyr Thr Cys Leu Leu Ala Ala Ile Cys Phe Phe>

   2590      2600      2610      2620      2630      2640
      TTT GCA TTT AAA TCA CGA AAA CTG CCA GAG AAC TTT ACT GAG GCT AAG TTC ATC ACC TTC
      Phe Ala Phe Lys Ser Arg Lys Leu Pro Glu Asn Phe Thr Glu Ala Lys Phe Ile Thr Phe>

   2650      2660      2670      2680      2690      2700
      AGC ATG CTC ATC TTC TTC ATC GTC TGG ATC TCT TTC ATC CCT GCC TAC TTC AGC ACT TAC
      Ser Met Leu Ile Phe Phe Ile Val Trp Ile Ser Phe Ile Pro Ala Tyr Phe Ser Thr Tyr>
```

FIG. 10C 2710 2720 2730 2740 2750 2760
GGA AAG TTT GTG TCG GCT GTG GAG GTC ATC GCC ATA CTA GCC TCC AGC TTT GGC CTG CTG
Gly Lys Phe Val Ser Ala Val Glu Val Ile Ala Ile Leu Ala Ser Ser Phe Gly Leu Leu>

2770 2780 2790 2800 2810 2820
GCC TGT ATT TTC TTC AAT AAA GTC TAC ATC ATC CTC TTC AAA CCG TCC AGG AAC ACT ATA
Ala Cys Ile Phe Phe Asn Lys Val Tyr Ile Ile Leu Phe Lys Pro Ser Arg Asn Thr Ile>

2830 2840 2850 2860 2870 2880
GAG GAG GTT CGC TGT AGC ACT GCG GCC CAT TCT TTC AAA GTG GCA GCC AAG GCC ACT CTG
Glu Glu Val Arg Cys Ser Thr Ala Ala His Ser Phe Lys Val Ala Ala Lys Ala Thr Leu>

2890 2900 2910 2920 2930 2940
AGA CAC AGC TCA GCC TCC AGG AAG AGG TCC AGC AGT GTG GGG GGA TCC TGT GCC TCA ACT
Arg His Ser Ser Ala Ser Arg Lys Arg Ser Ser Ser Val Gly Gly Ser Cys Ala Ser Thr>

2950 2960 2970 2980 2990 3000
CCC TCC TCA TCC ATC AGC CTC AAG ACC AAT GAC AAT GAC TCC CCA TCA GGT CAG CAG AGA
Pro Ser Ser Ser Ile Ser Leu Lys Thr Asn Asp Asn Asp Ser Pro Ser Gly Gln Gln Arg>

3010 3020 3030 3040 3050 3060
ATC CAT AAG CCA AGA GTA AGC TTT GGA AGT GGA ACA GTT ACT CTG TCC TTG AGC TTT GAG
Ile His Lys Pro Arg Val Ser Phe Gly Ser Gly Thr Val Thr Leu Ser Leu Ser Phe Glu>

3070 3080 3090 3100 3110 3120
GAG TCC AGA AAG AAT TCT ATG AAG TAG GGAAGTGTCTTTTGGTGGGCCGAGA
Glu Ser Arg Lys Asn Ser Met Lys ***> (SEQ ID NO: 10)

3130 3140 3150 3160 3170 3180 3190 3200
GCCTTGTCAAAACCTGAGTTGGTGTTGCATTCTTTGTTGGCTGGGTAGTTGGAGCAGAAATTATGATATTAAAAGCTTTG 3210 3220 3230 3240 3250 3260 3270 3280
ATGTATTCAGAATGGTGACACAGCATAGGTGGCCAAGATTCCATTATATTACAATAATCTGTGTTGTTCATTATGAGGAC 3290 3300 3310 3320 3330 3340 3350 3360
ATTTCAAAATGCTGAAAATCATCAAATACATAATTTACTGAGTTTTCTTGATAATCTTGAGAATAGAATAGCCTATTCAA 3370 3380 3390 3400 3410 3420 3430 3440
GTCATCGTTGAGCAGACATTAATTAACAATGATGTAATACTTTCCATACCTATTTTCTTTAACAATAGATTCACATTGTT 3450 3460 3470 3480 3490 3500 3510 3520
AAAGTTCAACTATGACCTGTAAAATACATGAGGTATAACAGGAGACAATAAAACTATGCATATCCTAGCTTCTGGGCCTG 3530 3540 3550 3560 3570 3580 3590 3600
AGTAGCAGGCAGTTTACTCTGGGCACGCTTTTCATCCAAACTTCCGAATGCTGCCCCCAATCCTAGTGAGGTTAAAGGCC 3610 3620 3630 3640 3650 3660 3670 3680
CAGTGCAGTCATATCTTTTCTCTAGGCACGCTTTTCATCCAAACTTCCGAATGCGGCTATATCAGTCTCTTTCCTACTGT 3690 3700 3710 3720 3730 3740 3750 3760
CTTTTTCATTAGGCCAGTGTTTAACAACCCTGGTCCTTAAGTACACACAACAGAGCACATTTTTGTTGTAGCCCTGGACA 3770 3780 3790 3800 3810 3820 3830 3840
ATCACTCCTCACTCAGCTCATTGAGGGCCTGATGATTAGTTGACAAGTTGAGTCGGGTGTGCTTGTCCAGGGTTACGATA 3850 3860 3870 3880 3890 3900 3910 3920
CAGATGTGTACTGTTGGGGGTGCTCGAGGACCAGGATTGGGAAACATTACATTAGGACTACTGTAGGTTCTTCAATATGG

FIG. 10D

```
      3930      3940      3950      3960      3970      3980      3990      4000
TGTCATACGGTCATATGGTGTCATATGGTGTCTGGTTGTTTTCTGCATATGTGTATTTCACCAAGTTACTGCACATGTTA

      4010      4020      4030
GACCTATACACTGGAATAAACATTTTTTTTC (SEQ ID NO: 9)
```

FIG. 10E

```
Sequence Range: 1 to 3824
        10        20        30        40        50        60        70        80
GTTCCAACAGCATATTTTTGTTGTATTTGCTTTGGTTTGTCTGAAATCAAGCATTATCAAGATCAAGAACAGCATGAGTC

        90       100       110       120       130       140       150       160
AGAAACAAGGCGACAGCCAGAGTCACTGGAGGGGACAAGACTGAGGTTAACTCTGAAGTCTAATGTGCTGAGAGGACAAG

       170       180           190         200         210         220
GCCCTCCTGAGAGCTGAACG ATG AGA TTT TAC CTG TAT TAC CTG GTG CTT TTG GGC TTC AGT TCT
                     Met Arg Phe Tyr Leu Tyr Tyr Leu Val Leu Leu Gly Phe Ser Ser>

   230         240         250         260         270         280
GTC ATC TCC ACC TAT GGG CCT CAT CAG AGA GCA CAG AAG ACT GGG GAT ATT CTG CTG GGC
Val Ile Ser Thr Tyr Gly Pro His Gln Arg Ala Gln Lys Thr Gly Asp Ile Leu Leu Gly>

   290         300         310         320         330         340
GGG CTG TTT CCA ATG CAC TTT GGT GTT ACC TCC AAA GAC CAA GAC CTG GCA GCG CGG CCA
Gly Leu Phe Pro Met His Phe Gly Val Thr Ser Lys Asp Gln Asp Leu Ala Ala Arg Pro>

   350         360         370         380         390         400
GAA TCC ACA GAG TGT GTT AGG TAC AAT TTC CGG GGA TTC CGT TGG CTT CAG GCC ATG ATT
Glu Ser Thr Glu Cys Val Arg Tyr Asn Phe Arg Gly Phe Arg Trp Leu Gln Ala Met Ile>

   410         420         430         440         450         460
TTT GCA ATA GAG GAG ATC AAC AAC AGC AGT ACT CTC CTG CCC AAC ATC ACA CTG GGC TAC
Phe Ala Ile Glu Glu Ile Asn Asn Ser Ser Thr Leu Leu Pro Asn Ile Thr Leu Gly Tyr>

   470         480         490         500         510         520
AGG ATC TTT GAC ACC TGC AAC ACC GTG TCC AAG GCC CTG GAG GCT ACC CTC AGT TTC GTA
Arg Ile Phe Asp Thr Cys Asn Thr Val Ser Lys Ala Leu Glu Ala Thr Leu Ser Phe Val>

   530         540         550         560         570         580
GCA CAG AAT AAG ATT GAC TCT CTG AAC TTG GAT GAA TTC TGT AAC TGC ACT GAT CAC ATC
Ala Gln Asn Lys Ile Asp Ser Leu Asn Leu Asp Glu Phe Cys Asn Cys Thr Asp His Ile>

   590         600         610         620         630         640
CCA TCG ACT ATA GCA GTG GTG GGG GCT TCT-GGG TCA GCG GTC TCC ACT GCT GTT GCC AAT
Pro Ser Thr Ile Ala Val Val Gly Ala Ser Gly Ser Ala Val Ser Thr Ala Val Ala Asn>

   650         660         670         680         690         700
CTG TTG GGC CTT TTC TAC ATC CCA CAG ATC AGC TAT GCC TCT TCC AGT CGC CTA CTA AGC
Leu Leu Gly Leu Phe Tyr Ile Pro Gln Ile Ser Tyr Ala Ser Ser Ser Arg Leu Leu Ser>

   710         720         730         740         750         760
AAC AAG AAC CAG TTC AAA TCC TTC ATG AGG ACC ATT CCC ACA GAT GAG CAC CAG GCC ACT
Asn Lys Asn Gln Phe Lys Ser Phe Met Arg Thr Ile Pro Thr Asp Glu His Gln Ala Thr>

   770         780         790         800         810         820
GCC ATG GCA GAT ATC ATC GAC TAC TTC CAA TGG AAT TGG GTC ATT GCA GTT GCG TCT GAT
Ala Met Ala Asp Ile Ile Asp Tyr Phe Gln Trp Asn Trp Val Ile Ala Val Ala Ser Asp>

   830         840         850         860         870         880
GAT GAG TAT GGA CGT CCG GGG ATT GAA AAA TTT GAG AAA GAG ATG GAA GAA CGA GAC ATT
Asp Glu Tyr Gly Arg Pro Gly Ile Glu Lys Phe Glu Lys Glu Met Glu Glu Arg Asp Ile>
```

FIG. 11A

```
890        900        910        920        930        940
TGT ATC CAT CTG AGT GAG CTG ATC TCT CAG TAC TTT GAG GAG TGG CAG ATC CAA GGA TTG
Cys Ile His Leu Ser Glu Leu Ile Ser Gln Tyr Phe Glu Glu Trp Gln Ile Gln Gly Leu>

950        960        970        980        990        1000
GTT GAC CGT ATT GAG AAC TCC TCA GCT AAA GTT ATA GTC GTT TTC GCC AGT GGG CCT GAC
Val Asp Arg Ile Glu Asn Ser Ser Ala Lys Val Ile Val Val Phe Ala Ser Gly Pro Asp>

1010       1020       1030       1040       1050       1060
ATT GAG CCT CTT ATT AAA GAG ATG GTC AGA CGG AAC ATC ACC GAC CGC ATC TGG TTG GCC
Ile Glu Pro Leu Ile Lys Glu Met Val Arg Arg Asn Ile Thr Asp Arg Ile Trp Leu Ala>

1070       1080       1090       1100       1110       1120
AGC GAG GCT TGG GCA ACC ACC TCC CTC ATC GCC AAA CCA GAG TAC CTT GAT GTT GTA GTT
Ser Glu Ala Trp Ala Thr Thr Ser Leu Ile Ala Lys Pro Glu Tyr Leu Asp Val Val Val>

1130       1140       1150       1160       1170       1180
GGG ACC ATT GGC TTT GCT CTC AGA GCA GGC GAA ATA CCT GGC TTC AAG GAC TTC TTA CAA
Gly Thr Ile Gly Phe Ala Leu Arg Ala Gly Glu Ile Pro Gly Phe Lys Asp Phe Leu Gln>

1190       1200       1210       1220       1230       1240
GAG GTC ACA CCA AAG AAA TCC AGC CAC AAT GAA TTT GTC AGG GAG TTT TGG GAG GAG ACT
Glu Val Thr Pro Lys Lys Ser Ser His Asn Glu Phe Val Arg Glu Phe Trp Glu Glu Thr>

1250       1260       1270       1280       1290       1300
TTT AAC TGC TAT CTG GAA GAC AGC CAG AGA CTG AGA GAC AGT GAG AAT GGG AGC ACC AGT
Phe Asn Cys Tyr Leu Glu Asp Ser Gln Arg Leu Arg Asp Ser Glu Asn Gly Ser Thr Ser>

1310       1320       1330       1340       1350       1360
TTC AGA CCA TTG TGT ACT GGC GAG GAG GAC ATT ATG GGT GCA GAG ACC CCA TAT CTG GAT
Phe Arg Pro Leu Cys Thr Gly Glu Glu Asp Ile Met Gly Ala Glu Thr Pro Tyr Leu Asp>

1370       1380       1390       1400       1410       1420
TAC ACT CAT CTT CGT ATT TCC TAT AAT GTG TAT GTT GCA GTT CAC TCC ATT GCA CAG GCC
Tyr Thr His Leu Arg Ile Ser Tyr Asn Val Tyr Val Ala Val His Ser Ile Ala Gln Ala>

1430       1440       1450       1460       1470       1480
CTA CAG GAC ATT CTC ACC TGC ATT CCT GGA CGG GGT TTT TTT TCC AAC AAC TCA TGT GCA
Leu Gln Asp Ile Leu Thr Cys Ile Pro Gly Arg Gly Phe Phe Ser Asn Asn Ser Cys Ala>

1490       1500       1510       1520       1530       1540
GAT ATA AAG AAA ATA GAA GCA TGG CAG GTT CTC AAG CAG CTC AGA CAT TTA AAC TTC TCA
Asp Ile Lys Lys Ile Glu Ala Trp Gln Val Leu Lys Gln Leu Arg His Leu Asn Phe Ser>

1550       1560       1570       1580       1590       1600
AAC AGT ATG GGA GAA AAG GTA CAT TTT GAT GAG AAT GCT GAT CCG TCA GGA AAC TAC ACC
Asn Ser Met Gly Glu Lys Val His Phe Asp Glu Asn Ala Asp Pro Ser Gly Asn Tyr Thr>

1610       1620       1630       1640       1650       1660
ATT ATC AAT TGG CAC CGG TCT CCT GAG GAT GGT TCT GTT GTG TTT GAA GAG GTC GGT TTC
Ile Ile Asn Trp His Arg Ser Pro Glu Asp Gly Ser Val Val Phe Glu Glu Val Gly Phe>

1670       1680       1690       1700       1710       1720
TAC AAC ATG CGA GCT AAG AGA GGA GTA CAA CTT TTC ATT GAT AAC ACA AAG ATT CTA TGG
Tyr Asn Met Arg Ala Lys Arg Gly Val Gln Leu Phe Ile Asp Asn Thr Lys Ile Leu Trp>
```

FIG. 11B

```
1730        1740         1750         1760         1770         1780
AAT GGA TAT AAT ACT GAG GTT CCA TTC TCT AAC TGT AGT GAA GAT TGT GAA CCA GGC ACC
Asn Gly Tyr Asn Thr Glu Val Pro Phe Ser Asn Cys Ser Glu Asp Cys Glu Pro Gly Thr>

1790        1800         1810         1820         1830         1840
AGA AAG GGG ATC ATA GAA AGC ATG CCA ACG TGT TGC TTT GAA TGT ACA GAA TGC TCA GAA
Arg Lys Gly Ile Ile Glu Ser Met Pro Thr Cys Cys Phe Glu Cys Thr Glu Cys Ser Glu>

1850        1860         1870         1880         1890         1900
GGA GAG TAT AGT GAT CAC AAA GAT GCC AGT GTT TGT ACC AAG TGT CCC AAT GAC TCA TGG
Gly Glu Tyr Ser Asp His Lys Asp Ala Ser Val Cys Thr Lys Cys Pro Asn Asp Ser Trp>

1910        1920         1930         1940         1950         1960
TCT AAT GAG AAC CAC ACA TCT TGT TTC CTG AAG GAG ATA GAG TTT CTG TCT TGG ACA GAG
Ser Asn Glu Asn His Thr Ser Cys Phe Leu Lys Glu Ile Glu Phe Leu Ser Trp Thr Glu>

1970        1980         1990         2000         2010         2020
CCC TTT GGG ATC GCC TTG GCA TTA TGC TCT GTG CTG GGG GTA TTC TTG ACA GCA TTC GTG
Pro Phe Gly Ile Ala Leu Ala Leu Cys Ser Val Leu Gly Val Phe Leu Thr Ala Phe Val>

2030        2040         2050         2060         2070         2080
ATG GGA GTG TTT ATC AAA TTT CGC AAC ACC CCA ATT GTT AAG GCC ACA AAC AGA GAG CTA
Met Gly Val Phe Ile Lys Phe Arg Asn Thr Pro Ile Val Lys Ala Thr Asn Arg Glu Leu>

2090        2100         2110         2120         2130         2140
TCC TAC CTC CTC CTG TTC TCA CTC ATC TGC TGT TTC TCC AGT TCC CTC ATC TTC ATT GGT
Ser Tyr Leu Leu Leu Phe Ser Leu Ile Cys Cys Phe Ser Ser Ser Leu Ile Phe Ile Gly>

2150        2160         2170         2180         2190         2200
GAA CCC CAG GAC TGG ACA TGC CGT CTA CGC CAG CCT GCA TTC GGG ATA AGT TTT GTT CTC
Glu Pro Gln Asp Trp Thr Cys Arg Leu Arg Gln Pro Ala Phe Gly Ile Ser Phe Val Leu>

2210        2220         2230         2240         2250         2260
TGC ATC TCC TGC ATC CTG GTA AAA ACT AAC CGA GTA CTT CTA GTG TTC GAA GCC AAG ATC
Cys Ile Ser Cys Ile Leu Val Lys Thr Asn Arg Val Leu Leu Val Phe Glu Ala Lys Ile>

2270        2280         2290         2300         2310         2320
CCC ACC AGT CTC CAT CGT AAG TGG TGG GGG CTA AAC TTG CAG TTC CTG TTA GTG TTC CTG
Pro Thr Ser Leu His Arg Lys Trp Trp Gly Leu Asn Leu Gln Phe Leu Leu Val Phe Leu>

2330        2340         2350         2360         2370         2380
TTC ACA TTT GTG CAA GTG ATG ATA TGT GTG GTC TGG CTT TAC AAT GCT CCT CCG GCG AGC
Phe Thr Phe Val Gln Val Met Ile Cys Val Val Trp Leu Tyr Asn Ala Pro Pro Ala Ser>

2390        2400         2410         2420         2430         2440
TAC AGG AAC CAT GAC ATT GAT GAG ATA ATT TTC ATT ACA TGC AAT GAG GGC TCT ATG ATG
Tyr Arg Asn His Asp Ile Asp Glu Ile Ile Phe Ile Thr Cys Asn Glu Gly Ser Met Met>

2450        2460         2470         2480         2490         2500
GCG CTT GGC TTC CTA ATT GGG TAC ACA TGC CTG CTG GCA GCC ATA TGC TTC TTC TTT GCA
Ala Leu Gly Phe Leu Ile Gly Tyr Thr Cys Leu Leu Ala Ala Ile Cys Phe Phe Phe Ala>

2510        2520         2530         2540         2550         2560
TTT AAA TCA CGA AAA CTG CCA GAG AAC TTT ACT GAG GCT AAG TTC ATC ACC TTC AGC ATG
Phe Lys Ser Arg Lys Leu Pro Glu Asn Phe Thr Glu Ala Lys Phe Ile Thr Phe Ser Met>
```

FIG. 11C

```
        2570         2580          2590         2600         2610         2620
CTC ATC TTC TTC ATC GTC TGG ATC TCT TTC ATC CCT GCC TAC TTC AGC ACT TAC GGA AAG
Leu Ile Phe Phe Ile Val Trp Ile Ser Phe Ile Pro Ala Tyr Phe Ser Thr Tyr Gly Lys>

        2630        2640          2650         2660         2670         2680
TTT GTG TCG GCT GTG GAG GTC ATC GCC ATA CTA GCC TCC AGC TTT GGC CTG CTG GCC TGT
Phe Val Ser Ala Val Glu Val Ile Ala Ile Leu Ala Ser Ser Phe Gly Leu Leu Ala Cys>

        2690        2700          2710         2720         2730
ATT TTC TTC AAT AAA GTC TAC ATC ATC CAT CAG CCT CAA GAC CAA TGA
Ile Phe Phe Asn Lys Val Tyr Ile Ile His Gln Pro Gln Asp Gln ***> (SEQ ID NO: 12)

      2740       2750       2760       2770       2780       2790       2800
CAATGACTCCCCATCAGGTCAGCAGAGAATCCATAAGCCAAGAGTAAGCTTTGGAAGTGGAACAGTT

       2810       2820       2830       2840       2850       2860       2870       2880
ACTCTGTCCTTGAGCTTTGAGGAGTCCAGAAAGAATTCTATGAAGTAGGGAAGTGTCTTTTGGTGGGCCGAGAGCCTTGT

       2890       2900       2910       2920       2930       2940       2950       2960
CAAAACCTGAGTTGGTGTTGCATTCTTTGTTGGCTGGGTAGTTGGAGCAGAAATTATGATATTAAAAGCTTTGATGTATT

       2970       2980       2990       3000       3010       3020       3030       3040
CAGAATGGTGACACAGCATAGGTGGCCAAGATTCCATTATATTACAATAATCTGTGTTGTTCATTATGAGGACATTTCAA

       3050       3060       3070       3080       3090       3100       3110       3120
AATGCTGAAAATCATCAAATACATAATTTACTGAGTTTTCTTGATAATCTTGAGAATAGAATAGCCTATTCAAGTCATCG

       3130       3140       3150       3160       3170       3180       3190       3200
TTGAGCAGACATTAATTAACAATGATGTAATACTTTCCATACCTATTTTCTTTAACAATAGATTCACATTGTTAAAGTTC

       3210       3220       3230       3240       3250       3260       3270       3280
AACTATGACCTGTAAAATACATGAGGTATAACAGGAGACAATAAAACTATGCATATCCTAGCTTCTGGGCCTGAGTAGCA

       3290       3300       3310       3320       3330       3340       3350       3360
GGCAGTTTACTCTGGGCACGCTTTTCATCCAAACTTCCGAATGCTGCCCCCAATCCTAGTGAGGTTAAAGGCCCAGTGCA

       3370       3380       3390       3400       3410       3420       3430       3440
GTCATATCTTTTCTCTAGGCACGCTTTTCATCCAAACTTCCGAATGCGGCTATATCAGTCTCTTTCCTACTGTCTTTTTC

       3450       3460       3470       3480       3490       3500       3510       3520
ATTAGGCCAGTGTTTAACAACCCTGGTCCTTGAGTACACACAACAGGGCACATTTTTGTTGTAGCCCTGGACAATCACTC

       3530       3540       3550       3560       3570       3580       3590       3600
CTCACTCAGCTCATTGAGGGCCTGATGATTAGTTGACAAGTTGGGTCAGGTGTGCTTGTCCAGGGTTACAATACAGATGT

       3610       3620       3630       3640       3650       3660       3670       3680
GTGCTGTTGGGGGTACTCGAGGACCAGGATTGGGAAACATTACATTAGGACTACTGTAGGTTCTTCAATATGGTGTCATA

       3690       3700       3710       3720       3730       3740       3750       3760
CGGTCATATGGTGTCATATGGTGTCTGGTTGTTTTCTGCATATGTGTATTTCACCAAGTTACTGCACATGTTAGACCTAT

       3770       3780       3790       3800       3810       3820
ACACTGGAATAAACATTTTTTTTCACAATGCATCCAATGACAATAAAATCACCATATGCCAATG (SEQ ID NO: 11)
```

FIG. 11D

```
SalmoKCaR 1 -TTCCAACAGCATATTTTTGTTGTATTTGCTTTGGTTTGT 39
SalmoKCaR 2 GTTCCAACAGCATATTTTTGTTGTATTTGCTTTGGTTTGT 40
SalmoKCaR 3 GTTCCAACAGCATATTTTTGTTGTATTTGCTTTGGTTTGT 40
Salmon A26  ---------------------------------------- 0
Salmon PCR  ---------------------------------------- 0

SalmoKCaR 1 CTGAAATCAAGCATTATCAAG------------------- 60
SalmoKCaR 2 CTGAAATCAAGCATTATCAAGGATTGAGCAAGACAACTGA 80
SalmoKCaR 3 CTGAAATCAAGCATTATCAAG------------------- 61
Salmon A26  ---------------------------------------- 0
Salmon PCR  ---------------------------------------- 0

SalmoKCaR 1 ---------------------------------------- 60
SalmoKCaR 2 GTTGTCAGACTAAGAATATACACATTTCCAGTTCTCTCTT 120
SalmoKCaR 3 ---------------------------------------- 61
Salmon A26  ---------------------------------------- 0
Salmon PCR  ---------------------------------------- 0

SalmoKCaR 1 ------------------------------ATCAAGAACA 70
SalmoKCaR 2 TAATGGACTTCTCACACTGATGTTCTTCAGATCAAGAACA 160
SalmoKCaR 3 ------------------------------ATCAAGAACA 71
Salmon A26  ---------------------------------------- 0
Salmon PCR  ---------------------------------------- 0

SalmoKCaR 1 GCATGAGTCAGAAACAAGGCGACAGCCAGAGTCACTGGAG 110
SalmoKCaR 2 GCATGAGTCAGAAACAAGGCGACAGCCAGAGTCACTGGAG 200
SalmoKCaR 3 GCATGAGTCAGAAACAAGGCGACAGCCAGAGTCACTGGAG 111
Salmon A26  ---------------------------------------- 0
Salmon PCR  ---------------------------------------- 0

SalmoKCaR 1 GGGACAAGACTGAGGTTAACTCTGAAGTCTAATGTGCTGA 150
SalmoKCaR 2 GGGACAAGACTGAGGTTAACTCTGAAGTCTAATGTGCTGA 240
SalmoKCaR 3 GGGACAAGACTGAGGTTAACTCTGAAGTCTAATGTGCTGA 151
Salmon A26  ---------------------------------------- 0
Salmon PCR  ---------------------------------------- 0

SalmoKCaR 1 GAGGACAAGGCCCTCCTGAGAGCTGAACGATGAGATTTTA 190
SalmoKCaR 2 GAGGACAAGGCCCTCCTGAGAGCTGAACGATGAGATTTTA 280
SalmoKCaR 3 GAGGACAAGGCCCTCCTGAGAGCTGAACGATGAGATTTTA 191
Salmon A26  ---------------------------------------- 0
Salmon PCR  ---------------------------------------- 0

SalmoKCaR 1 CCTGTATTACCTGGTGCTTTTGGGCTTCAGTTCTGTCATC 230
SalmoKCaR 2 CCTGTATTACCTGGTGCTTTTGGGCTTCAGTTCTGTCATC 320
SalmoKCaR 3 CCTGTATTACCTGGTGCTTTTGGGCTTCAGTTCTGTCATC 231
Salmon A26  ---------------------------------------- 0
Salmon PCR  ---------------------------------------- 0

SalmoKCaR 1 TCCACCTATGGGCCTCATCAGAGAGCACAGAAGACTGGGG 270
SalmoKCaR 2 TCCACCTATGGGCCTCATCAGAGAGCACAGAAGACTGGGG 360
SalmoKCaR 3 TCCACCTATGGGCCTCATCAGAGAGCACAGAAGACTGGGG 271
Salmon A26  ---------------------------------------- 0
Salmon PCR  ---------------------------------------- 0
```

FIG. 12A

```
SalmoKCaR 1  ATATTCTGCTGGGCGGGCTGTTTCCAATGCACTTTGGTGT 310
SalmoKCaR 2  ATATTCTGCTGGGCGGGCTGTTTCCAATGCACTTTGGTGT 400
SalmoKCaR 3  ATATTCTGCTGGGCGGGCTGTTTCCAATGCACTTTGGTGT 311
Salmon A26   ---------------------------------------- 0
Salmon PCR   ---------------------------------------- 0

SalmoKCaR 1  TACCTCCAAAGACCAAGACCTGGCAGCGCGGCCAGAATCC 350
SalmoKCaR 2  TACCTCCAAAGACCAAGACCTGGCAGCGCGGCCAGAATCC 440
SalmoKCaR 3  TACCTCCAAAGACCAAGACCTGGCAGCGCGGCCAGAATCC 351
Salmon A26   ---------------------------------------- 0
Salmon PCR   ---------------------------------------- 0

SalmoKCaR 1  ACAGAGTGTGTTAGGTACAATTTCCGGGGATTCCGTTGGC 390
SalmoKCaR 2  ACAGAGTGTGTTAGGTACAATTTCCGGGGATTCCGTTGGC 480
SalmoKCaR 3  ACAGAGTGTGTTAGGTACAATTTCCGGGGATTCCGTTGGC 391
Salmon A26   ---------------------------------------- 0
Salmon PCR   ---------------------------------------- 0

SalmoKCaR 1  TTCAGGCCATGATTTTTGCAATAGAGGAGATCAACAACAG 430
SalmoKCaR 2  TTCAGGCCATGATTTTTGCAATAGAGGAGATCAACAACAG 520
SalmoKCaR 3  TTCAGGCCATGATTTTTGCAATAGAGGAGATCAACAACAG 431
Salmon A26   ---------------------------------------- 0
Salmon PCR   ---------------------------------------- 0

SalmoKCaR 1  CAGTACTCTCCTGCCCAACATCACACTGGGCTACAGGATC 470
SalmoKCaR 2  CAGTACTCTCCTGCCCAACATCACACTGGGCTACAGGATC 560
SalmoKCaR 3  CAGTACTCTCCTGCCCAACATCACACTGGGCTACAGGATC 471
Salmon A26   ---------------------------------------- 0
Salmon PCR   ---------------------------------------- 0

SalmoKCaR 1  TTTGACACCTGCAACACCGTGTCCAAGGCCCTGGAGGCTA 510
SalmoKCaR 2  TTTGACACCTGCAACACCGTGTCCAAGGCCCTGGAGGCTA 600
SalmoKCaR 3  TTTGACACCTGCAACACCGTGTCCAAGGCCCTGGAGGCTA 511
Salmon A26   ---------------------------------------- 0
Salmon PCR   ---------------------------------------- 0

SalmoKCaR 1  CCCTCAGTTTCGTAGCACAGAATAAGATTGACTCTCTGAA 550
SalmoKCaR 2  CCCTCAGTTTCGTAGCACAGAATAAGATTGACTCTCTGAA 640
SalmoKCaR 3  CCCTCAGTTTCGTAGCACAGAATAAGATTGACTCTCTGAA 551
Salmon A26   ---------------------------------------- 0
Salmon PCR   ---------------------------------------- 0

SalmoKCaR 1  CTTGGATGAATTCTGTAACTGCACTGATCACATCCCATCG 590
SalmoKCaR 2  CTTGGATGAATTCTGTAACTGCACTGATCACATCCCATCG 680
SalmoKCaR 3  CTTGGATGAATTCTGTAACTGCACTGATCACATCCCATCG 591
Salmon A26   ---------------------------------------- 0
Salmon PCR   ---------------------------------------- 0

SalmoKCaR 1  ACTATAGCAGTGGTGGGGGCTTCTGGGTCAGCGGTCTCCA 630
SalmoKCaR 2  ACTATAGCAGTGGTGGGGGCTTCTGGGTCAGCGGTCTCCA 720
SalmoKCaR 3  ACTATAGCAGTGGTGGGGGCTTCTGGGTCAGCGGTCTCCA 631
Salmon A26   ---------------------------------------- 0
Salmon PCR   ---------------------------------------- 0
```

FIG. 12B

```
SalmoKCaR 1  CTGCTGTTGCCAATCTGTTGGGCCTTTTCTACATCCCACA  670
SalmoKCaR 2  CTGCTGTTGCCAATCTGTTGGGCCTTTTCTACATCCCACA  760
SalmoKCaR 3  CTGCTGTTGCCAATCTGTTGGGCCTTTTCTACATCCCACA  671
Salmon A26   ----------------------------------------  0
Salmon PCR   ----------------------------------------  0

SalmoKCaR 1  GATCAGCTATGCCTCTTCCAGTCGCCTACTAAGCAACAAG  710
SalmoKCaR 2  GATCAGCTATGCCTCTTCCAGTCGCCTACTAAGCAACAAG  800
SalmoKCaR 3  GATCAGCTATGCCTCTTCCAGTCGCCTACTAAGCAACAAG  711
Salmon A26   ----------------------------------------  0
Salmon PCR   ----------------------------------------  0

SalmoKCaR 1  AACCAGTTCAAATCCTTCATGAGGACCATTCCCACAGATG  750
SalmoKCaR 2  AACCAGTTCAAATCCTTCATGAGGACCATTCCCACAGATG  840
SalmoKCaR 3  AACCAGTTCAAATCCTTCATGAGGACCATTCCCACAGATG  751
Salmon A26   ----------------------------------------  0
Salmon PCR   ----------------------------------------  0

SalmoKCaR 1  AGCACCAGGCCACTGCCATGGCAGATATCATCGACTACTT  790
SalmoKCaR 2  AGCACCAGGCCACTGCCATGGCAGATATCATCGACTACTT  880
SalmoKCaR 3  AGCACCAGGCCACTGCCATGGCAGATATCATCGACTACTT  791
Salmon A26   ----------------------------------------  0
Salmon PCR   ----------------------------------------  0

SalmoKCaR 1  CCAATGGAATTGGGTCATTGCAGTTGCGTCTGATGATGAG  830
SalmoKCaR 2  CCAATGGAATTGGGTCATTGCAGTTGCGTCTGATGATGAG  920
SalmoKCaR 3  CCAATGGAATTGGGTCATTGCAGTTGCGTCTGATGATGAG  831
Salmon A26   ----------------------------------------  0
Salmon PCR   ----------------------------------------  0

SalmoKCaR 1  TATGGACGTCCGGGGATTGAAAAATTTGAGAAAGAGATGG  870
SalmoKCaR 2  TATGGACGTCCGGGGATTGAAAAATTTGAGAAAGAGATGG  960
SalmoKCaR 3  TATGGACGTCCGGGGATTGAAAAATTTGAGAAAGAGATGG  871
Salmon A26   ----------------------------------------  0
Salmon PCR   ----------------------------------------  0

SalmoKCaR 1  AAGAACGAGACATTTGTATCCATCTGAGTGAGCTGATCTC  910
SalmoKCaR 2  AAGAACGAGACATTTGTATCCATCTGAGTGAGCTGATCTC  1000
SalmoKCaR 3  AAGAACGAGACATTTGTATCCATCTGAGTGAGCTGATCTC  911
Salmon A26   ----------------------------------------  0
Salmon PCR   ----------------------------------------  0

SalmoKCaR 1  TCAGTACTTTGAGGAGTGGCAGATCCAAGGATTGGTTGAC  950
SalmoKCaR 2  TCAGTACTTTGAGGAGTGGCAGATCCAAGGATTGGTTGGC  1040
SalmoKCaR 3  TCAGTACTTTGAGGAGTGGCAGATCCAAGGATTGGTTGAC  951
Salmon A26   ----------------------------------------  0
Salmon PCR   ----------------------------------------  0

SalmoKCaR 1  CGTATTGAGAACTCCTCAGCTAAAGTTATAGTCGTTTTCG  990
SalmoKCaR 2  CGTATTGAGAACTCCTCAGCTAAAGTTATAGTCGTTTTCG  1080
SalmoKCaR 3  CGTATTGAGAACTCCTCAGCTAAAGTTATAGTCGTTTTCG  991
Salmon A26   ----------------------------------------  0
Salmon PCR   ----------------------------------------  0
```

FIG. 12C

```
SalmoKCaR 1  C C A G T G G G C C T G A C A T T G A G C C T C T T A T T A A A G A G A T G G T  1030
SalmoKCaR 2  C C A G T G G G C C T G A C A T T G A G C C T C T T A T T A A A G A G A T G G T  1120
SalmoKCaR 3  C C A G T G G G C C T G A C A T T G A G C C T C T T A T T A A A G A G A T G G T  1031
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  C A G A C G G A A C A T C A C C G A C C G C A T C T G G T T G G C C A G C G A G  1070
SalmoKCaR 2  C A G A C G G A A C A T C A C C G A C C G C A T C T G G T T G G C C A G C G A G  1160
SalmoKCaR 3  C A G A C G G A A C A T C A C C G A C C G C A T C T G G T T G G C C A G C G A G  1071
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  G C T T G G G C A A C C A C C T C C C T C A T C G C C A A A C C A G A G T A C C  1110
SalmoKCaR 2  G C T T G G G C A A C C A C C T C C C T C A T C G C C A A A C C A G A G T A C C  1200
SalmoKCaR 3  G C T T G G G C A A C C A C C T C C C T C A T C G C C A A A C C A G A G T A C C  1111
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  T T G A T G T T G T A G T T G G G A C C A T T G G C T T T G C T C T C A G A G C  1150
SalmoKCaR 2  T T G A T G T T G T A G T T G G G A C C A T T G G C T T T G C T C T C A G A G C  1240
SalmoKCaR 3  T T G A T G T T G T A G T T G G G A C C A T T G G C T T T G C T C T C A G A G C  1151
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  A G G C G A A A T A C C T G G C T T C A A G G A C T T C T T A C A A G A G G T C  1190
SalmoKCaR 2  A G G C G A A A T A C C T G G C T T C A A G G A C T T C T T A C A A G A G G T C  1280
SalmoKCaR 3  A G G C G A A A T A C C T G G C T T C A A G G A C T T C T T A C A A G A G G T C  1191
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  A C A C C A A A G A A A T C C A G C C A C A A T G A A T T T G T C A G G G A G T  1230
SalmoKCaR 2  A C A C C A A A G A A A T C C A G C C A C A A T G A A T T T G T C A G G G A G T  1320
SalmoKCaR 3  A C A C C A A A G A A A T C C A G C C A C A A T G A A T T T G T C A G G G A G T  1231
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  T T T G G G A G G A G A C T T T T A A C T G C T A T C T G G A A G A C A G C C A  1270
SalmoKCaR 2  T T T G G G A G G A G A C T T T T A A C T G C T A T C T G G A A G A C A G C C A  1360
SalmoKCaR 3  T T T G G G A G G A G A C T T T T A A C T G C T A T C T G G A A G A C A G C C A  1271
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  G A G A C T G A G A G A C A G T G A G A A T G G G A G C A C C A G T T T C A G A  1310
SalmoKCaR 2  G A G A C T G A G A G A C A G T G A G A A T G G G A G C A C C A G T T T C A G A  1400
SalmoKCaR 3  G A G A C T G A G A G A C A G T G A G A A T G G G A G C A C C A G T T T C A G A  1311
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  C C A T T G T G T A C T G G C G A G G A G G A C A T T A T G G G T G C A G A G A  1350
SalmoKCaR 2  C C A T T G T G T A C T G G C G A G G A G G A C A T T A T G G G T G C A G A G A  1440
SalmoKCaR 3  C C A T T G T G T A C T G G C G A G G A G G A C A T T A T G G G T G C A G A G A  1351
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0
```

FIG. 12D

```
SalmoKCaR 1  CCCCATATCTGGATTACACTCATCTTCGTATTTCCTATAA 1390
SalmoKCaR 2  CCCCATATCTGGATTACACTCATCTTCGTATTTCCTATAA 1480
SalmoKCaR 3  CCCCATATCTGGATTACACTCATCTTCGTATTTCCTATAA 1391
Salmon A26   ---------------------------------------- 0
Salmon PCR   ---------------------------------------- 0

SalmoKCaR 1  TGTGTATGTTGCAGTTCACTCCATTGCACAGGCCCTACAG 1430
SalmoKCaR 2  TGTGTATGTTGCAGTTCACTCCATTGCACAGGCCCTACAG 1520
SalmoKCaR 3  TGTGTATGTTGCAGTTCACTCCATTGCACAGGCCCTACAG 1431
Salmon A26   ---------------------------------------- 0
Salmon PCR   ---------------------------------------- 0

SalmoKCaR 1  GACATTCTCACCTGCATTCCTGGACGGGGTCTTTTTTCCA 1470
SalmoKCaR 2  GACATTCTCACCTGCATTCCTGGACGGGGTCTTTTTTCCA 1560
SalmoKCaR 3  GACATTCTCACCTGCATTCCTGGACGGGGTTTTTTTTCCA 1471
Salmon A26   ---------------------------------------- 0
Salmon PCR   ---------------------------------------- 0

SalmoKCaR 1  ACAACTCATGTGCAGATATAAAGAAAATAGAAGCATGGCA 1510
SalmoKCaR 2  ACAACTCATGTGCAGATATAAAGAAAATAGAAGCATGGCA 1600
SalmoKCaR 3  ACAACTCATGTGCAGATATAAAGAAAATAGAAGCATGGCA 1511
Salmon A26   ---------------------------------------- 0
Salmon PCR   ---------------------------------------- 0

SalmoKCaR 1  GGTTCTCAAGCAGCTCAGACATTTAAACTTCTCAAACAGT 1550
SalmoKCaR 2  GGTTCTCAAGCAGCTCAGACATTTAAACTTCTCAAACAGT 1640
SalmoKCaR 3  GGTTCTCAAGCAGCTCAGACATTTAAACTTCTCAAACAGT 1551
Salmon A26   ---------------------------------------- 0
Salmon PCR   ---------------------------------------- 0

SalmoKCaR 1  ATGGGAGAAAAGGTACATTTTGATGAGAATGCTGATCCGT 1590
SalmoKCaR 2  ATGGGAGAAAAGGTACATTTTGATGAGAATGCTGATCCGT 1680
SalmoKCaR 3  ATGGGAGAAAAGGTACATTTTGATGAGAATGCTGATCCGT 1591
Salmon A26   ---------------------------------------- 0
Salmon PCR   ---------------------------------------- 0

SalmoKCaR 1  CAGGAAACTACACCATTATCAATTGGCACCGGTCTCCTGA 1630
SalmoKCaR 2  CAGGAAACTACACCATTATCAATTGGCACCGGTCTCCTGA 1720
SalmoKCaR 3  CAGGAAACTACACCATTATCAATTGGCACCGGTCTCCTGA 1631
Salmon A26   ---------------------------------------- 0
Salmon PCR   ---------------------------------------- 0

SalmoKCaR 1  GGATGGTTCTGTTGTGTTTGAAGAGGTCGGTTTCTACAAC 1670
SalmoKCaR 2  GGATGGTTCTGTTGTGTTTGAAGAGGTCGGTTTCTACAAC 1760
SalmoKCaR 3  GGATGGTTCTGTTGTGTTTGAAGAGGTCGGTTTCTACAAC 1671
Salmon A26   ---------------------------------------- 0
Salmon PCR   ---------------------------------------- 0

SalmoKCaR 1  ATGCGAGCTAAGAGAGGAGTACAACTTTTCATTGATAACA 1710
SalmoKCaR 2  ATGCGAGCTAAGAGAGGAGTACAACTTTTCATTGATAACA 1800
SalmoKCaR 3  ATGCGAGCTAAGAGAGGAGTACAACTTTTCATTGATAACA 1711
Salmon A26   ---------------------------------------- 0
Salmon PCR   ---------------------------------------- 0
```

FIG. 12E

| | | |
|---|---|---|
| SalmoKCaR 1 | C A A A G A T T C T A T G G A A T G G A T A T A A T A C T G A G G T T C C A T T | 1750 |
| SalmoKCaR 2 | C A A A G A T T C T A T G G A A T G G A T A T A A T A C T G A G G T T C C A T T | 1840 |
| SalmoKCaR 3 | C A A A G A T T C T A T G G A A T G G A T A T A A T A C T G A G G T T C C A T T | 1751 |
| Salmon A26 | - - - - - - - - - - - - - - - - - - - - - - - - - - - - - - - - - - - - - - - - | 0 |
| Salmon PCR | - - - - - - - - - - - - - - - - - - - - - - - - - - - - - - - - - - - - - - - - | 0 |
| SalmoKCaR 1 | C T C T A A C T G T A G T G A A G A T T G T G A A C C A G G C A C C A G A A A G | 1790 |
| SalmoKCaR 2 | C T C T A A C T G T A G T G A A G A T T G T G A A C C A G G C A C C A G A A A G | 1880 |
| SalmoKCaR 3 | C T C T A A C T G T A G T G A A G A T T G T G A A C C A G G C A C C A G A A A G | 1791 |
| Salmon A26 | - - G T G A T C A C A A A G G T A A G A A A G A C A G T G A A A A A T C T G A A | 38 |
| Salmon PCR | - - - - - - - - - - - - - - - - - - - - - - - - - - - - - - - - - - - - - - - - | 0 |
| SalmoKCaR 1 | G G G A T C A T A G A A A G C A T G C C A A C G T G T T G C T T T G A A T G T A | 1830 |
| SalmoKCaR 2 | G G G A T C A T A G A A A G C A T G C C A A C G T G T T G C T T T G A A T G T A | 1920 |
| SalmoKCaR 3 | G G G A T C A T A G A A A G C A T G C C A A C G T G T T G C T T T G A A T G T A | 1831 |
| Salmon A26 | C T A C C C C A T T A T A T A A T C T G T T G C T A T T T C A T A T G T T T C T | 78 |
| Salmon PCR | - - - - - - - - - - - - - - - - - - - - - - - - - - - - - - - - - - - - - - - - | 0 |
| SalmoKCaR 1 | C A G A A T G C T C A G A A G G A G A G T A T A G T G A T C A C A A A G A T G C | 1870 |
| SalmoKCaR 2 | C A G A A T G C T C A G A A G G A G A G T A T A G T G A T C A C A A A G A T G C | 1960 |
| SalmoKCaR 3 | C A G A A T G C T C A G A A G G A G A G T A T A G T G A T C A C A A A G A T G C | 1871 |
| Salmon A26 | A T C A A T A A T A C A A A C A C T A C T T C T C T A T T C C T G C A G A T G C | 118 |
| Salmon PCR | - - - - - - - - - - - - - - - - - - - - - - - - - - - - - - - - - - - - - - - - | 0 |
| SalmoKCaR 1 | C A G T G T T T G T A C C A A G T G T C C C A A T G A C T C A T G G T C T A A T | 1910 |
| SalmoKCaR 2 | C A G T G T T T G T A C C A A G T G T C C C A A T G A C T C A T G G T C T A A T | 2000 |
| SalmoKCaR 3 | C A G T G T T T G T A C C A A G T G T C C C A A T G A C T C A T G G T C T A A T | 1911 |
| Salmon A26 | C A G T G T T T G T A C C A A G T G T C C C A A T G A C T C A T G G T C T A A T | 158 |
| Salmon PCR | - - - - - - - - - - - - - - - - - - - - - - - - - - - - - - - - - - - - - - - - | 0 |
| SalmoKCaR 1 | G A G A A C C A C A C A T C T T G T T T C C T G A A G G A G A T A G A G T T T C | 1950 |
| SalmoKCaR 2 | G A G A A C C A C A C A T C T T G T T T C C T G A A G G A G A T A G A G T T T C | 2040 |
| SalmoKCaR 3 | G A G A A C C A C A C A T C T T G T T T C C T G A A G G A G A T A G A G T T T C | 1951 |
| Salmon A26 | G A G A A C C A C A C A T C T T G T T T C C T G A A G G A G A T A G A G T T T C | 198 |
| Salmon PCR | - - - - - - - - - - - - - - - - - - - - - - - - - - - - - - - - - - - - - - - - | 0 |
| SalmoKCaR 1 | T G T C T T G G A C A G A G C C C T T T G G G A T C G C C T T G G C A T T A T G | 1990 |
| SalmoKCaR 2 | T G T C T T G G A C A G A G C C C T T T G G G A T C G C C T T G G C A T T A T G | 2080 |
| SalmoKCaR 3 | T G T C T T G G A C A G A G C C C T T T G G G A T C G C C T T G G C A T T A T G | 1991 |
| Salmon A26 | T G T C T T G G A C A G A G C C C T T T G G G A T C G C C T T G G C A T T A T G | 238 |
| Salmon PCR | - - - - - - - - - - - - - - - - - - - - - - - - - - - - C T T G G C A T T A T G | 12 |
| SalmoKCaR 1 | C T C T G T G C T G G G G G T A T T C T T G A C A G C A T T C G T G A T G G G A | 2030 |
| SalmoKCaR 2 | C T C T G T G C T G G G G G T A T T C T T G A C A G C A T T C G T G A T G G G A | 2120 |
| SalmoKCaR 3 | C T C T G T G C T G G G G G T A T T C T T G A C A G C A T T C G T G A T G G G A | 2031 |
| Salmon A26 | C T C T G T G C T G G G G G T A T T C T T G A C A G C A T T C G T G A T G G G A | 278 |
| Salmon PCR | C T C T G T G C T G G G G G T A T T C T T G A C A G C A T T C G T G A T G G G A | 52 |
| SalmoKCaR 1 | G T G T T T A T C A A A T T T C G C A A C A C C C C A A T T G T T A A G G C C A | 2070 |
| SalmoKCaR 2 | G T G T T T A T C A A A T T T C G C A A C A C C C C A A T T G T T A A G G C C A | 2160 |
| SalmoKCaR 3 | G T G T T T A T C A A A T T T C G C A A C A C C C C A A T T G T T A A G G C C A | 2071 |
| Salmon A26 | G T G T T T A T C A A A T T T C G C A A C A C C C C A A T T G T T A A G G C C A | 318 |
| Salmon PCR | G T G T T T A T C A A A T T T C G C A A C A C C C C A A T T G T T A A G G C C A | 92 |

FIG. 12F

SalmoKCaR 1 C A A A C A G A G A G C T A T C C T A C C T C C T C C T G T T C T C A C T C A T 2110
SalmoKCaR 2 C A A A C A G A G A G C T A T C C T A C C T C C T C C T G T T C T C A C T C A T 2200
SalmoKCaR 3 C A A A C A G A G A G C T A T C C T A C C T C C T C C T G T T C T C A C T C A T 2111
Salmon A26 C A A A C A G A G A G C T A T C C T A C C T C C T C C T G T T C T C A C T C A T 358
Salmon PCR C A A A C A G A G A G C T A T C C T A C C T C C T C C T G T T C T C A C T C A T 132

SalmoKCaR 1 C T G C T G T T T C T C C A G T T C C C T C A T C T T C A T T G G T G A A C C C 2150
SalmoKCaR 2 C T G C T G T T T C T C C A G T T C C C T C A T C T T C A T T G G T G A A C C C 2240
SalmoKCaR 3 C T G C T G T T T C T C C A G T T C C C T C A T C T T C A T T G G T G A A C C C 2151
Salmon A26 C T G C T G T T T C T C C A G T T C C C T C A T C T T C A T T G G T G A A C C C 398
Salmon PCR C T G C T G T T T C T C C A G T T C C C T C A T C T T C A T T G G T G A A C C C 172

SalmoKCaR 1 C A G G A C T G G A C A T G C C G T C T A C G C C A G C C T G C A T T C G G G A 2190
SalmoKCaR 2 C A G G A C T G G A C A T G C C G T C T A C G C C A G C C T G C A T T C G G G A 2280
SalmoKCaR 3 C A G G A C T G G A C A T G C C G T C T A C G C C A G C C T G C A T T C G G G A 2191
Salmon A26 C A G G A C T G G A C A T G C C G T C T A C G C C A G C C T G C A T T C G G G A 438
Salmon PCR C A G G A C T G G A C A T G C C G T C T A C G C C A G C C T G C A T T C G G G A 212

SalmoKCaR 1 T A A G T T T T G T T C T C T G C A T C T C C T G C A T C C T G G T A A A A A C 2230
SalmoKCaR 2 T A A G T T T T G T T C T C T G C A T C T C C T G C A T C C T G G T A A A A A C 2320
SalmoKCaR 3 T A A G T T T T G T T C T C T G C A T C T C C T G C A T C C T G G T A A A A A C 2231
Salmon A26 T A A G T T T T G T T C T C T G C A T C T C C T G C A T C C T G G T A A A A A C 478
Salmon PCR T A A G T T T T G T T C T C T G C A T C T C C T G C A T C C T G G T A A A A A C 252

SalmoKCaR 1 T A A C C G A G T A C T T C T A G T G T T C G A A G C C A A G A T C C C C A C C 2270
SalmoKCaR 2 T A A C C G A G T A C T T C T A G T G T T C G A A G C C A A G A T C C C C A C C 2360
SalmoKCaR 3 T A A C C G A G T A C T T C T A G T G T T C G A A G C C A A G A T C C C C A C C 2271
Salmon A26 T A A C C G A G T A C T T C T A G T G T T C G A A G C C A A G A T C C C C A C C 518
Salmon PCR T A A C C G A G T A C T T C T A G T G T T C G A A G C C A A G A T C C C C A C C 292

SalmoKCaR 1 A G T C T C C A T C G T A A G T G G T G G G G G C T A A A C T T G C A G T T C C 2310
SalmoKCaR 2 A G T C T C C A T C G T A A G T G G T G G G G G C T A A A C T T G C A G T T C C 2400
SalmoKCaR 3 A G T C T C C A T C G T A A G T G G T G G G G G C T A A A C T T G C A G T T C C 2311
Salmon A26 A G T C T C C A T C G T A A G T G G T G G G G G C T A A A C T T G C A G T T C C 558
Salmon PCR A G T C T C C A T C G T A A G T G G T G G G G G C T A A A C T T G C A G T T C C 332

SalmoKCaR 1 T G T T A G T G T T C C T G T T C A C A T T T G T G C A A G T G A T G A T A T G 2350
SalmoKCaR 2 T G T T A G T G T T C C T G T T C A C A T T T G T G C A A G T G A T G A T A T G 2440
SalmoKCaR 3 T G T T A G T G T T C C T G T T C A C A T T T G T G C A A G T G A T G A T A T G 2351
Salmon A26 T G T T A G T G T T C C T G T T C A C A T T T G T G C A A G T G A T G A T A T G 598
Salmon PCR T G T T A G T G T T C C T G T T C A C A T T T G T G C A A G T G A T G A T A T G 372

SalmoKCaR 1 T G T G G T C T G G C T T T A C A A T G C T C C T C C G G C G A G C T A C A G G 2390
SalmoKCaR 2 T G T G G T C T G G C T T T A C A A T G C T C C T C C G G C G A G C T A C A G G 2480
SalmoKCaR 3 T G T G G T C T G G C T T T A C A A T G C T C C T C C G G C G A G C T A C A G G 2391
Salmon A26 T G T G G T C T G G C T T T A C A A T G C T C C T C C G G C G A G C T A C A G G 638
Salmon PCR T G T G G T C T G G C T T T A C A A T G C T C C T C C G G C G A G C T A C A G G 412

SalmoKCaR 1 A A C C A T G A C A T T G A T G A G A T A A T T T T C A T T A C A T G C A A T G 2430
SalmoKCaR 2 A A C C A T G A C A T T G A T G A G A T A A T T T T C A T T A C A T G C A A T G 2520
SalmoKCaR 3 A A C C A T G A C A T T G A T G A G A T A A T T T T C A T T A C A T G C A A T G 2431
Salmon A26 A A C C A T G A C A T T G A T G A G A T A A T T T T C A T T A C A T G C A A T G 678
Salmon PCR A A C C A T G A C A T T G A T G A G A T A A T T T T C A T T A C A T G C A A T G 452

FIG. 12G

```
SalmoKCaR 1  A G G G C T C T A T G A T G G C G C T T G G C T T C C T A A T T G G G T A C A C  2470
SalmoKCaR 2  A G G G C T C T A T G A T G G C G C T T G G C T T C C T A A T T G G G T A C A C  2560
SalmoKCaR 3  A G G G C T C T A T G A T G G C G C T T G G C T T C C T A A T T G G G T A C A C  2471
Salmon A26   A G G G C T C T A T G A T G G C G C T T G G C T T C C T A A T T G G G T A C A C  718
Salmon PCR   A G G G C T C T A T G A T G G C G C T T G G C T T C C T A A T T G G G T A C A C  492

SalmoKCaR 1  A T G C C T G C T G G C A G C C A T A T G C T T C T T C T T T G C A T T T A A A  2510
SalmoKCaR 2  A T G C C T G C T G G C A G C C A T A T G C T T C T T C T T T G C A T T T A A A  2600
SalmoKCaR 3  A T G C C T G C T G G C A G C C A T A T G C T T C T T C T T T G C A T T T A A A  2511
Salmon A26   A T G C C T G C T G G C A G C C A T A T G C T T C T T C T T T G C A T T T A A A  758
Salmon PCR   A T G C C T G C T G G C A G C C A T A T R C T T C T T C T T T G C A T T T A A A  532

SalmoKCaR 1  T C A C G A A A A C T G C C A G A G A A C T T T A C T G A G G C T A A G T T C A  2550
SalmoKCaR 2  T C A C G A A A A C T G C C A G A G A A C T T T A C T G A G G C T A A G T T C A  2640
SalmoKCaR 3  T C A C G A A A A C T G C C A G A G A A C T T T A C T G A G G C T A A G T T C A  2551
Salmon A26   T C A C G A A A A C T G C C A G A G A A C T T T A C T G A G G C T A A G T T C A  798
Salmon PCR   T C A C G A A A A C T G C C A G A G A A C T T T A C T G A G G C T A A G T T C A  572

SalmoKCaR 1  T C A C C T T C A G C A T G C T C A T C T T C T T C A T C G T C T G G A T C T C  2590
SalmoKCaR 2  T C A C C T T C A G C A T G C T C A T C T T C T T C A T C G T C T G G A T C T C  2680
SalmoKCaR 3  T C A C C T T C A G C A T G C T C A T C T T C T T C A T C G T C T G G A T C T C  2591
Salmon A26   T C A C C T T C A G C A T G C T C A T C T T C T T C A T C G T C T G G A T C T C  838
Salmon PCR   T C A C C T T C A G C A T G C T C A T C T T (SEQ ID NO: 3)                      594

SalmoKCaR 1  T T T C A T C C C T G C C T A C T T C A G C A C T T A C G G A A A G T T T G T G  2630
SalmoKCaR 2  T T T C A T C C C T G C C T A C T T C A G C A C T T A C G G A A A G T T T G T G  2720
SalmoKCaR 3  T T T C A T C C C T G C C T A C T T C A G C A C T T A C G G A A A G T T T G T G  2631
Salmon A26   T T T C A T C C C T G C C T A C T T C A G C A C T T A C G G A A A G T T T G T G  878
Salmon PCR                                                                                594

SalmoKCaR 1  T C G G C T G T G G A G G T C A T C G C C A T A C T A G C C T C C A G C T T T G  2670
SalmoKCaR 2  T C G G C T G T G G A G G T C A T C G C C A T A C T A G C C T C C A G C T T T G  2760
SalmoKCaR 3  T C G G C T G T G G A G G T C A T C G C C A T A C T A G C C T C C A G C T T T G  2671
Salmon A26   T C G G C T G T G G A G G T C A T C G C C A T A C T A G C C T C C A G C T T T G  918
Salmon PCR                                                                                594

SalmoKCaR 1  G C C T G C T G G C C T G T A T T T T C T T C A A T A A A G T C T A C A T C A T  2710
SalmoKCaR 2  G C C T G C T G G C C T G T A T T T T C T T C A A T A A A G T C T A C A T C A T  2800
SalmoKCaR 3  G C C T G C T G G C C T G T A T T T T C T T C A A T A A A G T C T A C A T C A T  2711
Salmon A26   G C C T G C T G G C C T G T A T T T T C T T C A A T A A A G T C T A C A T C A T  958
Salmon PCR                                                                                594

SalmoKCaR 1  C C T C T T C A A A C C G T C C A G G A A C A C T A T A G A G G A G G T T C G C  2750
SalmoKCaR 2  C C T C T T C A A A C C G T C C A G G A A C A C T A T A G A G G A G G T T C G C  2840
SalmoKCaR 3  C C - - - - - - - - - - - - - - - - - - - - - - - - - - - - - - - - - - - - - -  2713
Salmon A26   C C T C T T C A A A C C G T C C A G G A A C A C T A T A G A G G A G G T T C G C  998
Salmon PCR                                                                                594

SalmoKCaR 1  T G T A G C A C T G C G G C C C A T T C T T T C A A A G T G G C A G C C A A G G  2790
SalmoKCaR 2  T G T A G C A C T G C G G C C C A T T C T T T C A A A G T G G C A G C C A A G G  2880
SalmoKCaR 3  - - - - - - - - - - - - - - - - - - - - - - - - - - - - - - - - - - - - - - - -  2713
Salmon A26   T G T A G C A C T G C G G C C C A T T C T T T C A A A G T G G C A G C C A A G G  1038
Salmon PCR                                                                                594
```

FIG. 12H

```
SalmoKCaR 1  C C A C T C T G A G A C A C A G C T C A G C C T C C A G G A A G A G G T C C A G  2830
SalmoKCaR 2  C C A C T C T G A G A C A C A G C T C A G C C T C C A G G A A G A G G T C C A G  2920
SalmoKCaR 3  - - - - - - - - - - - - - - - - - - - - - - - - - - - - - - - - - - - - - - - -  2713
Salmon A26   C C A C T C T G A G A C A C A G C T C A G C C T C C A G G A A G A G G T C C A G  1078
Salmon PCR                                                                                  594

SalmoKCaR 1  C A G T G T G G G G G G A T C C T G T G C C T C A A C T C C C T C C T C A T C C  2870
SalmoKCaR 2  C A G T G T G G G G G G A T C C T G T G C C T C A A C T C C C T C C T C A T C C  2960
SalmoKCaR 3  - - - - - - - - - - - - - - - - - - - - - - - - - - - - - - - - - - - - - - - -  2713
Salmon A26   C A G T G T G G G G G G A T C C T G T G C C T C A A C T C C C T C C T C A T C C  1118
Salmon PCR                                                                                  594

SalmoKCaR 1  A T C A G C C T C A A G A C C A A T G A C A A T G A C T C C C C A T C A G G T C  2910
SalmoKCaR 2  A T C A G C C T C A A G A C C A A T G A C A A T G A C T C C C C A T C A G G T C  3000
SalmoKCaR 3  A T C A G C C T C A A G A C C A A T G A C A A T G A C T C C C C A T C A G G T C  2753
Salmon A26   A T C A G C C T C A A G A C C A A T G A C A A T G A C T C C C C A T C A G G T C  1158
Salmon PCR                                                                                  594

SalmoKCaR 1  A G C A G A G A A T C C A T A A G C C A A G A G T A A G C T T T G G A A G T G G  2950
SalmoKCaR 2  A G C A G A G A A T C C A T A A G C C A A G A G T A A G C T T T G G A A G T G G  3040
SalmoKCaR 3  A G C A G A G A A T C C A T A A G C C A A G A G T A A G C T T T G G A A G T G G  2793
Salmon A26   A G C A G A G A A T C C A T A A G C C A A G A G T A A G C T T T G G A A G T G G  1198
Salmon PCR                                                                                  594

SalmoKCaR 1  A A C A G T T A C T C T G T C C T T G A G C T T T G A G G A G T C C A G A A A G  2990
SalmoKCaR 2  A A C A G T T A C T C T G T C C T T G A G C T T T G A G G A G T C C A G A A A G  3080
SalmoKCaR 3  A A C A G T T A C T C T G T C C T T G A G C T T T G A G G A G T C C A G A A A G  2833
Salmon A26   A A C A G T T A C T C T G T C C T T G A G C T T T G A G G A G T C C A G A A A G  1238
Salmon PCR                                                                                  594

SalmoKCaR 1  A A T T C T A T G A A G T A G G G A A G T G T C T T T T G G T G G G C C G A G A  3030
SalmoKCaR 2  A A T T C T A T G A A G T A G G G A A G T G T C T T T T G G T G G G C C G A G A  3120
SalmoKCaR 3  A A T T C T A T G A A G T A G G G A A G T G T C T T T T G G T G G G C C G A G A  2873
Salmon A26   A A T T C T A T G A A G T A G G G A A G T G T C T T T T G G T G G G C C G A G A  1278
Salmon PCR                                                                                  594

SalmoKCaR 1  G C C T T G T C A A A A C C T G A G T T G G T G T T G C A T T C T T T G T T G G  3070
SalmoKCaR 2  G C C T T G T C A A A A C C T G A G T T G G T G T T G C A T T C T T T G T T G G  3160
SalmoKCaR 3  G C C T T G T C A A A A C C T G A G T T G G T G T T G C A T T C T T T G T T G G  2913
Salmon A26   G C C T T G T C A A A A C C T G A G T T G G T G T T G C A T T C T T T G T T G G  1318
Salmon PCR                                                                                  594

SalmoKCaR 1  C T G G G T A G T T G G A G C A G A A A T T A T G A T A T T A A A A G C T T T G  3110
SalmoKCaR 2  C T G G G T A G T T G G A G C A G A A A T T A T G A T A T T A A A A G C T T T G  3200
SalmoKCaR 3  C T G G G T A G T T G G A G C A G A A A T T A T G A T A T T A A A A G C T T T G  2953
Salmon A26   C T G G G T A G T T G G A G C A G A A A T T A T G A T A T T A A A A G C T T T G  1358
Salmon PCR                                                                                  594

SalmoKCaR 1  A T G T A T T C A G A A T G G T G A C A C A G C A T A G G T G G C C A A G A T T  3150
SalmoKCaR 2  A T G T A T T C A G A A T G G T G A C A C A G C A T A G G T G G C C A A G A T T  3240
SalmoKCaR 3  A T G T A T T C A G A A T G G T G A C A C A G C A T A G G T G G C C A A G A T T  2993
Salmon A26   A T G T A T T C A G A A T G G T G A C A C A G C A T A G G T G G C C A A G A T T  1398
Salmon PCR                                                                                  594
```

FIG. 12I

```
SalmoKCaR 1   C C A T T A T A T T A C A A T A A T C T G T G T T G T T C A T T A T G A G G A C  3190
SalmoKCaR 2   C C A T T A T A T T A C A A T A A T C T G T G T T G T T C A T T A T G A G G A C  3280
SalmoKCaR 3   C C A T T A T A T T A C A A T A A T C T G T G T T G T T C A T T A T G A G G A C  3033
Salmon A26    C C A T T A T A T T A C A A T A A T C T G T G T T G T T C A T T A T G A G G A C  1438
Salmon PCR                                                                                   594

SalmoKCaR 1   A T T T C A A A A T G C T G A A A A T C A T C A A A T A C A T A A T T T A C T G  3230
SalmoKCaR 2   A T T T C A A A A T G C T G A A A A T C A T C A A A T A C A T A A T T T A C T G  3320
SalmoKCaR 3   A T T T C A A A A T G C T G A A A A T C A T C A A A T A C A T A A T T T A C T G  3073
Salmon A26    A T T T C A A A A T G C T G A A A A T C A T C A A A T A C A T A A T T T A C T G  1478
Salmon PCR                                                                                   594

SalmoKCaR 1   A G T T T T C T T G A T A A T C T T G A G A A T A G A A T A G C C T A T T C A A  3270
SalmoKCaR 2   A G T T T T C T T G A T A A T C T T G A G A A T A G A A T A G C C T A T T C A A  3360
SalmoKCaR 3   A G T T T T C T T G A T A A T C T T G A G A A T A G A A T A G C C T A T T C A A  3113
Salmon A26    A G T T T T C T T G A T A A T C T T G A G A A T A G A A T A G C C T A T T C A A  1518
Salmon PCR                                                                                   594

SalmoKCaR 1   G T C A T C G T T G A G C A G A C A T T A A T T A A C A A T G A T G T A A T A C  3310
SalmoKCaR 2   G T C A T C G T T G A G C A G A C A T T A A T T A A C A A T G A T G T A A T A C  3400
SalmoKCaR 3   G T C A T C G T T G A G C A G A C A T T A A T T A A C A A T G A T G T A A T A C  3153
Salmon A26    G T C A T C G T T G A G C A G A C A T T A A T T A A C A A T G A T G T A A T A C  1558
Salmon PCR                                                                                   594

SalmoKCaR 1   T T T C C A T A C C T A T T T T C T T T A A C A A T A G A T T C A C A T T G T T  3350
SalmoKCaR 2   T T T C C A T A C C T A T T T T C T T T A A C A A T A G A T T C A C A T T G T T  3440
SalmoKCaR 3   T T T C C A T A C C T A T T T T C T T T A A C A A T A G A T T C A C A T T G T T  3193
Salmon A26    T T T C C A T A C C T A T T T T C T T T A A C A A T A G A T T C A C A T T G T T  1598
Salmon PCR                                                                                   594

SalmoKCaR 1   A A A G T T C A A C T A T G A C C T G T A A A A T A C A T G A G G T A T A A C A  3390
SalmoKCaR 2   A A A G T T C A A C T A T G A C C T G T A A A A T A C A T G A G G T A T A A C A  3480
SalmoKCaR 3   A A A G T T C A A C T A T G A C C T G T A A A A T A C A T G A G G T A T A A C A  3233
Salmon A26    A A A G T T C A A C T A T G A C C T G T A A A A T A C A T G A G G T A T A A C A  1638
Salmon PCR                                                                                   594

SalmoKCaR 1   G G A G A C A A T A A A A C T A T G C A T A T C C T A G C T T C T G G G C C T G  3430
SalmoKCaR 2   G G A G A C A A T A A A A C T A T G C A T A T C C T A G C T T C T G G G C C T G  3520
SalmoKCaR 3   G G A G A C A A T A A A A C T A T G C A T A T C C T A G C T T C T G G G C C T G  3273
Salmon A26    G G A G A C A A T A A A A C T A T G C A T A T C C T A G C T T C T G G G C C T G  1678
Salmon PCR                                                                                   594

SalmoKCaR 1   A G T A G C A G G C A G T T T A C T C T G G G C A C G C T T T T C A T C C A A A  3470
SalmoKCaR 2   A G T A G C A G G C A G T T T A C T C T G G G C A C G C T T T T C A T C C A A A  3560
SalmoKCaR 3   A G T A G C A G G C A G T T T A C T C T G G G C A C G C T T T T C A T C C A A A  3313
Salmon A26    A G T A G C A G G C A G T T T A C T C T G G G C A C G C T T T T C A T C C A A A  1718
Salmon PCR                                                                                   594

SalmoKCaR 1   C T T C C G A A T G C T G C C C C C A A T C C T A G T G A G G T T A A A G G C C  3510
SalmoKCaR 2   C T T C C G A A T G C T G C C C C C A A T C C T A G T G A G G T T A A A G G C C  3600
SalmoKCaR 3   C T T C C G A A T G C T G C C C C C A A T C C T A G T G A G G T T A A A G G C C  3353
Salmon A26    C T T C C G A A T G C T G C C C C C A A T C C T A G T G A G G T T A A A G G C C  1758
Salmon PCR                                                                                   594
```

FIG. 12J

```
SalmoKCaR 1  CAGTGCAGTCATATCTTTTCTCTAGGCACGCTTTTCATCC  3550
SalmoKCaR 2  CAGTGCAGTCATATCTTTTCTCTAGGCACGCTTTTCATCC  3640
SalmoKCaR 3  CAGTGCAGTCATATCTTTTCTCTAGGCACGCTTTTCATCC  3393
Salmon A26   CAGTGCAGTCATATCTTTTCTCTAGGCACGCTTTTCATCC  1798
Salmon PCR                                             594

SalmoKCaR 1  AAACTTCCGAATGCGGCTATATCAGTCTCTTTCCTACTGT  3590
SalmoKCaR 2  AAACTTCCGAATGCGGCTATATCAGTCTCTTTCCTACTGT  3680
SalmoKCaR 3  AAACTTCCGAATGCGGCTATATCAGTCTCTTTCCTACTGT  3433
Salmon A26   AAACTTCCGAATGCGGCTATATCAGTCTCTTTCCTACTGT  1838
Salmon PCR                                             594

SalmoKCaR 1  CTTTTTCATTAGGCCAGTGTTTAACAACCCTGGTCCTTAA  3630
SalmoKCaR 2  CTTTTTCATTAGGCCAGTGTTTAACAACCCTGGTCCTTAA  3720
SalmoKCaR 3  CTTTTTCATTAGGCCAGTGTTTAACAACCCTGGTCCTTGA  3473
Salmon A26   CTTTTTCATTAGGCCAGTGTTTAACAACCCTGGTCCTTAA  1878
Salmon PCR                                             594

SalmoKCaR 1  GTACACACAACAGAGCACATTTTTGTTGTGGCCCTGGACA  3670
SalmoKCaR 2  GTACACACAACAGAGCACATTTTTGTTGTAGCCCTGGACA  3760
SalmoKCaR 3  GTACACACAACAGGGCACATTTTTGTTGTAGCCCTGGACA  3513
Salmon A26   GTACACACAACAGAACACATTTTTGTTGTAGCCCTGGACA  1918
Salmon PCR                                             594

SalmoKCaR 1  ATCACTCCTCACTCAGCTCATTGAGGGCCTGATGATTAGT  3710
SalmoKCaR 2  ATCACTCCTCACTCAGCTCATTGAGGGCCTGATGATTAGT  3800
SalmoKCaR 3  ATCACTCCTCACTCAGCTCATTGAGGGCCTGATGATTAGT  3553
Salmon A26   ATCACTCCTCACTCAGCTCATTGAGGGCCTGATGATTAGT  1958
Salmon PCR                                             594

SalmoKCaR 1  TGACAAGTTGAGTCGGGTGTGCTTGTCCGGGGTTGCAATA  3750
SalmoKCaR 2  TGACAAGTTGAGTCGGGTGTGCTTGTCCAGGGTTACGATA  3840
SalmoKCaR 3  TGACAAGTTGGGTCAGGTGTGCTTGTCCAGGGTTACAATA  3593
Salmon A26   TGACAAGTTGAATCAGGTGTGCTTGTCCAGGGTTACAATA  1998
Salmon PCR                                             594

SalmoKCaR 1  CAGATGTGTACTGTTGGGGGTACTCGAGGACCAGGATTGG  3790
SalmoKCaR 2  CAGATGTGTACTGTTGGGGGTGCTCGAGGACCAGGATTGG  3880
SalmoKCaR 3  CAGATGTGTGCTGTTGGGGGTACTCGAGGACCAGGATTGG  3633
Salmon A26   CAAATGTGTACTGTTGGGGGTAC (SEQ ID NO: 5)      2021
Salmon PCR                                             594

SalmoKCaR 1  GAAACATTACATTAGGACTACTGTAGGTTCTTCAATATGG  3830
SalmoKCaR 2  GAAACATTACATTAGGACTACTGTAGGTTCTTCAATATGG  3920
SalmoKCaR 3  GAAACATTACATTAGGACTACTGTAGGTTCTTCAATATGG  3673
Salmon A26                                             2021
Salmon PCR                                             594

SalmoKCaR 1  TGTCATACGGTCATATGGTGTCATATGGTGTCTGGTTGTT  3870
SalmoKCaR 2  TGTCATACGGTCATATGGTGTCATATGGTGTCTGGTTGTT  3960
SalmoKCaR 3  TGTCATACGGTCATATGGTGTCATATGGTGTCTGGTTGTT  3713
Salmon A26                                             2021
Salmon PCR                                             594
```

FIG. 12K

```
SalmoKCaR 1  T T C T G C A T A T G T G T A T T T C A C C A A G T T A C T G C A C A T G T T A  3910
SalmoKCaR 2  T T C T G C A T A T G T G T A T T T C A C C A A G T T A C T G C A C A T G T T A  4000
SalmoKCaR 3  T T C T G C A T A T G T G T A T T T C A C C A A G T T A C T G C A C A T G T T A  3753
Salmon A26                                                                                2021
Salmon PCR                                                                                594

SalmoKCaR 1  G A C C T A T A C A C T G G A A T A A A C A T T T T T T T T C (SEQ ID NO: 7)   3941
SalmoKCaR 2  G A C C T A T A C A C T G G A A T A A A C A T T T T T T T T C (SEQ ID NO: 9)   4031
SalmoKCaR 3  G A C C T A T A C A C T G G A A T A A A C A T T T T T T T T C A C A A T G C A T  3793
Salmon A26                                                                                2021
Salmon PCR                                                                                594

SalmoKCaR 1                                                                               3941
SalmoKCaR 2                                                                               4031
SalmoKCaR 3  C C A A T G A C A A T A A A A T C A C C A T A T G C C A A T G (SEQ ID NO: 11)    3824
Salmon A26                                                                                2021
Salmon PCR                                                                                594
```

FIG. 12L

```
SalmoKCaR 1  M R F Y L Y Y L V L L G F S S V I S T Y G P H Q R A Q K T G D I L L G G L F P M  40
SalmoKCaR 2  M R F Y L Y Y L V L L G F S S V I S T Y G P H Q R A Q K T G D I L L G G L F P M  40
SalmoKCaR 3  M R F Y L Y Y L V L L G F S S V I S T Y G P H Q R A Q K T G D I L L G G L F P M  40
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  H F G V T S K D Q D L A A R P E S T E C V R Y N F R G F R W L Q A M I F A I E E  80
SalmoKCaR 2  H F G V T S K D Q D L A A R P E S T E C V R Y N F R G F R W L Q A M I F A I E E  80
SalmoKCaR 3  H F G V T S K D Q D L A A R P E S T E C V R Y N F R G F R W L Q A M I F A I E E  80
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  I N N S S T L L P N I T L G Y R I F D T C N T V S K A L E A T L S F V A Q N K I  120
SalmoKCaR 2  I N N S S T L L P N I T L G Y R I F D T C N T V S K A L E A T L S F V A Q N K I  120
SalmoKCaR 3  I N N S S T L L P N I T L G Y R I F D T C N T V S K A L E A T L S F V A Q N K I  120
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  D S L N L D E F C N C T D H I P S T I A V V G A S G S A V S T A V A N L L G L F  160
SalmoKCaR 2  D S L N L D E F C N C T D H I P S T I A V V G A S G S A V S T A V A N L L G L F  160
SalmoKCaR 3  D S L N L D E F C N C T D H I P S T I A V V G A S G S A V S T A V A N L L G L F  160
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  Y I P Q I S Y A S S S R L L S N K N Q F K S F M R T I P T D E H Q A T A M A D I  200
SalmoKCaR 2  Y I P Q I S Y A S S S R L L S N K N Q F K S F M R T I P T D E H Q A T A M A D I  200
SalmoKCaR 3  Y I P Q I S Y A S S S R L L S N K N Q F K S F M R T I P T D E H Q A T A M A D I  200
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  I D Y F Q W N W V I A V A S D D E Y G R P G I E K F E K E M E E R D I C I H L S  240
SalmoKCaR 2  I D Y F Q W N W V I A V A S D D E Y G R P G I E K F E K E M E E R D I C I H L S  240
SalmoKCaR 3  I D Y F Q W N W V I A V A S D D E Y G R P G I E K F E K E M E E R D I C I H L S  240
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  E L I S Q Y F E E W Q I Q G L V D R I E N S S A K V I V V F A S G P D I E P L I  280
SalmoKCaR 2  E L I S Q Y F E E W Q I Q G L V G R I E N S S A K V I V V F A S G P D I E P L I  280
SalmoKCaR 3  E L I S Q Y F E E W Q I Q G L V D R I E N S S A K V I V V F A S G P D I E P L I  280
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  K E M V R R N I T D R I W L A S E A W A T T S L I A K P E Y L D V V V G T I G F  320
SalmoKCaR 2  K E M V R R N I T D R I W L A S E A W A T T S L I A K P E Y L D V V V G T I G F  320
SalmoKCaR 3  K E M V R R N I T D R I W L A S E A W A T T S L I A K P E Y L D V V V G T I G F  320
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  A L R A G E I P G F K D F L Q E V T P K K S S H N E F V R E F W E E T F N C Y L  360
SalmoKCaR 2  A L R A G E I P G F K D F L Q E V T P K K S S H N E F V R E F W E E T F N C Y L  360
SalmoKCaR 3  A L R A G E I P G F K D F L Q E V T P K K S S H N E F V R E F W E E T F N C Y L  360
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0
```

FIG. 13A

SalmoKCaR 1 E D S Q R L R D S E N G S T S F R P L C T G E E D I M G A E T P Y L D Y T H L R 400
SalmoKCaR 2 E D S Q R L R D S E N G S T S F R P L C T G E E D I M G A E T P Y L D Y T H L R 400
SalmoKCaR 3 E D S Q R L R D S E N G S T S F R P L C T G E E D I M G A E T P Y L D Y T H L R 400
Salmon A26 - - - - - - - - - - - - - - - - - - - - - - - - - - - - - - - - - - - - - - - - 0
Salmon PCR - - - - - - - - - - - - - - - - - - - - - - - - - - - - - - - - - - - - - - - - 0

SalmoKCaR 1 I S Y N V Y V A V H S I A Q A L Q D I L T C I P G R G L F S N N S C A D I K K I 440
SalmoKCaR 2 I S Y N V Y V A V H S I A Q A L Q D I L T C I P G R G L F S N N S C A D I K K I 440
SalmoKCaR 3 I S Y N V Y V A V H S I A Q A L Q D I L T C I P G R G F F S N N S C A D I K K I 440
Salmon A26 - - - - - - - - - - - - - - - - - - - - - - - - - - - - - - - - - - - - - - - - 0
Salmon PCR - - - - - - - - - - - - - - - - - - - - - - - - - - - - - - - - - - - - - - - - 0

SalmoKCaR 1 E A W Q V L K Q L R H L N F S N S M G E K V H F D E N A D P S G N Y T I I N W H 480
SalmoKCaR 2 E A W Q V L K Q L R H L N F S N S M G E K V H F D E N A D P S G N Y T I I N W H 480
SalmoKCaR 3 E A W Q V L K Q L R H L N F S N S M G E K V H F D E N A D P S G N Y T I I N W H 480
Salmon A26 - - - - - - - - - - - - - - - - - - - - - - - - - - - - - - - - - - - - - - - - 0
Salmon PCR - - - - - - - - - - - - - - - - - - - - - - - - - - - - - - - - - - - - - - - - 0

SalmoKCaR 1 R S P E D G S V V F E E V G F Y N M R A K R G V Q L F I D N T K I L W N G Y N T 520
SalmoKCaR 2 R S P E D G S V V F E E V G F Y N M R A K R G V Q L F I D N T K I L W N G Y N T 520
SalmoKCaR 3 R S P E D G S V V F E E V G F Y N M R A K R G V Q L F I D N T K I L W N G Y N T 520
Salmon A26 - - - - - - - - - - - - - - - - - - - - - - - - - - - - - - - - - - - - - - - - 0
Salmon PCR - - - - - - - - - - - - - - - - - - - - - - - - - - - - - - - - - - - - - - - - 0

SalmoKCaR 1 E V P F S N C S E D C E P G T R K G I I E S M P T C C F E C T E C S E G E Y S D 560
SalmoKCaR 2 E V P F S N C S E D C E P G T R K G I I E S M P T C C F E C T E C S E G E Y S D 560
SalmoKCaR 3 E V P F S N C S E D C E P G T R K G I I E S M P T C C F E C T E C S E G E Y S D 560
Salmon A26 - - - - - - - - - - - - - - - - - - - - - - - - - - - - - - - - - Y K H Y F S I 7
Salmon PCR - - - - - - - - - - - - - - - - - - - - - - - - - - - - - - - - - - - - - - - - 0

SalmoKCaR 1 H K D A S V C T K C P N D S W S N E N H T S C F L K E I E F L S W T E P F G I A 600
SalmoKCaR 2 H K D A S V C T K C P N D S W S N E N H T S C F L K E I E F L S W T E P F G I A 600
SalmoKCaR 3 H K D A S V C T K C P N D S W S N E N H T S C F L K E I E F L S W T E P F G I A 600
Salmon A26 P A D A S V C T K C P N D S W S N E N H T S C F L K E I E F L S W T E P F G I A 47
Salmon PCR - - - - - - - - - - - - - - - - - - - - - - - - - - - - - - - - - - - - - - - - 0

SalmoKCaR 1 L A L C S V L G V F L T A F V M G V F I K F R N T P I V K A T N R E L S Y L L L 640
SalmoKCaR 2 L A L C S V L G V F L T A F V M G V F I K F R N T P I V K A T N R E L S Y L L L 640
SalmoKCaR 3 L A L C S V L G V F L T A F V M G V F I K F R N T P I V K A T N R E L S Y L L L 640
Salmon A26 L A L C S V L G V F L T A F V M G V F I K F R N T P I V K A T N R E L S Y L L L 87
Salmon PCR L A L C S V L G V F L T A F V M G V F I K F R N T P I V K A T N R E L S Y L L L 40

SalmoKCaR 1 F S L I C C F S S S L I F I G E P Q D W T C R L R Q P A F G I S F V L C I S C I 680
SalmoKCaR 2 F S L I C C F S S S L I F I G E P Q D W T C R L R Q P A F G I S F V L C I S C I 680
SalmoKCaR 3 F S L I C C F S S S L I F I G E P Q D W T C R L R Q P A F G I S F V L C I S C I 680
Salmon A26 F S L I C C F S S S L I F I G E P Q D W T C R L R Q P A F G I S F V L C I S C I 127
Salmon PCR F S L I C C F S S S L I F I G E P Q D W T C R L R Q P A F G I S F V L C I S C I 80

SalmoKCaR 1 L V K T N R V L L V F E A K I P T S L H R K W W G L N L Q F L L V F L F T F V Q 720
SalmoKCaR 2 L V K T N R V L L V F E A K I P T S L H R K W W G L N L Q F L L V F L F T F V Q 720
SalmoKCaR 3 L V K T N R V L L V F E A K I P T S L H R K W W G L N L Q F L L V F L F T F V Q 720
Salmon A26 L V K T N R V L L V F E A K I P T S L H R K W W G L N L Q F L L V F L F T F V Q 167
Salmon PCR L V K T N R V L L V F E A K I P T S L H R K W W G L N L Q F L L V F L F T F V Q 120

FIG. 13B

| | | |
|---|---|---|
| SalmoKCaR 1 | V M I C V V W L Y N A P P A S Y R N H D I D E I I F I T C N E G S M M A L G F L | 760 |
| SalmoKCaR 2 | V M I C V V W L Y N A P P A S Y R N H D I D E I I F I T C N E G S M M A L G F L | 760 |
| SalmoKCaR 3 | V M I C V V W L Y N A P P A S Y R N H D I D E I I F I T C N E G S M M A L G F L | 760 |
| Salmon A26 | V M I C V V W L Y N A P P A S Y R N H D I D E I I F I T C N E G S M M A L G F L | 207 |
| Salmon PCR | V M I C V V W L Y N A P P A S Y R N H D I D E I I F I T C N E G S M M A L G F L | 160 |

| | | |
|---|---|---|
| SalmoKCaR 1 | I G Y T C L L A A I C F F F A F K S R K L P E N F T E A K F I T F S M L I F F I | 800 |
| SalmoKCaR 2 | I G Y T C L L A A I C F F F A F K S R K L P E N F T E A K F I T F S M L I F F I | 800 |
| SalmoKCaR 3 | I G Y T C L L A A I C F F F A F K S R K L P E N F T E A K F I T F S M L I F F I | 800 |
| Salmon A26 | I G Y T C L L A A I C F F F A F K S R K L P E N F T E A K F I T F S M L I F F I | 247 |
| Salmon PCR | I G Y T C L L A A I C F F F A F K S R K L P E N F T E A K F I T F S M L I | 197 |

| | | |
|---|---|---|
| SalmoKCaR 1 | V W I S F I P A Y F S T Y G K F V S A V E V I A I L A S S F G L L A C I F F N K | 840 |
| SalmoKCaR 2 | V W I S F I P A Y F S T Y G K F V S A V E V I A I L A S S F G L L A C I F F N K | 840 |
| SalmoKCaR 3 | V W I S F I P A Y F S T Y G K F V S A V E V I A I L A S S F G L L A C I F F N K | 840 |
| Salmon A26 | V W I S F I P A Y F S T Y G K F V S A V E V I A I L A S S F G L L A C I F F N K | 287 |
| Salmon PCR | | 197 |

| | | |
|---|---|---|
| SalmoKCaR 1 | V Y I I L F K P S R N T I E E V R C S T A A H S F K V A A K A T L R H S S A S R | 880 |
| SalmoKCaR 2 | V Y I I L F K P S R N T I E E V R C S T A A H S F K V A A K A T L R H S S A S R | 880 |
| SalmoKCaR 3 | V Y I I H Q P Q D Q | 850 |
| Salmon A26 | V Y I I L F K P S R N T I E E V R C S T A A H S F K V A A K A T L R H S S A S R | 327 |
| Salmon PCR | | 197 |

| | | |
|---|---|---|
| SalmoKCaR 1 | K R S S S V G G S C A S T P S S S I S L K T N D N D S P S G Q Q R I H K P R V S | 920 |
| SalmoKCaR 2 | K R S S S V G G S C A S T P S S S I S L K T N D N D S P S G Q Q R I H K P R V S | 920 |
| SalmoKCaR 3 | | 850 |
| Salmon A26 | K R S S S V G G S C A S T P S S S I S L K T N D N D S P S G Q Q R I H K P R V S | 367 |
| Salmon PCR | | 197 |

| | | |
|---|---|---|
| SalmoKCaR 1 | F G S G T V T L S L S F E E S R K N S M K (SEQ ID NO: 8) | 941 |
| SalmoKCaR 2 | F G S G T V T L S L S F E E S R K N S M K (SEQ ID NO: 10) | 941 |
| SalmoKCaR 3 | | 850 |
| Salmon A26 | F G S G T V T L S L S F E E S R K N S M K (SEQ ID NO: 12) | 388 |
| Salmon PCR | | 197 |

FIG. 13C

```
SalmoKCaR 1 -TTCCAACAGCATATTTTTGTTGTATTTGCTTTGGTTTGT 39
SalmoKCaR 2 GTTCCAACAGCATATTTTTGTTGTATTTGCTTTGGTTTGT 40
SalmoKCaR 3 GTTCCAACAGCATATTTTTGTTGTATTTGCTTTGGTTTGT 40

SalmoKCaR 1 CTGAAATCAAGCATTATCAAG------------------- 60
SalmoKCaR 2 CTGAAATCAAGCATTATCAAGGATTGAGCAAGACAACTGA 80
SalmoKCaR 3 CTGAAATCAAGCATTATCAAG------------------- 61

SalmoKCaR 1 ---------------------------------------- 60
SalmoKCaR 2 GTTGTCAGACTAAGAATATACACATTTCCAGTTCTCTCTT 120
SalmoKCaR 3 ---------------------------------------- 61

SalmoKCaR 1 ------------------------------ATCAAGAACA 70
SalmoKCaR 2 TAATGGACTTCTCACACTGATGTTCTTCAGATCAAGAACA 160
SalmoKCaR 3 ------------------------------ATCAAGAACA 71

SalmoKCaR 1 GCATGAGTCAGAAACAAGGCGACAGCCAGAGTCACTGGAG 110
SalmoKCaR 2 GCATGAGTCAGAAACAAGGCGACAGCCAGAGTCACTGGAG 200
SalmoKCaR 3 GCATGAGTCAGAAACAAGGCGACAGCCAGAGTCACTGGAG 111

SalmoKCaR 1 GGGACAAGACTGAGGTTAACTCTGAAGTCTAATGTGCTGA 150
SalmoKCaR 2 GGGACAAGACTGAGGTTAACTCTGAAGTCTAATGTGCTGA 240
SalmoKCaR 3 GGGACAAGACTGAGGTTAACTCTGAAGTCTAATGTGCTGA 151

SalmoKCaR 1 GAGGACAAGGCCCTCCTGAGAGCTGAACGATGAGATTTTA 190
SalmoKCaR 2 GAGGACAAGGCCCTCCTGAGAGCTGAACGATGAGATTTTA 280
SalmoKCaR 3 GAGGACAAGGCCCTCCTGAGAGCTGAACGATGAGATTTTA 191

SalmoKCaR 1 CCTGTATTACCTGGTGCTTTTGGGCTTCAGTTCTGTCATC 230
SalmoKCaR 2 CCTGTATTACCTGGTGCTTTTGGGCTTCAGTTCTGTCATC 320
SalmoKCaR 3 CCTGTATTACCTGGTGCTTTTGGGCTTCAGTTCTGTCATC 231

SalmoKCaR 1 TCCACCTATGGGCCTCATCAGAGAGCACAGAAGACTGGGG 270
SalmoKCaR 2 TCCACCTATGGGCCTCATCAGAGAGCACAGAAGACTGGGG 360
SalmoKCaR 3 TCCACCTATGGGCCTCATCAGAGAGCACAGAAGACTGGGG 271

SalmoKCaR 1 ATATTCTGCTGGGCGGGCTGTTTCCAATGCACTTTGGTGT 310
SalmoKCaR 2 ATATTCTGCTGGGCGGGCTGTTTCCAATGCACTTTGGTGT 400
SalmoKCaR 3 ATATTCTGCTGGGCGGGCTGTTTCCAATGCACTTTGGTGT 311

SalmoKCaR 1 TACCTCCAAAGACCAAGACCTGGCAGCGCGGCCAGA ATCC 350
SalmoKCaR 2 TACCTCCAAAGACCAAGACCTGGCAGCGCGGCCAGA ATCC 440
SalmoKCaR 3 TACCTCCAAAGACCAAGACCTGGCAGCGCGGCCAGA ATCC 351

SalmoKCaR 1 ACAGAGTGTGTTAGGTACAATTTCCGGGGATTCCGT TGGC 390
SalmoKCaR 2 ACAGAGTGTGTTAGGTACAATTTCCGGGGATTCCGT TGGC 480
SalmoKCaR 3 ACAGAGTGTGTTAGGTACAATTTCCGGGGATTCCGT TGGC 391

SalmoKCaR 1 TTCAGGCCATGATTTTTGCAATAGAGGAGATCAACA ACAG 430
SalmoKCaR 2 TTCAGGCCATGATTTTTGCAATAGAGGAGATCAACA ACAG 520
SalmoKCaR 3 TTCAGGCCATGATTTTTGCAATAGAGGAGATCAACA ACAG 431

SalmoKCaR 1 CAGTACTCTCCTGCCCAACATCACACTGGGCTACAG GATC 470
SalmoKCaR 2 CAGTACTCTCCTGCCCAACATCACACTGGGCTACAG GATC 560
SalmoKCaR 3 CAGTACTCTCCTGCCCAACATCACACTGGGCTACAG GATC 471
```

FIG. 15A

SalmoKCaR 1 T T T G A C A C C T G C A A C A C C G T G T C C A A G G C C C T G G A G G C T A 510
SalmoKCaR 2 T T T G A C A C C T G C A A C A C C G T G T C C A A G G C C C T G G A G G C T A 600
SalmoKCaR 3 T T T G A C A C C T G C A A C A C C G T G T C C A A G G C C C T G G A G G C T A 511

SalmoKCaR 1 C C C T C A G T T T C G T A G C A C A G A A T A A G A T T G A C T C T C T G A A 550
SalmoKCaR 2 C C C T C A G T T T C G T A G C A C A G A A T A A G A T T G A C T C T C T G A A 640
SalmoKCaR 3 C C C T C A G T T T C G T A G C A C A G A A T A A G A T T G A C T C T C T G A A 551

SalmoKCaR 1 C T T G G A T G A A T T C T G T A A C T G C A C T G A T C A C A T C C C A T C G 590
SalmoKCaR 2 C T T G G A T G A A T T C T G T A A C T G C A C T G A T C A C A T C C C A T C G 680
SalmoKCaR 3 C T T G G A T G A A T T C T G T A A C T G C A C T G A T C A C A T C C C A T C G 591

SalmoKCaR 1 A C T A T A G C A G T G G T G G G G G C T T C T G G G T C A G C G G T C T C C A 630
SalmoKCaR 2 A C T A T A G C A G T G G T G G G G G C T T C T G G G T C A G C G G T C T C C A 720
SalmoKCaR 3 A C T A T A G C A G T G G T G G G G G C T T C T G G G T C A G C G G T C T C C A 631

SalmoKCaR 1 C T G C T G T T G C C A A T C T G T T G G G C C T T T T C T A C A T C C C A C A 670
SalmoKCaR 2 C T G C T G T T G C C A A T C T G T T G G G C C T T T T C T A C A T C C C A C A 760
SalmoKCaR 3 C T G C T G T T G C C A A T C T G T T G G G C C T T T T C T A C A T C C C A C A 671

SalmoKCaR 1 G A T C A G C T A T G C C T C T T C C A G T C G C C T A C T A A G C A A C A A G 710
SalmoKCaR 2 G A T C A G C T A T G C C T C T T C C A G T C G C C T A C T A A G C A A C A A G 800
SalmoKCaR 3 G A T C A G C T A T G C C T C T T C C A G T C G C C T A C T A A G C A A C A A G 711

SalmoKCaR 1 A A C C A G T T C A A A T C C T T C A T G A G G A C C A T T C C C A C A G A T G 750
SalmoKCaR 2 A A C C A G T T C A A A T C C T T C A T G A G G A C C A T T C C C A C A G A T G 840
SalmoKCaR 3 A A C C A G T T C A A A T C C T T C A T G A G G A C C A T T C C C A C A G A T G 751

SalmoKCaR 1 A G C A C C A G G C C A C T G C C A T G G C A G A T A T C A T C G A C T A C T T 790
SalmoKCaR 2 A G C A C C A G G C C A C T G C C A T G G C A G A T A T C A T C G A C T A C T T 880
SalmoKCaR 3 A G C A C C A G G C C A C T G C C A T G G C A G A T A T C A T C G A C T A C T T 791

SalmoKCaR 1 C C A A T G G A A T T G G G T C A T T G C A G T T G C G T C T G A T G A T G A G 830
SalmoKCaR 2 C C A A T G G A A T T G G G T C A T T G C A G T T G C G T C T G A T G A T G A G 920
SalmoKCaR 3 C C A A T G G A A T T G G G T C A T T G C A G T T G C G T C T G A T G A T G A G 831

SalmoKCaR 1 T A T G G A C G T C C G G G G A T T G A A A A A T T T G A G A A A G A G A T G G 870
SalmoKCaR 2 T A T G G A C G T C C G G G G A T T G A A A A A T T T G A G A A A G A G A T G G 960
SalmoKCaR 3 T A T G G A C G T C C G G G G A T T G A A A A A T T T G A G A A A G A G A T G G 871

SalmoKCaR 1 A A G A A C G A G A C A T T T G T A T C C A T C T G A G T G A G C T G A T C T C 910
SalmoKCaR 2 A A G A A C G A G A C A T T T G T A T C C A T C T G A G T G A G C T G A T C T C 1000
SalmoKCaR 3 A A G A A C G A G A C A T T T G T A T C C A T C T G A G T G A G C T G A T C T C 911

SalmoKCaR 1 T C A G T A C T T T G A G G A G T G G C A G A T C C A A G G A T T G G T T G A C 950
SalmoKCaR 2 T C A G T A C T T T G A G G A G T G G C A G A T C C A A G G A T T G G T T G G C 1040
SalmoKCaR 3 T C A G T A C T T T G A G G A G T G G C A G A T C C A A G G A T T G G T T G A C 951

SalmoKCaR 1 C G T A T T G A G A A C T C C T C A G C T A A A G T T A T A G T C G T T T T C G 990
SalmoKCaR 2 C G T A T T G A G A A C T C C T C A G C T A A A G T T A T A G T C G T T T T C G 1080
SalmoKCaR 3 C G T A T T G A G A A C T C C T C A G C T A A A G T T A T A G T C G T T T T C G 991

SalmoKCaR 1 C C A G T G G G C C T G A C A T T G A G C C T C T T A T T A A A G A G A T G G T 1030
SalmoKCaR 2 C C A G T G G G C C T G A C A T T G A G C C T C T T A T T A A A G A G A T G G T 1120
SalmoKCaR 3 C C A G T G G G C C T G A C A T T G A G C C T C T T A T T A A A G A G A T G G T 1031

FIG. 15B

SalmoKCaR 1 C A G A C G G A A C A T C A C C G A C C G C A T C T G G T T G G C C A G C G A G 1070
SalmoKCaR 2 C A G A C G G A A C A T C A C C G A C C G C A T C T G G T T G G C C A G C G A G 1160
SalmoKCaR 3 C A G A C G G A A C A T C A C C G A C C G C A T C T G G T T G G C C A G C G A G 1071

SalmoKCaR 1 G C T T G G G C A A C C A C C T C C C T C A T C G C C A A A C C A G A G T A C C 1110
SalmoKCaR 2 G C T T G G G C A A C C A C C T C C C T C A T C G C C A A A C C A G A G T A C C 1200
SalmoKCaR 3 G C T T G G G C A A C C A C C T C C C T C A T C G C C A A A C C A G A G T A C C 1111

SalmoKCaR 1 T T G A T G T T G T A G T T G G G A C C A T T G G C T T T G C T C T C A G A G C 1150
SalmoKCaR 2 T T G A T G T T G T A G T T G G G A C C A T T G G C T T T G C T C T C A G A G C 1240
SalmoKCaR 3 T T G A T G T T G T A G T T G G G A C C A T T G G C T T T G C T C T C A G A G C 1151

SalmoKCaR 1 A G G C G A A A T A C C T G G C T T C A A G G A C T T C T T A C A A G A G G T C 1190
SalmoKCaR 2 A G G C G A A A T A C C T G G C T T C A A G G A C T T C T T A C A A G A G G T C 1280
SalmoKCaR 3 A G G C G A A A T A C C T G G C T T C A A G G A C T T C T T A C A A G A G G T C 1191

SalmoKCaR 1 A C A C C A A A G A A A T C C A G C C A C A A T G A A T T T G T C A G G G A G T 1230
SalmoKCaR 2 A C A C C A A A G A A A T C C A G C C A C A A T G A A T T T G T C A G G G A G T 1320
SalmoKCaR 3 A C A C C A A A G A A A T C C A G C C A C A A T G A A T T T G T C A G G G A G T 1231

SalmoKCaR 1 T T T G G G A G G A G A C T T T T A A C T G C T A T C T G G A A G A C A G C C A 1270
SalmoKCaR 2 T T T G G G A G G A G A C T T T T A A C T G C T A T C T G G A A G A C A G C C A 1360
SalmoKCaR 3 T T T G G G A G G A G A C T T T T A A C T G C T A T C T G G A A G A C A G C C A 1271

SalmoKCaR 1 G A G A C T G A G A G A C A G T G A G A A T G G G A G C A C C A G T T T C A G A 1310
SalmoKCaR 2 G A G A C T G A G A G A C A G T G A G A A T G G G A G C A C C A G T T T C A G A 1400
SalmoKCaR 3 G A G A C T G A G A G A C A G T G A G A A T G G G A G C A C C A G T T T C A G A 1311

SalmoKCaR 1 C C A T T G T G T A C T G G C G A G G A G G A C A T T A T G G G T G C A G A G A 1350
SalmoKCaR 2 C C A T T G T G T A C T G G C G A G G A G G A C A T T A T G G G T G C A G A G A 1440
SalmoKCaR 3 C C A T T G T G T A C T G G C G A G G A G G A C A T T A T G G G T G C A G A G A 1351

SalmoKCaR 1 C C C C A T A T C T G G A T T A C A C T C A T C T T C G T A T T T C C T A T A A 1390
SalmoKCaR 2 C C C C A T A T C T G G A T T A C A C T C A T C T T C G T A T T T C C T A T A A 1480
SalmoKCaR 3 C C C C A T A T C T G G A T T A C A C T C A T C T T C G T A T T T C C T A T A A 1391

SalmoKCaR 1 T G T G T A T G T T G C A G T T C A C T C C A T T G C A C A G G C C C T A C A G 1430
SalmoKCaR 2 T G T G T A T G T T G C A G T T C A C T C C A T T G C A C A G G C C C T A C A G 1520
SalmoKCaR 3 T G T G T A T G T T G C A G T T C A C T C C A T T G C A C A G G C C C T A C A G 1431

SalmoKCaR 1 G A C A T T C T C A C C T G C A T T C C T G G A C G G G G T C T T T T T T C C A 1470
SalmoKCaR 2 G A C A T T C T C A C C T G C A T T C C T G G A C G G G G T C T T T T T T C C A 1560
SalmoKCaR 3 G A C A T T C T C A C C T G C A T T C C T G G A C G G G G T T T T T T T T C C A 1471

SalmoKCaR 1 A C A A C T C A T G T G C A G A T A T A A A G A A A A T A G A A G C A T G G C A 1510
SalmoKCaR 2 A C A A C T C A T G T G C A G A T A T A A A G A A A A T A G A A G C A T G G C A 1600
SalmoKCaR 3 A C A A C T C A T G T G C A G A T A T A A A G A A A A T A G A A G C A T G G C A 1511

SalmoKCaR 1 G G T T C T C A A G C A G C T C A G A C A T T T A A A C T T C T C A A A C A G T 1550
SalmoKCaR 2 G G T T C T C A A G C A G C T C A G A C A T T T A A A C T T C T C A A A C A G T 1640
SalmoKCaR 3 G G T T C T C A A G C A G C T C A G A C A T T T A A A C T T C T C A A A C A G T 1551

SalmoKCaR 1 A T G G G A G A A A A G G T A C A T T T T G A T G A G A A T G C T G A T C C G T 1590
SalmoKCaR 2 A T G G G A G A A A A G G T A C A T T T T G A T G A G A A T G C T G A T C C G T 1680
SalmoKCaR 3 A T G G G A G A A A A G G T A C A T T T T G A T G A G A A T G C T G A T C C G T 1591

FIG. 15C

| | | |
|---|---|---|
| SalmoKCaR 1 | C A G G A A A C T A C A C C A T T A T C A A T T G G C A C C G G T C T C C T G A | 1630 |
| SalmoKCaR 2 | C A G G A A A C T A C A C C A T T A T C A A T T G G C A C C G G T C T C C T G A | 1720 |
| SalmoKCaR 3 | C A G G A A A C T A C A C C A T T A T C A A T T G G C A C C G G T C T C C T G A | 1631 |
| SalmoKCaR 1 | G G A T G G T T C T G T T G T G T T T G A A G A G G T C G G T T T C T A C A A C | 1670 |
| SalmoKCaR 2 | G G A T G G T T C T G T T G T G T T T G A A G A G G T C G G T T T C T A C A A C | 1760 |
| SalmoKCaR 3 | G G A T G G T T C T G T T G T G T T T G A A G A G G T C G G T T T C T A C A A C | 1671 |
| SalmoKCaR 1 | A T G C G A G C T A A G A G A G G A G T A C A A C T T T T C A T T G A T A A C A | 1710 |
| SalmoKCaR 2 | A T G C G A G C T A A G A G A G G A G T A C A A C T T T T C A T T G A T A A C A | 1800 |
| SalmoKCaR 3 | A T G C G A G C T A A G A G A G G A G T A C A A C T T T T C A T T G A T A A C A | 1711 |
| SalmoKCaR 1 | C A A A G A T T C T A T G G A A T G G A T A T A A T A C T G A G G T T C C A T T | 1750 |
| SalmoKCaR 2 | C A A A G A T T C T A T G G A A T G G A T A T A A T A C T G A G G T T C C A T T | 1840 |
| SalmoKCaR 3 | C A A A G A T T C T A T G G A A T G G A T A T A A T A C T G A G G T T C C A T T | 1751 |
| SalmoKCaR 1 | C T C T A A C T G T A G T G A A G A T T G T G A A C C A G G C A C C A G A A A G | 1790 |
| SalmoKCaR 2 | C T C T A A C T G T A G T G A A G A T T G T G A A C C A G G C A C C A G A A A G | 1880 |
| SalmoKCaR 3 | C T C T A A C T G T A G T G A A G A T T G T G A A C C A G G C A C C A G A A A G | 1791 |
| SalmoKCaR 1 | G G G A T C A T A G A A A G C A T G C C A A C G T G T T G C T T T G A A T G T A | 1830 |
| SalmoKCaR 2 | G G G A T C A T A G A A A G C A T G C C A A C G T G T T G C T T T G A A T G T A | 1920 |
| SalmoKCaR 3 | G G G A T C A T A G A A A G C A T G C C A A C G T G T T G C T T T G A A T G T A | 1831 |
| SalmoKCaR 1 | C A G A A T G C T C A G A A G G A G A G T A T A G T G A T C A C A A A G A T G C | 1870 |
| SalmoKCaR 2 | C A G A A T G C T C A G A A G G A G A G T A T A G T G A T C A C A A A G A T G C | 1960 |
| SalmoKCaR 3 | C A G A A T G C T C A G A A G G A G A G T A T A G T G A T C A C A A A G A T G C | 1871 |
| SalmoKCaR 1 | C A G T G T T T G T A C C A A G T G T C C C A A T G A C T C A T G G T C T A A T | 1910 |
| SalmoKCaR 2 | C A G T G T T T G T A C C A A G T G T C C C A A T G A C T C A T G G T C T A A T | 2000 |
| SalmoKCaR 3 | C A G T G T T T G T A C C A A G T G T C C C A A T G A C T C A T G G T C T A A T | 1911 |
| SalmoKCaR 1 | G A G A A C C A C A C A T C T T G T T T C C T G A A G G A G A T A G A G T T T C | 1950 |
| SalmoKCaR 2 | G A G A A C C A C A C A T C T T G T T T C C T G A A G G A G A T A G A G T T T C | 2040 |
| SalmoKCaR 3 | G A G A A C C A C A C A T C T T G T T T C C T G A A G G A G A T A G A G T T T C | 1951 |
| SalmoKCaR 1 | T G T C T T G G A C A G A G C C C T T T G G G A T C G C C T T G G C A T T A T G | 1990 |
| SalmoKCaR 2 | T G T C T T G G A C A G A G C C C T T T G G G A T C G C C T T G G C A T T A T G | 2080 |
| SalmoKCaR 3 | T G T C T T G G A C A G A G C C C T T T G G G A T C G C C T T G G C A T T A T G | 1991 |
| SalmoKCaR 1 | C T C T G T G C T G G G G G T A T T C T T G A C A G C A T T C G T G A T G G G A | 2030 |
| SalmoKCaR 2 | C T C T G T G C T G G G G G T A T T C T T G A C A G C A T T C G T G A T G G G A | 2120 |
| SalmoKCaR 3 | C T C T G T G C T G G G G G T A T T C T T G A C A G C A T T C G T G A T G G G A | 2031 |
| SalmoKCaR 1 | G T G T T T A T C A A A T T T C G C A A C A C C C C A A T T G T T A A G G C C A | 2070 |
| SalmoKCaR 2 | G T G T T T A T C A A A T T T C G C A A C A C C C C A A T T G T T A A G G C C A | 2160 |
| SalmoKCaR 3 | G T G T T T A T C A A A T T T C G C A A C A C C C C A A T T G T T A A G G C C A | 2071 |
| SalmoKCaR 1 | C A A A C A G A G A G C T A T C C T A C C T C C T C C T G T T C T C A C T C A T | 2110 |
| SalmoKCaR 2 | C A A A C A G A G A G C T A T C C T A C C T C C T C C T G T T C T C A C T C A T | 2200 |
| SalmoKCaR 3 | C A A A C A G A G A G C T A T C C T A C C T C C T C C T G T T C T C A C T C A T | 2111 |
| SalmoKCaR 1 | C T G C T G T T T C T C C A G T T C C C T C A T C T T C A T T G G T G A A C C C | 2150 |
| SalmoKCaR 2 | C T G C T G T T T C T C C A G T T C C C T C A T C T T C A T T G G T G A A C C C | 2240 |
| SalmoKCaR 3 | C T G C T G T T T C T C C A G T T C C C T C A T C T T C A T T G G T G A A C C C | 2151 |

FIG. 15D

```
SalmoKCaR 1  C A G G A C T G G A C A T G C C G T C T A C G C C A G C C T G C A T T C G G G A  2190
SalmoKCaR 2  C A G G A C T G G A C A T G C C G T C T A C G C C A G C C T G C A T T C G G G A  2280
SalmoKCaR 3  C A G G A C T G G A C A T G C C G T C T A C G C C A G C C T G C A T T C G G G A  2191

SalmoKCaR 1  T A A G T T T T G T T C T C T G C A T C T C C T G C A T C C T G G T A A A A A C  2230
SalmoKCaR 2  T A A G T T T T G T T C T C T G C A T C T C C T G C A T C C T G G T A A A A A C  2320
SalmoKCaR 3  T A A G T T T T G T T C T C T G C A T C T C C T G C A T C C T G G T A A A A A C  2231

SalmoKCaR 1  T A A C C G A G T A C T T C T A G T G T T C G A A G C C A A G A T C C C C A C C  2270
SalmoKCaR 2  T A A C C G A G T A C T T C T A G T G T T C G A A G C C A A G A T C C C C A C C  2360
SalmoKCaR 3  T A A C C G A G T A C T T C T A G T G T T C G A A G C C A A G A T C C C C A C C  2271

SalmoKCaR 1  A G T C T C C A T C G T A A G T G G T G G G G G C T A A A C T T G C A G T T C C  2310
SalmoKCaR 2  A G T C T C C A T C G T A A G T G G T G G G G G C T A A A C T T G C A G T T C C  2400
SalmoKCaR 3  A G T C T C C A T C G T A A G T G G T G G G G G C T A A A C T T G C A G T T C C  2311

SalmoKCaR 1  T G T T A G T G T T C C T G T T C A C A T T T G T G C A A G T G A T G A T A T G  2350
SalmoKCaR 2  T G T T A G T G T T C C T G T T C A C A T T T G T G C A A G T G A T G A T A T G  2440
SalmoKCaR 3  T G T T A G T G T T C C T G T T C A C A T T T G T G C A A G T G A T G A T A T G  2351

SalmoKCaR 1  T G T G G T C T G G C T T T A C A A T G C T C C T C C G G C G A G C T A C A G G  2390
SalmoKCaR 2  T G T G G T C T G G C T T T A C A A T G C T C C T C C G G C G A G C T A C A G G  2480
SalmoKCaR 3  T G T G G T C T G G C T T T A C A A T G C T C C T C C G G C G A G C T A C A G G  2391

SalmoKCaR 1  A A C C A T G A C A T T G A T G A G A T A A T T T T C A T T A C A T G C A A T G  2430
SalmoKCaR 2  A A C C A T G A C A T T G A T G A G A T A A T T T T C A T T A C A T G C A A T G  2520
SalmoKCaR 3  A A C C A T G A C A T T G A T G A G A T A A T T T T C A T T A C A T G C A A T G  2431

SalmoKCaR 1  A G G G C T C T A T G A T G G C G C T T G G C T T C C T A A T T G G G T A C A C  2470
SalmoKCaR 2  A G G G C T C T A T G A T G G C G C T T G G C T T C C T A A T T G G G T A C A C  2560
SalmoKCaR 3  A G G G C T C T A T G A T G G C G C T T G G C T T C C T A A T T G G G T A C A C  2471

SalmoKCaR 1  A T G C C T G C T G G C A G C C A T A T G C T T C T T C T T T G C A T T T A A A  2510
SalmoKCaR 2  A T G C C T G C T G G C A G C C A T A T G C T T C T T C T T T G C A T T T A A A  2600
SalmoKCaR 3  A T G C C T G C T G G C A G C C A T A T G C T T C T T C T T T G C A T T T A A A  2511

SalmoKCaR 1  T C A C G A A A A C T G C C A G A G A A C T T T A C T G A G G C T A A G T T C A  2550
SalmoKCaR 2  T C A C G A A A A C T G C C A G A G A A C T T T A C T G A G G C T A A G T T C A  2640
SalmoKCaR 3  T C A C G A A A A C T G C C A G A G A A C T T T A C T G A G G C T A A G T T C A  2551

SalmoKCaR 1  T C A C C T T C A G C A T G C T C A T C T T C T T C A T C G T C T G G A T C T C  2590
SalmoKCaR 2  T C A C C T T C A G C A T G C T C A T C T T C T T C A T C G T C T G G A T C T C  2680
SalmoKCaR 3  T C A C C T T C A G C A T G C T C A T C T T C T T C A T C G T C T G G A T C T C  2591

SalmoKCaR 1  T T T C A T C C C T G C C T A C T T C A G C A C T T A C G G A A A G T T T G T G  2630
SalmoKCaR 2  T T T C A T C C C T G C C T A C T T C A G C A C T T A C G G A A A G T T T G T G  2720
SalmoKCaR 3  T T T C A T C C C T G C C T A C T T C A G C A C T T A C G G A A A G T T T G T G  2631

SalmoKCaR 1  T C G G C T G T G G A G G T C A T C G C C A T A C T A G C C T C C A G C T T T G  2670
SalmoKCaR 2  T C G G C T G T G G A G G T C A T C G C C A T A C T A G C C T C C A G C T T T G  2760
SalmoKCaR 3  T C G G C T G T G G A G G T C A T C G C C A T A C T A G C C T C C A G C T T T G  2671

SalmoKCaR 1  G C C T G C T G G C C T G T A T T T T C T T C A A T A A A G T C T A C A T C A T  2710
SalmoKCaR 2  G C C T G C T G G C C T G T A T T T T C T T C A A T A A A G T C T A C A T C A T  2800
SalmoKCaR 3  G C C T G C T G G C C T G T A T T T T C T T C A A T A A A G T C T A C A T C A T  2711
```

FIG. 15E

| | | |
|---|---|---|
| SalmoKCaR 1 | CCTCTTCAAACCGTCCAGGAACACTATAGAGGAGGTTCGC | 2750 |
| SalmoKCaR 2 | CCTCTTCAAACCGTCCAGGAACACTATAGAGGAGGTTCGC | 2840 |
| SalmoKCaR 3 | CC-------------------------------------- | 2713 |
| SalmoKCaR 1 | TGTAGCACTGCGGCCCATTCTTTCAAAGTGGCAGCCAAGG | 2790 |
| SalmoKCaR 2 | TGTAGCACTGCGGCCCATTCTTTCAAAGTGGCAGCCAAGG | 2880 |
| SalmoKCaR 3 | ---------------------------------------- | 2713 |
| SalmoKCaR 1 | CCACTCTGAGACACAGCTCAGCCTCCAGGAAGAGGTCCAG | 2830 |
| SalmoKCaR 2 | CCACTCTGAGACACAGCTCAGCCTCCAGGAAGAGGTCCAG | 2920 |
| SalmoKCaR 3 | ---------------------------------------- | 2713 |
| SalmoKCaR 1 | CAGTGTGGGGGGATCCTGTGCCTCAACTCCCTCCTCATCC | 2870 |
| SalmoKCaR 2 | CAGTGTGGGGGGATCCTGTGCCTCAACTCCCTCCTCATCC | 2960 |
| SalmoKCaR 3 | ---------------------------------------- | 2713 |
| SalmoKCaR 1 | ATCAGCCTCAAGACCAATGACAATGACTCCCCATCAGGTC | 2910 |
| SalmoKCaR 2 | ATCAGCCTCAAGACCAATGACAATGACTCCCCATCAGGTC | 3000 |
| SalmoKCaR 3 | ATCAGCCTCAAGACCAATGACAATGACTCCCCATCAGGTC | 2753 |
| SalmoKCaR 1 | AGCAGAGAATCCATAAGCCAAGAGTAAGCTTTGGAAGTGG | 2950 |
| SalmoKCaR 2 | AGCAGAGAATCCATAAGCCAAGAGTAAGCTTTGGAAGTGG | 3040 |
| SalmoKCaR 3 | AGCAGAGAATCCATAAGCCAAGAGTAAGCTTTGGAAGTGG | 2793 |
| SalmoKCaR 1 | AACAGTTACTCTGTCCTTGAGCTTTGAGGAGTCCAGAAAG | 2990 |
| SalmoKCaR 2 | AACAGTTACTCTGTCCTTGAGCTTTGAGGAGTCCAGAAAG | 3080 |
| SalmoKCaR 3 | AACAGTTACTCTGTCCTTGAGCTTTGAGGAGTCCAGAAAG | 2833 |
| SalmoKCaR 1 | AATTCTATGAAGTAGGGAAGTGTCTTTTGGTGGGCCGAGA | 3030 |
| SalmoKCaR 2 | AATTCTATGAAGTAGGGAAGTGTCTTTTGGTGGGCCGAGA | 3120 |
| SalmoKCaR 3 | AATTCTATGAAGTAGGGAAGTGTCTTTTGGTGGGCCGAGA | 2873 |
| SalmoKCaR 1 | GCCTTGTCAAAACCTGAGTTGGTGTTGCATTCTTTGTTGG | 3070 |
| SalmoKCaR 2 | GCCTTGTCAAAACCTGAGTTGGTGTTGCATTCTTTGTTGG | 3160 |
| SalmoKCaR 3 | GCCTTGTCAAAACCTGAGTTGGTGTTGCATTCTTTGTTGG | 2913 |
| SalmoKCaR 1 | CTGGGTAGTTGGAGCAGAAATTATGATATTAAAAGCTTTG | 3110 |
| SalmoKCaR 2 | CTGGGTAGTTGGAGCAGAAATTATGATATTAAAAGCTTTG | 3200 |
| SalmoKCaR 3 | CTGGGTAGTTGGAGCAGAAATTATGATATTAAAAGCTTTG | 2953 |
| SalmoKCaR 1 | ATGTATTCAGAATGGTGACACAGCATAGGTGGCCAAGATT | 3150 |
| SalmoKCaR 2 | ATGTATTCAGAATGGTGACACAGCATAGGTGGCCAAGATT | 3240 |
| SalmoKCaR 3 | ATGTATTCAGAATGGTGACACAGCATAGGTGGCCAAGATT | 2993 |
| SalmoKCaR 1 | CCATTATATTACAATAATCTGTGTTGTTCATTATGAGGAC | 3190 |
| SalmoKCaR 2 | CCATTATATTACAATAATCTGTGTTGTTCATTATGAGGAC | 3280 |
| SalmoKCaR 3 | CCATTATATTACAATAATCTGTGTTGTTCATTATGAGGAC | 3033 |
| SalmoKCaR 1 | ATTTCAAAATGCTGAAAATCATCAAATACATAATTTACTG | 3230 |
| SalmoKCaR 2 | ATTTCAAAATGCTGAAAATCATCAAATACATAATTTACTG | 3320 |
| SalmoKCaR 3 | ATTTCAAAATGCTGAAAATCATCAAATACATAATTTACTG | 3073 |
| SalmoKCaR 1 | AGTTTTCTTGATAATCTTGAGAATAGAATAGCCTATTCAA | 3270 |
| SalmoKCaR 2 | AGTTTTCTTGATAATCTTGAGAATAGAATAGCCTATTCAA | 3360 |
| SalmoKCaR 3 | AGTTTTCTTGATAATCTTGAGAATAGAATAGCCTATTCAA | 3113 |

FIG. 15F

```
SalmoKCaR 1 G T C A T C G T T G A G C A G A C A T T A A T T A A C A A T G A T G T A A T A C 3310
SalmoKCaR 2 G T C A T C G T T G A G C A G A C A T T A A T T A A C A A T G A T G T A A T A C 3400
SalmoKCaR 3 G T C A T C G T T G A G C A G A C A T T A A T T A A C A A T G A T G T A A T A C 3153

SalmoKCaR 1 T T T C C A T A C C T A T T T T C T T T A A C A A T A G A T T C A C A T T G T T 3350
SalmoKCaR 2 T T T C C A T A C C T A T T T T C T T T A A C A A T A G A T T C A C A T T G T T 3440
SalmoKCaR 3 T T T C C A T A C C T A T T T T C T T T A A C A A T A G A T T C A C A T T G T T 3193

SalmoKCaR 1 A A A G T T C A A C T A T G A C C T G T A A A A T A C A T G A G G T A T A A C A 3390
SalmoKCaR 2 A A A G T T C A A C T A T G A C C T G T A A A A T A C A T G A G G T A T A A C A 3480
SalmoKCaR 3 A A A G T T C A A C T A T G A C C T G T A A A A T A C A T G A G G T A T A A C A 3233

SalmoKCaR 1 G G A G A C A A T A A A A C T A T G C A T A T C C T A G C T T C T G G G C C T G 3430
SalmoKCaR 2 G G A G A C A A T A A A A C T A T G C A T A T C C T A G C T T C T G G G C C T G 3520
SalmoKCaR 3 G G A G A C A A T A A A A C T A T G C A T A T C C T A G C T T C T G G G C C T G 3273

SalmoKCaR 1 A G T A G C A G G C A G T T T A C T C T G G G C A C G C T T T T C A T C C A A A 3470
SalmoKCaR 2 A G T A G C A G G C A G T T T A C T C T G G G C A C G C T T T T C A T C C A A A 3560
SalmoKCaR 3 A G T A G C A G G C A G T T T A C T C T G G G C A C G C T T T T C A T C C A A A 3313

SalmoKCaR 1 C T T C C G A A T G C T G C C C C C A A T C C T A G T G A G G T T A A A G G C C 3510
SalmoKCaR 2 C T T C C G A A T G C T G C C C C C A A T C C T A G T G A G G T T A A A G G C C 3600
SalmoKCaR 3 C T T C C G A A T G C T G C C C C C A A T C C T A G T G A G G T T A A A G G C C 3353

SalmoKCaR 1 C A G T G C A G T C A T A T C T T T T C T C T A G G C A C G C T T T T C A T C C 3550
SalmoKCaR 2 C A G T G C A G T C A T A T C T T T T C T C T A G G C A C G C T T T T C A T C C 3640
SalmoKCaR 3 C A G T G C A G T C A T A T C T T T T C T C T A G G C A C G C T T T T C A T C C 3393

SalmoKCaR 1 A A A C T T C C G A A T G C G G C T A T A T C A G T C T C T T T C C T A C T G T 3590
SalmoKCaR 2 A A A C T T C C G A A T G C G G C T A T A T C A G T C T C T T T C C T A C T G T 3680
SalmoKCaR 3 A A A C T T C C G A A T G C G G C T A T A T C A G T C T C T T T C C T A C T G T 3433

SalmoKCaR 1 C T T T T T C A T T A G G C C A G T G T T T A A C A A C C C T G G T C C T T A A 3630
SalmoKCaR 2 C T T T T T C A T T A G G C C A G T G T T T A A C A A C C C T G G T C C T T A A 3720
SalmoKCaR 3 C T T T T T C A T T A G G C C A G T G T T T A A C A A C C C T G G T C C T T G A 3473

SalmoKCaR 1 G T A C A C A C A A C A G A G C A C A T T T T T G T T G T G G C C C T G G A C A 3670
SalmoKCaR 2 G T A C A C A C A A C A G A G C A C A T T T T T G T T G T A G C C C T G G A C A 3760
SalmoKCaR 3 G T A C A C A C A A C A G G G C A C A T T T T T G T T G T A G C C C T G G A C A 3513

SalmoKCaR 1 A T C A C T C C T C A C T C A G C T C A T T G A G G G C C T G A T G A T T A G T 3710
SalmoKCaR 2 A T C A C T C C T C A C T C A G C T C A T T G A G G G C C T G A T G A T T A G T 3800
SalmoKCaR 3 A T C A C T C C T C A C T C A G C T C A T T G A G G G C C T G A T G A T T A G T 3553

SalmoKCaR 1 T G A C A A G T T G A G T C G G G T G T G C T T G T C C G G G G T T G C A A T A 3750
SalmoKCaR 2 T G A C A A G T T G A G T C G G G T G T G C T T G T C C A G G G T T A C G A T A 3840
SalmoKCaR 3 T G A C A A G T T G G G T C A G G T G T G C T T G T C C A G G G T T A C A A T A 3593

SalmoKCaR 1 C A G A T G T G T A C T G T T G G G G G T A C T C G A G G A C C A G G A T T G G 3790
SalmoKCaR 2 C A G A T G T G T A C T G T T G G G G G T G C T C G A G G A C C A G G A T T G G 3880
SalmoKCaR 3 C A G A T G T G T G C T G T T G G G G G T A C T C G A G G A C C A G G A T T G G 3633

SalmoKCaR 1 G A A A C A T T A C A T T A G G A C T A C T G T A G G T T C T T C A A T A T G G 3830
SalmoKCaR 2 G A A A C A T T A C A T T A G G A C T A C T G T A G G T T C T T C A A T A T G G 3920
SalmoKCaR 3 G A A A C A T T A C A T T A G G A C T A C T G T A G G T T C T T C A A T A T G G 3673
```

FIG. 15G

```
SalmoKCaR 1 T G T C A T A C G G T C A T A T G G T G T C A T A T G G T G T C T G G T T G T T 3870
SalmoKCaR 2 T G T C A T A C G G T C A T A T G G T G T C A T A T G G T G T C T G G T T G T T 3960
SalmoKCaR 3 T G T C A T A C G G T C A T A T G G T G T C A T A T G G T G T C T G G T T G T T 3713

SalmoKCaR 1 T T C T G C A T A T G T G T A T T T C A C C A A G T T A C T G C A C A T G T T A 3910
SalmoKCaR 2 T T C T G C A T A T G T G T A T T T C A C C A A G T T A C T G C A C A T G T T A 4000
SalmoKCaR 3 T T C T G C A T A T G T G T A T T T C A C C A A G T T A C T G C A C A T G T T A 3753

SalmoKCaR 1 G A C C T A T A C A C T G G A A T A A A C A T T T T T T T T C                   3941
SalmoKCaR 2 G A C C T A T A C A C T G G A A T A A A C A T T T T T T T T C                   4031
SalmoKCaR 3 G A C C T A T A C A C T G G A A T A A A C A T T T T T T T T C A C A A T G C A T 3793

SalmoKCaR 1                                                                             3941
SalmoKCaR 2                                                                             4031
SalmoKCaR 3 C C A A T G A C A A T A A A A T C A C C A T A T G C C A A T G                   3824
```

FIG. 15H

```
HuPCaR         M A F Y S C C W V L L A L T W H - - - - T S A Y S P S Q P A Q K K G D I I L G G 36
SKCaR          M A Q L H C Q L L F L G F T L L Q S Y N V S G Y G P N Q R A Q K K G D I I L G G 40
SalmoKCaR 1    M R F Y L Y Y L V L L G F S S V - - - - I S T Y G P H Q R A Q K T G D I L L G G 36
SalmoKCaR 2    M R F Y L Y Y L V L L G F S S V - - - - I S T Y G P H Q R A Q K T G D I L L G G 36
SalmoKCaR 3    M R F Y L Y Y L V L L G F S S V - - - - I S T Y G P H Q R A Q K T G D I L L G G 36

HuPCaR         L F P I H F G V A A K D Q D L K S R P E S V E C I R Y N F R G F R W L Q A M I F 76
SKCaR          L F P I H F G V A A K D Q D L K S R P E A T K C I R Y N F R G F R W L Q A M I F 80
SalmoKCaR 1    L F P M H F G V T S K D Q D L A A R P E S T E C V R Y N F R G F R W L Q A M I F 76
SalmoKCaR 2    L F P M H F G V T S K D Q D L A A R P E S T E C V R Y N F R G F R W L Q A M I F 76
SalmoKCaR 3    L F P M H F G V T S K D Q D L A A R P E S T E C V R Y N F R G F R W L Q A M I F 76

HuPCaR         A I E E I N S S P A L L P N L T L G Y R I F D T C N T V S K A L E A T L S F V A 116
SKCaR          A I E E I N N S M T F L P N I T L G Y R I F D T C N T V S K A L E A T L S F V A 120
SalmoKCaR 1    A I E E I N N S S T L L P N I T L G Y R I F D T C N T V S K A L E A T L S F V A 116
SalmoKCaR 2    A I E E I N N S S T L L P N I T L G Y R I F D T C N T V S K A L E A T L S F V A 116
SalmoKCaR 3    A I E E I N N S S T L L P N I T L G Y R I F D T C N T V S K A L E A T L S F V A 116

HuPCaR         Q N K I D S L N L D E F C N C S E H I P S T I A V V G A T G S G V S T A V A N L 156
SKCaR          Q N K I D S L N L D E F C N C S D H I P S T I A V V G A T G S G I S T A V A N L 160
SalmoKCaR 1    Q N K I D S L N L D E F C N C T D H I P S T I A V V G A S G S A V S T A V A N L 156
SalmoKCaR 2    Q N K I D S L N L D E F C N C T D H I P S T I A V V G A S G S A V S T A V A N L 156
SalmoKCaR 3    Q N K I D S L N L D E F C N C T D H I P S T I A V V G A S G S A V S T A V A N L 156

HuPCaR         L G L F Y I P Q V S Y A S S S R L L S N K N Q F K S F L R T I P N D E H C A T A 196
SKCaR          L G L F Y I P Q V S Y A S S S R L L S N K N E Y K A F L R T I P N D E Q Q A T A 200
SalmoKCaR 1    L G L F Y I P Q I S Y A S S S R L L S N K N Q F K S F M R T I P T D E H Q A T A 196
SalmoKCaR 2    L G L F Y I P Q I S Y A S S S R L L S N K N Q F K S F M R T I P T D E H Q A T A 196
SalmoKCaR 3    L G L F Y I P Q I S Y A S S S R L L S N K N Q F K S F M R T I P T D E H Q A T A 196

HuPCaR         M A D I I E Y F R W N W V G T I A A D D D Y G R P G I E K F R E E A E E R D I C 236
SKCaR          M A E I I E H F Q W N W V G T L A A D D D Y G R P G I D K F R E E A V K R D I C 240
SalmoKCaR 1    M A D I I D Y F Q W N W V I A V A S D D E Y G R P G I E K F E K E M E E R D I C 236
SalmoKCaR 2    M A D I I D Y F Q W N W V I A V A S D D E Y G R P G I E K F E K E M E E R D I C 236
SalmoKCaR 3    M A D I I D Y F Q W N W V I A V A S D D E Y G R P G I E K F E K E M E E R D I C 236

HuPCaR         I D F S E L I S Q Y S D E E E I Q M V V E V I Q N S T A K V I V V F S S G P D L 276
SKCaR          I D F S E M I S Q Y Y T Q K Q L E F I A D V I Q N S S A K V I V V F S N G P D L 280
SalmoKCaR 1    I H L S E L I S Q Y F E E W Q I Q G L V D R I E N S S A K V I V V F A S G P D I 276
SalmoKCaR 2    I H L S E L I S Q Y F E E W Q I Q G L V G R I E N S S A K V I V V F A S G P D I 276
SalmoKCaR 3    I H L S E L I S Q Y F E E W Q I Q G L V D R I E N S S A K V I V V F A S G P D I 276

HuPCaR         E P L I K E I V P R N I T G K I W L A S E A W A S S S L I A M P Q Y F H V V G G 316
SKCaR          E P L I Q E I V R R N I T D R I W L A S E A W A S S S L I A K P E Y F H V V G G 320
SalmoKCaR 1    E P L I K E M V R R N I T D R I W L A S E A W A T T S L I A K P E Y L D V V V G 316
SalmoKCaR 2    E P L I K E M V R R N I T D R I W L A S E A W A T T S L I A K P E Y L D V V V G 316
SalmoKCaR 3    E P L I K E M V R R N I T D R I W L A S E A W A T T S L I A K P E Y L D V V V G 316

HuPCaR         T I G F A L K A G Q I P G F R E F L K K V H P P K S V N N G F A K E F W E E T F 356
SKCaR          T I G F A L R A G R I P G F N K F L K E V H P S R S S D N G F V K E F W E E T F 360
SalmoKCaR 1    T I G F A L R A G E I P G F K D F L Q E V T P K K S S H N E F V R E F W E E T F 356
SalmoKCaR 2    T I G F A L R A G E I P G F K D F L Q E V T P K K S S H N E F V R E F W E E T F 356
SalmoKCaR 3    T I G F A L R A G E I P G F K D F L Q E V T P K K S S H N E F V R E F W E E T F 356
```

FIG. 16A

```
HuPCaR       M C H L Q E G A - - - - K G P L P V D T F L A G H E E S G D R F S N S S T A F P 392
SKCaR        N C Y F T E K T L T Q L K N S K V P S H G P A A Q G D G S K A G N S R R T A L R 400
SalmoKCaR 1  N C Y L E D S Q - - - - R L R D S - - - - - - - - - - - - - - - E N G S T S F R 377
SalmoKCaR 2  N C Y L E D S Q - - - - R L R D S - - - - - - - - - - - - - - - E N G S T S F R 377
SalmoKCaR 3  N C Y L E D S Q - - - - R L R D S - - - - - - - - - - - - - - - E N G S T S F R 377

HuPCaR       P L C T G D E N I S S V E T P Y I D Y T N L R I S Y N V Y L A V Y S I A N A L Q 432
SKCaR        H P C T G E E N I T S V E T P Y L D Y T H L R I S Y N V Y V A V Y S I A H A L Q 440
SalmoKCaR 1  P L C T G E E D I M G A E T P Y L D Y T H L R I S Y N V Y V A V H S I A Q A L Q 417
SalmoKCaR 2  P L C T G E E D I M G A E T P Y L D Y T H L R I S Y N V Y V A V H S I A Q A L Q 417
SalmoKCaR 3  P L C T G E E D I M G A E T P Y L D Y T H L R I S Y N V Y V A V H S I A Q A L Q 417

HuPCaR       D I Y T C L P G R G L F T N G S C A D I K K V E A W Q V L K H L R N L N F T N N 472
SKCaR        D I H S C K P G T G I F A N G S C A D I K K V E A W Q V L N H L L H L K F T N S 480
SalmoKCaR 1  D I L T C I P G R G L F S N N S C A D I K K I E A W Q V L K Q L R H L N F S N S 457
SalmoKCaR 2  D I L T C I P G R G L F S N N S C A D I K K I E A W Q V L K Q L R H L N F S N S 457
SalmoKCaR 3  D I L T C I P G R G F F S N N S C A D I K K I E A W Q V L K Q L R H L N F S N S 457

HuPCaR       M G E Q V T F D E C G D L V G N Y S I I N W H L S P E D G S I V F K E V G Y Y N 512
SKCaR        M G E Q V D F D D Q G D L K G N Y T I I N W Q L S A E D E S V L F H E V G N Y N 520
SalmoKCaR 1  M G E K V H F D E N A D P S G N Y T I I N W H R S P E D G S V V F E E V G F Y N 497
SalmoKCaR 2  M G E K V H F D E N A D P S G N Y T I I N W H R S P E D G S V V F E E V G F Y N 497
SalmoKCaR 3  M G E K V H F D E N A D P S G N Y T I I N W H R S P E D G S V V F E E V G F Y N 497

HuPCaR       V Y A K K G E R L F I N E E K I L W S G F S R E V P F S N C S R D C L A G T R K 552
SKCaR        A Y A K P S D R L N I N E K K I L W S G F S K V V P F S N C S R D C V P G T R K 560
SalmoKCaR 1  M R A K R G V Q L F I D N T K I L W N G Y N T E V P F S N C S E D C E P G T R K 537
SalmoKCaR 2  M R A K R G V Q L F I D N T K I L W N G Y N T E V P F S N C S E D C E P G T R K 537
SalmoKCaR 3  M R A K R G V Q L F I D N T K I L W N G Y N T E V P F S N C S E D C E P G T R K 537

HuPCaR       G I I E G E P T C C F E C V E C P D G E Y S D E T D A S A C N K C P D D F W S N 592
SKCaR        G I I E G E P T C C F E C M A C A E G E F S D E N D A S A C T K C P N D F W S N 600
SalmoKCaR 1  G I I E S M P T C C F E C T E C S E G E Y S D H K D A S V C T K C P N D S W S N 577
SalmoKCaR 2  G I I E S M P T C C F E C T E C S E G E Y S D H K D A S V C T K C P N D S W S N 577
SalmoKCaR 3  G I I E S M P T C C F E C T E C S E G E Y S D H K D A S V C T K C P N D S W S N 577

HuPCaR       E N H T S C I A K E I E F L S W T E P F G I A L T L F A V L G I S L T A F V L G 632
SKCaR        E N H T S C I A K E I E Y L S W T E P F G I A L T I F A V L G I L I T S F V L G 640
SalmoKCaR 1  E N H T S C F L K E I E F L S W T E P F G I A L A L C S V L G V F L T A F V M G 617
SalmoKCaR 2  E N H T S C F L K E I E F L S W T E P F G I A L A L C S V L G V F L T A F V M G 617
SalmoKCaR 3  E N H T S C F L K E I E F L S W T E P F G I A L A L C S V L G V F L T A F V M G 617

HuPCaR       V F I K F R N T P I V K A T N R E L S Y L L L F S L L C C F S S S L F F I G E P 672
SKCaR        V F I K F R N T P I V K A T N R E L S Y L L L F S L I C C F S S S L I F I G E P 680
SalmoKCaR 1  V F I K F R N T P I V K A T N R E L S Y L L L F S L I C C F S S S L I F I G E P 657
SalmoKCaR 2  V F I K F R N T P I V K A T N R E L S Y L L L F S L I C C F S S S L I F I G E P 657
SalmoKCaR 3  V F I K F R N T P I V K A T N R E L S Y L L L F S L I C C F S S S L I F I G E P 657

HuPCaR       Q D W T C R L R Q P A F G I S F V L C I S C I L V K T N R V L L V F E A K I P T 712
SKCaR        R D W T C R L R Q P A F G I S F V L C I S C I L V K T N R V L L V F E A K I P T 720
SalmoKCaR 1  Q D W T C R L R Q P A F G I S F V L C I S C I L V K T N R V L L V F E A K I P T 697
SalmoKCaR 2  Q D W T C R L R Q P A F G I S F V L C I S C I L V K T N R V L L V F E A K I P T 697
SalmoKCaR 3  Q D W T C R L R Q P A F G I S F V L C I S C I L V K T N R V L L V F E A K I P T 697
```

FIG. 16B

```
HuPCaR       S F M F K W W G L N L Q F L L V F L C T F N Q I V I C V I W L Y T A P P S S Y R  752
SKCaR        S L H R K W V G L N L Q F L L V F L C I L V Q I V T C I I W L Y T A P P S S Y R  760
SalmoKCaR 1  S L H R K W W G L N L Q F L L V F L F T F V Q V M I C V V W L Y N A P P A S Y R  737
SalmoKCaR 2  S L H R K W W G L N L Q F L L V F L F T F V Q V M I C V V W L Y N A P P A S Y R  737
SalmoKCaR 3  S L H R K W W G L N L Q F L L V F L F T F V Q V M I C V V W L Y N A P P A S Y R  737

HuPCaR       N Q E L E D E I I F I T C N E G S L M A L G F L I G Y T C L L A A I C F F F A F  792
SKCaR        N H E L E D E V I F I T C D E G S L M A L G F L I G Y T C L L A A I C F F F A F  800
SalmoKCaR 1  N H D I - D E I I F I T C N E G S M M A L G F L I G Y T C L L A A I C F F F A F  776
SalmoKCaR 2  N H D I - D E I I F I T C N E G S M M A L G F L I G Y T C L L A A I C F F F A F  776
SalmoKCaR 3  N H D I - D E I I F I T C N E G S M M A L G F L I G Y T C L L A A I C F F F A F  776

HuPCaR       K S R K L P E N F N E A K F I T F S M L I F F I V W I S F I P A Y A S T Y G K F  832
SKCaR        K S R K L P E N F N E A K F I T F S M L I F F I V W I S F I P A Y V S T Y G K F  840
SalmoKCaR 1  K S R K L P E N F T E A K F I T F S M L I F F I V W I S F I P A Y F S T Y G K F  816
SalmoKCaR 2  K S R K L P E N F T E A K F I T F S M L I F F I V W I S F I P A Y F S T Y G K F  816
SalmoKCaR 3  K S R K L P E N F T E A K F I T F S M L I F F I V W I S F I P A Y F S T Y G K F  816

HuPCaR       V S A V E V I A I L A A S F G L L A C I F F N K I Y I I L F K P S R N T I E E V  872
SKCaR        V S A V E V I A I L A S S F G L L G C I Y F N K C Y I I L F K P C R N T I E E V  880
SalmoKCaR 1  V S A V E V I A I L A S S F G L L A C I F F N K V Y I I L F K P S R N T I E E V  856
SalmoKCaR 2  V S A V E V I A I L A S S F G L L A C I F F N K V Y I I L F K P S R N T I E E V  856
SalmoKCaR 3  V S A V E V I A I L A S S F G L L A C I F F N K V Y I I - - - - - - - - - - - -  844

HuPCaR       R C S T A A N A F K V A A R A T L R R S N V S R K R S S S L G G S T G S T P S S  912
SKCaR        R C S T A A H A F K V A A R A T L R R S A A S R K R S S S L C G S T I S S P A S  920
SalmoKCaR 1  R C S T A A H S F K V A A K A T L R H S S A S R K R S S S V G G S C A S T P S S  896
SalmoKCaR 2  R C S T A A H S F K V A A K A T L R H S S A S R K R S S S V G G S C A S T P S S  896
SalmoKCaR 3  - - - - - - - - - - - - - - - - - - - - - - - - - - - - - - - - - - - - - - - -  844

HuPCaR       S I S S K S N S E D P F P R P E R Q K Q Q Q P L A L T Q Q E Q Q Q Q P L T L P Q  952
SKCaR        S T C G P G L T M E - - - - - - - - - - - - - - - - - - - - - - - - - - - - - -  930
SalmoKCaR 1  S I S L K T N D N D S P S G Q Q R I H K P R - - - - - - - - - - - - - - - - - -  918
SalmoKCaR 2  S I S L K T N D N D S P S G Q Q R I H K P R - - - - - - - - - - - - - - - - - -  918
SalmoKCaR 3  - - - - - - - - - - - - - - - - - - - - - - - - - - - - - - - - - - - - - - - -  844

HuPCaR       Q Q R S Q Q Q P R C K Q K V I F G S G T V T F S L S F D E P Q K N A M A N R N S  992
SKCaR        - - - - - M Q R C S T Q K V S F G S G T V T L S L S F E E T G R Y A T L S R T A  965
SalmoKCaR 1  - - - - - - - - - - - - - - - - - - - - - - - - - - - - - - - - - - - - - - - -  918
SalmoKCaR 2  - - - - - - - - - - - - - - - - - - - - - - - - - - - - - - - - - - - - - - - -  918
SalmoKCaR 3  - - - - - - - - - - - - - - - - - - - - - - - - - - - - - - - - - - - - - - - -  844

HuPCaR       T N Q N S L E A Q K S S D T L T A N Q P L L P L Q C G E T D L D L T V Q E T G L  1032
SKCaR        R S R N S A D G R S G D D L P S R H H D Q G P P Q K C E P Q - - - - - - - - - -  995
SalmoKCaR 1  - - - - - - - - - - - - - - - - - - - - - - - - - - - - - - - - - - - - - - - -  918
SalmoKCaR 2  - - - - - - - - - - - - - - - - - - - - - - - - - - - - - - - - - - - - - - - -  918
SalmoKCaR 3  - - - - - - - - - - - - - - - - - - - - - - - - - - - - - - - - - - - - - - - -  844

HuPCaR       Q G P V G G D Q R P E V E D P E E L S P A L V V S S S Q S F V I S G G G S T V T  1072
SKCaR        - - - - - - - - - - - - - - P A N D A R Y K A A P T K G T L E S P G G S K E R P  1021
SalmoKCaR 1  - - - - - - - - - - - - - - - - - - - - - - V S F G S G T V T L S L S F E E S R  936
SalmoKCaR 2  - - - - - - - - - - - - - - - - - - - - - - V S F G S G T V T L S L S F E E S R  936
SalmoKCaR 3  - - - - - - - - - - - - - - - - - - - - - - - - - - - - - - - - - - - - - - - -  844
```

FIG. 16C

| | | |
|---|---|---|
| HuPCaR | E N V V N S | 1078 |
| SKCaR | T T M E E T | 1027 |
| SalmoKCaR 1 | K N S M K | 941 |
| SalmoKCaR 2 | K N S M K | 941 |
| SalmoKCaR 3 | H Q P Q D Q | 850 |

FIG. 16D

Saltwater – Panels A, C, E
Top Row
Well 1 Ladder
2 Gill
3 Nasal Lamellae
4 Urinary Bladder
5 Kidney
6 Stomach
7 Pyloric Caeca
8 Prox. Intestine
9 Dist. Intestine
10 Brain
11 Pituitary
12 Olfactory Bulb
13 Liver
14 Muscle
Bottom Row
Well 1 Ladder
2 Water
3
4
5
6
7 SalmoKCaR #1
8
9 SalmoKCaR #2
10
11
12 SalmoKCaR #3
13
14

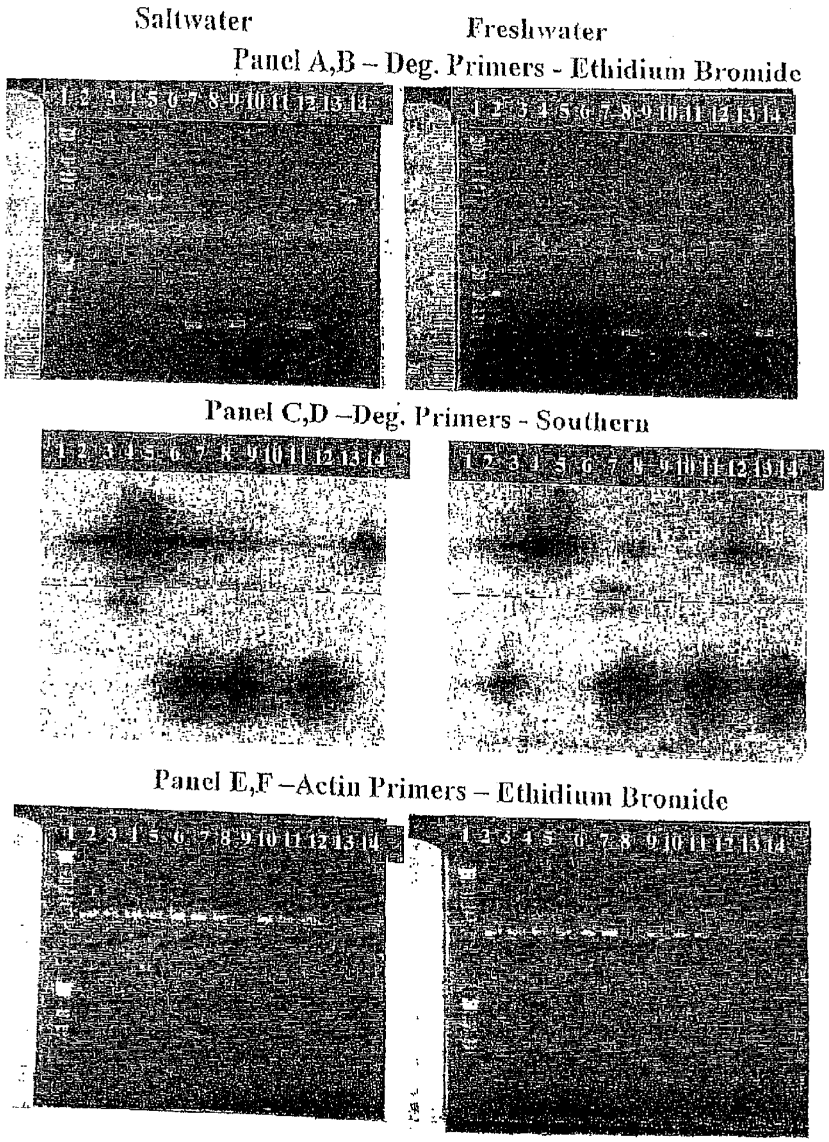

Freshwater – Panels B, D, F
Top Row
Well 1 Ladder
2 Gill
3 Nasal Lamellae
4 Urinary Bladder
5 Kidney
6 Stomach
7 Pyloric Caeca
8 Prox. Intestine
9 Dist. Intestine
10 Brain
11 Pituitary
12 Olfactory Bulb
13 Liver
14 Muscle
Bottom Row
Well 1 Ladder
2 Water
3 Ovary
4
5
6
7
8 SalmoKCaR #1
9
10
11 SalmoKCaR #2
12
13
14 SalmoKCaR #3

FIG. 17A-F

Saltwater Freshwater

Panels A, B – SalmoKCaR #3 Primers - Ethidium Bromide

Panels C, D – SalmoKCaR #3 Primers - Southern

Panels E,F – Actin Primers – Ethidium Bromide

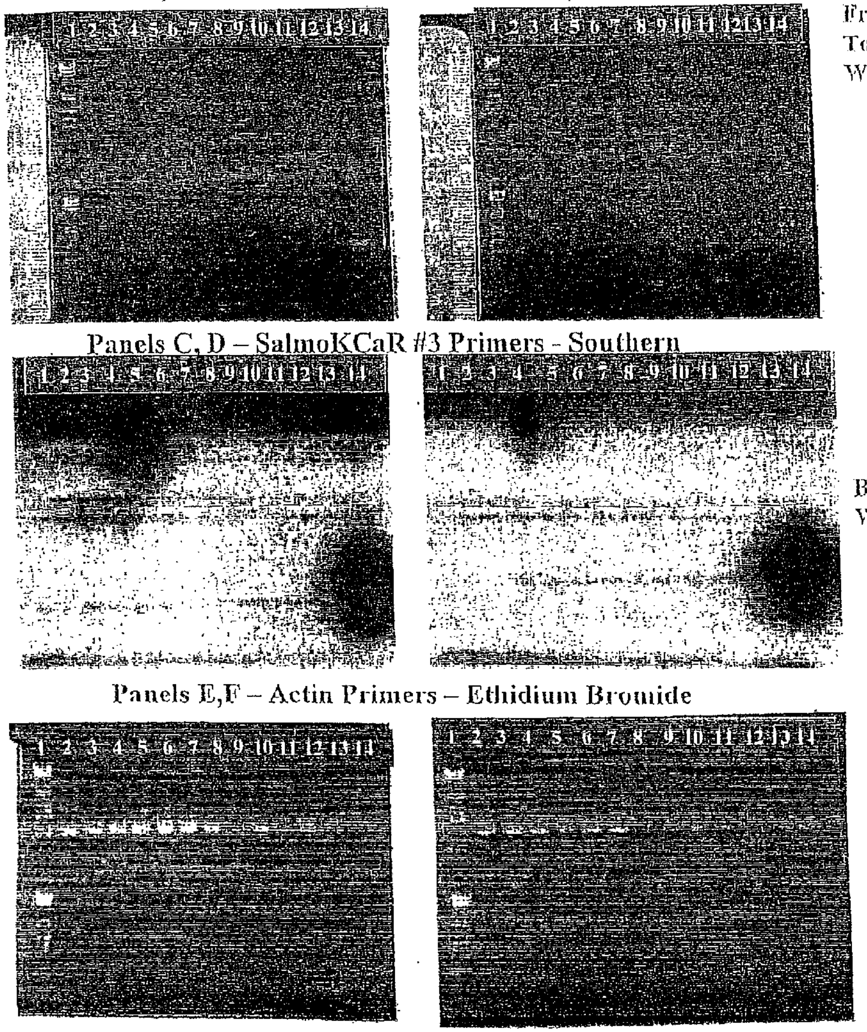

Saltwater-Panels A, C, E
Top Row
Well 1 Ladder
2 Gill
3 Nasal Lamellae
4 Urinary Bladder
5 Kidney
6 Stomach
7 Pyloric Caeca
8 Prox. Intestine
9 Dist. Intestine
10 Brain
11 Pituitary
12 Olfactory Bulb
13 Liver
14 Muscle
Bottom Row
Well 1 Ladder
2 Water
3
4
5
6
7
8 SalmoKCaR #1
9
10
11 SalmoKCaR #2
12
13
14 SalmoKCaR #3

Freshwater- Panels B, D, F
Top Row
Well 1 Ladder
2 Gill
3 Nasal Lamellae
4 Urinary Bladder
5 Kidney
6 Stomach
7 Pyloric Caeca
8 Prox. Intestine
9 Dist. Intestine
10 Brain
11 Pituitary
12 Olfactory Bulb
13 Liver
14 Muscle
Bottom Row
Well 1 Ladder
2 Water
3 Ovary
4
5
6
7
8 SalmoKCaR #1
9
10
11 SalmoKCaR #2
12
13
14 SalmoKCaR #3

FIG. 20A-F

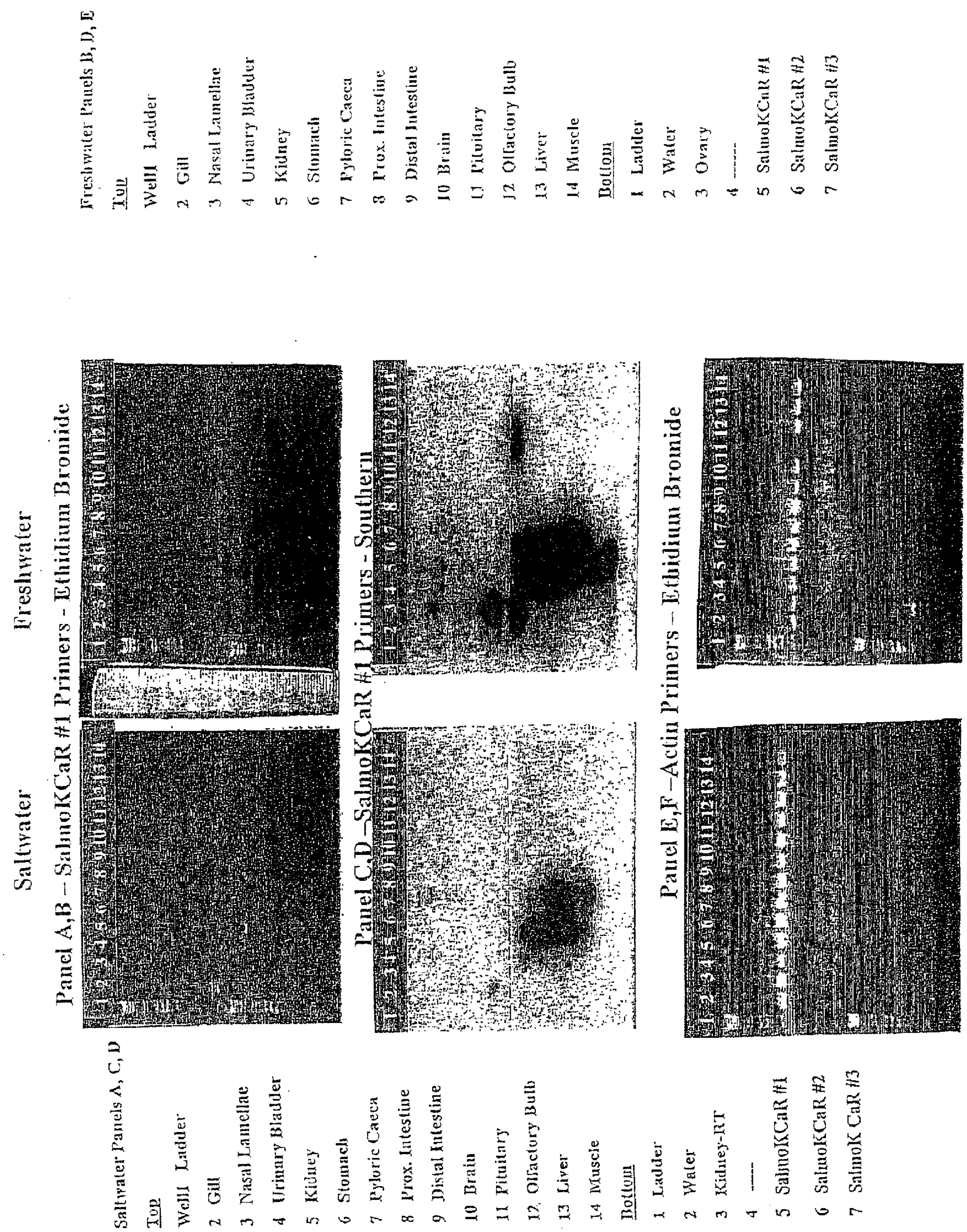
FIG. 21A-F

Saltwater Freshwater

Panel A,B – SalmoKCaR #2 Primers - Ethidium Bromide

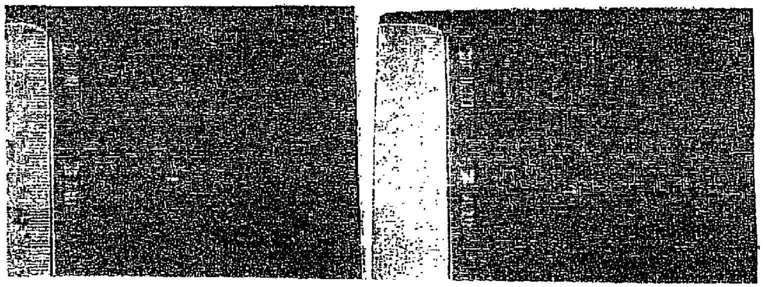

Panel C,D –SalmoKCaR #1 Primers - Southern

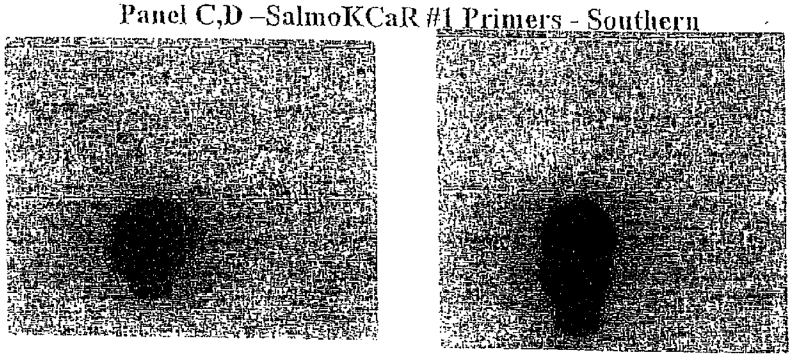

Panel E,F –Actin Primers - Ethidium Bromide

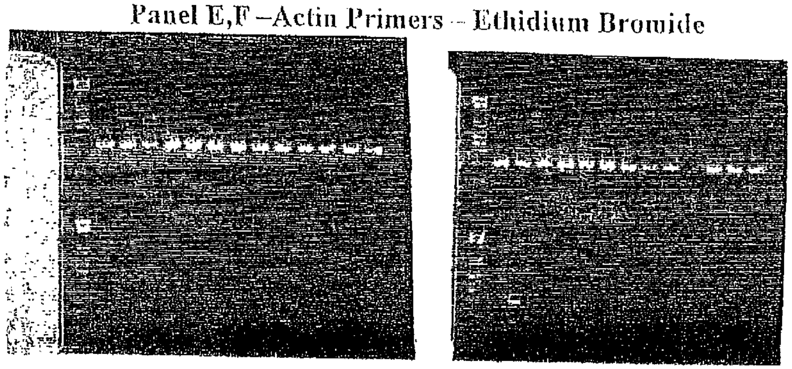

Saltwater Panels A, C, D

Top

Well1 Ladder

2 Gill

3 Nasal Lamellae

4 Urinary Bladder

5 Kidney

6 Stomach

7 Pyloric Caeca

8 Prox. Intestine

9 Distal Intestine

10 Brain

11 Pituitary

12 Olfactory Bulb

13 Liver

14 Muscle

Bottom

1 Ladder

2 Water

3 Kidney-RT

4 -----

5 SalmoKCaR #1

6 SalmoKCaR #2

7 SalmoKCaR #3

Freshwater Panels B, D, E

Top

Well1 Ladder

2 Gill

3 Nasal Lamellae

4 Urinary Bladder

5 Kidney

6 Stomach

7 Pyloric Caeca

8 Prox. Intestine

9 Distal Intestine

10 Brain

11 Pituitary

12 Olfactory Bulb

13 Liver

14 Muscle

Bottom

1 Ladder

2 Water

3 Ovary

4 -----

5 SalmoKCaR #1

6 SalmoKCaR #2

7 SalmoKCaR #3

FIG. 22A-F

PVCR Expression in Atlantic Salmon Tissues

EtBr 1 2 3 4 5 6 7 8 9 10

SB 1 2 3 4 5 6 7 8 9 10

Key:
Atlantic Salmon
1. Gill
2. Nasal Lamellae
3. Urinary Bladder
4. Kidney
5. Intestine
6. Stomach
7. Liver
8. Brain
9. Water Blank
10. Positive Control FIG. 35: PVCR Localization in Atlantic Salmon Olfactory Bulb Nerve and Lamellae
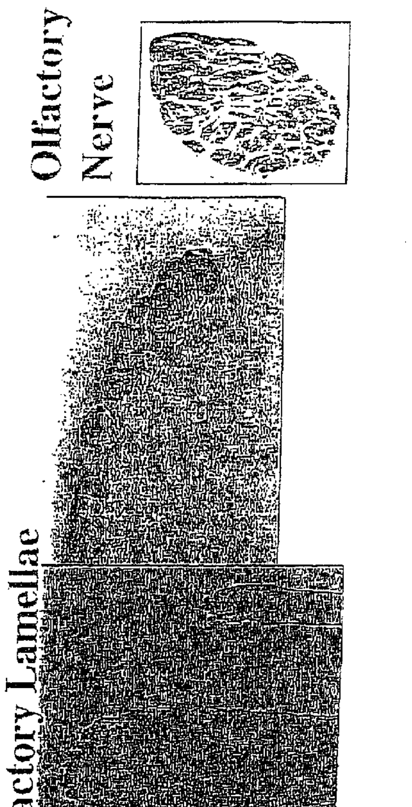
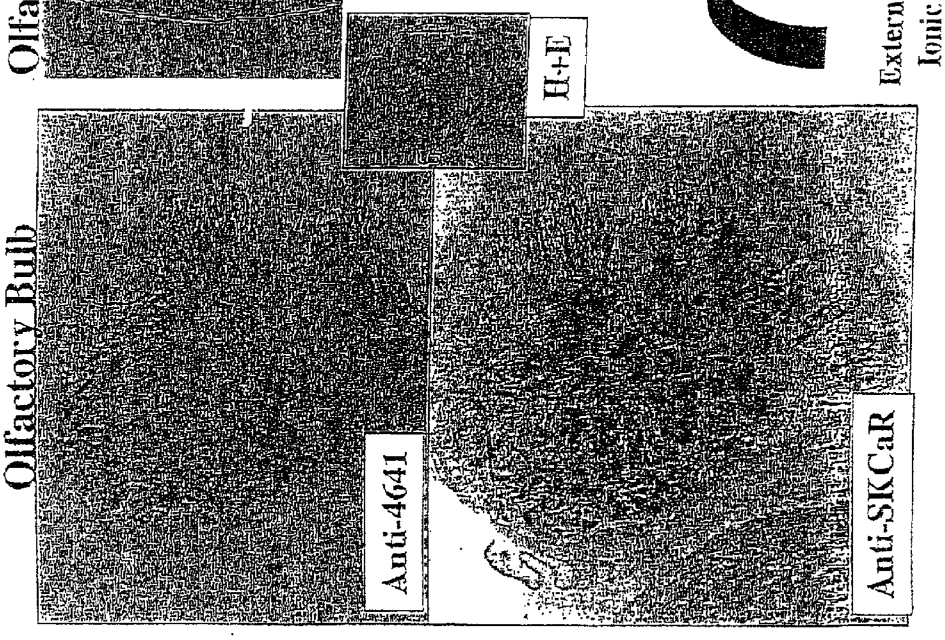
FIG. 36: Schematic of PVCR Function
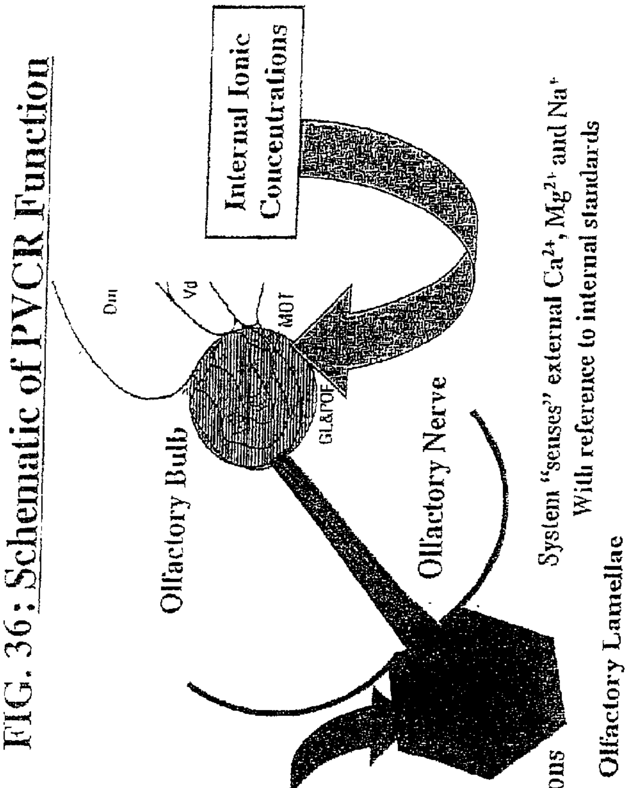

FIG. 37A: PVCR Protein is Expressed Days After Hatching of Atlantic Salmon
Developing Nasal Lamellae
In Atlantic Salmon Larvae
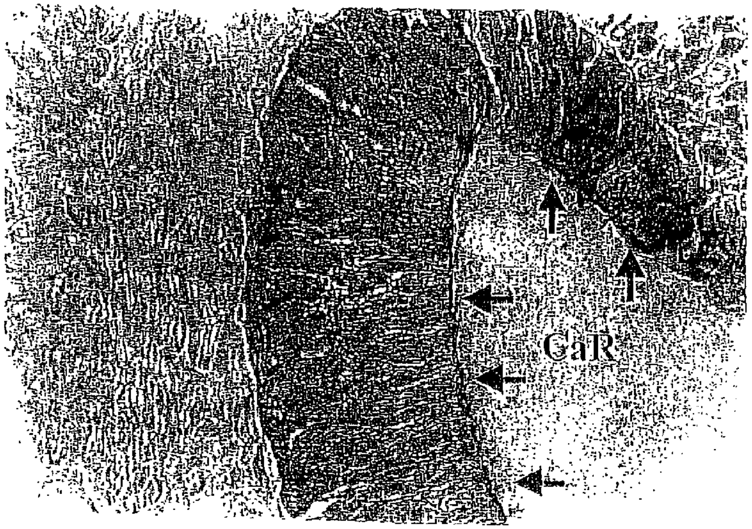
Developing Olfactory Bulb and
Skin in Atlantic Salmon Larvae
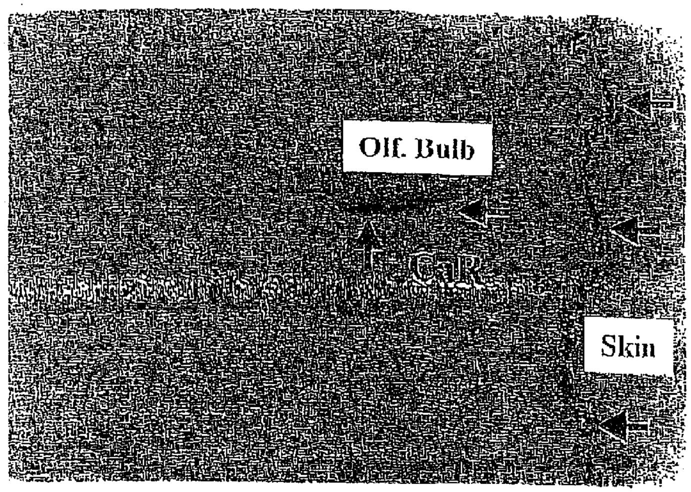

FIG. 38: PVCR localization in Nasal Lamellae of Dogfish Shark (Squalus acanthias)
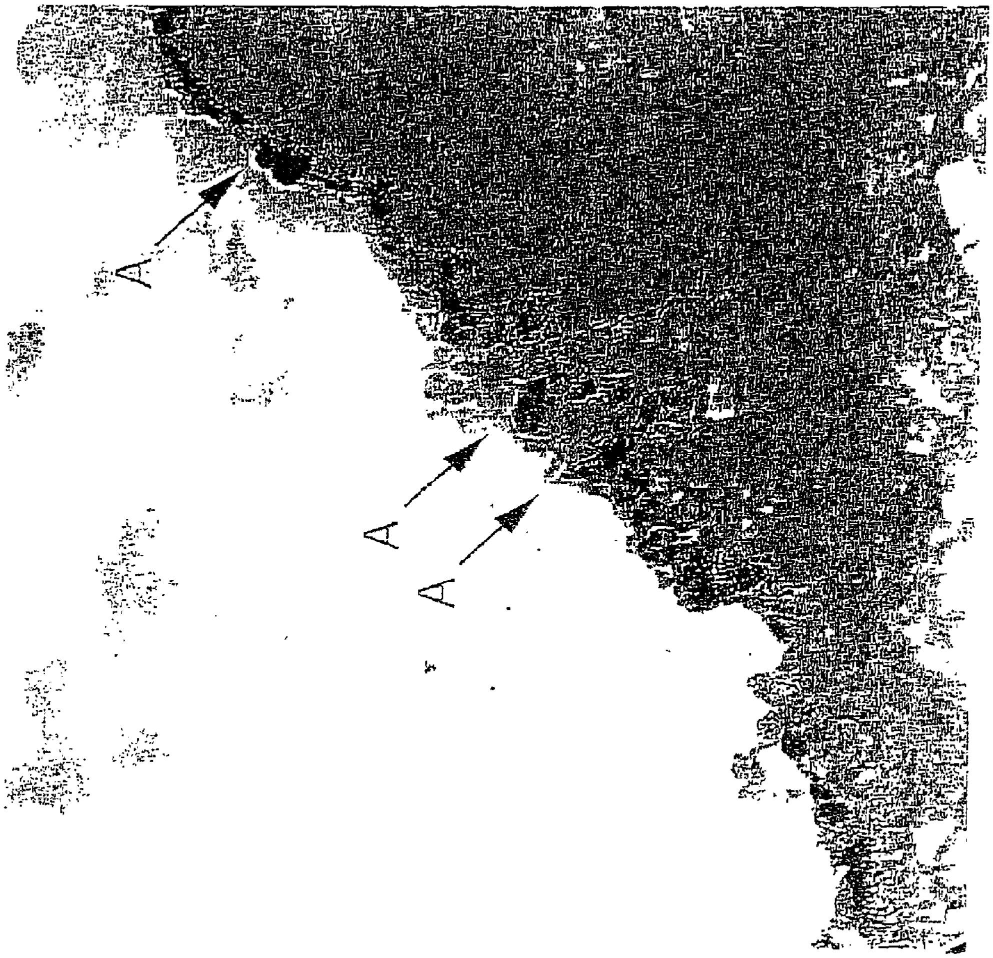

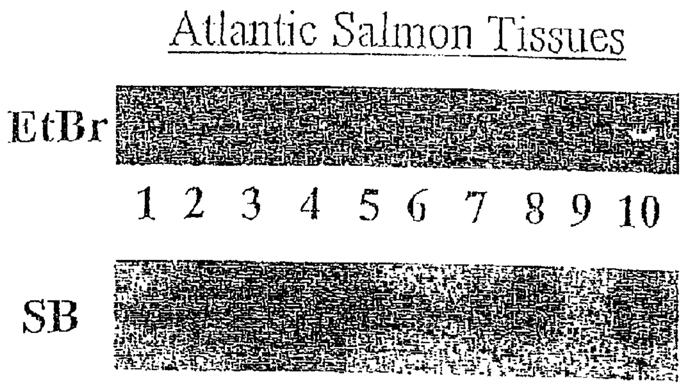
Key:
Atlantic Salmon
1. Gill
2. Nasal Lamellae
3. Urinary Bladder
4. Kidney
5. Intestine
6. Stomach
7. Liver
8. Brain
9. Water Blank
10. Positive Control
FIG. 39: RT-PCR of salmon tissues showing abundant PVCR mRNA in nasal lamellae of freshwater adapted Atlantic salmon.

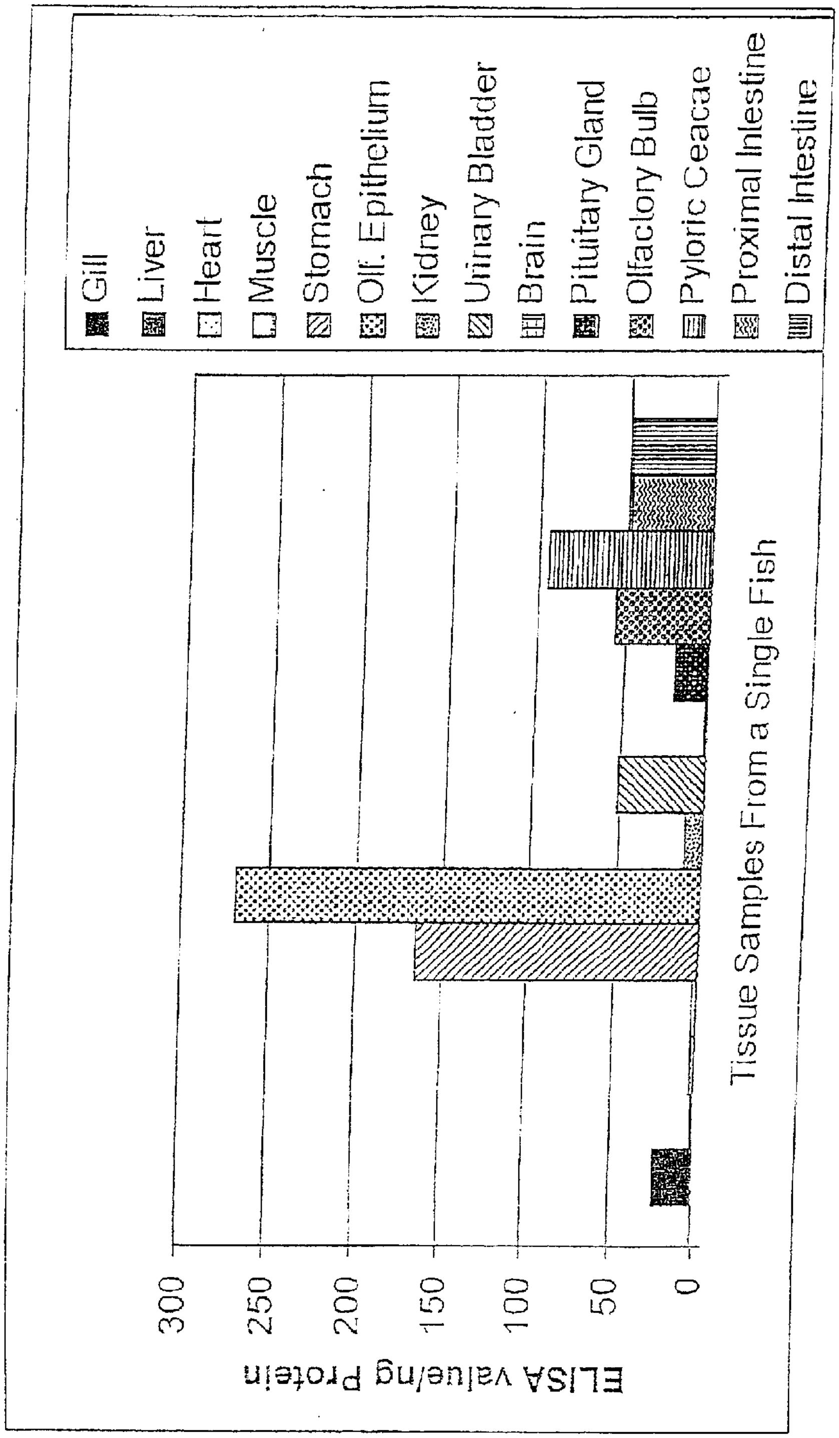
FIG. 40: Quantitation of PVCR content of 14 different tissues of juvenile Atlantic salmon using solid phase ELISA assay performed in a 96 well plate.

FIG. 41: High Resistance Electrode Olfactory Recordings of Freshwater Adapted Atlantic Salmon
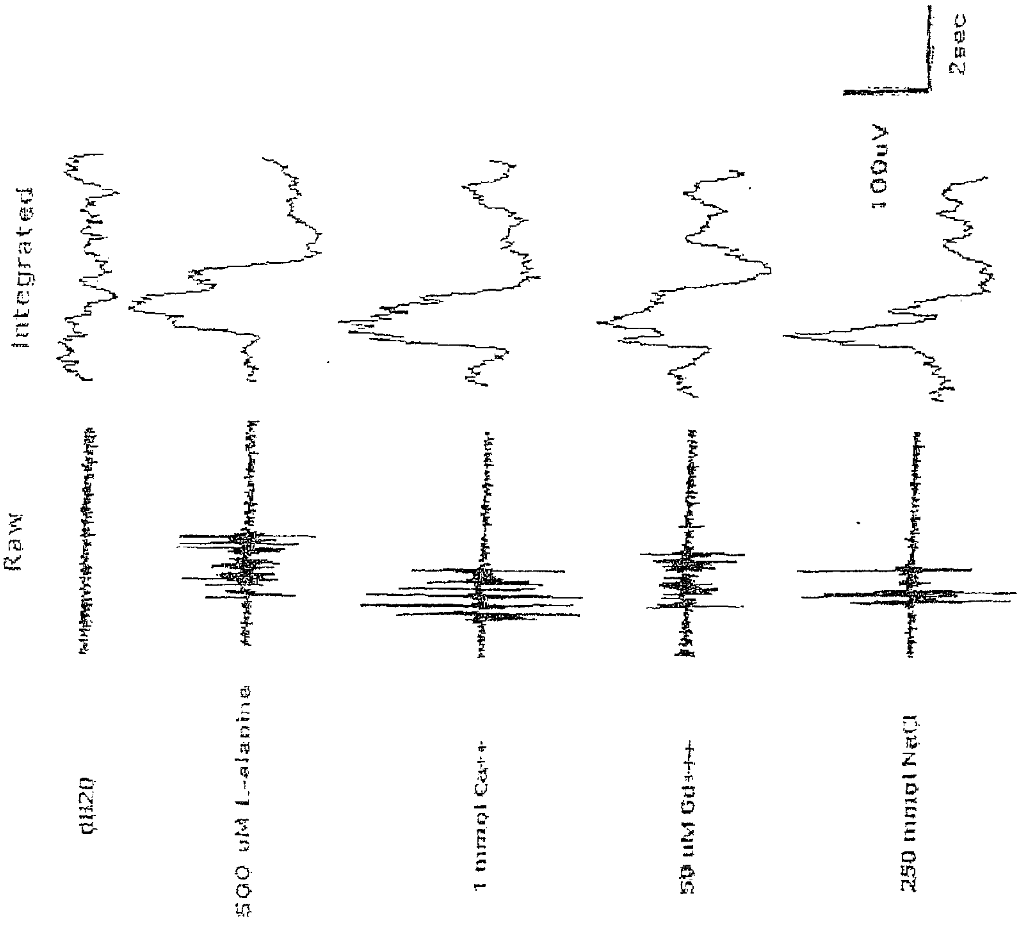

FIG. 43: Modulation of Olfactory Nerve Impulses from a Repellant by PYCR Agonist Repeated Stimulation of Preparation with Single Continuous Recording

SEQUENCE LISTING

<160> NUMBER OF SEQ ID NOS: 28

<210> SEQ ID NO 1
<211> LENGTH: 4134
<212> TYPE: DNA
<213> ORGANISM: Squalus acanthias

<400> SEQUENCE: 1
aattccgttg ctgtcggttc agtccaagtc tcctccagtg caaaatgaga aatggtggtc 60
gccattacag gaacatgcac tacatctgtg ttaatgaaat attgtcagtt atctgaaggt 120
tattaaaatg tttctgcaag gatggcttca cgagaaatca attctgcacg ttttcccatt 180
gtcattgtat gaataactga ccaaagggat gtaacaaaat ggaacaaagc tgaggaccac 240
gttcaccctt tcttggagca tacgatcaac cctgaaggag atggaagact tgaggaggaa 300
atggggattg atcttccagg agttctgctg taaagcgatc cctcaccatt acaaagataa 360
gcagaaatcc tccaggcatc ctctgtaaac gggctggcgt agtgtggctt ggtcaaggaa 420
cagagacagg gctgcacaat ggctcagctt cactgccaac tcttattctt gggatttaca 480
ctcctacagt cgtacaatgt ctcagggtat ggtccaaacc aaagggccca gaagaaagga 540
gacatcatac tgggaggtct cttcccaata cactttggag tagccgccaa ggatcaggac 600
ttaaaatcga gaccggaggc gacaaaatgt attcggtaca attttcgagg cttccgatgg 660
ctccaggcga tgatattcgc aattgaagag attaacaaca gtatgacttt cctgcccaat 720
atcaccctgg gatatcgcat atttgacacg tgtaacaccg tgtccaaggc gctagaggca 780
acactcagct ttgtggccca gaacaaaatc gactcgctga acttagatga gttctgtaac 840
tgctctgacc atatcccatc cacaatagca gtggtcgggg caaccgggtc aggaatctcc 900
acggctgtgg ccaatctatt gggattattt tacattccac aggtcagcta tgcctcctcg 960
agcaggctgc tcagcaacaa gaatgagtac aaggccttcc tgaggaccat ccccaatgat 1020
gagcaacagg ccacggccat ggccgagatc atcgagcact tccagtggaa ctgggtggga 1080
accctggcag ccgacgatga ctatggccgc ccaggcattg acaagttccg ggaggaggcc 1140
gttaagaggg acatctgtat tgacttcagt gagatgatct ctcagtacta cacccagaag 1200
cagttggagt tcatcgccga cgtcatccag aactcctcgg ccaaggtcat cgtggtcttc 1260
tccaatggcc ccgacctgga gccgctcatc caggagatag ttcggagaaa catcaccgat 1320
cggatctggc tggccagcga ggcttgggcc agctcttcgc tcattgccaa gccagagtac 1380
ttccacgtgg tcggcggcac catcggcttc gctctcaggg cggggcgtat cccagggttc 1440
aacaagttcc tgaaggaggt ccaccccagc aggtcctcgg acaatgggtt tgtcaaggag 1500
ttctgggagg agaccttcaa ctgctacttc accgagaaga ccctgacgca gctgaagaat 1560
tccaaggtgc cctcgcacgg accggcggct caaggggacg gctccaaggc ggggaactcc 1620
agacggacag ccctacgcca cccctgcact ggggaggaga acatcaccag cgtggagacc 1680
ccctacctgg attatacaca cctgaggatc tcctacaatg tatacgtggc cgtctactcc 1740
attgctcacg ccctgcaaga catccactct tgcaaacccg gcacgggcat ctttgcaaac 1800
ggatcttgtg cagatattaa aaaagttgag gcctggcagg tcctcaacca tctgctgcat 1860
ctgaagttta ccaacagcat gggtgagcag gttgactttg acgatcaagg tgacctcaag 1920
gggaactaca ccattatcaa ctggcagctc tccgcagagg atgaatcggt gttgttccat 1980
gaggtgggca actacaacgc ctacgctaag cccagtgacc gactcaacat caacgaaaag 2040

-continued

```
aaaatcctct ggagtggctt ctccaaagtg gttcctttct ccaactgcag tcgagactgt   2100
gtgccgggca ccaggaaggg gatcatcgag ggggagccca cctgctgctt tgaatgcatg   2160
gcatgtgcag agggagagtt cagtgatgaa aacgatgcaa gtgcgtgtac aaagtgcccg   2220
aatgatttct ggtcgaatga gaaccacacg tcgtgcatcg ccaaggagat cgagtacctg   2280
tcgtggacgg agcccttcgg gatcgctctg accatcttcg ccgtactggg catcctgatc   2340
acctccttcg tgctgggggt cttcatcaag ttcaggaaca ctcccatcgt gaaggccacc   2400
aaccgggagt tgtcctacct gctgctcttc tccctcatct gctgcttctc cagctcgctc   2460
atcttcatcg gcgagcccag ggactggacc tgtcggctcc gccaaccggc ctttggcatc   2520
agcttcgtcc tgtgcatctc ctgcatcctg gtgaagacca accgggtgct gctggtcttc   2580
gaggccaaga tccccaccag cctccaccgc aagtgggtgg gcctcaacct gcagttcctc   2640
ctggtcttcc tctgcatcct ggtgcaaatc gtcacctgca tcatctggct ctacaccgcg   2700
cctccctcca gctacaggaa ccatgagctg gaggacgagg tcatcttcat cacctgcgac   2760
gagggctcgc tcatggcgct gggcttcctc atcggctaca cctgcctcct cgccgccatc   2820
tgcttcttct tcgccttcaa gtcccgtaag ctgccggaga acttcaacga ggctaagttc   2880
atcaccttca gcatgttgat cttcttcatc gtctggatct ccttcatccc cgcctatgtc   2940
agcacctacg gcaagtttgt gtcggccgtg gaggtgattg ccatcctggc ctccagcttc   3000
gggctgctgg gctgcattta cttcaacaag tgttacatca tcctgttcaa gccgtgccgt   3060
aacaccatcg aggaggtgcg ctgcagcacg gcggcccacg ccttcaaggt ggcggcccgg   3120
gccaccctcc ggcgcagcgc cgcgtctcgc aagcgctcca gcagcctgtg cggctccacc   3180
atctcctcgc ccgcctcgtc cacctgcggg ccgggcctca ccatggagat gcagcgctgc   3240
agcacgcaga aggtcagctt cggcagcggc accgtcaccc tgtcgctcag cttcgaggag   3300
acaggccgat acgccaccct cagccgcacg gcccgcagca ggaactcggc ggatggccgc   3360
agcggcgacg acctgccatc tagacaccac gaccagggcc cgcctcagaa atgcgagccc   3420
cagcccgcca acgatgcccg atacaaggcg gcgccgacca agggcaccct agagtcgccg   3480
ggcggcagca aggagcgccc cacaactatg gaggaaacct aatccaactc ctccatcaac   3540
cccaagaaca tcctccacgg cagcaccgtc gacaactgac atcaactcct aaccggtggc   3600
tgcccaacct ctcccctctc cggcactttg cgttttgctg aagattgcag catctgcagt   3660
tcctttttatc cctgattttc tgacttggat atttactagt gtgcgatgga atatcacaac   3720
ataatgagtt gcacaattag gtgagcagag ttgtgtcaaa gtatctgaac tatctgaagt   3780
atctgaacta ctttattctc tcgaattgta ttacaaacat ttgaagtatt tttagtgaca   3840
ttatgttcta acattgtcaa gataatttgt tacaacatat aaggtaccac ctgaagcagt   3900
gactgagatt gccactgtga tgacagaact gttttataac atttatcatt gaaacctgga   3960
ttgcaacagg aatataatga ctgtaacaaa aaaattgttg attatcttaa aaatgcaaat   4020
tgtaatcaga tgtgtaaaat tggtaattac ttctgtacat taaatgcata tttcttgata   4080
aaaaaaaaaa aaaaaaaaaa aaaaaaaaaa aaaaaagcgg cccgacagca acgg         4134
```

<210> SEQ ID NO 2
<211> LENGTH: 1027
<212> TYPE: PRT
<213> ORGANISM: Squalus acanthias

<400> SEQUENCE: 2

-continued

```
Met Ala Gln Leu His Cys Gln Leu Leu Phe Leu Gly Phe Thr Leu Leu
1               5                   10                  15

Gln Ser Tyr Asn Val Ser Gly Tyr Gly Pro Asn Gln Arg Ala Gln Lys
            20                  25                  30

Lys Gly Asp Ile Ile Leu Gly Gly Leu Phe Pro Ile His Phe Gly Val
        35                  40                  45

Ala Ala Lys Asp Gln Asp Leu Lys Ser Arg Pro Glu Ala Thr Lys Cys
    50                  55                  60

Ile Arg Tyr Asn Phe Arg Gly Phe Arg Trp Leu Gln Ala Met Ile Phe
65                  70                  75                  80

Ala Ile Glu Glu Ile Asn Asn Ser Met Thr Phe Leu Pro Asn Ile Thr
                85                  90                  95

Leu Gly Tyr Arg Ile Phe Asp Thr Cys Asn Thr Val Ser Lys Ala Leu
            100                 105                 110

Glu Ala Thr Leu Ser Phe Val Ala Gln Asn Lys Ile Asp Ser Leu Asn
        115                 120                 125

Leu Asp Glu Phe Cys Asn Cys Ser Asp His Ile Pro Ser Thr Ile Ala
    130                 135                 140

Val Val Gly Ala Thr Gly Ser Gly Ile Ser Thr Ala Val Ala Asn Leu
145                 150                 155                 160

Leu Gly Leu Phe Tyr Ile Pro Gln Val Ser Tyr Ala Ser Ser Ser Arg
                165                 170                 175

Leu Leu Ser Asn Lys Asn Glu Tyr Lys Ala Phe Leu Arg Thr Ile Pro
            180                 185                 190

Asn Asp Glu Gln Gln Ala Thr Ala Met Ala Glu Ile Ile Glu His Phe
        195                 200                 205

Gln Trp Asn Trp Val Gly Thr Leu Ala Ala Asp Asp Asp Tyr Gly Arg
    210                 215                 220

Pro Gly Ile Asp Lys Phe Arg Glu Glu Ala Val Lys Arg Asp Ile Cys
225                 230                 235                 240

Ile Asp Phe Ser Glu Met Ile Ser Gln Tyr Tyr Thr Gln Lys Gln Leu
                245                 250                 255

Glu Phe Ile Ala Asp Val Ile Gln Asn Ser Ser Ala Lys Val Ile Val
            260                 265                 270

Val Phe Ser Asn Gly Pro Asp Leu Glu Pro Leu Ile Gln Glu Ile Val
        275                 280                 285

Arg Arg Asn Ile Thr Asp Arg Ile Trp Leu Ala Ser Glu Ala Trp Ala
    290                 295                 300

Ser Ser Ser Leu Ile Ala Lys Pro Glu Tyr Phe His Val Val Gly Gly
305                 310                 315                 320

Thr Ile Gly Phe Ala Leu Arg Ala Gly Arg Ile Pro Gly Phe Asn Lys
                325                 330                 335

Phe Leu Lys Glu Val His Pro Ser Arg Ser Ser Asp Asn Gly Phe Val
            340                 345                 350

Lys Glu Phe Trp Glu Glu Thr Phe Asn Cys Tyr Phe Thr Glu Lys Thr
        355                 360                 365

Leu Thr Gln Leu Lys Asn Ser Lys Val Pro Ser His Gly Pro Ala Ala
    370                 375                 380

Gln Gly Asp Gly Ser Lys Ala Gly Asn Ser Arg Arg Thr Ala Leu Arg
385                 390                 395                 400

His Pro Cys Thr Gly Glu Glu Asn Ile Thr Ser Val Glu Thr Pro Tyr
                405                 410                 415

Leu Asp Tyr Thr His Leu Arg Ile Ser Tyr Asn Val Tyr Val Ala Val
```

-continued

```
            420                 425                 430

Tyr Ser Ile Ala His Ala Leu Gln Asp Ile His Ser Cys Lys Pro Gly
        435                 440                 445

Thr Gly Ile Phe Ala Asn Gly Ser Cys Ala Asp Ile Lys Lys Val Glu
    450                 455                 460

Ala Trp Gln Val Leu Asn His Leu Leu His Leu Lys Phe Thr Asn Ser
465                 470                 475                 480

Met Gly Glu Gln Val Asp Phe Asp Asp Gln Gly Asp Leu Lys Gly Asn
                485                 490                 495

Tyr Thr Ile Ile Asn Trp Gln Leu Ser Ala Glu Asp Glu Ser Val Leu
            500                 505                 510

Phe His Glu Val Gly Asn Tyr Asn Ala Tyr Ala Lys Pro Ser Asp Arg
        515                 520                 525

Leu Asn Ile Asn Glu Lys Lys Ile Leu Trp Ser Gly Phe Ser Lys Val
    530                 535                 540

Val Pro Phe Ser Asn Cys Ser Arg Asp Cys Val Pro Gly Thr Arg Lys
545                 550                 555                 560

Gly Ile Ile Glu Gly Glu Pro Thr Cys Cys Phe Glu Cys Met Ala Cys
                565                 570                 575

Ala Glu Gly Glu Phe Ser Asp Glu Asn Asp Ala Ser Ala Cys Thr Lys
            580                 585                 590

Cys Pro Asn Asp Phe Trp Ser Asn Glu Asn His Thr Ser Cys Ile Ala
        595                 600                 605

Lys Glu Ile Glu Tyr Leu Ser Trp Thr Glu Pro Phe Gly Ile Ala Leu
    610                 615                 620

Thr Ile Phe Ala Val Leu Gly Ile Leu Ile Thr Ser Phe Val Leu Gly
625                 630                 635                 640

Val Phe Ile Lys Phe Arg Asn Thr Pro Ile Val Lys Ala Thr Asn Arg
                645                 650                 655

Glu Leu Ser Tyr Leu Leu Leu Phe Ser Leu Ile Cys Cys Phe Ser Ser
            660                 665                 670

Ser Leu Ile Phe Ile Gly Glu Pro Arg Asp Trp Thr Cys Arg Leu Arg
        675                 680                 685

Gln Pro Ala Phe Gly Ile Ser Phe Val Leu Cys Ile Ser Cys Ile Leu
    690                 695                 700

Val Lys Thr Asn Arg Val Leu Leu Val Phe Glu Ala Lys Ile Pro Thr
705                 710                 715                 720

Ser Leu His Arg Lys Trp Val Gly Leu Asn Leu Gln Phe Leu Leu Val
                725                 730                 735

Phe Leu Cys Ile Leu Val Gln Ile Val Thr Cys Ile Ile Trp Leu Tyr
            740                 745                 750

Thr Ala Pro Pro Ser Ser Tyr Arg Asn His Glu Leu Glu Asp Glu Val
        755                 760                 765

Ile Phe Ile Thr Cys Asp Glu Gly Ser Leu Met Ala Leu Gly Phe Leu
    770                 775                 780

Ile Gly Tyr Thr Cys Leu Leu Ala Ala Ile Cys Phe Phe Phe Ala Phe
785                 790                 795                 800

Lys Ser Arg Lys Leu Pro Glu Asn Phe Asn Glu Ala Lys Phe Ile Thr
                805                 810                 815

Phe Ser Met Leu Ile Phe Phe Ile Val Trp Ile Ser Phe Ile Pro Ala
            820                 825                 830

Tyr Val Ser Thr Tyr Gly Lys Phe Val Ser Ala Val Glu Val Ile Ala
        835                 840                 845
```

-continued

```
Ile Leu Ala Ser Ser Phe Gly Leu Leu Gly Cys Ile Tyr Phe Asn Lys
    850                 855                 860

Cys Tyr Ile Ile Leu Phe Lys Pro Cys Arg Asn Thr Ile Glu Glu Val
865                 870                 875                 880

Arg Cys Ser Thr Ala Ala His Ala Phe Lys Val Ala Ala Arg Ala Thr
                885                 890                 895

Leu Arg Arg Ser Ala Ala Ser Arg Lys Arg Ser Ser Ser Leu Cys Gly
            900                 905                 910

Ser Thr Ile Ser Ser Pro Ala Ser Ser Thr Cys Gly Pro Gly Leu Thr
        915                 920                 925

Met Glu Met Gln Arg Cys Ser Thr Gln Lys Val Ser Phe Gly Ser Gly
    930                 935                 940

Thr Val Thr Leu Ser Leu Ser Phe Glu Glu Thr Gly Arg Tyr Ala Thr
945                 950                 955                 960

Leu Ser Arg Thr Ala Arg Ser Arg Asn Ser Ala Asp Gly Arg Ser Gly
                965                 970                 975

Asp Asp Leu Pro Ser Arg His His Asp Gln Gly Pro Pro Gln Lys Cys
            980                 985                 990

Glu Pro Gln Pro Ala Asn Asp Ala  Arg Tyr Lys Ala Ala  Pro Thr Lys
        995                 1000                1005

Gly Thr  Leu Glu Ser Pro Gly  Gly Ser Lys Glu Arg  Pro Thr Thr
    1010                1015                1020

Met Glu  Glu Thr
    1025


<210> SEQ ID NO 3
<211> LENGTH: 594
<212> TYPE: DNA
<213> ORGANISM: Salmo salar

<400> SEQUENCE: 3

cttggcatta tgctctgtgc tgggggtatt cttgacagca ttcgtgatgg gagtgtttat     60

caaatttcgc aacaccccaa ttgttaaggc cacaaacaga gagctatcct acctcctcct    120

gttctcactc atctgctgtt tctccagttc cctcatcttc attggtgaac cccaggactg    180

gacatgccgt ctacgccagc ctgcattcgg gataagtttt gttctctgca tctcctgcat    240

cctggtaaaa actaaccgag tacttctagt gttcgaagcc aagatcccca ccagtctcca    300

tcgtaagtgg tgggggctaa acttgcagtt cctgttagtg ttcctgttca catttgtgca    360

agtgatgata tgtgtggtct ggctttacaa tgctcctccg gcgagctaca ggaaccatga    420

cattgatgag ataattttca ttacatgcaa tgagggctct atgatggcgc ttggcttcct    480

aattgggtac acatgcctgc tggcagccat atrcttcttc tttgcattta aatcacgaaa    540

actgccagag aactttactg aggctaagtt catcaccttc agcatgctca tctt          594


<210> SEQ ID NO 4
<211> LENGTH: 197
<212> TYPE: PRT
<213> ORGANISM: Salmo salar
<220> FEATURE:
<221> NAME/KEY: misc_feature
<222> LOCATION: (171)..(171)
<223> OTHER INFORMATION: Xaa = Any Amino Acid

<400> SEQUENCE: 4

Leu Ala Leu Cys Ser Val Leu Gly Val Phe Leu Thr Ala Phe Val Met
1               5                   10                  15
```

-continued

```
Gly Val Phe Ile Lys Phe Arg Asn Thr Pro Ile Val Lys Ala Thr Asn
            20                  25                  30

Arg Glu Leu Ser Tyr Leu Leu Leu Phe Ser Leu Ile Cys Cys Phe Ser
        35                  40                  45

Ser Ser Leu Ile Phe Ile Gly Glu Pro Gln Asp Trp Thr Cys Arg Leu
    50                  55                  60

Arg Gln Pro Ala Phe Gly Ile Ser Phe Val Leu Cys Ile Ser Cys Ile
65                  70                  75                  80

Leu Val Lys Thr Asn Arg Val Leu Leu Val Phe Glu Ala Lys Ile Pro
                85                  90                  95

Thr Ser Leu His Arg Lys Trp Trp Gly Leu Asn Leu Gln Phe Leu Leu
            100                 105                 110

Val Phe Leu Phe Thr Phe Val Gln Val Met Ile Cys Val Val Trp Leu
        115                 120                 125

Tyr Asn Ala Pro Pro Ala Ser Tyr Arg Asn His Asp Ile Asp Glu Ile
    130                 135                 140

Ile Phe Ile Thr Cys Asn Glu Gly Ser Met Met Ala Leu Gly Phe Leu
145                 150                 155                 160

Ile Gly Tyr Thr Cys Leu Leu Ala Ala Ile Xaa Phe Phe Phe Ala Phe
                165                 170                 175

Lys Ser Arg Lys Leu Pro Glu Asn Phe Thr Glu Ala Lys Phe Ile Thr
            180                 185                 190

Phe Ser Met Leu Ile
        195
```

<210> SEQ ID NO 5
<211> LENGTH: 2021
<212> TYPE: DNA
<213> ORGANISM: Salmo salar

<400> SEQUENCE: 5

```
gtgatcacaa aggtaagaaa gacagtgaaa aatctgaact accccattat ataatctgtt     60

gctatttcat atgtttctat caataataca aacactactt ctctattcct gcagatgcca    120

gtgtttgtac caagtgtccc aatgactcat ggtctaatga gaaccacaca tcttgtttcc    180

tgaaggagat agagtttctg tcttggacag agccctttgg gatcgccttg gcattatgct    240

ctgtgctggg ggtattcttg acagcattcg tgatgggagt gtttatcaaa tttcgcaaca    300

ccccaattgt taaggccaca aacagagagc tatcctacct cctcctgttc tcactcatct    360

gctgtttctc cagttccctc atcttcattg gtgaacccca ggactggaca tgccgtctac    420

gccagcctgc attcgggata agttttgttc tctgcatctc ctgcatcctg gtaaaaacta    480

accgagtact tctagtgttc gaagccaaga tccccaccag tctccatcgt aagtggtggg    540

ggctaaactt gcagttcctg ttagtgttcc tgttcacatt tgtgcaagtg atgatatgtg    600

tggtctggct ttacaatgct cctccggcga gctacaggaa ccatgacatt gatgagataa    660

ttttcattac atgcaatgag ggctctatga tggcgcttgg cttcctaatt gggtacacat    720

gcctgctggc agccatatgc ttcttctttg catttaaatc acgaaaactg ccagagaact    780

ttactgaggc taagttcatc accttcagca tgctcatctt cttcatcgtc tggatctctt    840

tcatccctgc ctacttcagc acttacggaa agtttgtgtc ggctgtggag gtcatcgcca    900

tactagcctc cagctttggc ctgctggcct gtattttctt caataaagtc tacatcatcc    960

tcttcaaacc gtccaggaac actatagagg aggttcgctg tagcactgcg gcccattctt   1020
```

-continued

```
tcaaagtggc agccaaggcc actctgagac acagctcagc ctccaggaag aggtccagca   1080

gtgtgggggg atcctgtgcc tcaactccct cctcatccat cagcctcaag accaatgaca   1140

atgactcccc atcaggtcag cagagaatcc ataagccaag agtaagcttt ggaagtggaa   1200

cagttactct gtccttgagc tttgaggagt ccagaaagaa ttctatgaag tagggaagtg   1260

tcttttggtg ggccgagagc cttgtcaaaa cctgagttgg tgttgcattc tttgttggct   1320

gggtagttgg agcagaaatt atgatattaa aagctttgat gtattcagaa tggtgacaca   1380

gcataggtgg ccaagattcc attatattac aataatctgt gttgttcatt atgaggacat   1440

ttcaaaatgc tgaaaatcat caaatacata atttactgag ttttcttgat aatcttgaga   1500

atagaatagc ctattcaagt catcgttgag cagacattaa ttaacaatga tgtaatactt   1560

tccataccta ttttctttaa caatagattc acattgttaa agttcaacta tgacctgtaa   1620

aatacatgag gtataacagg agacaataaa actatgcata tcctagcttc tgggcctgag   1680

tagcaggcag tttactctgg gcacgctttt catccaaact tccgaatgct gcccccaatc   1740

ctagtgaggt taaaggccca gtgcagtcat atcttttctc taggcacgct tttcatccaa   1800

acttccgaat gcggctatat cagtctcttt cctactgtct ttttcattag gccagtgttt   1860

aacaaccctg gtccttaagt acacacaaca gaacacattt ttgttgtagc cctggacaat   1920

cactcctcac tcagctcatt gagggcctga tgattagttg acaagttgaa tcaggtgtgc   1980

ttgtccaggg ttacaataca aatgtgtact gttgggggta c                        2021


210> SEQ ID NO 6
<211> LENGTH: 388
<212> TYPE: PRT
<213> ORGANISM: Salmo salar

<400> SEQUENCE: 6

Tyr Lys His Tyr Phe Ser Ile Pro Ala Asp Ala Ser Val Cys Thr Lys
1               5                   10                  15

Cys Pro Asn Asp Ser Trp Ser Asn Glu Asn His Thr Ser Cys Phe Leu
            20                  25                  30

Lys Glu Ile Glu Phe Leu Ser Trp Thr Glu Pro Phe Gly Ile Ala Leu
        35                  40                  45

Ala Leu Cys Ser Val Leu Gly Val Phe Leu Thr Ala Phe Val Met Gly
    50                  55                  60

Val Phe Ile Lys Phe Arg Asn Thr Pro Ile Val Lys Ala Thr Asn Arg
65                  70                  75                  80

Glu Leu Ser Tyr Leu Leu Leu Phe Ser Leu Ile Cys Cys Phe Ser Ser
                85                  90                  95

Ser Leu Ile Phe Ile Gly Glu Pro Gln Asp Trp Thr Cys Arg Leu Arg
            100                 105                 110

Gln Pro Ala Phe Gly Ile Ser Phe Val Leu Cys Ile Ser Cys Ile Leu
        115                 120                 125

Val Lys Thr Asn Arg Val Leu Leu Val Phe Glu Ala Lys Ile Pro Thr
    130                 135                 140

Ser Leu His Arg Lys Trp Trp Gly Leu Asn Leu Gln Phe Leu Leu Val
145                 150                 155                 160

Phe Leu Phe Thr Phe Val Gln Val Met Ile Cys Val Val Trp Leu Tyr
                165                 170                 175

Asn Ala Pro Pro Ala Ser Tyr Arg Asn His Asp Ile Asp Glu Ile Ile
            180                 185                 190

Phe Ile Thr Cys Asn Glu Gly Ser Met Met Ala Leu Gly Phe Leu Ile
```

-continued

```
        195                 200                 205

Gly Tyr Thr Cys Leu Leu Ala Ala Ile Cys Phe Phe Phe Ala Phe Lys
    210                 215                 220

Ser Arg Lys Leu Pro Glu Asn Phe Thr Glu Ala Lys Phe Ile Thr Phe
225                 230                 235                 240

Ser Met Leu Ile Phe Phe Ile Val Trp Ile Ser Phe Ile Pro Ala Tyr
                245                 250                 255

Phe Ser Thr Tyr Gly Lys Phe Val Ser Ala Val Glu Val Ile Ala Ile
            260                 265                 270

Leu Ala Ser Ser Phe Gly Leu Leu Ala Cys Ile Phe Phe Asn Lys Val
        275                 280                 285

Tyr Ile Ile Leu Phe Lys Pro Ser Arg Asn Thr Ile Glu Glu Val Arg
    290                 295                 300

Cys Ser Thr Ala Ala His Ser Phe Lys Val Ala Ala Lys Ala Thr Leu
305                 310                 315                 320

Arg His Ser Ser Ala Ser Arg Lys Arg Ser Ser Ser Val Gly Gly Ser
                325                 330                 335

Cys Ala Ser Thr Pro Ser Ser Ser Ile Ser Leu Lys Thr Asn Asp Asn
            340                 345                 350

Asp Ser Pro Ser Gly Gln Gln Arg Ile His Lys Pro Arg Val Ser Phe
        355                 360                 365

Gly Ser Gly Thr Val Thr Leu Ser Leu Ser Phe Glu Glu Ser Arg Lys
    370                 375                 380

Asn Ser Met Lys
385


<210> SEQ ID NO 7
<211> LENGTH: 3941
<212> TYPE: DNA
<213> ORGANISM: Salmo salar

<400> SEQUENCE: 7

ttccaacagc atatttttgt tgtatttgct ttggtttgtc tgaaatcaag cattatcaag      60

atcaagaaca gcatgagtca gaaacaaggc gacagccaga gtcactggag gggacaagac     120

tgaggttaac tctgaagtct aatgtgctga gaggacaagg ccctcctgag agctgaacga     180

tgagatttta cctgtattac ctggtgcttt tgggcttcag ttctgtcatc tccacctatg     240

ggcctcatca gagagcacag aagactgggg atattctgct gggcgggctg tttccaatgc     300

actttggtgt tacctccaaa gaccaagacc tggcagcgcg gccagaatcc acagagtgtg     360

ttaggtacaa tttccgggga ttccgttggc ttcaggccat gatttttgca atagaggaga     420

tcaacaacag cagtactctc ctgcccaaca tcacactggg ctacaggatc tttgacacct     480

gcaacaccgt gtccaaggcc ctggaggcta ccctcagttt cgtagcacag aataagattg     540

actctctgaa cttggatgaa ttctgtaact gcactgatca catcccatcg actatagcag     600

tggtgggggc ttctgggtca gcggtctcca ctgctgttgc caatctgttg ggccttttct     660

acatcccaca gatcagctat gcctcttcca gtcgcctact aagcaacaag aaccagttca     720

aatccttcat gaggaccatt cccacagatg agcaccaggc cactgccatg gcagatatca     780

tcgactactt ccaatggaat tgggtcattg cagttgcgtc tgatgatgag tatggacgtc     840

cggggattga aaaatttgag aaagagatgg aagaacgaga catttgtatc catctgagtg     900

agctgatctc tcagtacttt gaggagtggc agatccaagg attggttgac cgtattgaga     960

actcctcagc taaagttata gtcgttttcg ccagtgggcc tgacattgag cctcttatta    1020
```

-continued

```
aagagatggt cagacggaac atcaccgacc gcatctggtt ggccagcgag gcttgggcaa   1080
ccacctccct catcgccaaa ccagagtacc ttgatgttgt agttgggacc attggctttg   1140
ctctcagagc aggcgaaata cctggcttca aggacttctt acaagaggtc acaccaaaga   1200
aatccagcca caatgaattt gtcagggagt tttgggagga gacttttaac tgctatctgg   1260
aagacagcca gagactgaga gacagtgaga atgggagcac cagtttcaga ccattgtgta   1320
ctggcgagga ggacattatg ggtgcagaga ccccatatct ggattacact catcttcgta   1380
tttcctataa tgtgtatgtt gcagttcact ccattgcaca ggccctacag gacattctca   1440
cctgcattcc tggacggggt ctttttttcca acaactcatg tgcagatata aagaaaatag   1500
aagcatggca ggttctcaag cagctcagac atttaaactt ctcaaacagt atgggagaaa   1560
aggtacattt tgatgagaat gctgatccgt caggaaacta caccattatc aattggcacc   1620
ggtctcctga ggatggttct gttgtgtttg aagaggtcgg tttctacaac atgcgagcta   1680
agagaggagt acaacttttc attgataaca caaagattct atggaatgga tataatactg   1740
aggttccatt ctctaactgt agtgaagatt gtgaaccagg caccagaaag gggatcatag   1800
aaagcatgcc aacgtgttgc tttgaatgta cagaatgctc agaaggagag tatagtgatc   1860
acaaagatgc cagtgtttgt accaagtgtc ccaatgactc atggtctaat gagaaccaca   1920
catcttgttt cctgaaggag atagagtttc tgtcttggac agagcccttt gggatcgcct   1980
tggcattatg ctctgtgctg gggtattctt tgacagcatt cgtgatggga gtgtttatca   2040
aatttcgcaa caccccaatt gttaaggcca caaacagaga gctatcctac ctcctcctgt   2100
tctcactcat ctgctgtttc tccagttccc tcatcttcat tggtgaaccc caggactgga   2160
catgccgtct acgccagcct gcattcggga taagttttgt tctctgcatc tcctgcatcc   2220
tggtaaaaac taaccgagta cttctagtgt tcgaagccaa gatccccacc agtctccatc   2280
gtaagtggtg gggctaaac ttgcagttcc tgttagtgtt cctgttcaca tttgtgcaag   2340
tgatgatatg tgtggtctgg ctttacaatg ctcctccggc gagctacagg aaccatgaca   2400
ttgatgagat aattttcatt acatgcaatg agggctctat gatggcgctt ggcttcctaa   2460
ttgggtacac atgcctgctg gcagccatat gcttcttctt tgcatttaaa tcacgaaaac   2520
tgccagagaa ctttactgag gctaagttca tcaccttcag catgctcatc ttcttcatcg   2580
tctggatctc tttcatccct gcctacttca gcacttacgg aaagtttgtg tcggctgtgg   2640
aggtcatcgc catactagcc tccagctttg gcctgctggc ctgtattttc ttcaataaag   2700
tctacatcat cctcttcaaa ccgtccagga acactataga ggaggttcgc tgtagcactg   2760
cggcccattc tttcaaagtg gcagccaagg ccactctgag acacagctca gcctccagga   2820
agaggtccag cagtgtgggg ggatcctgtg cctcaactcc ctcctcatcc atcagcctca   2880
agaccaatga caatgactcc ccatcaggtc agcagagaat ccataagcca agagtaagct   2940
ttggaagtgg aacagttact ctgtccttga gctttgagga gtccagaaag aattctatga   3000
agtagggaag tgtcttttgg tgggccgaga gccttgtcaa aacctgagtt ggtgttgcat   3060
tctttgttgg ctgggtagtt ggagcagaaa ttatgatatt aaaagctttg atgtattcag   3120
aatggtgaca cagcataggt ggccaagatt ccattatatt acaataatct gtgttgttca   3180
ttatgaggac atttcaaaat gctgaaaatc atcaaataca taatttactg agttttcttg   3240
ataatcttga gaatagaata gcctattcaa gtcatcgttg agcagacatt aattaacaat   3300
gatgtaatac tttccatacc tattttcttt aacaatagat tcacattgtt aaagttcaac   3360
```

-continued

```
tatgacctgt aaaatacatg aggtataaca ggagacaata aaactatgca tatcctagct   3420

tctgggcctg agtagcaggc agtttactct gggcacgctt ttcatccaaa cttccgaatg   3480

ctgcccccaa tcctagtgag gttaaaggcc cagtgcagtc atatcttttc tctaggcacg   3540

cttttcatcc aaacttccga atgcggctat atcagtctct ttcctactgt ctttttcatt   3600

aggccagtgt ttaacaaccc tggtccttaa gtacacacaa cagagcacat ttttgttgtg   3660

gccctggaca atcactcctc actcagctca ttgagggcct gatgattagt tgacaagttg   3720

agtcgggtgt gcttgtccgg ggttgcaata cagatgtgta ctgttggggg tactcgagga   3780

ccaggattgg gaaacattac attaggacta ctgtaggttc ttcaatatgg tgtcatacgg   3840

tcatatggtg tcatatggtg tctggttgtt ttctgcatat gtgtatttca ccaagttact   3900

gcacatgtta gacctataca ctggaataaa catttttttt c                       3941
```

<210> SEQ ID NO 8
<211> LENGTH: 941
<212> TYPE: PRT
<213> ORGANISM: Salmo salar

<400> SEQUENCE: 8

```
Met Arg Phe Tyr Leu Tyr Tyr Leu Val Leu Leu Gly Phe Ser Ser Val
1               5                   10                  15

Ile Ser Thr Tyr Gly Pro His Gln Arg Ala Gln Lys Thr Gly Asp Ile
            20                  25                  30

Leu Leu Gly Gly Leu Phe Pro Met His Phe Gly Val Thr Ser Lys Asp
        35                  40                  45

Gln Asp Leu Ala Ala Arg Pro Glu Ser Thr Glu Cys Val Arg Tyr Asn
    50                  55                  60

Phe Arg Gly Phe Arg Trp Leu Gln Ala Met Ile Phe Ala Ile Glu Glu
65                  70                  75                  80

Ile Asn Asn Ser Ser Thr Leu Leu Pro Asn Ile Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Thr Asp His Ile Pro Ser Thr Ile Ala Val Val Gly Ala
    130                 135                 140

Ser Gly Ser Ala Val Ser Thr Ala Val Ala Asn Leu Leu Gly Leu Phe
145                 150                 155                 160

Tyr Ile Pro Gln Ile Ser Tyr Ala Ser Ser Ser Arg Leu Leu Ser Asn
                165                 170                 175

Lys Asn Gln Phe Lys Ser Phe Met Arg Thr Ile Pro Thr Asp Glu His
            180                 185                 190

Gln Ala Thr Ala Met Ala Asp Ile Ile Asp Tyr Phe Gln Trp Asn Trp
        195                 200                 205

Val Ile Ala Val Ala Ser Asp Asp Glu Tyr Gly Arg Pro Gly Ile Glu
    210                 215                 220

Lys Phe Glu Lys Glu Met Glu Glu Arg Asp Ile Cys Ile His Leu Ser
225                 230                 235                 240

Glu Leu Ile Ser Gln Tyr Phe Glu Glu Trp Gln Ile Gln Gly Leu Val
                245                 250                 255

Asp Arg Ile Glu Asn Ser Ser Ala Lys Val Ile Val Val Phe Ala Ser
            260                 265                 270
```

-continued

```
Gly Pro Asp Ile Glu Pro Leu Ile Lys Glu Met Val Arg Arg Asn Ile
        275                 280                 285

Thr Asp Arg Ile Trp Leu Ala Ser Glu Ala Trp Ala Thr Thr Ser Leu
    290                 295                 300

Ile Ala Lys Pro Glu Tyr Leu Asp Val Val Val Gly Thr Ile Gly Phe
305                 310                 315                 320

Ala Leu Arg Ala Gly Glu Ile Pro Gly Phe Lys Asp Phe Leu Gln Glu
                325                 330                 335

Val Thr Pro Lys Lys Ser Ser His Asn Glu Phe Val Arg Glu Phe Trp
            340                 345                 350

Glu Glu Thr Phe Asn Cys Tyr Leu Glu Asp Ser Gln Arg Leu Arg Asp
        355                 360                 365

Ser Glu Asn Gly Ser Thr Ser Phe Arg Pro Leu Cys Thr Gly Glu Glu
    370                 375                 380

Asp Ile Met Gly Ala Glu Thr Pro Tyr Leu Asp Tyr Thr His Leu Arg
385                 390                 395                 400

Ile Ser Tyr Asn Val Tyr Val Ala Val His Ser Ile Ala Gln Ala Leu
                405                 410                 415

Gln Asp Ile Leu Thr Cys Ile Pro Gly Arg Gly Leu Phe Ser Asn Asn
            420                 425                 430

Ser Cys Ala Asp Ile Lys Lys Ile Glu Ala Trp Gln Val Leu Lys Gln
        435                 440                 445

Leu Arg His Leu Asn Phe Ser Asn Ser Met Gly Glu Lys Val His Phe
    450                 455                 460

Asp Glu Asn Ala Asp Pro Ser Gly Asn Tyr Thr Ile Ile Asn Trp His
465                 470                 475                 480

Arg Ser Pro Glu Asp Gly Ser Val Val Phe Glu Glu Val Gly Phe Tyr
                485                 490                 495

Asn Met Arg Ala Lys Arg Gly Val Gln Leu Phe Ile Asp Asn Thr Lys
            500                 505                 510

Ile Leu Trp Asn Gly Tyr Asn Thr Glu Val Pro Phe Ser Asn Cys Ser
        515                 520                 525

Glu Asp Cys Glu Pro Gly Thr Arg Lys Gly Ile Ile Glu Ser Met Pro
    530                 535                 540

Thr Cys Cys Phe Glu Cys Thr Glu Cys Ser Glu Gly Glu Tyr Ser Asp
545                 550                 555                 560

His Lys Asp Ala Ser Val Cys Thr Lys Cys Pro Asn Asp Ser Trp Ser
                565                 570                 575

Asn Glu Asn His Thr Ser Cys Phe Leu Lys Glu Ile Glu Phe Leu Ser
            580                 585                 590

Trp Thr Glu Pro Phe Gly Ile Ala Leu Ala Leu Cys Ser Val Leu Gly
        595                 600                 605

Val Phe Leu Thr Ala Phe Val Met Gly Val Phe Ile Lys Phe Arg Asn
    610                 615                 620

Thr Pro Ile Val Lys Ala Thr Asn Arg Glu Leu Ser Tyr Leu Leu Leu
625                 630                 635                 640

Phe Ser Leu Ile Cys Cys Phe Ser Ser Ser Leu Ile Phe Ile Gly Glu
                645                 650                 655

Pro Gln Asp Trp Thr Cys Arg Leu Arg Gln Pro Ala Phe Gly Ile Ser
            660                 665                 670

Phe Val Leu Cys Ile Ser Cys Ile Leu Val Lys Thr Asn Arg Val Leu
        675                 680                 685

Leu Val Phe Glu Ala Lys Ile Pro Thr Ser Leu His Arg Lys Trp Trp
```

-continued

```
690                 695                 700

Gly Leu Asn Leu Gln Phe Leu Leu Val Phe Leu Phe Thr Phe Val Gln
705                 710                 715                 720

Val Met Ile Cys Val Val Trp Leu Tyr Asn Ala Pro Pro Ala Ser Tyr
                725                 730                 735

Arg Asn His Asp Ile Asp Glu Ile Ile Phe Ile Thr Cys Asn Glu Gly
            740                 745                 750

Ser Met Met Ala Leu Gly Phe Leu Ile Gly Tyr Thr Cys Leu Leu Ala
        755                 760                 765

Ala Ile Cys Phe Phe Phe Ala Phe Lys Ser Arg Lys Leu Pro Glu Asn
    770                 775                 780

Phe Thr Glu Ala Lys Phe Ile Thr Phe Ser Met Leu Ile Phe Phe Ile
785                 790                 795                 800

Val Trp Ile Ser Phe Ile Pro Ala Tyr Phe Ser Thr Tyr Gly Lys Phe
                805                 810                 815

Val Ser Ala Val Glu Val Ile Ala Ile Leu Ala Ser Ser Phe Gly Leu
            820                 825                 830

Leu Ala Cys Ile Phe Phe Asn Lys Val Tyr Ile Ile Leu Phe Lys Pro
        835                 840                 845

Ser Arg Asn Thr Ile Glu Glu Val Arg Cys Ser Thr Ala Ala His Ser
    850                 855                 860

Phe Lys Val Ala Ala Lys Ala Thr Leu Arg His Ser Ser Ala Ser Arg
865                 870                 875                 880

Lys Arg Ser Ser Ser Val Gly Gly Ser Cys Ala Ser Thr Pro Ser Ser
                885                 890                 895

Ser Ile Ser Leu Lys Thr Asn Asp Asn Asp Ser Pro Ser Gly Gln Gln
            900                 905                 910

Arg Ile His Lys Pro Arg Val Ser Phe Gly Ser Gly Thr Val Thr Leu
        915                 920                 925

Ser Leu Ser Phe Glu Glu Ser Arg Lys Asn Ser Met Lys
    930                 935                 940


<210> SEQ ID NO 9
<211> LENGTH: 4031
<212> TYPE: DNA
<213> ORGANISM: Salmo salar

<400> SEQUENCE: 9

gttccaacag catatttttg ttgtatttgc tttggtttgt ctgaaatcaa gcattatcaa      60

ggattgagca agacaactga gttgtcagac taagaatata cacatttcca gttctctctt     120

taatggactt ctcacactga tgttcttcag atcaagaaca gcatgagtca gaaacaaggc     180

gacagccaga gtcactggag gggacaagac tgaggttaac tctgaagtct aatgtgctga     240

gaggacaagg ccctcctgag agctgaacga tgagatttta cctgtattac ctggtgcttt     300

tgggcttcag ttctgtcatc tccacctatg ggcctcatca gagagcacag aagactgggg     360

atattctgct gggcgggctg tttccaatgc actttggtgt tacctccaaa gaccaagacc     420

tggcagcgcg gccagaatcc acagagtgtg ttaggtacaa tttccgggga ttccgttggc     480

ttcaggccat gatttttgca atagaggaga tcaacaacag cagtactctc ctgcccaaca     540

tcacactggg ctacaggatc tttgacacct gcaacaccgt gtccaaggcc ctggaggcta     600

ccctcagttt cgtagcacag aataagattg actctctgaa cttggatgaa ttctgtaact     660

gcactgatca catcccatcg actatagcag tggtgggggc ttctgggtca gcggtctcca     720
```

-continued

```
ctgctgttgc caatctgttg ggccttttct acatcccaca gatcagctat gcctcttcca    780
gtcgcctact aagcaacaag aaccagttca aatccttcat gaggaccatt cccacagatg    840
agcaccaggc cactgccatg gcagatatca tcgactactt ccaatggaat tgggtcattg    900
cagttgcgtc tgatgatgag tatggacgtc cggggattga aaaatttgag aaagagatgg    960
aagaacgaga catttgtatc catctgagtg agctgatctc tcagtacttt gaggagtggc   1020
agatccaagg attggttggc cgtattgaga actcctcagc taaagttata gtcgttttcg   1080
ccagtgggcc tgacattgag cctcttatta aagagatggt cagacggaac atcaccgacc   1140
gcatctggtt ggccagcgag gcttgggcaa ccacctccct catcgccaaa ccagagtacc   1200
ttgatgttgt agttgggacc attggctttg ctctcagagc aggcgaaata cctggcttca   1260
aggacttctt acaagaggtc acaccaaaga aatccagcca caatgaattt gtcagggagt   1320
tttgggagga gacttttaac tgctatctgg aagacagcca gagactgaga gacagtgaga   1380
atgggagcac cagtttcaga ccattgtgta ctggcgagga ggacattatg ggtgcagaga   1440
ccccatatct ggattacact catcttcgta tttcctataa tgtgtatgtt gcagttcact   1500
ccattgcaca ggccctacag gacattctca cctgcattcc tggacggggt ctttttttcca   1560
acaactcatg tgcagatata aagaaaatag aagcatggca ggttctcaag cagctcagac   1620
atttaaactt ctcaaacagt atgggagaaa aggtacattt tgatgagaat gctgatccgt   1680
caggaaacta caccattatc aattggcacc ggtctcctga ggatggttct gttgtgtttg   1740
aagaggtcgg tttctacaac atgcgagcta agagaggagt acaacttttc attgataaca   1800
caaagattct atggaatgga tataatactg aggttccatt ctctaactgt agtgaagatt   1860
gtgaaccagg caccagaaag ggatcatag aaagcatgcc aacgtgttgc tttgaatgta   1920
cagaatgctc agaaggagag tatagtgatc acaaagatgc cagtgtttgt accaagtgtc   1980
ccaatgactc atggtctaat gagaaccaca catcttgttt cctgaaggag atagagtttc   2040
tgtcttggac agagcccttt gggatcgcct tggcattatg ctctgtgctg gggggtattct   2100
tgacagcatt cgtgatggga gtgtttatca aatttcgcaa caccccaatt gttaaggcca   2160
caaacagaga gctatcctac ctcctcctgt tctcactcat ctgctgtttc tccagttccc   2220
tcatcttcat tggtgaaccc caggactgga catgccgtct acgccagcct gcattcggga   2280
taagttttgt tctctgcatc tcctgcatcc tggtaaaaac taaccgagta cttctagtgt   2340
tcgaagccaa gatccccacc agtctccatc gtaagtggtg gggggctaaac ttgcagttcc   2400
tgttagtgtt cctgttcaca tttgtgcaag tgatgatatg tgtggtctgg ctttacaatg   2460
ctcctccggc gagctacagg aaccatgaca ttgatgagat aattttcatt acatgcaatg   2520
agggctctat gatggcgctt ggcttcctaa ttgggtacac atgcctgctg gcagccatat   2580
gcttcttctt tgcatttaaa tcacgaaaac tgccagagaa ctttactgag gctaagttca   2640
tcaccttcag catgctcatc ttcttcatcg tctggatctc tttcatccct gcctacttca   2700
gcacttacgg aaagtttgtg tcggctgtgg aggtcatcgc catactagcc tccagctttg   2760
gcctgctggc ctgtattttc ttcaataaag tctacatcat cctcttcaaa ccgtccagga   2820
acactataga ggaggttcgc tgtagcactg cggcccattc tttcaaagtg gcagccaagg   2880
ccactctgag acacagctca gcctccagga agaggtccag cagtgtgggg ggatcctgtg   2940
cctcaactcc ctcctcatcc atcagcctca agaccaatga caatgactcc ccatcaggtc   3000
agcagagaat ccataagcca agagtaagct ttggaagtgg aacagttact ctgtccttga   3060
gctttgagga gtccagaaag aattctatga agtagggaag tgtcttttgg tgggccgaga   3120
```

-continued

```
gccttgtcaa aacctgagtt ggtgttgcat tctttgttgg ctgggtagtt ggagcagaaa   3180

ttatgatatt aaaagctttg atgtattcag aatggtgaca cagcataggt ggccaagatt   3240

ccattatatt acaataatct gtgttgttca ttatgaggac atttcaaaat gctgaaaatc   3300

atcaaataca taatttactg agttttcttg ataatcttga gaatagaata gcctattcaa   3360

gtcatcgttg agcagacatt aattaacaat gatgtaatac tttccatacc tattttcttt   3420

aacaatagat tcacattgtt aaagttcaac tatgacctgt aaaatacatg aggtataaca   3480

ggagacaata aaactatgca tatcctagct tctgggcctg agtagcaggc agtttactct   3540

gggcacgctt ttcatccaaa cttccgaatg ctgcccccaa tcctagtgag gttaaaggcc   3600

cagtgcagtc atatcttttc tctaggcacg cttttcatcc aaacttccga atgcggctat   3660

atcagtctct ttcctactgt ctttttcatt aggccagtgt ttaacaaccc tggtccttaa   3720

gtacacacaa cagagcacat ttttgttgta gccctggaca atcactcctc actcagctca   3780

ttgagggcct gatgattagt tgacaagttg agtcgggtgt gcttgtccag ggttacgata   3840

cagatgtgta ctgttggggg tgctcgagga ccaggattgg gaaacattac attaggacta   3900

ctgtaggttc ttcaatatgg tgtcatacgg tcatatggtg tcatatggtg tctggttgtt   3960

ttctgcatat gtgtatttca ccaagttact gcacatgtta gacctataca ctggaataaa   4020

catttttttt c                                                        4031
```

```
<210> SEQ ID NO 10
<211> LENGTH: 941
<212> TYPE: PRT
<213> ORGANISM: Salmo salar

<400> SEQUENCE: 10

Met Arg Phe Tyr Leu Tyr Tyr Leu Val Leu Leu Gly Phe Ser Ser Val
1               5                   10                  15

Ile Ser Thr Tyr Gly Pro His Gln Arg Ala Gln Lys Thr Gly Asp Ile
            20                  25                  30

Leu Leu Gly Gly Leu Phe Pro Met His Phe Gly Val Thr Ser Lys Asp
        35                  40                  45

Gln Asp Leu Ala Ala Arg Pro Glu Ser Thr Glu Cys Val Arg Tyr Asn
    50                  55                  60

Phe Arg Gly Phe Arg Trp Leu Gln Ala Met Ile Phe Ala Ile Glu Glu
65                  70                  75                  80

Ile Asn Asn Ser Ser Thr Leu Leu Pro Asn Ile Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Thr Asp His Ile Pro Ser Thr Ile Ala Val Val Gly Ala
    130                 135                 140

Ser Gly Ser Ala Val Ser Thr Ala Val Ala Asn Leu Leu Gly Leu Phe
145                 150                 155                 160

Tyr Ile Pro Gln Ile Ser Tyr Ala Ser Ser Ser Arg Leu Leu Ser Asn
                165                 170                 175

Lys Asn Gln Phe Lys Ser Phe Met Arg Thr Ile Pro Thr Asp Glu His
            180                 185                 190

Gln Ala Thr Ala Met Ala Asp Ile Ile Asp Tyr Phe Gln Trp Asn Trp
        195                 200                 205
```

-continued

```
Val Ile Ala Val Ala Ser Asp Asp Glu Tyr Gly Arg Pro Gly Ile Glu
    210                 215                 220

Lys Phe Glu Lys Glu Met Glu Glu Arg Asp Ile Cys Ile His Leu Ser
225                 230                 235                 240

Glu Leu Ile Ser Gln Tyr Phe Glu Glu Trp Gln Ile Gln Gly Leu Val
                245                 250                 255

Gly Arg Ile Glu Asn Ser Ser Ala Lys Val Ile Val Val Phe Ala Ser
            260                 265                 270

Gly Pro Asp Ile Glu Pro Leu Ile Lys Glu Met Val Arg Arg Asn Ile
        275                 280                 285

Thr Asp Arg Ile Trp Leu Ala Ser Glu Ala Trp Ala Thr Thr Ser Leu
    290                 295                 300

Ile Ala Lys Pro Glu Tyr Leu Asp Val Val Val Gly Thr Ile Gly Phe
305                 310                 315                 320

Ala Leu Arg Ala Gly Glu Ile Pro Gly Phe Lys Asp Phe Leu Gln Glu
                325                 330                 335

Val Thr Pro Lys Lys Ser Ser His Asn Glu Phe Val Arg Glu Phe Trp
            340                 345                 350

Glu Glu Thr Phe Asn Cys Tyr Leu Glu Asp Ser Gln Arg Leu Arg Asp
        355                 360                 365

Ser Glu Asn Gly Ser Thr Ser Phe Arg Pro Leu Cys Thr Gly Glu Glu
    370                 375                 380

Asp Ile Met Gly Ala Glu Thr Pro Tyr Leu Asp Tyr Thr His Leu Arg
385                 390                 395                 400

Ile Ser Tyr Asn Val Tyr Val Ala Val His Ser Ile Ala Gln Ala Leu
                405                 410                 415

Gln Asp Ile Leu Thr Cys Ile Pro Gly Arg Gly Leu Phe Ser Asn Asn
            420                 425                 430

Ser Cys Ala Asp Ile Lys Lys Ile Glu Ala Trp Gln Val Leu Lys Gln
        435                 440                 445

Leu Arg His Leu Asn Phe Ser Asn Ser Met Gly Glu Lys Val His Phe
    450                 455                 460

Asp Glu Asn Ala Asp Pro Ser Gly Asn Tyr Thr Ile Ile Asn Trp His
465                 470                 475                 480

Arg Ser Pro Glu Asp Gly Ser Val Val Phe Glu Glu Val Gly Phe Tyr
                485                 490                 495

Asn Met Arg Ala Lys Arg Gly Val Gln Leu Phe Ile Asp Asn Thr Lys
            500                 505                 510

Ile Leu Trp Asn Gly Tyr Asn Thr Glu Val Pro Phe Ser Asn Cys Ser
        515                 520                 525

Glu Asp Cys Glu Pro Gly Thr Arg Lys Gly Ile Ile Glu Ser Met Pro
    530                 535                 540

Thr Cys Cys Phe Glu Cys Thr Glu Cys Ser Glu Gly Glu Tyr Ser Asp
545                 550                 555                 560

His Lys Asp Ala Ser Val Cys Thr Lys Cys Pro Asn Asp Ser Trp Ser
                565                 570                 575

Asn Glu Asn His Thr Ser Cys Phe Leu Lys Glu Ile Glu Phe Leu Ser
            580                 585                 590

Trp Thr Glu Pro Phe Gly Ile Ala Leu Ala Leu Cys Ser Val Leu Gly
        595                 600                 605

Val Phe Leu Thr Ala Phe Val Met Gly Val Phe Ile Lys Phe Arg Asn
    610                 615                 620
```

-continued

```
Thr Pro Ile Val Lys Ala Thr Asn Arg Glu Leu Ser Tyr Leu Leu Leu
625                 630                 635                 640

Phe Ser Leu Ile Cys Cys Phe Ser Ser Ser Leu Ile Phe Ile Gly Glu
                645                 650                 655

Pro Gln Asp Trp Thr Cys Arg Leu Arg Gln Pro Ala Phe Gly Ile Ser
            660                 665                 670

Phe Val Leu Cys Ile Ser Cys Ile Leu Val Lys Thr Asn Arg Val Leu
        675                 680                 685

Leu Val Phe Glu Ala Lys Ile Pro Thr Ser Leu His Arg Lys Trp Trp
    690                 695                 700

Gly Leu Asn Leu Gln Phe Leu Leu Val Phe Leu Phe Thr Phe Val Gln
705                 710                 715                 720

Val Met Ile Cys Val Val Trp Leu Tyr Asn Ala Pro Pro Ala Ser Tyr
                725                 730                 735

Arg Asn His Asp Ile Asp Glu Ile Ile Phe Ile Thr Cys Asn Glu Gly
            740                 745                 750

Ser Met Met Ala Leu Gly Phe Leu Ile Gly Tyr Thr Cys Leu Leu Ala
        755                 760                 765

Ala Ile Cys Phe Phe Phe Ala Phe Lys Ser Arg Lys Leu Pro Glu Asn
    770                 775                 780

Phe Thr Glu Ala Lys Phe Ile Thr Phe Ser Met Leu Ile Phe Phe Ile
785                 790                 795                 800

Val Trp Ile Ser Phe Ile Pro Ala Tyr Phe Ser Thr Tyr Gly Lys Phe
                805                 810                 815

Val Ser Ala Val Glu Val Ile Ala Ile Leu Ala Ser Ser Phe Gly Leu
            820                 825                 830

Leu Ala Cys Ile Phe Phe Asn Lys Val Tyr Ile Ile Leu Phe Lys Pro
        835                 840                 845

Ser Arg Asn Thr Ile Glu Glu Val Arg Cys Ser Thr Ala Ala His Ser
    850                 855                 860

Phe Lys Val Ala Ala Lys Ala Thr Leu Arg His Ser Ser Ala Ser Arg
865                 870                 875                 880

Lys Arg Ser Ser Ser Val Gly Gly Ser Cys Ala Ser Thr Pro Ser Ser
                885                 890                 895

Ser Ile Ser Leu Lys Thr Asn Asp Asn Asp Ser Pro Ser Gly Gln Gln
            900                 905                 910

Arg Ile His Lys Pro Arg Val Ser Phe Gly Ser Gly Thr Val Thr Leu
        915                 920                 925

Ser Leu Ser Phe Glu Glu Ser Arg Lys Asn Ser Met Lys
    930                 935                 940
```

<210> SEQ ID NO 11
<211> LENGTH: 3824
<212> TYPE: DNA
<213> ORGANISM: Salmo salar

<400> SEQUENCE: 11

```
gttccaacag catatttttg ttgtatttgc tttggtttgt ctgaaatcaa gcattatcaa      60

gatcaagaac agcatgagtc agaaacaagg cgacagccag agtcactgga ggggacaaga     120

ctgaggttaa ctctgaagtc taatgtgctg agaggacaag gccctcctga gagctgaacg     180

atgagatttt acctgtatta cctggtgctt ttgggcttca gttctgtcat ctccacctat     240

gggcctcatc agagagcaca gaagactggg gatattctgc tgggcgggct gtttccaatg     300

cactttggtg ttacctccaa agaccaagac ctggcagcgc ggccagaatc cacagagtgt     360
```

-continued

```
gttaggtaca atttccgggg attccgttgg cttcaggcca tgatttttgc aatagaggag    420
atcaacaaca gcagtactct cctgcccaac atcacactgg gctacaggat ctttgacacc    480
tgcaacaccg tgtccaaggc cctggaggct accctcagtt tcgtagcaca gaataagatt    540
gactctctga acttggatga attctgtaac tgcactgatc acatcccatc gactatagca    600
gtggtggggg cttctgggtc agcggtctcc actgctgttg ccaatctgtt gggccttttc    660
tacatcccac agatcagcta tgcctcttcc agtcgcctac taagcaacaa gaaccagttc    720
aaatccttca tgaggaccat tcccacagat gagcaccagg ccactgccat ggcagatatc    780
atcgactact tccaatggaa ttgggtcatt gcagttgcgt ctgatgatga gtatggacgt    840
ccggggattg aaaaatttga gaaagagatg gaagaacgag acatttgtat ccatctgagt    900
gagctgatct ctcagtactt tgaggagtgg cagatccaag gattggttga ccgtattgag    960
aactcctcag ctaaagttat agtcgttttc gccagtgggc ctgacattga gcctcttatt   1020
aaagagatgg tcagacggaa catcaccgac cgcatctggt tggccagcga ggcttgggca   1080
accacctccc tcatcgccaa accagagtac cttgatgttg tagttgggac cattggcttt   1140
gctctcagag caggcgaaat acctggcttc aaggacttct tacaagaggt cacaccaaag   1200
aaatccagcc acaatgaatt tgtcagggag ttttgggagg agacttttaa ctgctatctg   1260
gaagacagcc agagactgag agacagtgag aatgggagca ccagtttcag accattgtgt   1320
actggcgagg aggacattat gggtgcagag accccatatc tggattacac tcatcttcgt   1380
atttcctata atgtgtatgt tgcagttcac tccattgcac aggccctaca ggacattctc   1440
acctgcattc ctggacgggg tttttttcc aacaactcat gtgcagatat aaagaaaata   1500
gaagcatggc aggttctcaa gcagctcaga catttaaact tctcaaacag tatgggagaa   1560
aaggtacatt ttgatgagaa tgctgatccg tcaggaaact acaccattat caattggcac   1620
cggtctcctg aggatggttc tgttgtgttt gaagaggtcg gtttctacaa catgcgagct   1680
aagagaggag tacaactttt cattgataac acaaagattc tatggaatgg atataatact   1740
gaggttccat tctctaactg tagtgaagat tgtgaaccag gcaccagaaa ggggatcata   1800
gaaagcatgc caacgtgttg ctttgaatgt acagaatgct cagaaggaga gtatagtgat   1860
cacaaagatg ccagtgtttg taccaagtgt cccaatgact catggtctaa tgagaaccac   1920
acatcttgtt tcctgaagga gatagagttt ctgtcttgga cagagccctt tgggatcgcc   1980
ttggcattat gctctgtgct gggggtattc ttgacagcat tcgtgatggg agtgtttatc   2040
aaatttcgca acaccccaat tgttaaggcc acaaacagag agctatccta cctcctcctg   2100
ttctcactca tctgctgttt ctccagttcc ctcatcttca ttggtgaacc ccaggactgg   2160
acatgccgtc tacgccagcc tgcattcggg ataagttttg ttctctgcat ctcctgcatc   2220
ctggtaaaaa ctaaccgagt acttctagtg ttcgaagcca agatccccac cagtctccat   2280
cgtaagtggt gggggctaaa cttgcagttc ctgttagtgt tcctgttcac atttgtgcaa   2340
gtgatgatat gtgtggtctg gctttacaat gctcctccgg cgagctacag gaaccatgac   2400
attgatgaga taattttcat tacatgcaat gagggctcta tgatggcgct tggcttccta   2460
attgggtaca catgcctgct ggcagccata tgcttcttct ttgcatttaa atcacgaaaa   2520
ctgccagaga actttactga ggctaagttc atcaccttca gcatgctcat cttcttcatc   2580
gtctggatct ctttcatccc tgcctacttc agcacttacg gaaagtttgt gtcggctgtg   2640
gaggtcatcg ccatactagc ctccagcttt ggcctgctgg cctgtatttt cttcaataaa   2700
```

-continued

```
gtctacatca tccatcagcc tcaagaccaa tgacaatgac tccccatcag gtcagcagag   2760

aatccataag ccaagagtaa gctttggaag tggaacagtt actctgtcct tgagctttga   2820

ggagtccaga aagaattcta tgaagtaggg aagtgtcttt tggtgggccg agagccttgt   2880

caaaacctga gttggtgttg cattctttgt tggctgggta gttggagcag aaattatgat   2940

attaaaagct ttgatgtatt cagaatggtg acacagcata ggtggccaag attccattat   3000

attacaataa tctgtgttgt tcattatgag gacatttcaa aatgctgaaa atcatcaaat   3060

acataattta ctgagttttc ttgataatct tgagaataga atagcctatt caagtcatcg   3120

ttgagcagac attaattaac aatgatgtaa tactttccat acctattttc tttaacaata   3180

gattcacatt gttaaagttc aactatgacc tgtaaaatac atgaggtata acaggagaca   3240

ataaaactat gcatatccta gcttctgggc ctgagtagca ggcagtttac tctgggcacg   3300

cttttcatcc aaacttccga atgctgcccc caatcctagt gaggttaaag gcccagtgca   3360

gtcatatctt ttctctaggc acgcttttca tccaaacttc cgaatgcggc tatatcagtc   3420

tctttcctac tgtctttttc attaggccag tgtttaacaa ccctggtcct tgagtacaca   3480

caacagggca catttttgtt gtagccctgg acaatcactc ctcactcagc tcattgaggg   3540

cctgatgatt agttgacaag ttgggtcagg tgtgcttgtc cagggttaca atacagatgt   3600

gtgctgttgg gggtactcga ggaccaggat tgggaaacat tacattagga ctactgtagg   3660

ttcttcaata tggtgtcata cggtcatatg gtgtcatatg gtgtctggtt gttttctgca   3720

tatgtgtatt tcaccaagtt actgcacatg ttagacctat acactggaat aaacattttt   3780

tttcacaatg catccaatga caataaaatc accatatgcc aatg                      3824
```

```
<210> SEQ ID NO 12
<211> LENGTH: 850
<212> TYPE: PRT
<213> ORGANISM: Salmo salar

<400> SEQUENCE: 12

Met Arg Phe Tyr Leu Tyr Tyr Leu Val Leu Leu Gly Phe Ser Ser Val
1               5                   10                  15

Ile Ser Thr Tyr Gly Pro His Gln Arg Ala Gln Lys Thr Gly Asp Ile
            20                  25                  30

Leu Leu Gly Gly Leu Phe Pro Met His Phe Gly Val Thr Ser Lys Asp
        35                  40                  45

Gln Asp Leu Ala Ala Arg Pro Glu Ser Thr Glu Cys Val Arg Tyr Asn
    50                  55                  60

Phe Arg Gly Phe Arg Trp Leu Gln Ala Met Ile Phe Ala Ile Glu Glu
65                  70                  75                  80

Ile Asn Asn Ser Ser Thr Leu Leu Pro Asn Ile Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Thr Asp His Ile Pro Ser Thr Ile Ala Val Val Gly Ala
    130                 135                 140

Ser Gly Ser Ala Val Ser Thr Ala Val Ala Asn Leu Leu Gly Leu Phe
145                 150                 155                 160

Tyr Ile Pro Gln Ile Ser Tyr Ala Ser Ser Ser Arg Leu Leu Ser Asn
                165                 170                 175
```

-continued

```
Lys Asn Gln Phe Lys Ser Phe Met Arg Thr Ile Pro Thr Asp Glu His
            180                 185                 190

Gln Ala Thr Ala Met Ala Asp Ile Ile Asp Tyr Phe Gln Trp Asn Trp
        195                 200                 205

Val Ile Ala Val Ala Ser Asp Asp Glu Tyr Gly Arg Pro Gly Ile Glu
    210                 215                 220

Lys Phe Glu Lys Glu Met Glu Glu Arg Asp Ile Cys Ile His Leu Ser
225                 230                 235                 240

Glu Leu Ile Ser Gln Tyr Phe Glu Glu Trp Gln Ile Gln Gly Leu Val
                245                 250                 255

Asp Arg Ile Glu Asn Ser Ser Ala Lys Val Ile Val Val Phe Ala Ser
            260                 265                 270

Gly Pro Asp Ile Glu Pro Leu Ile Lys Glu Met Val Arg Arg Asn Ile
        275                 280                 285

Thr Asp Arg Ile Trp Leu Ala Ser Glu Ala Trp Ala Thr Thr Ser Leu
    290                 295                 300

Ile Ala Lys Pro Glu Tyr Leu Asp Val Val Val Gly Thr Ile Gly Phe
305                 310                 315                 320

Ala Leu Arg Ala Gly Glu Ile Pro Gly Phe Lys Asp Phe Leu Gln Glu
                325                 330                 335

Val Thr Pro Lys Lys Ser Ser His Asn Glu Phe Val Arg Glu Phe Trp
            340                 345                 350

Glu Glu Thr Phe Asn Cys Tyr Leu Glu Asp Ser Gln Arg Leu Arg Asp
        355                 360                 365

Ser Glu Asn Gly Ser Thr Ser Phe Arg Pro Leu Cys Thr Gly Glu Glu
    370                 375                 380

Asp Ile Met Gly Ala Glu Thr Pro Tyr Leu Asp Tyr Thr His Leu Arg
385                 390                 395                 400

Ile Ser Tyr Asn Val Tyr Val Ala Val His Ser Ile Ala Gln Ala Leu
                405                 410                 415

Gln Asp Ile Leu Thr Cys Ile Pro Gly Arg Gly Phe Phe Ser Asn Asn
            420                 425                 430

Ser Cys Ala Asp Ile Lys Lys Ile Glu Ala Trp Gln Val Leu Lys Gln
        435                 440                 445

Leu Arg His Leu Asn Phe Ser Asn Ser Met Gly Glu Lys Val His Phe
    450                 455                 460

Asp Glu Asn Ala Asp Pro Ser Gly Asn Tyr Thr Ile Ile Asn Trp His
465                 470                 475                 480

Arg Ser Pro Glu Asp Gly Ser Val Val Phe Glu Glu Val Gly Phe Tyr
                485                 490                 495

Asn Met Arg Ala Lys Arg Gly Val Gln Leu Phe Ile Asp Asn Thr Lys
            500                 505                 510

Ile Leu Trp Asn Gly Tyr Asn Thr Glu Val Pro Phe Ser Asn Cys Ser
        515                 520                 525

Glu Asp Cys Glu Pro Gly Thr Arg Lys Gly Ile Ile Glu Ser Met Pro
    530                 535                 540

Thr Cys Cys Phe Glu Cys Thr Glu Cys Ser Glu Gly Glu Tyr Ser Asp
545                 550                 555                 560

His Lys Asp Ala Ser Val Cys Thr Lys Cys Pro Asn Asp Ser Trp Ser
                565                 570                 575

Asn Glu Asn His Thr Ser Cys Phe Leu Lys Glu Ile Glu Phe Leu Ser
            580                 585                 590

Trp Thr Glu Pro Phe Gly Ile Ala Leu Ala Leu Cys Ser Val Leu Gly
```

-continued

```
        595                 600                 605

Val Phe Leu Thr Ala Phe Val Met Gly Val Phe Ile Lys Phe Arg Asn
    610                 615                 620

Thr Pro Ile Val Lys Ala Thr Asn Arg Glu Leu Ser Tyr Leu Leu Leu
625                 630                 635                 640

Phe Ser Leu Ile Cys Cys Phe Ser Ser Ser Leu Ile Phe Ile Gly Glu
                645                 650                 655

Pro Gln Asp Trp Thr Cys Arg Leu Arg Gln Pro Ala Phe Gly Ile Ser
            660                 665                 670

Phe Val Leu Cys Ile Ser Cys Ile Leu Val Lys Thr Asn Arg Val Leu
        675                 680                 685

Leu Val Phe Glu Ala Lys Ile Pro Thr Ser Leu His Arg Lys Trp Trp
    690                 695                 700

Gly Leu Asn Leu Gln Phe Leu Leu Val Phe Leu Phe Thr Phe Val Gln
705                 710                 715                 720

Val Met Ile Cys Val Val Trp Leu Tyr Asn Ala Pro Pro Ala Ser Tyr
                725                 730                 735

Arg Asn His Asp Ile Asp Glu Ile Ile Phe Ile Thr Cys Asn Glu Gly
            740                 745                 750

Ser Met Met Ala Leu Gly Phe Leu Ile Gly Tyr Thr Cys Leu Leu Ala
        755                 760                 765

Ala Ile Cys Phe Phe Phe Ala Phe Lys Ser Arg Lys Leu Pro Glu Asn
    770                 775                 780

Phe Thr Glu Ala Lys Phe Ile Thr Phe Ser Met Leu Ile Phe Phe Ile
785                 790                 795                 800

Val Trp Ile Ser Phe Ile Pro Ala Tyr Phe Ser Thr Tyr Gly Lys Phe
                805                 810                 815

Val Ser Ala Val Glu Val Ile Ala Ile Leu Ala Ser Ser Phe Gly Leu
            820                 825                 830

Leu Ala Cys Ile Phe Phe Asn Lys Val Tyr Ile Ile His Gln Pro Gln
        835                 840                 845

Asp Gln
    850


<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13

tgtcktggac ggagccctty ggratcgc                                          28


<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14

ggckggratg aargakatcc aracratgaa g                                      31


<210> SEQ ID NO 15
<211> LENGTH: 16
<212> TYPE: PRT
<213> ORGANISM: Artificial Sequence
```

-continued

<220> FEATURE:
<223> OTHER INFORMATION: peptide for Sal-1 antibody production

<400> SEQUENCE: 15

Cys Thr Asn Asp Asn Asp Ser Pro Ser Gly Gln Gln Arg Ile His Lys
1 5 10 15

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
caagcattat caagatcaag 20

<210> SEQ ID NO 17
<211> LENGTH: 17
<212> TYPE: DNA
<213> ORGANISM: Artificial Sequence
<220> FEATURE:
<223> OTHER INFORMATION: primer

<400> SEQUENCE: 17
ctcagagtgg ccttggc 17

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
cagttctctc tttaatggac 20

<210> SEQ ID NO 19
<211> LENGTH: 17
<212> TYPE: DNA
<213> ORGANISM: Artificial Sequence
<220> FEATURE:
<223> OTHER INFORMATION: primer

<400> SEQUENCE: 19
ctcagagtgg ccttggc 17

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
agtctacatc atccatcagc c 21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gattttattg tcattggatg c 21

-continued

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
tggaagatga aatcgccgc 19

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
gtggtggtga aactgtaacc gc 22

<210> SEQ ID NO 24
<211> LENGTH: 23
<212> TYPE: PRT
<213> ORGANISM: Artificial Sequence
<220> FEATURE:
<223> OTHER INFORMATION: peptide for 4641 antibody production

<400> SEQUENCE: 24

```
Ala Asp Asp Asp Tyr Gly Arg Pro Gly Ile Glu Lys Phe Arg Glu Glu
1               5                   10                  15

Ala Glu Glu Arg Asp Ile Cys
            20
```

<210> SEQ ID NO 25
<211> LENGTH: 22
<212> TYPE: PRT
<213> ORGANISM: Artificial Sequence
<220> FEATURE:
<223> OTHER INFORMATION: peptide for 4641 antibody production

<400> SEQUENCE: 25

```
Asp Asp Tyr Gly Arg Pro Gly Ile Glu Lys Phe Arg Glu Glu Ala Glu
1               5                   10                  15

Glu Arg Asp Ile Cys Ile
            20
```

<210> SEQ ID NO 26
<211> LENGTH: 17
<212> TYPE: PRT
<213> ORGANISM: Artificial Sequence
<220> FEATURE:
<223> OTHER INFORMATION: peptide for SKCaR antibody production

<400> SEQUENCE: 26

```
Ala Arg Ser Arg Asn Ser Ala Asp Gly Arg Ser Gly Asp Asp Leu Pro
1               5                   10                  15

Cys
```

<210> SEQ ID NO 27
<211> LENGTH: 18
<212> TYPE: PRT
<213> ORGANISM: Artificial Sequence
<220> FEATURE:
<223> OTHER INFORMATION: peptide for Sal-ADD antibody production -continued

<400> SEQUENCE: 27

```
Cys Ser Asp Asp Glu Tyr Gly Arg Pro Gly Ile Glu Lys Phe Glu Lys
1               5                   10                  15

Glu Met
```

<210> SEQ ID NO 28
<211> LENGTH: 1078
<212> TYPE: PRT
<213> ORGANISM: Homo sapiens

<400> SEQUENCE: 28

```
Met Ala Phe Tyr Ser Cys Cys Trp Val Leu Leu Ala Leu Thr Trp His
1               5                   10                  15

Thr Ser Ala Tyr Ser Pro Ser Gln Pro Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Cys Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Met Val Val
                245                 250                 255

Glu Val Ile Gln Asn Ser Thr Ala Lys Val Ile Val Val Phe Ser Ser
            260                 265                 270

Gly Pro Asp Leu Glu Pro Leu Ile Lys Glu Ile Val Pro Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335
```

-continued

```
Val His Pro Pro Lys Ser Val Asn Asn Gly Phe Ala Lys Glu Phe Trp
            340                 345                 350

Glu Glu Thr Phe Met Cys His Leu Gln Glu Gly Ala Lys Gly Pro Leu
        355                 360                 365

Pro Val Asp Thr Phe Leu Ala Gly His Glu Glu Ser Gly Asp Arg Phe
    370                 375                 380

Ser Asn Ser Ser Thr Ala Phe Pro Pro Leu Cys Thr Gly Asp Glu Asn
385                 390                 395                 400

Ile Ser Ser Val Glu Thr Pro Tyr Ile Asp Tyr Thr Asn Leu Arg Ile
                405                 410                 415

Ser Tyr Asn Val Tyr Leu Ala Val Tyr Ser Ile Ala Asn Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
    450                 455                 460

Arg Asn Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
        595                 600                 605

Thr Glu Pro Phe Gly Ile Ala Leu Thr Leu Phe Ala Val Leu Gly Ile
    610                 615                 620

Ser Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
        675                 680                 685

Val Leu Cys Ile Ser Cys Ile Leu Val Lys Thr Asn Arg Val Leu Leu
    690                 695                 700

Val Phe Glu Ala Lys Ile Pro Thr Ser Phe Met Phe Lys Trp Trp Gly
705                 710                 715                 720

Leu Asn Leu Gln Phe Leu Leu Val Phe Leu Cys Thr Phe Asn Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys Asn Glu Gly
```

-continued

```
        755                 760                 765

Ser Leu Met Ala Leu Gly Phe Leu Ile Gly Tyr Thr Cys Leu Leu Ala
    770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
        835                 840                 845

Leu Ala Cys Ile Phe Phe Asn Lys Ile Tyr Ile Ile Leu Phe Lys Pro
    850                 855                 860

Ser Arg Asn Thr Ile Glu Glu Val Arg Cys Ser Thr Ala Ala Asn Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Arg Pro Glu
        915                 920                 925

Arg Gln Lys Gln Gln Gln Pro Leu Ala Leu Thr Gln Gln Glu Gln Gln
    930                 935                 940

Gln Gln Pro Leu Thr Leu Pro Gln Gln Gln Arg Ser Gln Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala Asn Arg Asn Ser
            980                 985                 990

Thr Asn Gln Asn Ser Leu Glu Ala  Gln Lys Ser Ser Asp  Thr Leu Thr
        995                 1000                1005

Ala Asn  Gln Pro Leu Leu Pro  Leu Gln Cys Gly Glu  Thr Asp Leu
    1010                1015                1020

Asp Leu  Thr Val Gln Glu Thr  Gly Leu Gln Gly Pro  Val Gly Gly
    1025                1030                1035

Asp Gln  Arg Pro Glu Val Glu  Asp Pro Glu Glu Leu  Ser Pro Ala
    1040                1045                1050

Leu Val  Val Ser Ser Ser Gln  Ser Phe Val Ile Ser  Gly Gly Gly
    1055                1060                1065

Ser Thr  Val Thr Glu Asn Val  Val Asn Ser
    1070                1075
```

POLYVALENT CATION-SENSING RECEPTOR IN ATLANTIC SALMON

RELATED APPLICATIONS

This application is a continuation-in-part of U.S. application Ser. No. 10/121,441, filed Apr. 11, 2002, now abandoned, which is a continuation-in-part of International Application No. PCT/US01/31704, which designated the United States and was filed on Oct. 11, 2001, not yet published, which claims the benefit of U.S. Provisional Application No. 60/240,392, filed on Oct. 12, 2000, and U.S. Provisional Application No. 60/240,003, filed on Oct. 12, 2000. The entire teachings of the above applications are incorporated herein by reference.

BACKGROUND OF THE INVENTION

In nature, anadromous fish like salmon live most of their adulthood in seawater, but swim upstream to freshwater for the purpose of breeding. As a result, anadromous fish hatch from their eggs and are born in freshwater. As these fish grow, they swim downstream and gradually adapt to the seawater.

Currently, wild Atlantic salmon are classified as endangered species in multiple areas of their native habitats. Among the reasons for their decline has been man made alterations in freshwater conditions in their native streams that have produced multiple problems with their migration, spawning, smoltification and survival. One problem complicating the effective restoration of wild Atlantic salmon is the lack of a fundamental understanding of how these deleterious environmental conditions effect the salmon's ability to home to freshwater streams from the ocean, interchangeably adapt to freshwater and seawater as well as feed and grow in both salinity environments.

Despite the decline of wild populations, the global aquaculture industry has utilized Atlantic salmon as one of chief fish species for large-scale marine farming operations. At the present time, large scale breeding programs of Atlantic salmon provide for high quality fish used in production by selection of specific traits among them rapid growth, seawater adaptability, flesh quality and taste.

However, fish hatcheries have experienced some difficulty in raising salmon because the window of time in which the pre-adult salmon adapts to seawater (e.g., undergoes smoltification) is short-lived, and can be difficult to pinpoint. As a result, these hatcheries can experience significant morbidity and mortality when transferring salmon from freshwater to seawater. Additionally, many of the salmon that do survive the transfer from freshwater to seawater are stressed, and consequently, experience decreased feeding, and increased susceptibility to disease. Therefore, salmon often do not grow well after they are transferred to seawater.

The aquaculture industry loses millions of dollars each year due to problems it encounters in transferring salmon from freshwater to seawater. Therefore, a need exists to gain a better understanding of the biological processes of salmon that are related to smoltification and adaptation to varying salinities, including seawater. In particular, a need exists to identify genes that play an important role in these areas.

SUMMARY OF THE INVENTION

The present invention relates to genes that allow fish to sense and adapt to ion concentrations in the surrounding environment. Modulating one or more of these genes allow anadromous fish like salmon to better adapt to seawater during smoltification, which in turn allows salmon to grow faster and stronger after transfer to seawater. A gene, called a PolyValent Cation-sensing Receptor (PVCR), has been isolated in several species of fish, and in particular, in Atlantic Salmon. In fact, three forms of the PVCR have been isolated in Atlantic Salmon, and have been termed, "SalmoKCaR" genes and individually referred to as "SalmoKCaR#1", "SalmoKCaR#2" and "SalmoKCaR#3". "PVCR" and "SalmoKCaR" are used interchangeably when referring to Atlantic Salmon. These three genes work together to alter the salmon's sensitivity to the surrounding ion concentrations, as further described herein.

The invention embodies nucleic acid molecules (e.g., RNA, genomic DNA and cDNA) having nucleic acid sequences of SalmoKCaR#1 (SEQ ID NO: 7), SalmoKCaR#2 (SEQ ID NO: 9), or SalmoKCaR#3 (SEQ ID NO: 11). The invention also embodies polypeptide molecules having amino acid sequences of SalmoKCaR#1 (SEQ ID NO: 8), SalmoKCaR#2 (SEQ ID NO: 10), or SalmoKCaR#3 (SEQ ID NO: 12). The present invention, in particular, encompasses isolated nucleic acid molecules having nucleic acid sequences of SEQ ID NO: 7, 9, or 11; the complementary strand thereof; the coding region of SEQ ID NO: 7, 9, or 11; or the complementary strand thereof. The present invention also embodies nucleic acid molecules that encode polypeptides having an amino acid sequence of SEQ ID NO: 8, 10, or 12. The present invention, in another embodiment, includes isolated polypeptide molecules having amino acid sequences that comprise SEQ ID NO: 8, 10, or 12; or amino acid sequences encoded by the nucleic acid sequence of SEQ ID NO: 7, 9, or 11.

In one embodiment, the present invention pertains to isolated nucleic acid molecules that have a nucleic acid sequence with at least about 70% (e.g., 75%, 80%, 85%, 90%, or 95%) identity with SEQ ID NO: 7, 9, or 11, or the coding region of SEQ ID NO: 7, 9, or 11. Such a nucleic acid sequence encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; altering water intake; altering water absorption; or altering urine output.

The present invention further includes nucleic acid molecules that hybridize with SalmoKCaR#1, SalmoKCaR#2, or SalmoKCaR#3, but not to the Shark Kidney Calcium Receptor Related Protein (SKCaR) nucleic acid sequence. SKCaR is a PVCR isolated from dogfish shark. Specifically, the present invention relates to an isolated nucleic acid molecule that contains a nucleic acid sequence that hybridizes under high stringency conditions to SEQ ID NO: 7, 9, or 11; or the coding region of SEQ ID NO: 7, 9, or 11; but excluding those that hybridize to SEQ ID NO: 1 under the same conditions.

The present invention also includes probes, vectors, viruses, plasmids, and host cells that contain the nucleic acid sequences, as described herein. In particular, the present invention includes probes (e.g., nucleic acid probes or DNA probes) having a sequence from SEQ ID NO: 7, but not SEQ ID NO: 1. The present invention encompasses nucleic acid or peptide molecules purified or obtained from clones deposited with American Type Culture Collection (ATCC), Accession No: PTA-4190, PTA-4191, or PTA-4192.

In another embodiment, the present invention includes isolated polypeptide molecules having at least about 70% (e.g., 75%, 80%, 85%, 90%, or 95%) identity with SEQ ID NO: 8, 10, or 12; or an amino acid sequence encoded by the nucleic acid sequence of SEQ ID NO: 7, 9, or 11. These polypeptide molecules have one or more of the following functions: sensing at least one SalmoKCaR modulator in serum or in the surrounding environment; adapting to at least one SalmoKCaR modulator present in the serum or surrounding environment; imprinting Atlantic Salmon with an odorant; altering water intake; altering water absorption; or altering urine output.

Additionally, the present invention relates to antibodies that specifically bind to or are produced in reaction to polypeptide molecules described herein. The invention further includes fusion proteins that contain one of the polypeptide molecules described herein, and a portion of an immunoglobulin.

The present invention also pertains to assays for determining the presence or absence of a SalmoKCaR in a sample by contacting the sample to be tested with an antibody specific to at least a portion of the SalmoKCaR polypeptide sufficiently to allow formation of a complex between SalmoKCaR and the antibody, and detecting the presence or absence of the complex formation. Another assay for determining the presence or absence of a nucleic acid molecule that encodes SalmoKCaR in a sample involves contacting the sample to be tested with a nucleic acid probe that hybridizes under high stringency conditions to a nucleic acid molecule having a sequence of SEQ ID NO: 7, 9, or 11, sufficiently to allow hybridization between the sample and the probe; and detecting the SalmoKCaR nucleic acid molecule in the sample. Such assay methods also include methods for determining whether a compound is a modulator of SalmoKCaR. These methods include contacting a compound to be tested with a cell that contains SalmoKCaR nucleic acid molecules and/or expresses SalmoKCaR proteins, and determining whether compounds are modulators by measuring the expression level or activity (e.g., phosphorylation, dimerization, proteolysis or intracellular signal transduction) of SalmoKCaR proteins. In one embodiment, one can measure changes that occur in one or more intracellular signal transduction systems that are altered by activation of the expressed proteins coded for by a single or combination of nucleic acids. Such methods can also encompass contacting a compound to be tested with a cell that comprises one or more of SalmoKCaR nucleic acid molecules; and determining the level of expression of said nucleic acid molecule. An increase or decrease in the expression level, as compared to a control, indicates that the compound is a modulator.

Lastly, the present invention relates to transgenic fish encoding a SalmoKCaR polypeptide or having one or more nucleic acid molecules that contain the SalmoKCaR nucleic acid sequence, as described herein.

The present invention allows for a number of advantages, including the ability to more efficiently grow Atlantic Salmon, and in particular, transfer them to seawater with increased growth and reduce mortality. The technology of the present invention also allows for assaying or testing these salmon to determine if they are ready for transfer to seawater, so that they can be transferred at the optimal time. The technology of the present invention provides for the imprinting of salmon with an odorant so that the salmon, once imprinted, can later more easily recognize and/or distinguish the odorant. For example, an attractant that has been used to imprint salmon can be added to feed so that the salmon will consume more feed and grow at a faster rate. A number of additional advantages for the present invention exist and are apparent from the description provided herein.

BRIEF DESCRIPTION OF THE FIGURES

FIGS. 1A–E show the annotated nucleotide sequence (SEQ ID NO: 1) and the deduced amino acids sequence (SEQ ID NO: 2) of SKCaR with the Open Reading Frame (ORF) starting at nucleotide (nt) 439 and ending at 3516.

FIGS. 7A and 7B show an annotated partial nucleotide sequence (SEQ ID NO: 3) and the deduced amino acids sequence (SEQ ID NO: 4) of an Atlantic salmon polyvalent cation-sensing receptor protein.

FIGS. 8A–8C show a second annotated partial nucleotide sequence (SEQ ID NO: 5) and the deduced amino acids sequence (SEQ ID NO: 6) of an Atlantic salmon polyvalent cation-sensing receptor protein.

FIGS. 9A–E show the nucleic acid (SEQ ID NO: 7) and amino acid (SEQ ID NO: 8) sequences of a full length Atlantic Salmon PVCR, SalmoKCaR#1 with the ORF starting at nt 180 and ending at 3005.

FIGS. 10A–E show the nucleic acid (SEQ ID NO: 9) and amino acid (SEQ ID NO: 10) sequences of a full length Atlantic Salmon PVCR, SalmoKCaR#2 with the ORF starting at nt 270 and ending at 3095.

FIGS. 11A–D show the nucleic acid (SEQ ID NO: 11) and amino acid (SEQ ID NO: 12) sequences of a full length Atlantic Salmon PVCR, SalmoKCaR#3 with the ORF starting at nt 181 and ending at 2733.

FIGS. 12A–L are an alignment showing nucleic acid sequences of two partial Atlantic Salmon Clones (SEQ ID NO: 3 and 5), SalmoKCaR#1 (SEQ ID NO: 7), SalmoKCaR#2 (SEQ ID NO: 9), and SalmoKCaR#3 (SEQ ID NO: 11).

FIGS. 13A–C are an alignment showing amino acid sequences of two partial Atlantic Salmon Clones (SEQ ID NO: 4 and 6), SalmoKCaR#1 (SEQ ID NO: 8), SalmoKCaR#2 (SEQ ID NO: 10), and SalmoKCaR#3 (SEQ ID NO: 12).

FIGS. 15A–H are an alignment of the full length nucleic acid sequences of SalmoKCaR#1, 2, and 3 (SEQ ID NO: 7, 9, and 11, respectively). Alignment obtained using Clustal method with weighted residue weight table.

FIGS. 16A–D are an alignment of the full length amino acid sequences of Human Parathyroid Calcium Receptor (HuPCaR) (SEQ ID NO: 28), SKCaR (SEQ ID NO: 2), SalmoKCaR#1 (SEQ ID NO: 8), SalmoKCaR#2 (SEQ ID NO: 10) and SalmoKCaR#3 (SEQ ID NO: 12). Alignment obtained using Clustal method with PAM250 residue weight table.

FIGS. 17A–F are graphical representations comparing six photographs of Reverse Transcriptase Polymerase Chain Reaction (RT-PCR) analysis of freshwater (FIGS. 17B, D and F) and seawater (FIGS. 17A, C and E) adapted Atlantic salmon tissues (gill, nasal lamellae, urinary bladder, kidney, stomach, pyloric caeca, proximal intestine, distal intestine, brain, pituitary gland, olfactory bulb, liver and muscle) using either degenerate PVCR (FIGS. 17A–D) or salmon actin PCR primers (FIGS. 17E, F). Wells 1–14 for FIGS. 17A–F, top row, are designated as follows: ladder, gill, nasal lamellae, urinary bladder, kidney, stomach, pyloric caeca, proximal intestine, distal intestine, brain, pituitary gland, olfactory bulb, liver and muscle, respectively. Wells 1, 2, 7, 9, and 12, bottom row, for FIGS. 17A, C, and E are designated as ladder, water, SalmoKCaR #1, SalmoKCaR#2 and SalmoKCaR#3, respectively, and wells 1, 2, 3, 7, 9, and 12, bottom row, for FIGS. 17B, D, and F are designated as ladder, water, ovary, SalmoKCaR #1, SalmoKCaR#2 and SalmoKCaR#3, respectively.

FIGS. 20A–F are graphical representations comparing six photographs showing RT-PCR analysis of freshwater (FIGS. 20B, D and F) and seawater (FIGS. 20A, C and E) adapted Atlantic salmon tissues using either SalmoKCaR #3 specific PCR (FIGS. 20A–D) primers or salmon actin PCR primers (FIGS. 20E,F). Wells 1–14 for FIGS. 20A–F, top row, are designated as follows: ladder, gill, nasal lamellae, urinary bladder, kidney, stomach, pyloric caeca, proximal intestine, distal intestine, brain, pituitary gland, olfactory bulb, liver and muscle, respectively. Wells 1, 2, 8, 11, and 14, bottom row, for FIGS. 20A, C, and E are designated as ladder, water, SalmoKCaR #1, SalmoKCaR#2 and SalmoKCaR#3, respectively, and wells 1, 2, 3, 8, 11, and 14, bottom row, for FIGS. 20B, D, and F are designated as ladder, water, ovary, SalmoKCaR #1, SalmoKCaR#2 and SalmoKCaR#3, respectively.

FIGS. 21A–F are graphical representations comparing six photographs showing RT-PCR analysis of freshwater (FIGS. 21B, D and F) and seawater (FIGS. 21A, C and E) adapted Atlantic salmon tissues using either SalmoKCaR #1 specific PCR primers or salmon actin PCR primers. Wells 1–14 for FIGS. 21A–F, top row, are designated as follows: ladder, gill, nasal lamellac, urinary bladder, kidney, stomach, pyloric caeca, proximal intestine, distal intestine, brain, pituitary gland, olfactory bulb, liver and muscle, respectively. Wells 1, 2, 3, 5, 6, and 7. bottom row, for FIGS. 21A, C, and E are designated as ladder, water, Kidney-RT, SalmoKCaR #1, SalmoKCaR#2 and SalmoKCaR#3, respectively, and wells 1, 2, 3, 5, 6, and 7, bottom row, for FIGS. 21B, D, and F are designated as ladder, water, ovary, SalmoKCaR #1, SalmoKCaR#2 and SalmoKCaR#3, respectively.

FIGS. 22A–F are graphical representations comparing six photographs showing RT-PCR analysis of freshwater (FIGS. 22B, D and F) and seawater (FIGS. 22A, C and E) adapted Atlantic salmon tissues using either SalmoKCaR #2 specific PCR primers (FIGS. 22A–D) or salmon actin PCR primers (FIGS. 22E, F). Wells 1–14 for FIGS. 22A–F, top row, are designated as follows: ladder, gill, nasal lamellae, urinary bladder, kidney, stomach, pyloric caeca, proximal intestine, distal intestine, brain, pituitary gland, olfactory bulb, liver and muscle, respectively. Wells 1, 2, 3, 5, 6, and 7. bottom row, for FIGS. 22A, C, and E are designated as ladder, water, Kidney-RT, SalmoKCaR #1, SalmoKCaR#2 and SalmoKCaR#3, respectively, and wells 1, 2, 3, 5, 6, and 7, bottom row, for FIGS. 22B, D, and F are designated as ladder, water, ovary, SalmoKCaR #1, SalmoKCaR#2 and SalmoKCaR#3, respectively.

FIG. 35 is a series of photographs of immunocytochemistry showing the SalmoKCaR localization of Atlantic Salmon Olfactory Bulb Nerve and Lamellae using an anti-SalmoKCaR antibody.

FIG. 36 is a schematic illustrating the effect of external and internal ionic concentrations on the olfactory lamellae in response to SalmoKCaR modulators.

FIG. 37A is a photograph of immunocytochemistry showing the SalmoKCaR protein expression in the developing nasal lamellae (Panel A) and olfactory bulb (Panel B) after hatching of Atlantic salmon using an anti-SalmoKCaR antibody.

FIG. 38 is a photograph of immunocytochemistry showing the PVCR localization in nasal lamellae of dogfish shark using an anti-PVCR antibody.

FIG. 39 is a photograph of a Southern blot of RT-PCR analyses of tissues from Atlantic Salmon showing the presence of SalmoKCaR mRNA in nasal lamellae of freshwater adapted fish. Wells 1–10 are designated as follows: gill, nasal lamellae, urinary bladder, kidney, intestine, stomach, liver, brain, water (blank) and positive control, respectively.

FIG. 40 is a histogram illustrating the amount of SalmoKCaR protein, as determined by an ELISA (ng) for various tissue samples (gill, liver, heart, muscle, stomach, olfactory epithelium, kidney, urinary bladder, brain, pituitary gland, olfactory bulb, pyloric ceacae, proximal intestine, and distal intestine).

FIG. 41 shows the raw and integrated recordings from high resistance electrodes of freshwater adapted Atlantic Salmon when exposed to 500 $\mu$M L-alanine, 1 mmol calcium, 50 $\mu$M Gadolinium, and 250 mmol of NaCl. The figures show the existence of an olfactory recording in response to L-alanine, calcium, gadolinium, and NaCl.

DETAILED DESCRIPTION OF THE INVENTION

Figure 2:
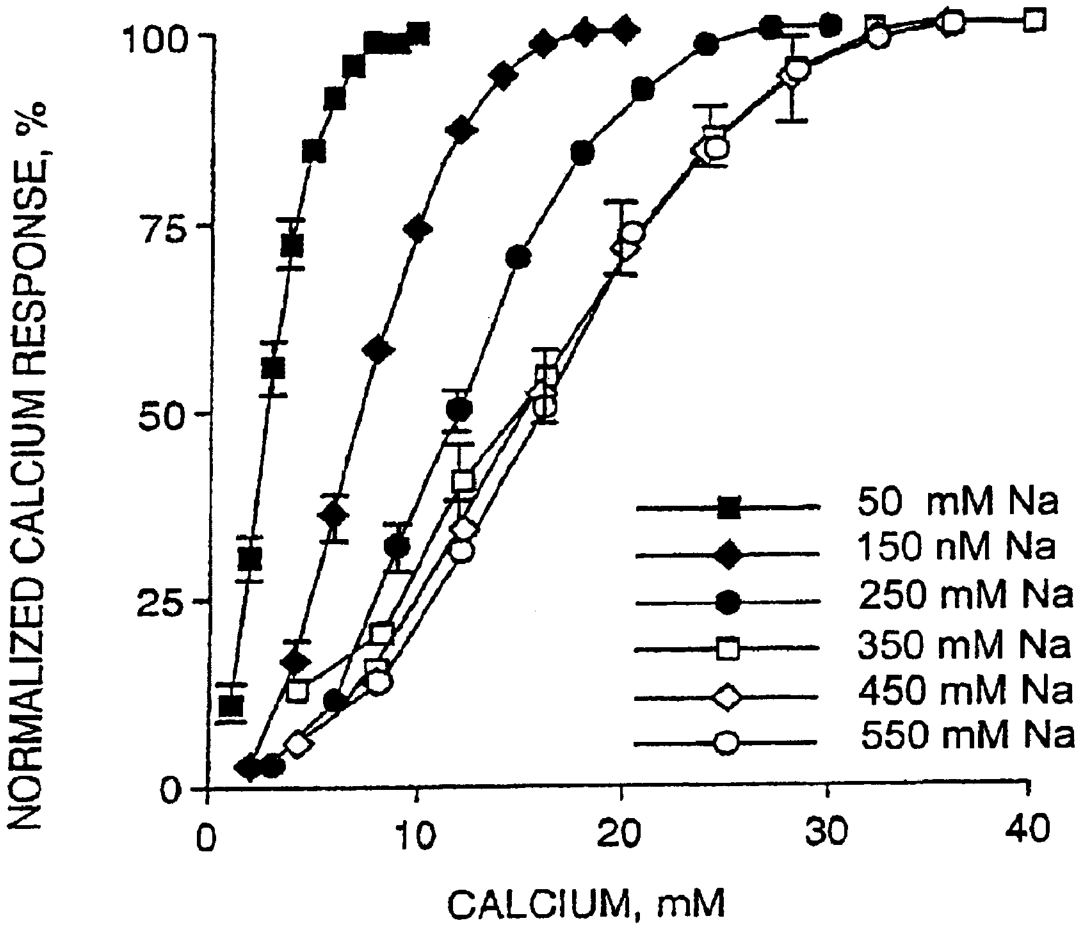
FIG. 2 is a graphical representation showing a normalized calcium response (%) against the amount of Calcium (mM) of the SKCaR-I protein when modulated by alternations in extracellular NaCl concentrations.

The present invention relates to three novel isolated sequences from PVCR genes, SalmoKCaR#1, SalmoKCaR#2, and SalmoKCaR#3, in Atlantic Salmon. These genes encode three polypeptide sequences that are also the subject of the present invention. These polypeptide sequences allow for or assist in several functions including sensing at least one SalmoKCaR modulator in serum or in the surrounding environment; adapting to at least one SalmoKCaR modulator present in the serum or surrounding environment; imprinting Atlantic Salmon with an odorant; altering water intake; altering water absorption; or altering urine output.

Uses of the Present Invention

One use of the present invention relates to methods for improving the raising of salmon and/or methods for preparing salmon for transfer from freshwater to seawater. These methods involve adding one or more PVCR (e.g., SalmoKCaR) modulators to the freshwater (e.g., calcium and/or magnesium), and adding a specially made or modified feed to the freshwater for consumption by the fish. The feed contains a sufficient amount of sodium chloride (NaCl) and/or a SalmoKCaR modulator (e.g., an amino acid like tryptophan) to significantly increase levels of the SalmoKCaR modulator in the serum. During this process, the serum level of the SalmoKCaR modulator significantly increases in the salmon, and causes modulated (e.g., increased and/or decreased) SalmoKCaR expression and/or altered SalmoKCaR sensitivity. This process prepares salmon for transfer to seawater, so that they can better adapt to seawater once they are transferred. The details of how to carry out this process is described in the Exemplification Section. In particular, the Exemplification describes two processes. Briefly, Process I involves adding calcium and magnesium to the water, and providing feed containing NaCl; and Process II includes adding calcium and magnesium to the water, and providing feed having both NaCl and tryptophan. Studies performed and described in Example 7 show that Atlantic Salmon maintained in freshwater and subjected to Process I had a survival rate of 91%, and those Atlantic Salmon subjected to Process II had a survival rate of 99%; as compared to control fish having a survival rate of only 67% after transfer to seawater. Similarly, in the same experiment, five days after transfer to seawater, Atlantic Salmon subjected to Process I had a survival rate of 90%, while Atlantic Salmon subjected to Process II had a survival rate of 99%. The control fish had a survival rate of only 50% after being transferred to seawater. Furthermore, experiments described in Example 6 demonstrate that modulated expression of one or more SalmoKCaR genes occurs in various tissues during Process I and Process II. Process I and II, as described herein, modulate the SalmoKCaR genes and allow for increased food consumption, growth and survival; and decreased morbidity and susceptibility to disease.

Process I and II likely have further utility in restoration of wild Atlantic salmon populations. Since a major cause of mortality of wild Atlantic salmon smolt is loss or capture by predators as they are adapting to seawater in river estuaries, treatment of wild Atlantic salmon produced in large numbers, as part of river restocking programs would boost the productivity and survival of fish produced in such programs. Moreover, several studies have shown that salmon smolt are also poisoned by exposure to heavy metals ($Al^{3+}$, $Zn^{2+}$, $Cu^{2+}$) that contaminate their native rivers in both the US and other countries such as Norway. These highly deleterious effects on salmon are manifested principally in rivers with low natural $Ca^{2+}$ concentrations. Thus, treatment of wild strains of Atlantic salmon produced in restocking hatcheries with either Process I or Process II would render these treated smolt less susceptible to the effects of heavy metals since the smoltification process in these treated smolt was much further advanced that in untreated fish. Use of Process I or II to treat Atlantic salmon that would be released into rivers also have commercial utility in large-scale ocean ranching programs where large numbers of salmon smolt are released and captured for human consumption upon their return from 1–3 years in the ocean.

Similarly, since expression of the SalmoKCaR genes changes during Process I and Process II, assaying these genes allows one to determine if the salmon are ready for transfer to seawater. Examples of such assays are ELISAs, radioimmunoassays (RIAs), southern blots and RT-PCR assays, which are described herein in detail. The salmon are subjected to either Process I or Process II for a period of time in freshwater before being transferred to seawater. The SalmoKCaR genes, or polypeptides encoded by these genes, can be assayed for determining the optimal time period for maintaining the salmon in the freshwater, before transfer to seawater. Using methods described herein, salmon can be assayed to determine if modulated levels of the SalmoKCaR genes and/or polypeptides have occurred, as compared to controls. For example, when fish that are maintained in freshwater and subjected to either Process I or Process II and changes in one or more of SalmoKCaR genes and/or polypeptide levels in at least one tissue are modulated such that they mimic changes in the same genes and/or polypeptide levels that would be seen in fish adapted to seawater, then this group of fish are ready to be transferred to seawater. In one experiment, the increased expression of SalmoKCaR genes in the kidney of Atlantic Salmon subjected to Process II was similar to the increased expression in the same tissue for Atlantic Salmon already adapted to seawater, but dissimilar to expression to Atlantic Salmon adapted to freshwater (i.e., no increased expression in the kidney water fish was seen). See Example 6. When levels of SalmoKCaR genes and/or polypeptide encoded by these genes are similar to those levels seen in fish that have been transferred to seawater, then in the experiments described herein, the transfer of these salmon result in several benefits including increased survival and growth. Also, the optimal time periods for subjecting salmon to Process I or Process II are generally between 4–6 weeks, but vary depending on the strain of salmon or process used. Hence, the assays described herein can be used to determine the optimal amount of time for subjecting the salmon to either Process I or Process II before transferring to seawater.

Additionally, comparison of the SalmoKCaR #3 sequence with data generated from site directed mutagenesis studies of mammalian CaRs indicates that the SalmoKCaR #3 protein likely generates a dominant negative effect on the other SalmoKCaR #1 and #2 proteins when they are expressed together in the same cell. This dominant negative effect of SalmoKCaR #3 occurs since it lacks that necessary carboxyl terminal domain to propagate signals generated by the binding of PVCR agonists. Interactions between the fully functional SalmoKCaR #1 or #2 proteins and SalmoKCaR #3 would cause a marked reduction in the sensitivity of the SalmoKCaR #1 or #2 proteins. In one experiment, it was found that increased expression of SalmoKCaR#3 was seen in tissues readily exposed to high concentrations of calcium and magnesium in the surrounding environment (e.g., gill and nasal lamellae) or tissues that excrete high concentrations of calcium and magnesium (e.g., urinary bladder and kidney). Therefore, such assays can be used to determine levels of the individual SalmoKCaR genes, and compare expression levels to one another, and to individual levels of these genes of seawater adapted salmon to determine whether the salmon being tested are ready for transfer to seawater.

Uses of nucleic acids of the present invention include one or more of the following: (1) producing receptor proteins which can be used, for example, for structure determination, to assay a molecule's activity, and to obtain antibodies binding to the receptor; (2) being sequenced to determine a receptor's nucleotide sequence which can be used, for example, as a basis for comparison with other receptors to determine one or more of the following: conserved sequences; unique nucleotide sequences for normal and altered receptors; and nucleotide sequences to be used as target sites for antisense nucleic acids, ribozymes, or PCR amplification primers; (3) as hybridization detection probes to detect the presence of a native receptor and/or a related receptor in a sample, as further described herein to determine the presence or level of SalmoKCaR in a sample for, e.g., assessing whether salmon are ready for transfer to seawater; (4) as PCR primers to generate particular nucleic acid sequence sequences, for example, to generate sequences to be used as hybridization detection probes; and (5) for determining and isolating additional aquatic PVCR homologs in other species.

Another use for nucleic acid sequences of SalmoKCaRs #1, #2 or #3 is as probes for the screening of Atlantic salmon broodstock, eggs, sperm, embryos or larval and juvenile fish as part of breeding programs. Use of SalmoKCaR probes would enable identification of desirable traits such as enhanced salinity responsiveness, homing, growth in seawater or freshwater or improve the feed utilization that were due to or associated with naturally occurring or induced mutations of SalmoKCaR genes. Nucleic acid sequences of SalmoKCaRs #1, #2 or #3 can also be used as probes for screening of wild Atlantic salmon in various regions as a tool to identify specific strains of fish from both sea run and land locked strains. Such strains could then be used to interbreed with existing commercial strains to produce further improvements in fish performance.

The structural-functional data generated via study of recombinant SalmoKCaRs after their expression in cells. as functional proteins can be used to identify desirable alternations in the function of SalmoKCaR proteins that could then be screened for as part of genetic selection-broodstock enhancement program.

Cell lines expressing SalmoKCaR proteins, either individually or in various combinations, would have utility and value as a means to assay various compounds, chemicals and water conditions that occur both in the natural and commercial environments. Utilization of transfected cells expressing SalmoKCaR #1–3 proteins either alone or in various combinations can be used in screening methods to identify both naturally occurring and commercially synthesized compounds that would enhance the performance of wild or commercially produced Atlantic salmon including salinity adaption, feeding, growth and maturation, flesh quality, homing to areas of spawning, recognition of specific odorants as part of imprinting, utilization of nutrients with improved efficiency and altered behavior. Such screening assay would be a vast improvement over existing assays where large numbers of fish are required and their end response (e.g., behavior, feeding, growth, survival or appearance is altered) to a given compound produce complicated assays that have many problems with data interpretation. Transfected cells expressing SalmoKCaR #1–3 proteins either alone or in various combinations can also be used in screening methods to screen for specific water conditions including pH, ionic strength and composition of various compounds dissolved in the water to alter the function of SalmoKCaR proteins and thus lead to improved salinity responses in various life stages of Atlantic salmon. Such assays would be designed to determine the interactions and effects of these conditions on SalmoKCaR proteins without having to test the effects of such compounds on either whole living fish or some tissue explants.

Fragments of recombinant SalmoKCaR proteins also provide a utility as modulators of PVCR function that could be added to water, applied to tissue surfaces such as gills or skin or injected into fish via standard techniques. The present invention is also useful in immunization of any one of the various life stages of Atlantic salmon (eggs, embryo, larval or juvenile or adult fish with either whole or fragments of recombinant SalmoKCaR proteins to create antibody responses that would, in turn, alter SalmoKCaR mediated functions of fish.

The present invention is not limited to the uses described in this section. Based on the data and information described herein, additional uses of the present invention may be readily appreciated by one of skill in the art.

The SalmoKCaR Polypeptides and its Function

The present invention relates to isolated polypeptide molecules that have been isolated in Atlantic Salmon including three full length sequences. The present invention includes polypeptide molecules that contain the sequence of any one of the full length SalmoKCaR amino acid sequence (SEQ ID NO: 8, 10, or 12). See FIGS. 9, 10 and 11. The present invention also pertains polypeptide molecules that are encoded by nucleic acid molecules having the sequence of any one of the isolated full length SalmoKCaR nucleic acid sequences (SEQ ID NO: 7, 9, or 11).

SalmoKCaR polypeptides referred to herein as "isolated" are polypeptides that separated away from other proteins and cellular material of their source of origin. Isolated SalmoKCaR proteins include essentially pure protein, proteins produced by chemical synthesis, by combinations of biological and chemical synthesis and by recombinant methods. The proteins of the present invention have been isolated and characterized as to its physical characteristics using laboratory techniques common to protein purification, for example, salting out, immunoprecipation, column chromatography, high pressure liquid chromatography or electrophoresis. SalmoKCaR proteins are found in many tissues in fish including gill, nasal lamellae, urinary bladder, kidney, stomach, pyloric caeca, proximal intestine, distal intestine, brain, pituitary gland, olfactory bulb, liver, muscle, skin and brain.

The present invention also encompasses SalmoKCaR proteins and polypeptides having amino acid sequences analogous to the amino acid sequences of SalmoKCaR polypeptides. Such polypeptides are defined herein as SalmoKCaR analogs (e.g., homologues), or mutants or derivatives. “Analogous” or “homolgous” amino acid sequences refer to amino acid sequences with sufficient identity of any one of the SalmoKCaR amino acid sequences so as to possess the biological activity of any one of the native SalmoKCaR polypeptides. For example, an analog polypeptide can be produced with “silent” changes in the amino acid sequence wherein one, or more, amino acid residues differ from the amino acid residues of any one of the SalmoKCaR protein, yet still possesses the function or biological activity of the SalmoKCaR. Examples of such differences include additions, deletions or substitutions of residues of the amino acid sequence of SalmoKCaR. Also encompassed by the present invention are analogous polypeptides that exhibit greater, or lesser, biological activity of any one of the SalmoKCaR proteins of the present invention. Such polypeptides can be made by mutating (e.g., substituting, deleting or adding) one or more amino acid or nucleic acid residues to any of the isolated SalmoKCaR molecules described herein. Such mutations can be performed using methods described herein and those known in the art. In particular, the present invention relates to homologous polypeptide molecules having at least about 70% (e.g., 75%, 80%, 85%, 90% or 95%) identity or similarity with SEQ ID NO: 8, 10, or 12. Percent “identity” refers to the amount of identical nucleotides or amino acids between two nucleotides or amino acid sequences, respectfully. As used herein, “percent similarity” refers to the amount of similar or conservative amino acids between two amino acid sequences. Each of the SalmoKCaR polypeptides are homologous to one another.

The percent identity when comparing one SalmoKCaR amino acid sequence to another are as follows:

Percent Identity for Amino Acid Sequences*

| Query Sequence | SalmoKCaR#1 | SalmoKCaR#2 | SalmoKCaR#3 |
|---|---|---|---|
| SalmoKCaR#1 | N/A | 99.9% | 89.6% |
| SalmoKCaR#2 | 99.9% | N/A | 89.5% |
| SalmoKCaR#3 | 99.2% | 99.1% | N/A |

*Note that the percentages are based on the number of aa’s in the target sequence.

The polypeptides of the present invention, including the full length sequences, the partial sequences, functional fragments and homologues, allow for or assist in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; altering water intake; altering water absorption; altering urine output. These and additional functions of the polypeptides are further described herein, and illustrated by the Exemplification. The term “sense” or “sensing” refers to the SalmoKCaR’s ability to alter its expression and/or sensitivity in response to a SalmoKCaR modulator.

Homologous polypeptides can be determined using methods known to those of skill in the art. Initial homology searches can be performed at NCBI against the GenBank, EMBL and SwissProt databases using, for example, the BLAST network service. Altschuler, S. F., et al., *J. Mol. Biol.,* 215:403 (1990), Altschuler, S. F., *Nucleic Acids Res.,* 25:3389–3402 (1998). Computer analysis of nucleotide sequences can be performed using the MOTIFS and the FindPatterns subroutines of the Genetics Computing Group (GCG, version 8.0) software. Protein and/or nucleotide comparisons were performed according to Higgins and Sharp (Higgins, D. G. and Sharp, P. M., *Gene,* 73:237–244 (1988) e.g., using default parameters).

The SalmoKCaR proteins of the present invention also encompass biologically active or functional polypeptide fragments of the full length SalmoKCaR proteins. Such fragments can include the partial isolated amino acid sequences (SEQ ID NO: 15 and 27), or part of the full-length amino acid sequence (SEQ ID NO: 8, 10, or 12), yet possess the function or biological activity of the full length sequence. For example, polypeptide fragments comprising deletion mutants of the SalmoKCaR proteins can be designed and expressed by well-known laboratory methods. Fragments, homologues, or analogous polypeptides can be evaluated for biological activity, as described herein.

In one embodiment, the function or biological activity relates to preparing salmon for transfer to seawater. The method for preparing Atlantic Salmon for transfer to seawater includes adding at least one SalmoKCaR modulator (e.g., PVCR modulator) to the freshwater, and adding a specially made or modified feed to the freshwater for consumption by the fish. The feed contains a sufficient amount of sodium chloride (NaCl) (e.g., between about 1% and about 10% by weight, or about 10,000 mg/kg to about 100,000 mg/kg) to significantly increase levels of the SalmoKCaR modulator in the serum. This amount of NaCl in the feed causes or induces the Atlantic Salmon to drink more freshwater. Since the freshwater contains a SalmoKCaR modulator and the salmon ingest increased amounts of it, the serum level of the SalmoKCaR modulator significantly increases in the salmon, and causes modulated (e.g., increased and/or decreased) SalmoKCaR expression and/or altered SalmoKCaR sensitivity. One function or activity of the SalmoKCaR genes is to sense SalmoKCaR modulators in the serum. The SalmoKCaR expression is altered by the SalmoKCaR modulators in the serum, which provides the ability for the salmon to better adapt to seawater, undergo smoltification, survive, grow, consume food and/or to be less susceptible to disease.

A “PVCR modulator” or “SalmoKCaR modulator” refers to a compound which modulates (e.g., increases and/or decreases) expression of SalmoKCaR, or alters the sensitivity or responsiveness of SalmoKCaR genes. Such compounds include, but are not limited to, SalmoKCaR agonists (e.g., inorganic polycations, organic polycations and amino acids), Type II calcimimetics, and compounds that indirectly alter PVCR expression (e.g., 1,25 dihydroxyvitamin D in concentrations of about 3,000–10,000 International Units /kg feed), cytokines such as Interleukin Beta, and Macrophage Chemotatic Peptide-1 (MCP-1)). Examples of Type II calcimimetics, which increase and/or decrease expression, and/or sensitivity of the SalmoKCaR genes, are, for example, NPS-R-467 and NPS-R-568 from NPS Pharmaceutical Inc., (Salt Lake, Utah, U.S. Pat. Nos. 5,962,314; 5,763,569; 5,858,684; 5,981,599; 6,001,884) which can be administered in concentrations of between about 0.1 $\mu$M and about 100 $\mu$M feed or water. See Nemeth, E. F. et al., *PNAS* 95: 4040–4045 (1998). Examples of inorganic polycations are divalent cations including calcium at a concentration between about 2.0 and about 10.0 mM and magnesium at a concentration between about 0.5 and about 10.0 mM; and trivalent cations including, but not limited to, gadolinium (Gd3+) at a concentration between about 1 and about 500 $\mu$M. Organic polycations include, but are not limited to, aminoglycosides such as neomycin or gentamicin in concentrations of between about 1 and about 8 gm/kg feed as well as organic polycations including polyamines (e.g., polyarginine, polylysine, polyhistidine, polyornithine, spermine, spermidine, cadaverine, putrescine, copolymers of poly arginine/histidine, poly lysine/arginine in concentrations of between about 10 μM and 10 mM feed). See Brown, E. M. et al., *Endocrinology* 128:3047–3054 (1991); Quinn, S. J. et al., *Am. J. Physiol.* 273: C1315–1323 (1997). Additionally, SalmoKCaR agonists include amino acids such as L-Tryptophan L-Tyrosine, L-Phenylalanine, L-Alanine, L-Serine, L-Arginine, L-Histidine, L-Leucine, L-Isoleucine, L-Aspartic acid, L-Glutamic acid, L-Glycine, L-Lysine, L-Methionine, L-Asparagine, L-Proline, L-Glutamine, L-Threonine, L-Valine, and L-Cysteine at concentrations of between about 1 and about 10 gm/kg feed. See Conigrave, A. D., et al., *PNAS* 97: 4814–4819 (2000). Amino acids, in one embodiment, are also defined as those amino acids that can be sensed by at least one SalmoKCaR in the presence of low levels of extracellular calcium (e.g., between about 1 mM and about 10 mM). In the presence of extracellular calcium, the SalmoKCaR in organs or tissues such as the intestine, pyloric caeca, or kidney can better sense amino acids. The molar concentrations refer to free or ionized concentrations of the SalmoKCaR modulator in the freshwater, and do not include amounts of bound SalmoKCaR modulator (e.g., SalmoKCaR modulator bound to negatively charged particles including glass, proteins, or plastic surfaces). Any combination of these modulators can be added to the water or to the feed (in addition to the NaCl, as described herein), so long as the combination modulates expression and/or sensitivity of one or more of the SalmoKCaR genes.

Figure 34:
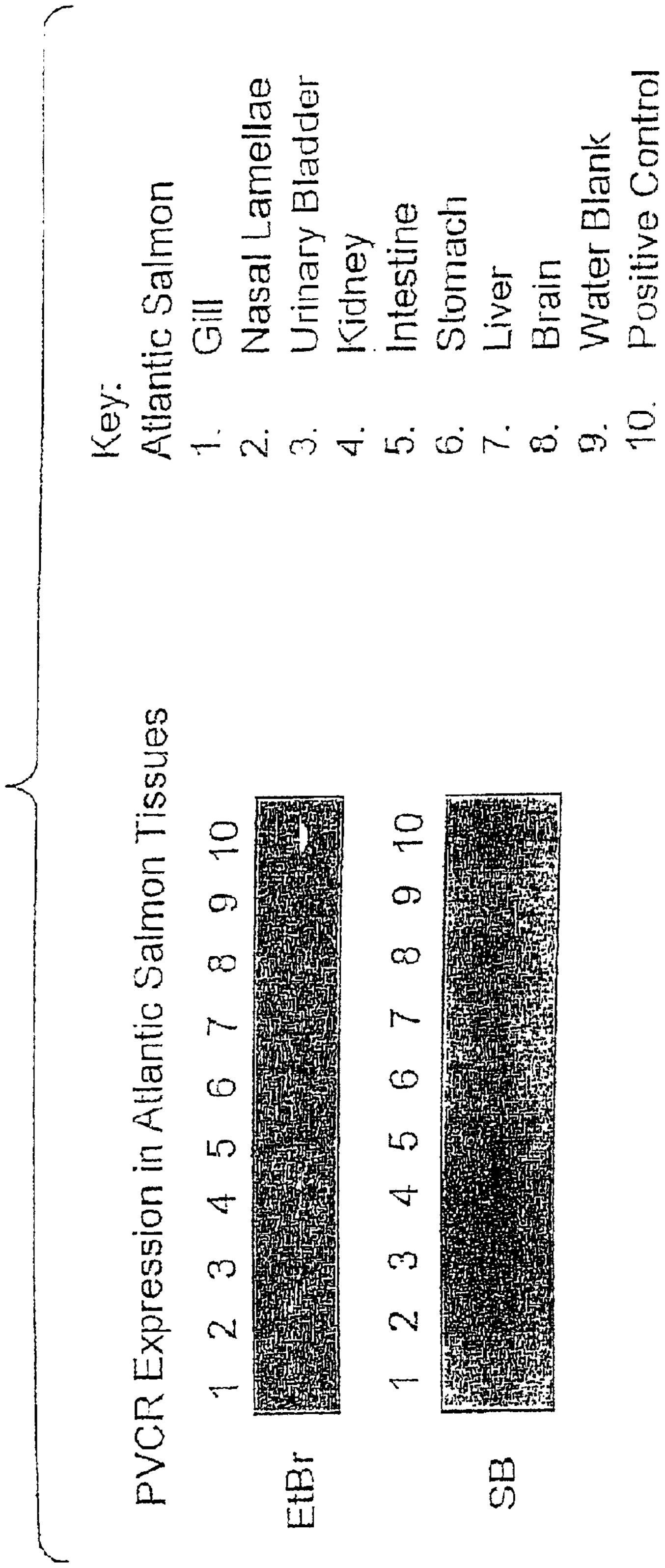
FIG. 34 is a photograph of a RT-PCR amplification of a partial SalmoKCaR mRNA transcript from various tissues (gill, nasal lamellae, urinary bladder, kidney, intestine, stomach, liver, and brain (Wells 1–8, respectively)) of Atlantic Salmon. RT-PCR reactions were separated by gel electrophoresis and either stained in ethidium bromide (EtBr) or transferred to a membrane and Southern Blotted (SB) using a 32P-labeled 653 basepair (bp) genomic DNA fragment from the Atlantic salmon SalmoKCaR gene. Wells 9 and 10 are water (blank) and positive control, respectively.

Another function of the SalmoKCaR polypeptides involves imprinting Atlantic Salmon with an odorant (e.g., an attractant or repellant). Atlantic Salmon can be imprinted with an odorant so that, when the fish are later exposed to the odorant, they can more easily distinguish the odorant or are sensitized to the odorant. The SalmoKCaR polypeptides can work, for example, with one or more olfactory receptors to modify the generation of the nerve impulse during sensing of an odorant. Generation of this nerve impulse occurs upon binding of the odorant to the olfactory lamellae in the fish. The SalmoKCaR modulator alters the olfactory sensing of the salmon to the odorant. In some cases, the presence of a (e.g., at least one) SalmoKCaR modulator in freshwater reversibly reduces or ablates the fish's ability to sense certain odorants. In other cases it can be heightened or increased. By exposing the salmon in freshwater having a SalmoKCaR modulator to an odorant, the fish have an altered response which depending on the modulator would consist of either a decreased or heightened response to the odorant. Briefly, these imprinting methods involve adding at least one SalmoKCaR modulator (e.g., calcium and magnesium) to the freshwater in an amount sufficient to modulate expression and/or sensitivity of at least one SalmoKCaR gene; and adding feed for fish consumption to the freshwater. The feed contains at least one an attractant (e.g., alanine); an amount of NaCl sufficient to contribute to a significantly increased level of the SalmoKCaR modulator in serum of the Atlantic Salmon; and optionally a SalmoKCaR modulator (e.g., tryptophan). The odorant can also be added to the water, instead of the feed. Salmon that has been imprinted with an attractant consume more feed having this attractant and, as a result, grow faster. The imprinting process occurs during various developmental stages of salmon including the larval stage and the smoltification stage. Localizations of SalmoKCaR proteins and detection of SalmoKCaR expression using RT-PCR in various organs involved in the imprinting process including olfactory lamellae, olfactory bulb and brain is provided for both larval (Example 13) and smolt stages (FIGS. 34 and 35). The process of imprinting the salmon with an odorant refers to creating a lasting effect or impression on the fish so that the fish are sensitized to the odorant or can distinguish the odorant. Being sensitized to the odorant refers to the fish's ability to more easily recognize or recall the odorant. Distinguishing an odorant refers to the fish's ability to differentiate among one or more odorants, or have a preference for one odorant over another.

An odorant is a compound that binds to olfactory receptors and causes fish to sense odorants. Generation of an olfactory nerve impulse occurs upon binding of the odorant to the olfactory lamellae. A fish odorant is either a fish attractant or fish repellant. A fish attractant is a compound to which fish are attracted. The sensitivity of the attractant is modulated, at least in part, by the sensitivity and/or expression of the SalmoKCaR genes in the olfactory apparatus of the fish in response to a SalmoKCaR modulator. Examples of attractants in some fish include amino acids (e.g., L-Tryptophan L-Tyrosine, L-Phenylalanine, L-Alanine, L-Serine, L-Arginine, L-Histidine, L-Leucine, L-Isoleucine, L-Aspartic acid, L-Glutamic acid, L-Glycine, L-Lysine, L-Methionine, L-Asparagine, L-Proline, L-Glutamine, L-Threonine, L-Valine, and L-Cysteine), nucleotides (e.g., inosine monophosphate), organic compounds (e.g., glycine-betaine and trimethylamine oxide), or a combination thereof. Similarly, a fish repellant is a compound that fish are repelled by, and the sensitivity of the fish to the repellant is altered through expression and/or sensitivity of a SalmoKCaR gene in the olfactory apparatus of the fish in the presence of a SalmoKCaR modulator. An example of a repellant is a "finger rinse" which is a mixture of mammalian oils and fatty acids produced by the epidermal cells of the skin, and is left behind after human fingers are rinsed with an aqueous solution. Methods for performing a finger rinse is known in the art and is described in more detailed in the Exemplification Section.

Additionally, the function of SalmoKCaR polypeptides includes its ability to sense or adapt to ion concentrations in the surrounding environment. The SalmoKCaR polypeptides sense various SalmoKCaR modulators including calcium, magnesium and/or sodium. The SalmoKCaR polypeptides are modulated by varying ion concentrations. For instance, any one of the SalmoKCaR polypeptides can be modulated (e.g., increased or decreased) in response to a change in ion concentration (e.g., calcium, magnesium, or sodium). Responses to changes in ion concentrations of Atlantic Salmon containing the SalmoKCaR polypeptides include the ability to adapt to the changing ion concentration. Such responses include the amount the fish drinks, the amount of urine output, and the amount of water absorption. Responses also include changes in biological processes that affect its ability to excrete contaminants.

More specifically, methods are available to regulate salinity tolerance in fish by modulating (e.g., increasing, decreasing or maintaining the expression) the activity of one or more of the SalmoKCaR proteins present in cells involved in ion transport. For example, salinity tolerance of fish adapted (or acclimated) to freshwater can be increased by activating one or more of the SalmoKCaR polypeptides, for example, by increasing the expression of one or more of SalmoKCaR genes, resulting in the secretion of ions and seawater adaption. Alternatively, the salinity tolerance of fish adapted to seawater can be decreased by inhibiting one or more of the SalmoKCaR proteins, resulting in alterations in the absorption of ions and freshwater adaption.

"Salinity" refers to the concentration of various ions in a surrounding aquatic environment. In particular, salinity refers to the ionic concentration of calcium, magnesium and/or sodium (e.g., sodium chloride). "Normal salinity" levels refers to the range of ionic concentrations of typical water environment in which an aquatic species naturally lives. Normal salinity or normal seawater concentrations are about 10 mM Ca, about 40 mM Mg, and about 450 mM NaCl. "Salinity tolerance" refers to the ability of a fish to live or survive in a salinity environment that is different than the salinity of its natural environment. Modulations of the PVCR allows fish to live in about four times and one-fiftieth, preferably, twice and one-tenth the normal salinity.

The ability of anadromous fish (Atlantic salmon, trout and Arctic char) as well as euryhaline fish (flounders, alewives, eels) to traverse from freshwater to seawater environments and back again is of key importance to their lifecycles in the natural environment. Both types of fish have to undergo similar physiological changes including alterations in their urine output, altering water intake and water absorption. Both types of fish utilize environments of either freshwater (Atlantic salmon) or partial salinity (flounders) to spawn and allow for the development of larval fish into juvenile forms that then undergo changes to migrate into full strength seawater. Both types of fish utilize PVCRs to sense when adult fish have arrived in a salinity environment suitable for spawning and to guide their return back to full strength seawater. Similarly, their resulting offspring utilize PVCRs to control various organs allowing for their normal development in fresh or brackish (partial strength seawater) water and subsequently to regulate the physiological changes that permit these fish to migrate into full strength seawater.

The following experiment was done in Summer and Winter Flounder, but is applicable to Atlantic Salmon because both species of fish have PVCRs which respond to ion concentrations in a similar manner. Summer and Winter Flounder were adapted to live in 1/10th seawater (100 mOsm/kg) by reduction in salinity from 450 mM NaCl to 45 mM NaCl over an interval of 8 hrs. Summer and Winter Flounder can be maintained in 1/10 or twice the salinity for over a period of 6 months. After a 10 day interval where the Summer and Winter Flounder were fed a normal diet, the distribution of the PVCR in their urinary bladder epithelial cells was examined using immunocytochemistry. PVCR immunostaining is reduced and localized primarily to the apical membrane of epithelial cells in the urinary bladder. In contrast, the distribution of PVCR in epithelial cells lining the urinary bladders of control flounders continuously exposed to full strength seawater is more abundant and present in both the apical membranes as well as in punctate sequences throughout the cell. These data are consistent with previous Northern data where more PVCR protein is present in the urinary bladders of seawater fish vs fish adapted to brackish water. These data show that PVCR protein is expressed in epithelial cells that line the urinary bladder where the PVCR protein comes into direct contact with the urine that is being formed by the kidney. Due to its location in the cell membrane of these epithelial cells, the PVCR proteins can "sense" changes in the urine's composition on a continuous basis. Depending on the specific ionic concentrations of the urine, the PVCR protein alters the transport of ions across the epithelium of the urinary bladder and, in this way, determines the final composition of the urine. This composition and the amount of water and NaCl absorbed from the urine are critical to salinity regulation in fish.

As urinary magnesium and calcium concentrations increase when fish are present in full strength sea water, activation of apical PVCR protein causes reduction in urinary bladder water transport. The invention provides methods to facilitate euryhaline adaptation of fish to occur, and improve the adaption. More specifically, methods are now available to regulate salinity tolerance in fish by modulating (e.g., alternating, activating and or expressing) the activity of the PVCR protein present in epithelial cells involved in ion transport, as well as in endocrine and nervous tissue. For example, salinity tolerance of fish adapted (or acclimated) to fresh water can be increased by activating the PVCR, for example, by increasing the expression of PVCR in selected epithelial cells, resulting in the secretion of ions and seawater adaption. Specifically, this would involve regulatory events controlling the conversion of epithelial cells of the gill, intestine and kidney. In the kidney, PVCR activation facilitates excretion of divalent metal ions including calcium and magnesium by renal tubules. In the gill, PVCR activation reduces reabsorption of ions by gill cells that occurs in fresh water and promote the net excretion of ions by gill epithelia that occurs in salt water. In the intestine, PVCR activation will permit reabsorption of water and ions across the G.I. tract after their ingestion by fish.

Alternatively, the salinity tolerance of fish adapted to seawater can be deceased by modulating one or more of the SalmoKCaR polypeptides, for example by decreasing the expression of one or more of the SalmoKCaR genes while others may be increased. The net result of these changes would be alterations in the absorption of ions that facilitate the adaption to freshwater conditions.

In another example, Winter and Summer Flounder were maintained in at least twice the normal salinity or 1/10 the normal salinity. See Exemplification. These fish can be maintained in these environments for long periods of time (e.g., over 3 months, over 6 months, or over 1 year). These limits were defined by decreasing or increasing the ionic concentrations of calcium, magnesium, and sodium, keeping a constant ratio between the ions. These salinity limits can be further defined by increasing and/or decreasing an individual ion concentration, thereby changing the ionic concentration ratio among the ions. Increasing and/or decreasing individual ion concentrations can increase and/or decrease salinity tolerance. "Hypersalinity" or "above normal salinity" levels refers to a level of at least one ion concentration that is above the level found in normal salinity. "Hyposalinity" or "below normal salinity" levels refers to a level of at least one ion concentration that is below the level found in normal salinity.

Maintaining fish in a hypersalinity environment also results in fish with a reduced number of parasites or bacteria. Preferably, the parasites and/or bacteria are reduced to a level that is safe for human consumption, raw or cooked. More preferably, the parasites and/or bacteria are reduced to having essentially no parasites and few bacteria. These fish must be maintained in a hypersalinity environment long enough to rid the fish of these parasites or bacteria, (e.g., for at least a few days or at least a few weeks).

The host range of many parasites is limited by exposure to water salinity. For example, Diphyllobothrium species commonly known as fish tapeworms, is encountered in the flesh of fish, primarily fresh water or certain euryhaline species. Foodborne Pathogenic Microorganisms and Natural Toxins Handbook, 1991. U.S. Food and Drug Administration Center for Food Safety and Applied Nutrition, the teachings of which are incorporated herein by reference in their entirety. In contrast, its presence in the flesh of completely marine species is much reduced or absent. Since summer flounder can survive and thrive at salinity extremes as high as 58 ppt (1.8 times normal seawater) for extended periods in recycling water, exposure of summer flounder to hypersalinity conditions might be used as a "biological" remediation process to ensure that no Diphyllobothrium species are present in the GI tract of summer flounder prior to their sale as product.

Data from Cole et al., (*J. Biol. Chem.* 272:12008–12013 (1997)), show that winter flounder elaborate an antimicrobial peptide from their skin to prevent bacterial infections. Their data reveals that in the absence of pleurocidin, *Escherichia coli* are killed by high concentrations of NaCl. In contrast, low concentrations of NaCl (<300 mM NaCl) allow *E. coli* to grow and under these conditions pleurocidin presumably helps to kill them. These data provide evidence of NaCl killing of *E. coli*, as well as highlight possible utility of bacterial elimination in fish.

Similarly, maintaining fish in a hyposalinity environment results in a fish with a reduced amount of contaminants (e.g., hydrocarbons, amines or antibiotics). Preferably, the contaminants are reduced to a level that is safe for human consumption, raw or cooked fish. More preferable, the contaminants are reduced to having essentially very little contaminants left in the fish. These fish must be maintained in a hyposalinity environment long enough to rid the fish of these contaminants, (e.g., for at least a few days or a few weeks).

Organic amines, such as trimethylamine oxide (TMAO) produce a "fishy" taste in seafood. They are excreted via the kidney in flounder. (Krogh, A., Osmotic Regulation in Aquatic Animals, Cambridge University Press, Cambridge, U.K. pgs 1–233 (1939), the teachings of which are incorporated herein by reference in their entirety). TMAO is synthesized by marine organisms consumed by fish that accumulate the TMAO in their tissues. Depending on the species of fish, the muscle content of TMAO and organic amines is either large accounting for the "strong" taste of bluefish and herring or small such as in milder tasting flounder.

The presence of SalmoKCaR in brain reflects both its involvement in basic neurotransmitter release via synaptic vesicles (Brown, E. M. et al., *New England J. of Med.,* 333:234–240 (1995)), as well as its activity to trigger various hormonal and behavioral changes that are necessary for adaptation to either fresh water or marine environments. For example, increases in water ingestion by fish upon exposure to salt water is mediated by SalmoKCaR activation in a manner similar to that described for humans where PVCR activation by hypercalcemia in the subfornical organ of the brain cause an increase in water drinking behavior (Brown, E. M. et al., *New England J. of Med.,* 333:234–240 (1995)). In fish, processes involving both alterations in serum hormonal levels and behavioral changes are mediated by the brain. These include the reproductive and spawning activities of euryhaline fish in fresh water after their migration from salt water as well as detection of salinity of their environment for purposes of feeding, nesting, migration and spawning. The key events for successful reproduction in Atlantic salmon are to migrate to a specific streambed for spawning after 1–3 years of free-swimming existence on the open ocean. Successful achievement of this challenge depends on the combination of adult salmon being able to remember and navigate their way back to this original location as well as successful imprinting of larval and juvenile Atlantic salmon to odors present in freshwater in the freshwater streambed as well as the characteristics of the mouth of the river as the fish exit the river and enter the ocean. Sensing of salinity by PVCR and its modulation of the odorant detection system of salmon for detecting various odorants is critical to the achievement of these processes.

Data obtained recently from mammals now suggest that PVCR activation plays a pivotal role in coordinating these events. For example, alterations in plasma cortisol have been demonstrated to be critical for changes in ion transport necessary for adaptation of salmon smolts from fresh water to salt water (Veillette, P. A., et al, *Gen. and Comp. Physiol.,* 97:250–258 (1995)). As demonstrated recently in humans, plasma Adrenocorticotrophic Hormone (ACTH) levels that regulate plasma cortisol levels are altered by PVCR activation.

Additionally, the function or biological activity of the SalmoKCaR polypeptide or protein is defined, in one aspect, to mean the osmoregulatory activity of SalmoKCaR protein. Assay techniques to evaluate the biological activity of SalmoKCaR proteins and their analogs are described in Brown, et al., *New Eng. J. Med.,* 333:243 (1995); Riccardi, et al., *Proc. Nat. Acad. Sci USA,* 92:131–135 (1995); and Sands, et al., *J. Clinical Investigation* 99:1399–1405 (1997). The biological activity also includes the ability of the SalmoKCaR to modulate signal transduction pathways in specific cells. Thus, depending on the distribution and nature of various signal transduction pathway proteins that are expressed in cells, biologically active SalmoKCaR proteins can modulate cellular functions in either an inhibitory or stimulatory manner.

Biologically active derivatives or analogs of the above described SalmoKCaR polypeptides, referred to herein as peptide mimetics can be designed and produced by techniques known to those of skill in the art. (see e.g., U.S. Pat. Nos. 4,612,132; 5,643,873 and 5,654,276). These mimetics can be based, for example, on a specific SalmoKCaR amino acid sequence and maintain the relative position in space of the corresponding amino acid sequence. These peptide mimetics possess biological activity similar to the biological activity of the corresponding peptide compound, but possess a "biological advantage" over the corresponding SalmoKCaR amino acid sequence with respect to one, or more, of the following properties: solubility, stability and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic molecule. Modifications of peptides to produce peptide mimetics are described in U.S. Pat. Nos. 5,643,873 and 5,654,276. Other forms of the SalmoKCaR polypeptides, encompassed by the present invention, include those which are "functionally equivalent." This term, as used herein, refers to any nucleic acid sequence and its encoded amino acid, which mimics the biological activity of the SalmoKCaR polypeptides and/or functional domains thereof.

SalmoKCaR Nucleic Acid Sequences Plasmids, Vectors and Host Cells

The present invention, in one embodiment, includes an isolated full length nucleic acid molecule having a sequence of SalmoKCaR#1 (SEQ ID NO: 7), SalmoKCaR#2 (SEQ ID NO: 9) or SalmoKCaR#3 (SEQ ID NO: 11). See FIGS. 9, 10, and 11. The present invention includes sequences to the full length SalmoKCaR nucleic acid sequences, as well as the coding regions thereof. As shown in these figures, the ORF SalmoKCaR#1 begins at nt 180 and ends at nt 3005. For SalmoKCaR#2, it begins at nt 270 and ends at nt 3095, and for SalmoKCaR#3, the ORF begins at nt 181 and ends at nt 2733.

The present invention also encompasses isolated nucleic acid sequences that encode SalmoKCaR polypeptides, and in particular, those which encode a polypeptide molecule having an amino acid sequence of SEQ ID NO: 8, 10, or 12. The SalmoKCaR full length nucleic acid sequences encode polypeptides that allow or assist in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; altering water intake; altering water absorption; or altering urine output.

The present invention encompasses the SalmoKCaR full length nucleic acid sequences, SalmoKCaR#1 (SEQ ID NO: 7), SalmoKCaR#2 (SEQ ID NO: 9), and SalmoKCaR#3 (SEQ ID NO: 11), or polypeptides encoded by these sequences, which were deposited under the Budapest Treaty with the ATCC, 10801 University Boulevard, Manassas, Va. 20110–2209, U.S.A. on Mar. 29, 2002, under Accession Numbers PTA-4190, PTA-4191, and PTA-4192, respectively. These clones are plasmid DNA which can be transformed into *E. Coli* and cultured. The viability of the clones can be tested with ampicillin resistance. The sequences of the present invention can be purified from these deposits using techniques known in the art.

As used herein, an "isolated" gene or nucleotide sequence which is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. In vivo and in vitro RNA transcripts of the present invention are also encompassed by "isolated" nucleotide sequences. Such isolated nucleotide sequences are useful for the manufacture of the encoded SalmoKCaR polypeptide, as probes for isolating homologues sequences (e.g., from other mammalian species or other organisms), for gene mapping (e.g., by in situ hybridization), or for detecting the presence (e.g., by Southern blot analysis) or expression (e.g., by Northern blot analysis) of related genes in cells or tissue.

The SalmoKCaR nucleic acid sequences of the present invention include homologues nucleic acid sequences. "Analogous" or "homologous" nucleic acid sequences refer to nucleic acid sequences with sufficient identity of any one of the SalmoKCaR nucleic acid sequences, such that once encoded into polypeptides, they possess the biological activity of any one of the native SalmoKCaR polypeptides. For example, an analogous nucleic acid molecule can be produced with "silent" changes in the sequence wherein one, or more, nt differ from the nt of any one of the SalmoKCaR protein, yet, once encoded into a polypeptide, still possesses the function or biological activity of any one of the native SalmoKCaR. Examples of such differences include additions, deletions or substitutions. Also encompassed by the present invention are nucleic acid sequences that encode analogous polypeptides that exhibit greater, or lesser, biological activity of the SalmoKCaR proteins of the present invention. In particular, the present invention is directed to nucleic acid molecules having at least about 70% (e.g., 75%, 80%, 85%, 90% or 95%) identity with SEQ ID NO: 8, 10, or 12. Each of the SalmoKCaR genes are homologues to one another.

The percent identity for the SalmoKCaR nucleic acid sequences are as follows:

Percent Identity for Nucleic Acid Sequences

| Query Sequence | SalmoKCaR#1 | SalmoKCaR#2 | SalmoKCaR#3 |
|---|---|---|---|
| SalmoKCaR#1 | N/A | 99.8% | 95.8% |
| SalmoKCaR#2 | 97.6% | N/A | 93.6% |
| SalmoKCaR#3 | 98.7% | 98.7% | N/A |

The nucleic acid molecules of the present invention, including the full length sequences, the partial sequences, functional fragments and homologues, once encoded into polypeptides, allow for or assist in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; altering water intake; altering water absorption; or altering urine output. The homologous nucleic acid sequences can be determined using methods known to those of skill in the art, and by methods described herein including those described for determining homologous polypeptide sequences.

Also encompassed by the present invention are nucleic acid sequences, DNA or RNA, which are substantially complementary to the DNA sequences encoding the SalmoKCaR polypeptides and which specifically hybridize with their DNA sequences under conditions of stringency known to those of skill in the art. As defined herein, substantially complementary means that the nucleic acid need not reflect the exact sequence of the SalmoKCaR sequences, but must be sufficiently similar in sequence to permit hybridization with SalmoKCaR nucleic acid sequence under high stringency conditions. For example, non-complementary bases can be interspersed in a nucleotide sequence, or the sequences can be longer or shorter than the SalmoKCaR nucleic acid sequence, provided that the sequence has a sufficient number of bases complementary to the SalmoKCaR sequence to allow hybridization therewith. Conditions for stringency are described in e.g., Ausubel, F. M., et al., Current Protocols in Molecular Biology, (Current Protocol, 1994), and Brown, et al., *Nature,* 366:575 (1993); and further defined in conjunction with certain assays.

The SalmoKCaR sequence, or a fragment thereof, can be used as a probe to isolate additional homologues. Nucleic acids encoding SalmoKCaR polypeptides were identified by screening a cDNA library with a SalmoKCaR-specific probe under conditions known to those of skill in the art to identify homologous receptor proteins. For example, the full length sequences were isolated by screening Atlantic Salmon intestinal and kidney cDNA libraries with a probe consisting of a 653 nt PCR amplified genomic sequence (SEQ ID NO: 3). Techniques for the preparation and screening of a cDNA library are well-known to those of skill in the art. For example, techniques such as those described in Riccardi, et al., *Proc. Nat. Acad. Sci. USA,* 92:131–135 (1995), can be used. Positive clones can be isolated, subcloned and their sequences determined. Using the sequences of either a full length or several over-lapping partial cDNAs, the complete nucleotide sequence of the SalmoKCaR cDNA were obtained and the encoded amino acid sequence deduced. The sequences of the SalmoKCaRs can be compared to each other and other aquatic PVCRs to determine differences and similarities. Methods for screening and identifying homologues genes as described in e.g., Ausubel, F. M., et al., Current Protocols in Molecular Biology, (Current Protocol, 1994).

SalmoKCaR genes were isolated by Polymerase Chain Reaction (PCR) of genomic DNA with degenerate primers (SEQ ID NOS: 13 and 14) specific to a highly conserved sequence of calcium receptors that does not contain introns. For example, partial Atlantic Salmon clones were obtained by using degenerate primers that permit selective amplification of a sequence (nucleotides 2279–2934 of SKCaR) that is highly conserved in both mammalian and shark kidney calcium receptors. See Exemplification. The degenerate primers (SEQ ID NOS: 13 and 14) amplify a sequence of 653 base pairs that is present in the extracellular domain of calcium receptors. This 653 nt sequence refers to SEQ ID NO: 3 with the addition of the sequence of the primers. The resulting amplified 653 bp fragment was ligated into a cloning vector and transformed into bacterial cells for growth, purification and sequencing. Additionally, SalmoKCaR genes can be isolated by Reverse Transcriptase-Polymerase Chain Reaction (RT-PCR) after isolation of poly A+ RNA from aquatic species with the same or similar degenerate primers. Methods of PCR and RT-PCR are well characterized in the art (See generally, *PCR Technology: Principles and Applications for DNA Amplification* (ed. H. A. Erlich, Freeman Press, NY, N.Y., 1992); *PCR Protocols: A Guide to Methods and Applications* (Eds. Innis, et al., Academic Press, San Diego, Calif., 1990); Mattila, et al., *Nucleic Acids Res.,* 19:4967 (1991); Eckert, et al., *PCR Methods and Applications,* 1:17 (1991); PCR (eds. McPherson, et al., IRL Press, Oxford); and U.S. Pat. No. 4,683,202. Poly A+ RNA can be isolated from any tissue which contains one or more of SalmoKCaR polypeptides by standard methods as described. Preferred tissue for polyA+ RNA isolation can be determined using an antibody which is specific for the highly conserved sequence of calcium receptors, by standard methods. The partial genomic or CDNA sequences derived from a SalmoKCaR gene are unique and, thus, can be used as a unique probe to isolate the full-length cDNA from other species. Moreover, in one embodiment, this DNA fragment serves as a basis for specific assay kits for detection of SalmoKCaR expression in various tissues of Atlantic Salmon.

Also encompassed by the present invention are nucleic acid sequences, genomic DNA, cDNA, RNA or a combination thereof, which are substantially complementary to the DNA sequences encoding SalmoKCaR nucleic acid molecules and which specifically hybridize with the SalmoKCaR nucleic acid sequences under conditions of sufficient stringency (e.g., high stringency) to identify DNA sequences with substantial nucleic acid identity.

The present invention embodies nucleic acid molecules (e.g., probes or primers) that hybridize to SEQ ID NO: 7, 9, or 11 under high stringency conditions, as defined herein. In one aspect, the present invention includes molecules that hybridize to at least about 200 contiguous nucleotides or longer in length (e.g., 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000). Such molecules hybridize to one of the SalmoKCaR nucleic acid sequences (SEQ ID NO: 7, 9, or 11) under high stringency conditions. The present invention includes those molecules that hybridize with SalmoKCaR nucleic acid molecules and encode a polypeptide that has the functions or biological activity described herein.

Typically the nucleic acid probe comprises a nucleic acid sequence (e.g. SEQ ID NO: 7, 9, or 11) and is of sufficient length and complementarity to specifically hybridize to a nucleic acid sequence that encodes a SalmoKCaR polypeptide. For example, a nucleic acid probe can be at least about 5%, 10%, 20%, 30%, 40%, 50%, 60%, 70%, 80% or 90% the length of the SalmoKCaR nucleic acid sequence. The requirements of sufficient length and complementarity can be easily determined by one of skill in the art. Suitable hybridization conditions (e.g., high stringency conditions) are also described herein. Additionally, the present invention encompasses fragments that are biologically active SalmoKCaR polypeptides or nucleic acid sequences that encodes biologically active SalmoKCaR polypeptides, as described further herein.

Such fragments are useful as probes for assays described herein, and as experimental tools, or in the case of nucleic acid fragments, as primers. A preferred embodiment includes primers and probes which selectively hybridize to the nucleic acid constructs encoding any one of the SalmoKCaR proteins. For example, nucleic acid fragments which encode any one of the domains described herein are also implicated by the present invention.

Stringency conditions for hybridization refers to conditions of temperature and buffer composition which permit hybridization of a first nucleic acid sequence to a second nucleic acid sequence, wherein the conditions determine the degree of identity between those sequences which hybridize to each other. Therefore, “high stringency conditions” are those conditions wherein only nucleic acid sequences which are very similar to each other will hybridize. The sequences can be less similar to each other if they hybridize under moderate stringency conditions. Still less similarity is needed for two sequences to hybridize under low stringency conditions. By varying the hybridization conditions from a stringency level at which no hybridization occurs, to a level at which hybridization is first observed, conditions can be determined at which a given sequence will hybridize to those sequences that are most similar to it. The precise conditions determining the stringency of a particular hybridization include not only the ionic strength, temperature, and the concentration of destabilizing agents such as formamide, but also factors such as the length of the nucleic acid sequences, their base composition, the percent of mismatched base pairs between the two sequences, and the frequency of occurrence of subsets of the sequences (e.g., small stretches of repeats) within other non-identical sequences. Washing is the step in which conditions are set so as to determine a minimum level of similarity between the sequences hybridizing with each other. Generally, from the lowest temperature at which only homologous hybridization occurs, a 1% mismatch between two sequences results in a 1° C. decrease in the melting temperature ($T_m$) for any chosen SSC concentration. Generally, a doubling of the concentration of SSC results in an increase in the $T_m$ of about 17° C. Using these guidelines, the washing temperature can be determined empirically, depending on the level of mismatch sought. Hybridization and wash conditions are explained in *Current Protocols in Molecular Biology* (Ausubel, F. M. et al., eds., John Wiley & Sons, Inc., 1995, with supplemental updates) on pages 2.10.1 to 2.10.16, and 6.3.1 to 6.3.6.

High stringency conditions can employ hybridization at either (1) 1×SSC (10×SSC=3 M NaCl, 0.3 M $Na_3$-citrate.$2H_2O$ (88 g/liter), pH to 7.0 with 1 M HCl), 1% SDS (sodium dodecyl sulfate), 0.1–2 mg/ml denatured calf thymus DNA at 65° C., (2) 1×SSC, 50% formamide, 1% SDS, 0.1–2 mg/ml denatured calf thymus DNA at 42° C., (3) 1% bovine serum albumin (fraction V), 1 mM $Na_2$·EDTA, 0.5 M $NaHPO_4$ (pH 7.2) (1 M $NaHPO_4$=134 g $Na_2HPO_4.7H_2O$, 4 ml 85% $H_3PO_4$ per liter), 7% SDS, 0.1–2 mg/ml denatured calf thymus DNA at 65° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 42° C., (5) 5×SSC, 5× Denhardt's solution, 1% SDS, 100 μg/ml denatured calf thymus DNA at 65° C., or (6) 5×SSC, 5× Denhardt's solution, 50% formamide, 1% SDS, 100 μg/ml denatured calf thymus DNA at 42° C., with high stringency washes of either (1) 0.3–0.1×SSC, 0.1% SDS at 65° C., or (2) 1 mM $Na_2EDTA$, 40 mM $NaHPO_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 18 to about 49 base pairs in length, the $T_m$ in ° C.=(81.5° C.+16.6 ($log_{10}M$)+0.41(% G+C)−0.61 (% formamide)−500/L), where "M" is the molarity of monovalent cations (e.g., $Na^+$), and "L" is the length of the hybrid in base pairs.

Moderate stringency conditions can employ hybridization at either (1) 4×SSC, (10×SSC=3 M NaCl, 0.3 M $Na_3$-citrate.$2H_2O$ (88 g/liter), pH to 7.0 with 1 M HCl), 1% SDS (sodium dodecyl sulfate), 0.1–2 mg/ml denatured calf thymus DNA at 65° C., (2) 4×SSC, 50% formamide, 1% SDS, 0.1–2 mg/ml denatured calf thymus DNA at 42° C., (3) 1% bovine serum albumin (fraction V), 1 mM $Na_2$·EDTA, 0.5 M $NaHPO_4$ (pH 7.2) (1 M $NaHPO_4$=134 g $Na_2HPO_4.7H_2O$, 4 ml 85% $H_3PO_4$ per liter), 7% SDS, 0.1–2 mg/ml denatured calf thymus DNA at 65° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 42° C., (5) 5×SSC, 5× Denhardt's solution, 1% SDS, 100 μg/ml denatured calf thymus DNA at 65° C., or (6) 5×SSC, 5× Denhardt's solution, 50% formamide, 1% SDS, 100 μg/ml denatured calf thymus DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 18 to about 49 base pairs in length, the $T_m$ in ° C.=(81.5° C.+16.6($log_{10}M$)+0.41(% G+C)−0.61 (% formamide)−500/L), where "M" is the molarity of monovalent cations (e.g., $Na^+$), and "L" is the length of the hybrid in base pairs.

Low stringency conditions can employ hybridization at either (1) 4×SSC, (10×SSC=3 M NaCl, 0.3 M $Na_3$-citrate.$2H_2O$ (88 g/liter), pH to 7.0 with 1 M HCl), 1% SDS (sodium dodecyl sulfate), 0.1–2 mg/ml denatured calf thymus DNA at 50° C., (2) 6×SSC, 50% formamide, 1% SDS, 0.1–2 mg/ml denatured calf thymus DNA at 40° C., (3) 1% bovine serum albumin (fraction V), 1 mM $Na_2$.EDTA, 0.5 M $NaHPO_4$ (pH 7.2) (1 M $NaHPO_4$=134 g $Na_2HPO_4.7H_2O$, 4 ml 85% $H_3PO_4$ per liter), 7% SDS 0.1–2 mg/ml denatured calf thymus DNA at 50° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 40° C., (5) 5×SSC, 5× Denhardt's solution, 1% SDS, 100 μg/ml denatured calf thymus DNA at 50° C., or (6) 5×SSC, 5× Denhardt's solution, 50% formamide, 1% SDS, 100 μg/ml denatured calf thymus DNA at 40° C., with low stringency washes of either 2×SSC, 0.1% SDS at 50° C., or (2) 0.5% bovine serum albumin (fraction V), 1 mM $Na_2EDTA$, 40 mM $NaHPO_4$ (pH 7.2), 5% SDS. The above conditions are intended to be used for DNA-DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 18 to about 49 base pairs in length, the $T_m$ in ° C.=(81.5° C.+16.6($log_{10}M$)+0.41(% G+C)−061 (% formamide)−500/L), where "M" is the molarity of monovalent cations (e.g., $Na^+$), and "L" is the length of the hybrid in base pairs.

The SalmoKCaR nucleic acid sequence, or a fragment thereof, can also be used to isolate additional aquatic PVCR homologs. For example, a cDNA or genomic DNA library from the appropriate organism can be screened with labeled SalmoKCaR nucleic acid sequence to identify homologous genes as described in e.g., Ausebel, et al., Eds., *Current Protocols In Molecular Biology*, John Wiley & Sons, New York (1997).

In another embodiment, the present invention pertains to a method of isolating a SalmoKCaR nucleic acid comprising contacting an isolated nucleic acid with a SalmoKCaR-specific hybridization probe and identifying an aquatic PVCR. Methods for identifying a nucleic acid by hybridization are routine in the art (see *Current Protocols In Molecular Biology*, Ausubel, F. M. et al., Eds., John Wiley & Sons: New York, N.Y., (1997). The present method can optionally include a labeled SalmoKCaR probe.

The invention also provides vectors, plasmids or viruses containing one or more of the SalmoKCaR nucleic acid molecules. Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989).

Uses of plasmids, vectors or viruses containing the cloned SalmoKCaR receptors or receptor fragments include one or more of the following; (1) generation of hybridization probes for detection and measuring level of SalmoKCaR in tissue or isolation of SalmoKCaR homologs; (2) generation of SalmoKCaR MRNA or protein in vitro or in vivo; and (3) generation of transgenic non-human animals or recombinant host cells.

In one embodiment, the present invention encompasses host cells transformed with the plasmids, vectors or viruses described above. Nucleic acid molecules can be inserted into a construct which can, optionally, replicate and/or integrate into a recombinant host cell, by known methods. The host cell can be a eukaryote or prokaryote and includes, for example, yeast (such as *Pichia pastorius* or *Saccharomyces cerevisiae*), bacteria (such as *E. coli* or *Bacillus subtilis*), animal cells or tissue, insect Sf9 cells (such as baculoviruses infected SF9 cells) or mammalian cells (somatic or embryonic cells, Human Embryonic Kidney (HEK) cells, Chinese hamster ovary cells, HeLa cells, human 293 cells and monkey COS-7 cells). Host cells suitable in the present invention also include a fish cell, a mammalian cell, a bacterial cell, a yeast cell, an insect cell, and a plant cell.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a polypeptide. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example.

The host cell is then maintained under suitable conditions for expression and recovery of SalmoKCaR protein. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria broth, Superbroth, Dulbecco's Modified Eagles Media (DMEM), RPMI-1640, M199 and Grace's insect media. The growth media can contain a buffer, the selection of which is not critical to the invention. The pH of the buffered Media can be selected and is generally one tolerated by or optimal for growth for the host cell.

The host cell is maintained under a suitable temperature and atmosphere. Alternatively, the host cell is aerobic and the host cell is maintained under atmospheric conditions or other suitable conditions for growth. The temperature should also be selected so that the host cell tolerates the process and can be for example, between about 13°–40° C.

Antibodies, Fusion Proteins and Methods of Assessment of the SalmoKCaR Nucleic Acid and Amino Acid Molecules The present invention includes methods of detecting the levels of the SalmoKCaR nucleic acid levels (MRNA levels) and/or polypeptide levels to determine whether fish are ready for transfer from freshwater to seawater. The present invention also includes methods for assaying compounds that modulate SalmoKCaR nucleic acid levels, expression levels or activity of SalmoKCaR polypeptides. Activity of SalmoKCaR polypeptides includes, but is not limited to, phosphorylation of one or more of the SalmoKCaR polypeptides, dimerization of one of the SalmoKCaR polypeptides with a second SalmoKCaR polypeptide, proteolysis of one or more of the SalmoKCaR polypeptides, and/or increase or decrease in the intracellular signal transduction system or pathway of one or more of the SalmoKCaR polypeptides. The present invention also includes assaying activities, as known in the art. Methods that measure SalmoKCaR levels include several suitable assays. Suitable assays encompass immunological methods, such as FACS analysis, radioimmunoassay, flow cytometry, immunocytochemistry, enzyme-linked immunosorbent assays (ELISA) and chemiluminescence assays. Additionally, antibodies, or antibody fragments, can also be used to detect the presence of SalmoKCaR proteins and homologs in other tissues using standard immunohistological methods. For example, immunohistochemical studies were performed using the 1169 antibody which was raised against a portion of the shark kidney calcium receptor demonstrating localized expression in the olfactory organ. Antibodies are absorbed to determine the SalmoKCaR protein levels. Antibodies could be used in a kit to monitor the SalmoKCaR protein level of fish in aquaculture. Any method known now or developed later can be used for measuring SalmoKCaR expression.

Antibodies reactive with any one of the SalmoKCaR or portions thereof can be used. In a preferred embodiment, the antibodies specifically bind with SalmoKCaR polypeptides or a portion thereof. The antibodies can be polyclonal or monoclonal, and the term antibody is intended to encompass polyclonal and monoclonal antibodies, and functional fragments thereof. The terms polyclonal and monoclonal refer to the degree of homogeneity of an antibody preparation, and are not intended to be limited to particular methods of production.

In several of the preferred embodiments, immunological techniques detect SalmoKCaR levels by means of an anti-SalmoKCaR antibody (i.e., one or more antibodies). The term "anti-SalmoKCaR" antibody includes monoclonal and/or polyclonal antibodies, and mixtures thereof Anti-SalmoKCaR antibodies can be raised against appropriate immunogens, such as isolated and/or recombinant SalmoKCaR, analogs or portion thereof (including synthetic molecules, such as synthetic peptides). In one embodiment, antibodies are raised against an isolated and/or recombinant SalmoKCaR or portion thereof (e.g., a peptide) or against a host cell which expresses recombinant SalmoKCaR. In addition, cells expressing recombinant SalmoKCaR, such as transfected cells, can be used as immunogens or in a screen for antibody which binds receptor.

Any suitable technique can prepare the immunizing antigen and produce polyclonal or monoclonal antibodies. The art contains a variety of these methods (see e.g., Kohler et al., Nature, 256:495–497 (1975) and Eur. J. Immunol. 6:511–519 (1976); Milstein et al., Nature 266:550–552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, fusing a suitable immortal or myeloma cell line, such as SP2/0, with antibody producing cells can produce a hybridoma. Animals immunized with the antigen of interest provide the antibody producing cell, preferably cells from the spleen or lymph nodes. Selective culture conditions isolate antibody producing hybridoma cells while limiting dilution techniques produce them. Researchers can use suitable assays such as ELISA to select antibody producing cells with the desired specificity.

Other suitable methods can produce or isolate antibodies of the requisite specificity. Examples of other methods include selecting recombinant antibody from a library or relying upon immunization of transgenic animals such as mice. Such methods include immunization of various life-stages of Atlantic salmon to produce antibodies to native PVCR proteins and thereby alter their function or specificity.

According to the method, an assay can determine the level of SalmoKCaR in a biological sample. In determining the amounts of SalmoKCaR, an assay includes combining the sample to be tested with an antibody having specificity for the SalmoKCaR, under conditions suitable for formation of a complex between antibody and the SalmoKCaR, and detecting or measuring (directly or indirectly) the formation of a complex. The sample can be obtained directly or indirectly, and can be prepared by a method suitable for the particular sample and assay format selected.

In particular, tissue samples, e.g., gill tissue samples, can be taken from fish after they are anaesthetized with MS-222. The tissue samples are fixed by immersion in 2% paraformaldehyde in appropriate Ringers solution corresponding to the osmolality of the fish, washed in Ringers, then frozen in an embedding compound, e.g., O.C.T.™ (Miles, Inc., Elkahart, Ind., U.S.A.) using methylbutane cooled with liquid nitrogen. After cutting 8–10 micron tissue sections with a cryostat, individual sections are subjected to various staining protocols. For example, sections are: 1) blocked with goat serum or serum obtained from the same species of fish, 2) incubated with rabbit anti-CaR or anti-SalmoKCaR antiserum, and 3) washed and incubated with peroxidase-conjugated affinity-purified goat antirabbit antiserum. The locations of the bound peroxidase-conjugated goat antirabbit antiserum are then visualized by development of a rose-colored aminoethylcarbazole reaction product. Individual sections are mounted, viewed and photographed by standard light microscopy techniques. The anti-CaR antiserum used to detect fish SalmoKCaR protein is raised in rabbits using a 23-mer peptide corresponding to amino acids numbers 214–236 localized in the extracellular domain of the RaK-CaR protein. The sequence of the 23-mer peptide is: ADDDYGRPGIEKFREEAEERDIC (SEQ ID NO.: 24) A small peptide with the sequence DDYGRPGIEKFREE-AEERDICI (SEQ ID NO.: 25) or ARSRNSADGRSGD-DLPC (SEQ ID NO.: 26) can also be used to make antisera containing antibodies to SalmoKCaRs. Such antibodies can be monoclonal, polyclonal or chimeric.

Suitable labels can be detected directly, such as radioactive, fluorescent or chemiluminescent labels. They can also be indirectly detected using labels such as enzyme labels and other antigenic or specific binding partners like biotin. Examples of such labels include fluorescent labels such as fluorescein, rhodamine, chemiluminescent labels such as luciferase, radioisotope labels such as $^{32}P$, $^{125}I$, $^{131}I$, enzyme labels such as horseradish peroxidase, and alkaline phosphatase, β-galactosidase, biotin, avidin, spin labels, magnetic beads and the like. The detection of antibodies in a complex can also be done immunologically with a second antibody which is then detected (e.g., by means of a label). Conventional methods or other suitable methods can directly or indirectly label an antibody. Labeled primary and secondary antibodies can be obtained commercially or prepared using methods know to one of skill in the art (see Harlow, E. and D. Lane, 1988, *Antibodies: A Laboratory Manual*, (Cold Spring Harbor Laboratory: Cold Spring Harbor, N.Y.).

Using the immunocytochemistry method, the levels of SalmoKCaR in various tissues can be detected and examined as to whether they change in comparison to control. Modulated levels or the presence of SalmoKCaR expression in various tissues, as compared to a control, indicate that the fish or the population of fish from which a statistically significant amount of fish were tested, are ready for transfer to freshwater. A control refers to a level of SalmoKCaR, if any, from a fish that is not subjected to the steps of the present invention, e.g., not subjected to freshwater having a SalmoKCaR modulator and/or not fed a NaCl diet. For example, FIGS. 18 and 19 show that fish not subjected to the present invention had no detectable SalmoKCaR level, whereas fish that were subjected to the steps of the invention had SalmoKCaR levels that were easily detected.

In determining whether compounds are modulators, one can measure changes that occur in the expression levels of one or more the SalmoKCaR genes, or those that occur in one or more intracellular signal transduction systems or pathways. A signal transduction pathway is a pathway involved in the sensing and/or processing of stimuli. In particular, such pathways are altered by activation of the expressed proteins coded for by a single or combination of nucleic acids of the present invention.

The SalmoKCaR polypeptides can be in the form of a conjugate or a fusion protein, which can be manufactured by known methods. Fusion proteins can be manufactured according to known methods of recombinant DNA technology. For example, fusion proteins can be expressed from a nucleic acid molecule comprising sequences which code for a biologically active portion of the SalmoKCaR polypeptide and its fusion partner, for example a portion of an immunoglobulin molecule. For example, some embodiments can be produced by the intersection of a nucleic acid encoding immunoglobulin sequences into a suitable expression vector, phage vector, or other commercially available vectors. The resulting construct can be introduced into a suitable host cell for expression. Upon expression, the fusion proteins can be isolated or purified from a cell by means of an affinity matrix. By measurement of the alternations in the functions of transfected cells occurring as a result of expression of recombinant SalmoKCaR proteins, either the cells themselves or SalmoKCaR proteins produced from the cells can be utilized in a variety of screening assays that all have a high degree of utility over screening methods involving tests on the same PVCR proteins in whole fish.

The SalmoKCaRs can also be assayed by Northern blot analysis of mRNA from tissue samples. Northern blot analysis from various shark tissues has revealed that the highest degree of PVCR expression is in gill tissue, followed by the kidney and the rectal gland. There appear to be at least three distinct mRNA species of about 7 kb, 4.2 kb and 2.6 kb.

The SalmoKCaRs can also be assayed by hybridization, e.g., by hybridizing one of the SalmoKCaR sequences provided herein (e.g., SEQ ID NO: 7, 9 or 11) or an oligonucleotide derived from one of the sequences, to a DNA or RNA-containing tissue sample from a fish. Such a hybridization sequence can have a detectable label, e.g., radioactive, fluorescent, etc., attached to allow the detection of hybridization product. Methods for hybridization are well known, and such methods are provided in U.S. Pat. No. 5,837,490, by Jacobs et al., the entire teachings of which are herein incorporated by reference in their entirety. The design of the oligonucleotide probe should preferably follow these parameters: (a) it should be designed to an area of the sequence which has the fewest ambiguous bases ("N's"), if any, and (b) it should be designed to have a $T_m$ of approx. 80° C. (assuming 2° C. for each A or T and 4 degrees for each G or C).

Additionally, the above probes could be used in a kit to identify SalmoKCaR homologs and their expression in various fish tissue. The present invention also encompasses the isolation of SalmoKCaR homologs and their expression in various fish tissues with a kit containing primers specific for conserved sequences of SalmoKCaR nucleic acids and proteins.

The present invention encompasses detection of SalmoKCaRs with PCR methods using primers disclosed or derived from sequences described herein. For example, SalmoKCaRs can be detected by PCR using SEQ ID Nos: 13 and 14, as described in Example 6. PCR is the selective amplification of a target sequence by repeated rounds of nucleic acid replication utilizing sequence-specific primers and a thermostable polymerase. PCR allows recovery of entire sequences between two ends of known sequence. Methods of PCR are described herein and are known in the art.

In particular, the levels of SalmoKCaR nucleic acid can be determined in various tissues by Reverse Transcriptase-Polymerase Chain Reaction (RT-PCR) after isolation of poly A+ RNA from aquatic species. Methods of PCR and RT-PCR are well characterized in the art (See generally, PCR Technology: Principles and Applications for DNA Amplification (ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res., 19:4967 (1991); Eckert et al., PCR Methods and Applications, 1:17 (1991); PCR (eds. McPherson et al., IRL Press, Oxford); Ausebel, F. M. et al., Current Protocols in Molecular Biology, Greene Publishing Assoc. and Wiley-Interscience 1987, & Supp. 49, 2000; and U.S. Pat. No. 4,683,202). Briefly, mRNA is extracted from the tissue of interest and reverse transcribed. Subsequently, a PCR reaction is performed with SalmoKCaR-specific primers and the presence of the predicted SalmoKCaR product is determined, for example, by agarose gel electrophoresis. Examples of SalmoKCaR-specific primers are SEQ ID NO: 16–21. The product of the RT-PCR reaction that is performed with SalmoKCaR-specific primers is referred to herein as a RT-PCR product. The RT-PCR product can include nucleic acid molecules having part or all of the SalmoKCaR sequence. The RT-PCR product can optionally be radioactively labeled and the presence or amount of SalmoKCaR product can be determined using autoradiography. Two examples of commercially available fluorescent probes that can be used in such an assay are Molecular Beacons (Stratagene) and Taqman® (Applied Biosystems). Alternative methods of labeling and quantifying the RT-PCR product are well known to one of skill in the art (see Ausebel, F. M. et al., Current Protocols in Molecular Biology, Greene Publishing Assoc. and Wiley-Interscience 1987, & Supp. 49, 2000. Poly A+ RNA can be isolated from any tissue which contains at least one SalmoKCaR by standard methods. Such tissues include, for example, gill, nasal lamellae, urinary bladder, kidney, intestine, stomach, liver and brain.

Hence, the present invention includes kits for the detection of SalmoKCaR or the quantification of SalmoKCaR having either antibodies specific for SalmoKCaR or a portion thereof, or a nucleic acid sequence that can hybridize to the nucleic acid of SalmoKCaR.

Transgenic Fish

Alterations in the expression or sensitivity of SalmoKCaRs could also be accomplished by introduction of a suitable transgene. Suitable transgenes would include either the SalmoKCaR genes itself or modifier genes that would directly or indirectly influence SalmoKCaR gene expression. Methods for successful introduction, selection and expression of the transgene in fish oocytes, embryos and adults are described in Chen, T T et al., Transgenic Fish, *Trends in Biotechnology* 8:209–215 (1990).

The present invention is further and more specifically illustrated by the following Examples, which are not intended to be limiting in any way.

Exemplification

The following examples refer to Process I and Process II throughout. Process I is also referred to herein as "SUPERSMOLT™ I Process" or "APS Process I." APS stands for "AquaBio Products Sciences®, L.L.C." A "Process I" fish or smolt refers to a fish or smolt that has undergone the steps of Process I. A Process I smolt is also referred to as a "SUPERSMOLT™ I" or an "APS Process I" smolt. Likewise, Process II is also referred to herein as "SUPERSMOLT™ II Process" or "Process II." A "Process II" fish or smolt refers to a fish or smolt that has undergone the steps of Process II. A Process II smolt is also referred to as a "SUPERSMOLT™ II" or an "APS Process II" smolt.

Process I: Pre-adult anadromous fish (this includes both commercially produced S0, S1 or S2 smolts as well as smaller parr/smolt fish) are exposed to or maintained in freshwater containing either 2.0–10.0 mM Calcium and 0.5–10.0 mM Magnesium ions. This water is prepared by addition of calcium carbonate and/or chloride and magnesium chloride to the freshwater. Fish are fed with feed pellets containing 7% (weight/weight) NaCl. Fish are exposed to or maintained in this regimen of water mixture and feed for a total of 30–45 days, using standard hatchery care techniques. Water temperatures vary between 10–16° C. Fish are exposed to a constant photoperiod for the duration of Process I. A fluorescent light is used for the photoperiod.

Process II: Pre-adult anadromous fish (this includes both commercially produced S0, S1 or S2 smolts as well as smaller parr/smolt fish) are exposed to or maintained in freshwater containing 2.0–10.0 mM Calcium and 0.5–10.0 mM Magnesium ions. This water is prepared by addition of calcium carbonate and/or chloride and magnesium chloride to the freshwater. Fish are fed with feed pellets containing 7% (weight/weight) NaCl and either 2 gm or 4 gm of L-Tryptophan per kg of feed. Fish are exposed to or maintained in this regimen of water mixture and feed for a total of 30–45 days using standard hatchery care techniques. Water temperatures vary between 10–16° C. Fish are exposed to a constant photoperiod for the duration of Process II. A fluorescent light is used for the photoperiod.

EXAMPLE 1

Molecular Cloning of Shark Kidney Calcium Receptor Related Protein (SKCaR)

A shark λZAP cDNA library was manufactured using standard commercially available reagents with cDNA synthesized from poly A+ RNA isolated from shark kidney tissue as described and published in Siner et al. *Am. J. Physiol.* 270:C372–C381, 1996. The shark cDNA library was plated and resulting phage plaques screened using a $^{32}$P-labeled full length rat kidney CaR (RaKCaR) cDNA probe under intermediate stringency conditions (0.5×SSC, 0.1% SDS, 50° C.). Individual positive plaques were identified by autoradiography, isolated and rescued using phagemid infections to transfer cDNA to KS Bluescript vector. The complete nucleotide sequence, FIG. 1, (SEQ ID NO: 1) of the 4.1 kb shark kidney PVCR related protein (SKCaR) clone was obtained using commercially available automated sequencing service that performs nucleotide sequencing using the dideoxy chain termination technique. The deduced amino acid sequence (SEQ ID NO: 2) is shown in FIG. 1. Northern analyses were performed as described in Siner et. al. Am. J. Physiol. 270:C372–C381, 1996. The SKCAR nucleotide sequence was compared to others CaRs using commercially available nucleotide and protein database services including GENBANK and SWISS PIR.

EXAMPLE 2

Expression/Activation Studies of SKCaR in Human Embryonic Kidney (HEK) Cells PVCRs serve as salinity sensors in fish. These receptors are localized to the apical membranes of various cells within the fish's body (e.g., in the gills, intestine, kidney) that are known to be responsible for osmoregulation. A full-length cation receptor (CaR, also referred to as "PVCR") from the dogfish shark has been expressed in human HEK cells. This receptor was shown to respond to alterations in ionic compositions of NaCl, Ca2+ and Mg2+ in extracellular fluid bathing the HEK cells. The ionic concentrations encompassed the range which includes the transition from freshwater to seawater. Expression of PVCR MRNA is also increased in fish after their transfer from freshwater to seawater, and is modulated by PVCR agonists. Partial genomic clones of PVCRs have also been isolated from other fish species, including winter and summer flounder and lumpfish, by using nucleic acid amplification with degenerate primers.

In particular, the following was shown:

1. SKCaR encodes a functional ion receptor that is sensitive to both Mg2+ and Ca2+ as well as alterations in NaCl.
2. SKCaR's sensitivity to Ca2+, Mg2+ and NaCl occur in the range that is found in marine environments and is consistent with SKCaRs role as a salinity sensor.
3. SKCaR's sensitivity to Mg2+ is further modulated by Ca2+ such that SKCaR is capable to sensing various combinations of divalent and monovalent cations in seawater and freshwater. These data can be used to design novel electrolyte solutions to maintain fish in salinities different from those present in their natural environment.

SKCaR cDNA was ligated into the mammalian expression vector PCDNA II and transfected into HEK cells using standard techniques. The presence of SKCaR protein in transfected cells was verified by western blotting. Activation of SKCaR by extracellular Ca2+, Mg2+ or NaCl was quantified using a well characterized FURA 2 based assay where increases in intracellular Ca2+ produced by SKCaR activation are detected using methodology published previously by Bai, M., S. Quinn, S. Trvedi, O. Kifor, S. H. S. Pearce, M. R. Pollack, K. Krapcho, S. C. Hebert and E. M. Brown. *Expression and characterization of inactivating and activating mutations in the human Ca2+-sensing receptor. J. Biol. Chem.,* 32:19537–19545 (1996); and expressed as % normalized intracellular calcium response to receptor activation.

SKCaR is a functional extracellular Ca2+ sensor where its sensitivity is modulated by alterations in extracellular NaCl concentrations. As shown in FIG. 2, SKCaR is activated by increasing concentrations of extracellular Ca2+ where half maximal activation of SKCaR ranges between 1–15 mM depending on the extracellular concentration of NaCl. These are the exact ranges of Ca2+ (1–10 mM present in marine estuarian areas). Note that increasing concentrations of NaCl reduce the sensitivity of SKCaR to Ca2+. This alteration in SKCaR sensitivity to Ca2+ was not observed after addition of an amount of sucrose sufficient to alter the osmolality of the extracellular medium. This control experiment shows it is not alterations in cell osmolality effecting the changes observed.

Figure 4:
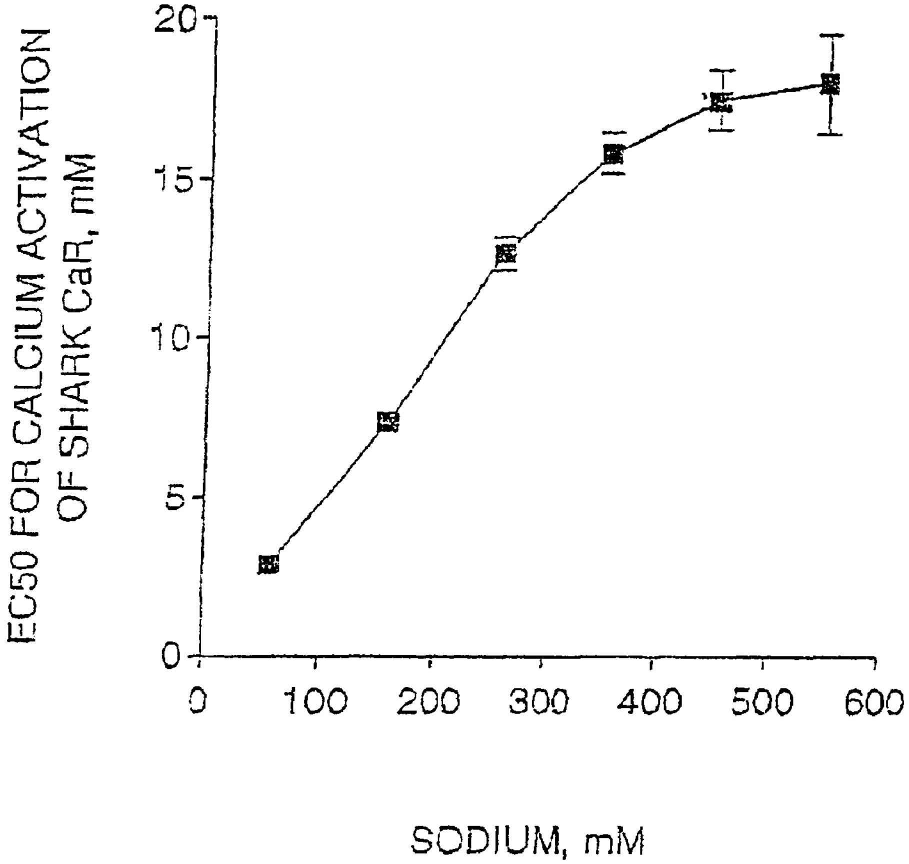
FIG. 4 is a graphical representation showing the EC50 for calcium activation of shark CaR (mM) against the amount of sodium (mM) of the SKCaR-I protein in increasing amounts of extracellular NaCl concentrations.

The half maximal activation ($EC_{50}$) by Ca2+ for SKCaR is reduced in increased concentrations of extracellular NaCl. See FIG. 4. The $EC_{50}$ for data shown on FIG. 4 is displayed as a function of increasing extracellular NaCl concentrations. Note the $EC_{50}$ for Ca2+ increases from less than 5 mM to approximately 18 mM as extracellular NaCl concentrations increase from 50 mM to 550 mM.

Figure 3:
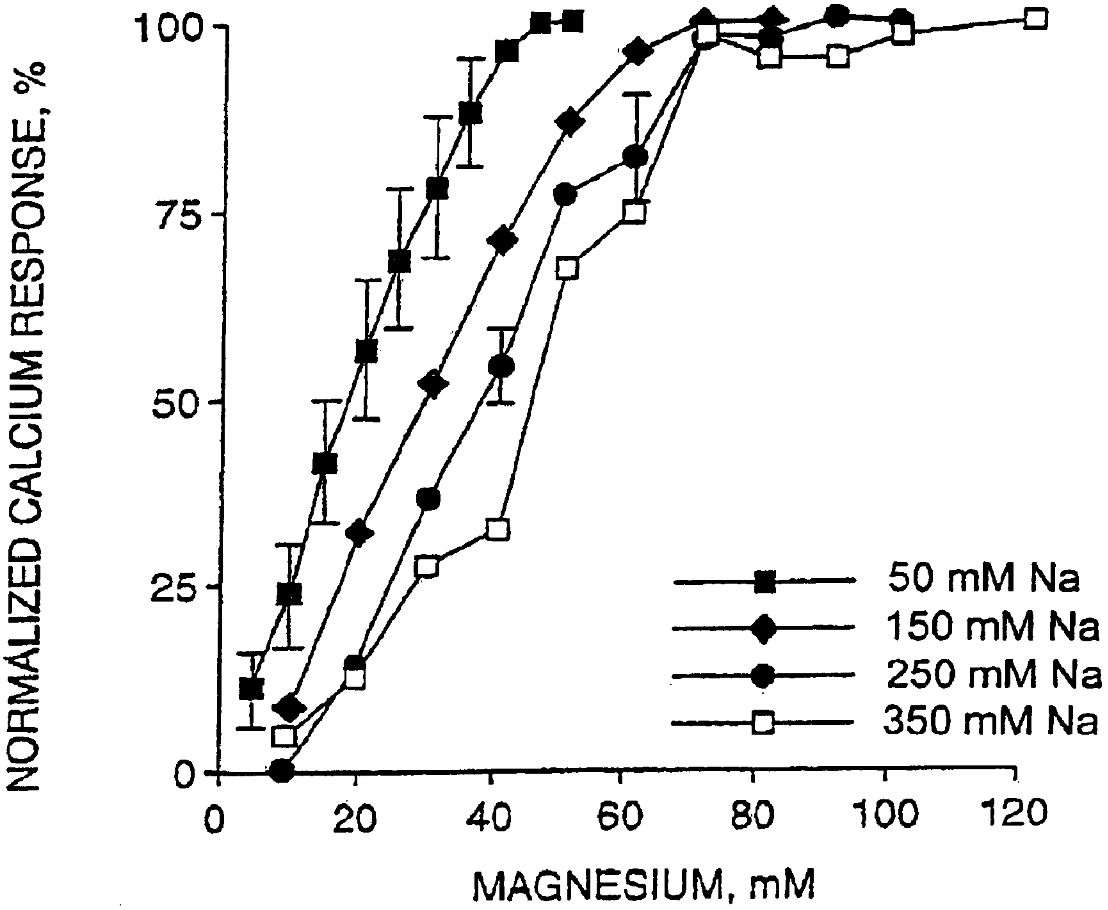
FIG. 3 is a graphical representation showing a normalized calcium response (%) against the amount of magnesium (mM) of the SKCaR protein in increasing amounts of extracellular NaCl concentrations.

SKCaR is a functional extracellular Mg2+ sensor where its sensitivity is modulated by alterations in extracellular NaCl concentrations. As shown in FIG. 3, SKCaR is activated in the range of 5–40 mM extracellular Mg2+ and is modulated in a manner similar to that shown in FIGS. 2 and 4 by increasing concentrations of extracellular NaCl. Similarly, this alteration in SKCaR sensitivity to Ca2+ was not observed after addition of an amount of sucrose sufficient to alter the osmolality of the extracellular medium.

Figure 5:
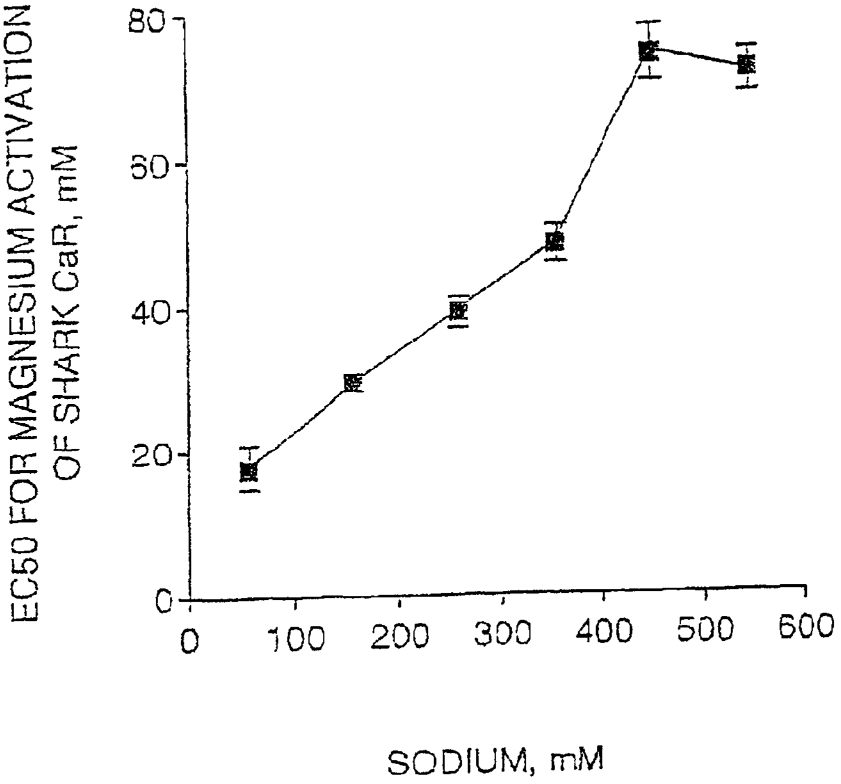
FIG. 5 is a graphical representation showing the EC50 for magnesium activation of shark CaR (mM) against the amount of sodium (mM) of the SKCaR protein in increasing amounts of extracellular NaCl concentrations.

The half maximal activation ($EC_{50}$) by Mg2+ for SKCaR is reduced in increased concentrations of extracellular NaCl. See FIG. 5. The $EC_{50}$ for data shown on FIG. 5 is displayed as a function of increasing extracellular NaCl concentrations. Note the $EC_{50}$ for Mg2+ increases from less than 20 mM to approximately 80 mM as extracellular NaCl concentrations increase from 50 mM to 550 mM.

Figure 6:
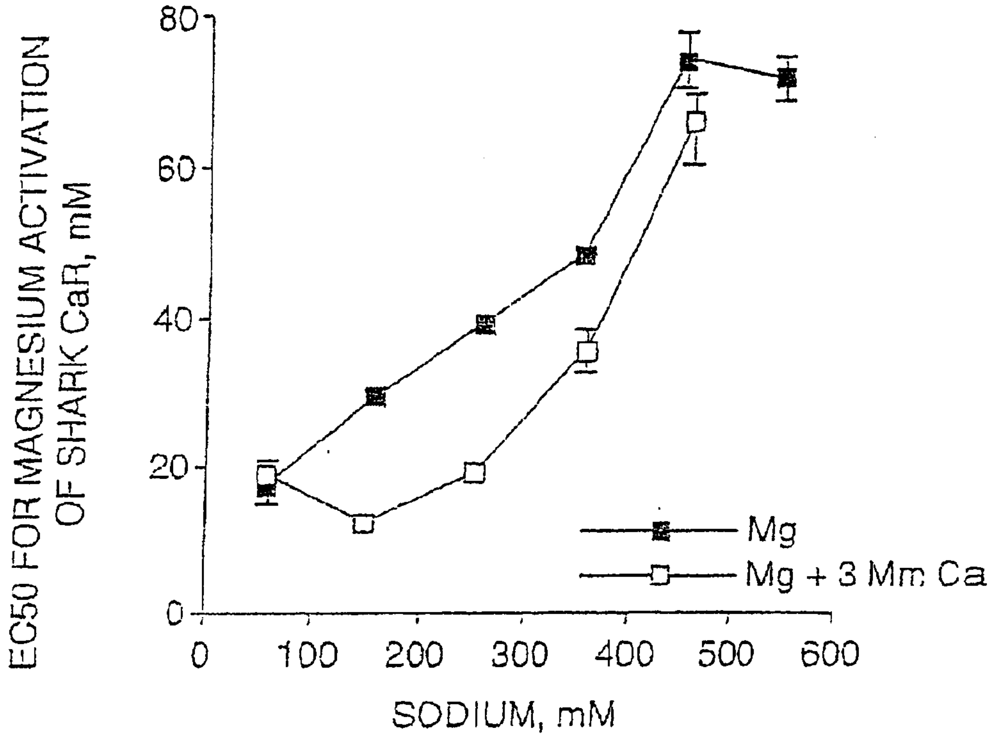
FIG. 6 is a graphical representation showing the EC50 for magnesium activation of shark CaR (mM) against the amount of sodium (mM) of the SKCaR protein in increasing amounts of extracellular NaCl concentrations and added amounts of calcium (3 mM).

Addition of 3 mM Ca2+ alters the sensitivity of SKCaR to Mg2+ and NaCl. See FIG. 6. The $EC_{50}$ for Mg2+ of SKCaR is modulated by increasing concentrations of NaCl as shown both in this FIG. 6 and in FIG. 5. Addition of 3mM Ca2+ to the extracellular solution alters the sensitivity characteristics of SKCaR as shown. Note the 3 mM Ca2+ increases the sensitivity of SKCaR to Mg2+ as a function of extracellular NaCl concentrations.

This method was also used to isolate partial genomic clones of PVCRs for Atlantic salmon and other species such as Arctic char and rainbow trout, as described herein. FIGS. 16A–D show the amino acid sequences and alignment for the PVCRs from three full length Atlantic salmon clones (SalmoKCar #1, #2, and #3) relative to the PVCR from the kidney of the dogfish shark (*Squalus acanthias*) (SKCaR) and human parathyroid calcium receptor (HuPCaR).

EXAMPLE 3

Defining Salinity Limits as an Assay to Identify Fish with Enhanced Salinity Responsive and Altered PVCR Function Both anadromous fish (Atlantic salmon, trout and Arctic char) and euryhaline fish (flounders, alewives, eels) traverse from freshwater to seawater environments and back again as part of their lifecycles in the natural environment. To successful accomplish this result; both types of fish have to undergo similar physiological changes including alterations in their urine output, altering water intake and water absorption. In some cases, naturally occurring mutations to PVCR would provide for altered salinity adaptation capabilities that would have significant value for both commercial and environmental restoration uses. For example, identification of selective traits associated with PVCR mediated salinity responses might allow identification of new strains of fish for commercial aquaculture. Similarly, identification of selected environmental parameters from a host of natural and man made variables that are the most important to improve the survival and successful restocking and/or ocean ranching of either wild Atlantic salmon or winter flounder would also be of great utility. To permit the identification of individual fish possessing enhanced salinity responsive characteristics, assays must be designed that enable these fish to survive while others not possessing these characteristics will either die or perform poorly. As described below, such assays would take advantage of the ability of these anadromous and euryhaline fish to withstand a wide range of salinities. Fish that were identified using such assays would then be propagated in breeding-selection programs.

Winter and Summer Flounder can be grown and maintained in recycling water systems. Groups of both winter (Pleuronectes americanus) and summer (Paralichthus dentalus) flounder were maintained in multiple modular recycling water system units that are composed of a single 1 meter fish tank maintained by a 1 meter biofilter tank located directly above it. The upper tank of each unit contains 168 sq. ft. of biofilter surface area that will support a maximum of 31 lbs of flounder, while maintaining optimal water purity and oxygenation conditions. Each unit is equipped with its own pump and temperature regulator apparatus. Both the temperature and photo-period of each unit can be independently regulated using black plastic curtains that partition each tank off from its neighbor. The inventors have a total of 12 independent modular units that permit 3 experiments each with 4 variables to be performed simultaneously. Using this experimental system, the following data have been obtained.

Salinity survival limits for winter and summer flounder with a constant ratio of divalent and monovalent ions were determined. The survival limit of both winter and summer flounder in waters of salinities greater than normal seawater (10 mM Ca2+, 50 mM Mg2+ and 450 mM NaCl) is water containing twice (20 mM Ca2+, 50 mM Mg2+ and 900 mM NaCl) the normal concentrations of ions present in normal seawater. In contrast, the survival limit of both winter and summer flounder in waters of salinity less than normal seawater is 10% seawater (1 mM Ca2+, 5 mM Mg2+ and 45 mM NaCl).

Use of a fully recycling water system permits growth of flounder at vastly different salinities. Groups of flounder (n=10) were adapted over a 15 day interval and maintained at either low salinity (LS) (e.g., at 10% normal seawater), normal seawater (NS) or hypersalinity (HS) (e.g., 2× seawater) for intervals of 3 months, under otherwise identical conditions. Survival among the 3 groups were comparable (all greater than 80%) and there were no differences in the electrolyte content of their respective sera.

EXAMPLE 4

Isolation of Partial Atlantic Salmon PVCRs

A partial PVCR gene of Atlantic Salmon was isolated as follows: sequences of shark kidney calcium receptor together with the nucleotide sequence of mammalian calcium receptors were used to design degenerate oligonucleotide primers, dSK-F3 (SEQ ID NO: 13) and dSK-R4 (SEQ ID NO: 14), to highly conserved regions in the transmembrane domain of polyvalent cation receptor proteins using standard methodologies (See G M Preston, *Polymerase chain reaction with degenerate oligonucleotide primers to clone gene family members*, Methods in Mol. Biol. Vol. 58 Edited by A. Harwood, Humana Press, pages 303–312, 1993). Using these primers, genomic DNA from the above species was amplified using standard PCR methodology. The PCR product (653 nt) was then purified by agarose gel electrophoresis and ligated into appropriate plasmid vector that was then transformed into a bacterial strain. After growth in liquid media, vectors and inserts are purified using standard techniques, analyzed by restriction enzyme analysis and sequenced. Using this methodology, a total of 8 nucleotide sequences from 8 fish species including Atlantic Salmon were amplified. Each clone is 594 nt (with-out primer sequences) and encodes a 197 amino acid sequence which corresponds to the conserved transmembrane domain of the calcium receptors.

Atlantic salmon partial PVCR nucleic acid sequence (SEQ ID NO: 3) is composed of 594 nucleotides (nt) containing an open reading frame encoding 197 amino acids (SEQ ID NO: 4) (FIG. 7).

EXAMPLE 5

Molecular Cloning of a Second Partial Atlantic Salmon PVCR

A second Atlantic salmon partial PVCR was isolated, as described herein. An Atlantic salmon λZAP cDNA library was manufactured using standard commercially available reagents with cDNA synthesized from poly A+ RNA isolated from Atlantic salmon intestine tissue according to manufacturers instructions (Stratagene, La Jolla, Calif.) and screened using the Atlantic salmon PCR product as a probe. A partial Atlantic salmon PVCR cDNA (SEQ ID NO: 5) is composed of 2021 nucleotides (nt) (FIG. 8A) containing an open reading frame encoding 388 amino acids (SEQ ID NO: 6) (FIG. 8B). The open reading frame encoded by SEQ ID NO: 5 begins at nucleotide position 87.

EXAMPLE 6

Molecular Cloning of 3 Full Length cDNA Clones from Kidney of Atlantic Salmon (Salmo Salar) and Determination of their Tissue Specific Expression in Various Salmon Tissues Modulated by Water Salinity In Example 5, a homology based approach was used to screen cDNA libraries under moderate stringency conditions to obtain a full length shark kidney PVCR clone (SKCaR). Using sequence information derived from Examples 4 and 5, both nucleotide (nt) and antibody probes were designed to detect PVCRs in other fish species. Using degenerate primers whose sequence was derived from knowledge of the nt sequence of SKCaR, PCR was utilized to amplify a series of genomic and cDNA (RT-PCR) sequences that contain partial nt and putative protein sequences of PVCRs from multiple fish including Atlantic salmon. See Examples 1, 4, and 5.

The data described in this Example show that the nt and putative protein sequences of 3 PVCR transcripts from Atlantic salmon kidney were isolated and characterized. Additionally, their tissue specific expression and modulation of tissue expression levels by alterations in water salinity were determined. This Example is divided into 2 parts: 1) isolation and sequence of 3 full length PVCR clones from salmon kidney (SalmoKCar#1 (SEQ ID NO: 7), SalmoKCar#2 (SEQ ID NO: 9) and SalmoKCar#3 (SEQ ID NO: 11)) and 2) use of RT-PCR analysis with degenerate and clone specific SalmoKCaR PCR primers to determine the tissue specific expression of these 3 transcripts in seawater vs. freshwater as well as the SuperSmolt™ process. Taken together, these data provide the framework for achieving a fundamental understanding of both PVCRs in salmonids as well as the their roles in the SuperSmolt™ process.

Part 1. Isolation and Sequence of 3 Full Length PVCR Clones from Salmon Kidney:

Materials and Methods: Total RNA was purified with Stat 60 reagent (Teltest B Friendswood, Tex.) and poly A+ purified with the Micro FastTrack Kit (Invitrogen, Carlsbad, Calif.). cDNA was then synthesized and fractionated whereby selected fractions were ligated and packaged as

| Primer sequences for PCR of PVCR clones: | |
|---|---|
| dSK-F3 5'-TGT CKT GGA CGG AGC CCT TYG GPA TCG C-3' | (SEQ ID NO:13) |
| dSK-R4 5'-GGC KGG RAT GAA RGA KAT CCA RAG RAT GAA G-3' | (SEQ ID NO:14) |

I=deoxyinosine, N=A+C+T+G, R=A+G, Y=C+T, M=A+C, K=T+G, S=C+G, W=A+T, H=A+T+C, B=T+C+G, D=A+T+G, V=A+C+G; Product from amplification=653 nt λZAP libraries (Stratagene, La Jolla, Calif.). Library phage were then plated and duplicate filter lifts performed that were screened under high stringency (0.1×SSC, 0.1% SDS @ 55° C.) with a $^{32}$P-labeled (RadPrime Kit, Invitrogen, Carlsbad, Calif.) genomic fragment of Atlantic salmon PVCR (653 nt sequence) amplified using protocols and reagents described in Examples 1, 4 and 5. Primary positive plaques were purified, excised and sequenced using commercial sequencing services (U. of Maine, Orono, Me.) and their sequences compared with those of other PVCRs using BLAST. (National Library of Medicine, Bethesda, Md.).

Results: A total of seven cDNA clones containing PVCR sequences were identified and purified from Atlantic Salmon kidney and intestine libraries. A total of three of the seven contain full length coding sequences for PVCR proteins together with 5' and 3' regulatory elements. For convenience, these clones are designated *Salmo salar* Kidney PVCRs (SalmoKCaRs) #1, #2 and #3 and their aligned nt and putative protein sequences are shown in FIGS. 12 and 13 respectively. The remaining 4 positive clones were partial PVCR clones very nearly identical to these 3 full-length SalmoKCaR clones. Comparison of the different nt sequences of these 3 clones reveals the following similarities and differences:

The SalmoKCaR #1 nucleic acid sequence (SEQ ID NO: 7) consists of 3941 nts of 5' and 3' regulatory elements together with full-length coding sequence for a 941 AA PVCR protein (SEQ ID NO: 8). See FIGS. 9A–E. The calculated molecular mass of this protein is 106,125 Daltons.

The SalmoKCaR #2 nucleic acid sequence (SEQ ID NO: 9) consists of 4031 nts of 5' and 3' regulatory elements together with full-length coding sequence for a 941 AA PVCR protein (SEQ ID NO: 10). See FIGS. 10A–E. The calculated molecular mass of this protein is 106, 180 Daltons.

The SalmoKCaR #3 nucleic acid sequence (SEQ ID NO: 11) consists of 3824 nts of 5' and 3' regulatory elements together with full-length coding sequence for a 850 AA PVCR protein (SEQ ID NO: 12). See FIGS. 11A–D. The calculated molecular mass of this protein is 96,538 Daltons.

FIGS. 12A–L and 13A–C show an alignment of between the two partial sequences of Atlantic Salmon PVCRs isolated and the 3 full length clones for both the nucleic acid and amino acid sequences, respectively. One partial nucleic acid sequence of an Atlantic Salmon PVCR, SEQ ID NO: 3, can be found in all three SalmoKCaR nucleic acid sequences between nt 1979 and 2572; nt 2069 and 2662; and nt 1980 and 2573 of SEQ ID NO: 7, 9, and 11, respectively. The second partial Atlantic Salmon clone, SEQ ID NO: 5, can also be found in all three SalmoKCaR nucleic acid sequences: between nt 1753 and 3773; 1843 and 3863, and 1754 and 3616 of SEQ ID NO: 7, 9, and 11, respectively. Similarly, the amino acid sequence of SEQ ID NO: 4 is found between aa 601 and 797 of each of SEQ ID NO: 8, 10, and 12. The amino acid sequence of the second Atlantic Salmon Clone, SEQ ID NO: 6, is found in each of the polypeptides: between aa 554 and 941 of SEQ ID NO: 8; between aa 554 and 941 of SEQ ID NO: 10; and between aa 554 and 850 of SEQ ID NO: 12. Note that the amino acid sequence of SEQ ID NO: 6 extends 91 aa past the end of SEQ ID NO: 12.

Additional differences between the partial Atlantic salmon PVCR (SEQ ID NO: 5) and full length PVCR (SEQ ID NO: 7, 9, or 11) include: nt 1–112 do not align with any corresponding sequence in SEQ ID NO: 7, 9, or 11. There are also 4 single nt base pair substitutions that are present in SEQ ID NO: 5 that are different than corresponding nt in full length SEQ ID NO: 7, 9, or 11. These include:

nt 1893 change from G to A
nt 1970 change from G to A
nt 1973 change from G to A
nt 2001 change from G to A.

Table 1 compares the overall % identity of nucleotides (nt) between cDNA clones that contain the SalmoKCaRs #1, 2 and 3 vs. shark kidney calcium receptor (SKCaR containing 4079 nts) or human parathyroid CaR (HuPCaR containing 3783 nts). Note that all 3 SalmoKCaR clones possess approximately a 56–57% nt identity to SKCaR and an approximately 50–55% nt identity to HuPCaR. However, in spite of the rather low overall % nt identity between the 3 SalmoKCaR clones and SKCaR, all 3 full length SalmoKCaR clones hybridize to full length SKCaR clone under high stringency conditions (0.5×SSC, 0.1% SDS @ 65° C.) (See FIG. 14).

The percentage identities between the aligned nucleotide sequences of the 3 full length SalmoKCaR clones (SEQ ID NO: 7, 9, 11) include:

A total of 99.8% of the nt of SEQ ID NO: 7 are identical to those of corresponding SEQ ID NO: 9. A total of 97.6% of the nt of SEQ ID NO: 9 are identical to those corresponding nt of SEQ ID NO: 7.

A total of 93.6% of the nt of SEQ ID NO: 9 are identical to those corresponding nt of SEQ ID NO: 11. A total of 98.7% of the nt of SEQ ID NO: 11 are identical to the corresponding nt present in SEQ ID NO: 9.

A total of 95.8% of the nt of SEQ ID NO: 7 are identical to the corresponding nt of SEQ ID NO: 11. A total of 98.7% of the nt of SEQ ID NO: 11 are identical to those corresponding in SEQ ID NO: 7.

TABLE 1

Comparison of the % nucleotide (nt) identity of the complete nt sequence of 3 SalmoKCaR clones #1, #2 and #3 (including 5' and 3' regulatory elements vs. either the SKCaR clone or the clone HuPCaR clone.

| | % NUCLEOTIDE IDENTITY | | |
|---|---|---|---|
| | SalmoKCaR #1 | SalmoKCaR #2 | SalmoKCaR #3 |
| SKCaR vs. | 56.2 | 56.5 | 57.2 |
| HuPCaR vs. | 55.0 | 54.9 | 50.9 |

Table 2 compares both the overall and domain-specific percent amino acid (% AA) identity for each of the SalmoKCaR clones vs. shark kidney PVCR (SKCaR-upper half) and human parathyroid CaR (HuPCaR-lower half). When compared to SKCaR, all 3 SalmoKCaR proteins possess approximately a 63–68% overall AA identity to SKCaR. However, their domain-specific identities show significant degrees of variation with the carboxyl terminal domain of the SalmoKCaR 3 being the most widely divergent. Not surprisingly, comparisons between the 3 SalmoKCaR proteins vs. HuPCaR reveal that the 7 transmembrane region possesses the highest degree of homology followed by the extracellular domain and finally the intracellular carboxy terminal domain.

The percentage identities between the aligned amino acid sequences of the 3 full length SalmoKCaR clones (SEQ ID NO: 8, 10, or 12) include:

A total of 99.9% of the aa of SEQ ID NO: 8 are identical to those corresponding aas in SEQ ID NO: 10. A total of 99.9% of the aa of SEQ ID NO: 10 are identical to corresponding aa in SEQ ID NO: 8.

A total of 89.5% of the aa of SEQ ID NO: 10 are identical to those corresponding aas in SEQ ID NO: 12. A total of 99.1% of the aa of SEQ ID NO: 12 are identical to those corresponding aa in SEQ ID NO: 10.

A total of 89.6% of the aa of SEQ ID NO: 8 are identical to those corresponding aas in SEQ ID NO: 12. A total of 99.2% of the aa of SEQ ID NO: 12 are identical to those corresponding aa of SEQ I) NO: 8.

TABLE 2

Comparison of % amino acid (AA) identities of 3 SalmoKCaR proteins vs. AA sequence of shark kidney CaR (SKCaR-Upper Half) and human parathyroid CaR (HuPCaR-Lower Half).

| | SalmoKCaR #1 | SalmoKCaR #2 | SalmoKCaR #3 |
|---|---|---|---|
| % AA Identity to SKCaR | | | |
| Overall Protein Domains | 68.4 | 68.3 | 24 63.3 |
| N-terminal Extracellular Ion Binding Domain | 70.0 | 69.8 | 70.0 |
| 7 Transmembrane Region | 87.2 | 87.2 | 86.4 |
| Carboxyl Terminal Intra-Cellular Domain | 31.8 | 31.8 | 0.0 |
| % AA Identity to HuPCaR | | | |
| Overall Protein Domains | 66.3 | 66.3 | 61.4 |
| N-terminal Extracellular Ion Binding Domain | 71.9 | 71.9 | 72.1 |
| 7 Transmembrane Region | 89.2 | 89.2 | 88.4 |
| Carboxyl Terminal Intra-Cellular Domain | 24.1 | 24.1 | 0 |

Figure 14:
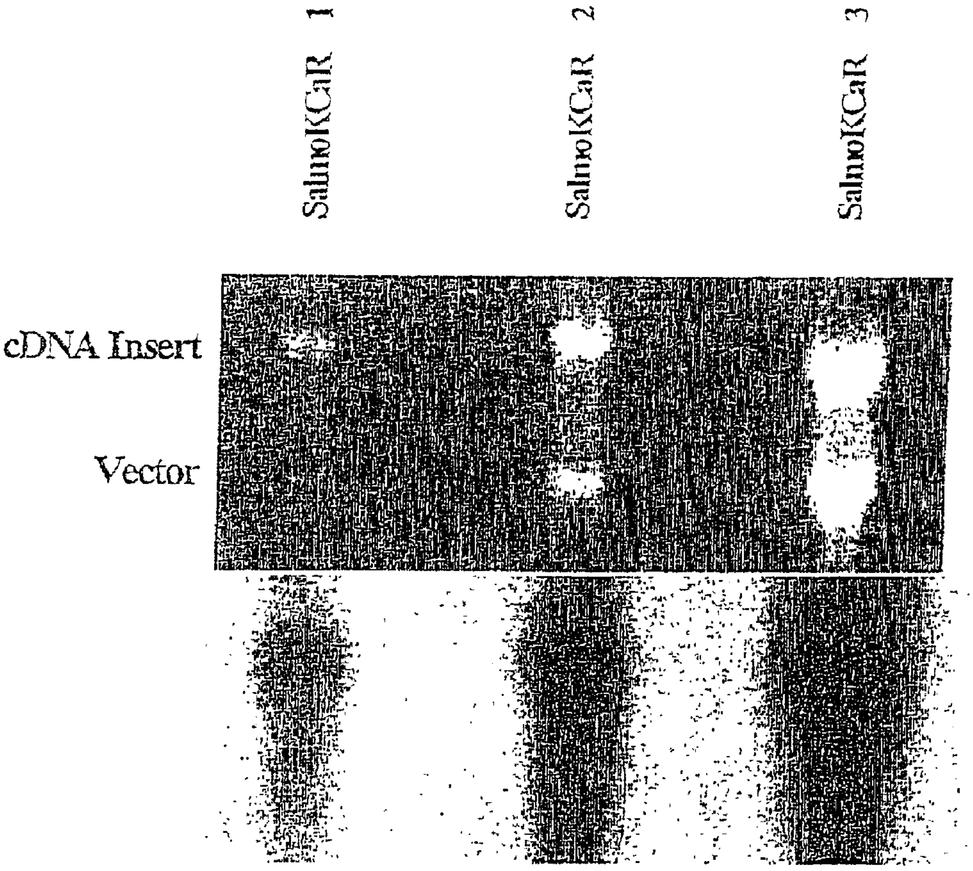
FIG. 14 is photograph showing a Southern blot in which SalmoKCaR#1, 2, and 3 hybridize to nucleic acid derived from SKCaR.

FIG. 14 shows all 3 unique SalmoKCaR clones hybridize to full length shark kidney CaR (SKCaR) under high stringency conditions (0.5×SSC, 0.1% SDS @ 65° C.). Representative autoradiogram of Southern blot was exposed for 30 min.

Site directed mutagenesis studies of mammalian CaRs, notably HuPCaR, have identified AAs that are particularly important in the various functions of CaRs. Cysteine AAs at AA#101 and AA#236 mediate dimerization of HuPCaR. HuPCaR and native CaRs in rat kidney exist primarily as dimers within the cell membrane where disulfide bond-mediated dimerization is required for normal agonist-mediated CaR activation. All 3 SalmoKCaRs possess Cys at AAs corresponding to HuPCaR AA#101 and AA#236 and presumably functions as dimers in a manner similar to mammalian CaRs.

Nucleotide Sequence Differences in the 5' and 3' Untranslated Regions or UTRs of SalmoKCaRs #1 #2 and #3:

FIG. 15 displays the aligned nucleotide sequences of SalmoKCaR clones #1, #2, and 3. As compared to Salmo-KCaR #1 and #3, SalmoKCaR #2 possesses an 89 nt insert in its 5' UTR. Differences between the 3' UTRs of the 3 SalmoKCaRs include a 36 nt insert just prior to the poly A tail in SalmoKCaR #3 as well as other single nt differences listed below where each difference is compared to the 2 other SalmoKCaR clones:

SalmoKCaR #1: nt 3660 A to G; nt 3739 A to G; nt 3745 A to G
SalmoKCaR #2: nt 3837 A to G; nt 3862 A to G
SalmoKCaR #3: nt 3472 A to G; nt 3487 A to G; nt 3564 A to G;
nt3568 G to A; nt3603 A to G; nt3786A to C. Although the functional significance of each of these nt differences in the 5' or 3' UTRs is unknown at the present time, each nt difference either individually or in combinations could represent a means for controlling either the stability or processing of the RNA transcript or its translation into each of the 3 Salmo-KCaR proteins.

Sequence Differences in the Coding Regions of SalmoK-CaRs #1, #2 and #3:

FIG. 16 displays the aligned AA sequences of SalmoK-CaRs #1, #2 and #3 as well as the Shark SKCaR protein and HuPCaR proteins. As compared to SalmoKCaR #1, Salmo-KCaR #2 possesses 2 different AA's present at AA#257 and AA#941 of its AA sequence. In contrast to SalmoKCaR #1 that possesses an Asp in AA#257, SalmoKCaR #2 possesses a Gly. The negative charge in this location may be important since both SKCaR and Fugu PVCR possess Asp at #257 while the mammalian CaRs, HuPCaR and RaKCaR possess a Glu. SalmoKCaR #3 also contains a Asp at AA#257.

At AA #443, SalmoKCaR #1 and #2 both possess a Leu whereas SalmoKCaR #3 contains a Phe. The conserved hydrophobic nature of the AA at this position appears to be important since Fugu PVCR also contains a Leu whereas SKCaR contains an Ile. As compared to SalmoKCaRs #1 or 2, SalmoKCaR #3 possesses a truncated carboxyl terminus as described below.

Sequence Differences in the Coding Regions of SalmoK-CaRs #1, #2 and #3 as Compared to Mammalian CaRs.

The putative AA sequences of SalmoKCaR #1, #2 and #3 proteins possess multiple differences in AAs at various positions throughout their extracellular, 7 transmembrane and carboxyl terminal domains when compared to mammalian CaRs such as HuPCaR (see aligned differences with HuPCaR in FIG. 16). While many of the differences between SalmoKCaR species and HuPCaR are conserved substitutions that preserve the overall net charge or hydrophobicity characteristics at that specific position in the PVCR protein, other substitutions may have functional consequences as based on previous structure-functional studies of mammalian CaRs. The actual functional consequences of these AA differences in SalmoKCaR proteins await expression studies by MariCal.

Differences between SalmoKCaR proteins vs. mammalian and other fish PVCRs include:

All 3 SalmoKCaRs possess a deletion of 15 AA's beginning at AA#369 as compared to either HuPCaR or RaKCaR. Fugu PVCR also exhibits a 19 AA deletion at the same location. In contrast, SKCaR does not exhibit any deletion in this area and thus is more similar to mammalian CaRs as compared to either SalmoKCaR or Fugu in this regard.

Another notable difference between SalmoKCaRs vs. mammalian CaRs and SKCaR is differences in AA#227 where mutagenesis studies have identified the presence of the positively charged Arg as important in CaR sensitivity since its alteration in HuPCaR to a Leu results in over a 2 fold reduction in $EC_{50}$ $Ca^{2+}$ from 4.0 mM to 9.3 mM but not $Gd^{3+}$ sensitivity. In contrast to mammalian CaRs and SKCaR, all 3 SalmoKCaRs possess a negatively charged Glu at AA#227. Fugu PVCR also exhibits the same Glu at AA#227. Interestingly, the AA sequence immediately following AA#227 is Glu-Glu-Ala in the mammalian HuPCaR and elasmobranch SKCaR whereas it is Lys-Glu-Met in all 3 SalmoKCaRs and Fugu.

Lastly, all 3 SalmoKCaR clones as well as Fugu possess an in frame deletion of a single AA at position #757 (between TM4 and 5) as compared to either mammalian CaRs or SKCaR.

SalmoKCaR #3 possesses a truncated carboxyl terminal domain as compared to either SalmoKCaRs #1 or #2. The number of AA that comprise the carboxyl terminal domains of the 3 SalmoKCaRs are different and include: SalmoKCaR #1–96 AA; SalmoKCaR #2–97 AA and SalmoKCaR #3–5 AA. Reduction in the 91–92AA's in SalmoKCaR #3 vs. SalmoKCaRs #1 or #2 would reduce its estimated molecular mass by 9,600 Daltons.

Studies from multiple site directed mutagenesis studies of HuPCaR reveal that alterations to the structure of the carboxyl terminal domain of PVCRs have profound effects on their function and sensitivity to ligands such as $Ca^{2+}$ and $Mg^{2+}$. Various truncations of the carboxyl terminal domain of HuPCaR have highlighted the importance of HuPCaR AAs#860–910. Truncation of the carboxyl terminal domain of HuPCaR to AAs less than AA#870 produced either an inactive receptor or a modified HuPCaR with a marked decrease in its affinity for extracellular $Ca^{2+}$ as well as a decrease in the apparent cooperativity of $Ca^{2+}$ dependent activation. While the exact functional characteristics of SalmoKCaR #3 remain to be determined using similar HEK transfection studies, these data derived from HuPCaR mutagenesis studies suggest that SalmoKCaR #3 protein is either inactive or exhibits a greatly reduced functional affinity for $Ca^{2+}$. Significant expression of SalmoKCaR #3 together with other SalmoKCaRs #1 or #2 could result in an overall reduction in the response to extracellular Ca2+due to so called dominant negative effects. These dominant negative effects could occur where SalmoKCaR#3 reduces the overall sensitivity of cells to $Ca^{2+}$ via combinations between SalmoKCaR #3 and SalmoKCaR #1 #2 to reduce the sensitivity of the latter PVCRs via cooperative interactions (dimers and higher oligomers) with them.

Certain mutagenesis studies also highlight the importance of the Threonine AA at AA#888 in mediation of HuPCaR's sensitivity to $Ca^{2+}$ and normal signal transduction. FIG. 16 shows that AA #888 is a Thr in all wild type CaR and PVCR proteins including HuPCaR, RaKCaR, SKCaR, BoPCaR and SalmoKCaR #1 and #2. SalmoKCaR #3 is missing Thr #888 because of its truncated tail. Of interest is also the presence of consensus sites for receptor kinase phosphorylation (Ser-Ser-Ser) that are present at AA#907–909 in HuPCaR, RaKCaR, SKCaR BoPCaR and SalmoKCaR #1 and #2. In contrast, Fugu PVCR possesses an Asn at AA#908 that would render its site nonrecongizable to protein kinases. A similar protein kinase site also appears in the region of AA#918–921 where HuPCaR, RaKCaR and BoPCaR possess a Ser-Ser-Ser motif. In contrast, SKCaR possesses an inactive site due to its sequence of Ala-Ser-Ser. Fugu PVCR and SalmoKCaR #1 and #2 also have intact Ser-Ser-Ser motifs at position AA #918–920 or #919–921. The exact functional significance of these Ser-Ser-Ser sites possessed by SalmoKCaR #1 and #2 await expression studies by MariCal.

The presence of Multiple Differences in the Nucleotide and Putative Protein Sequences of SalmoKCaR Clones #1–#3 Strongly Suggest the Presence of Multiple PVCR Genes within Atlantic Salmon:

Recent studies in rainbow trout provide direct evidence of the existence of multiple genes encoding two different forms of a specific type of protein, each of which are differentially expressed in specific tissues of trout. These proteins are aryl hydrocarbon receptor Type 2 (AhRs). Detailed studies on AhRs have shown the presence of 2 functional genes that produce different closely related AhR proteins, "Two forms of aryl hydrocarbon receptor type 2 in rainbow trout (Oncorhynchus mykiss)," by Abnet, C. C., et al., *J. Of Biological Chemistry* 274: 15159–15166, (1999). These two proteins are differentially expressed in various tissues where they perform closely related but distinct functions.

The presence of single nucleotide substitutions together with specific large scale alterations in the sequence of SalmoKCaR clones #1–3 including the gapping of large numbers of nucleotides and alterations in reading frame of the resulting SalmoKCaR transcript are not readily explainable on the basis of differential splicing of RNA transcripts derived from a single gene, or perhaps some complex process where different alleles of a single gene are present in salmon. Alternatively, these data suggest that there are multiple PVCR genes present in Atlantic salmon that work in concert to enable Atlantic salmon and likely other salmonids to carry out their lifecycle stages that include hatching as well as development of larval and juvenile phases in freshwater followed by smoltification and migration into seawater with a subsequent return to freshwater for spawning.

Detailed studies in mammals including mice and humans show the presence of a single functional PVCR gene. However, multiple published reports provide support for the possibility that multiple PVCR genes exist in fish, while only a single functional PVCR gene exists in mammals including humans. Support for multiple PVCR genes is provided by detailed studies of well characterized genes that have demonstrated that teleost fish including salmonids possess multiple sets of duplicated genes as compared to mammals. These duplicated genes have arisen as a result of either genomic duplication events occurring early in the evolutionary history of fishes with subsequent gene drop out or via more recent selective duplication of genes or some combination of both. Moreover, it is widely acknowledged that salmonids are polyploid with respect to other teleost fish and have undergone an additional genome duplication. This additional genomic duplication further heightens the possibility that multiple functional PVCR genes exist in salmonids particularly Atlantic salmon.

If the products of a duplicated gene are not important in the development, growth or maintenance of an organism, the nonfunctional gene accumulates natural mutations and is either inactivated becoming a pseudogene or lost from the genome altogether. However, multiple authors have provided evidence that preservation of duplicated genes likely involves changes in the developmental or tissue specific expression pattern of the duplicated vs. original gene or formation of a new functional gene protein product that would interact with the original gene product in novel ways. (See AhR data above). These data provide support for the possible roles of SalmoKCaR transcripts #1–3 as either differentially expressed in various tissues of Atlantic salmon as well as SalmoKCaR #3 exerting a dominant negative effect on the remaining functional SalmoKCaR proteins. As discussed below, such interactions amongst SalmoKCaR transcripts would provide Atlantic salmon and perhaps all salmonids with the ability to exploit a wide variety of freshwater and seawater environments.

Part 2: Use of RT-PCR and Northern Analysis to Determine the Expression of SalmoKCaR Clones #1, #2 and #3 in Various Tissues of Atlantic Salmon:

Background:

SalmoKCaR clones #1, #2 and #3 were originally isolated from a Atlantic salmon kidney cDNA library. To determine the pattern of tissue specific expression of these various SalmoKCaR clones, both degenerate (to amplify all Salmo PVCRs species) and SalmoKCaR primers that will specifically amplify either SalmoKCaR #1 or #2 or #3 were utilized. As shown in "Materials and Methods" Section below, these primers amplify DNA products of different sizes that can be distinguished by agarose gel electrophoresis. PCR on specific cDNA clones confirms that these primer pairs function exclusively on the clones for which they have been designed. Note that both the degenerate and SalmoKCaR #3 specific primers do not span an intron and therefore RNA was treated with DNAse to ensure that there was not amplification of contaminating genomic DNA in the results shown. Primers specific for SalmoKCaR #1 and #2 span introns and therefore DNAase treatment is not required to interpret these results. As a control, the amounts of mRNA added to each RT-PCR reaction was determined by separate amplification of actin using primers designed from the published sequence of Atlantic salmon actin (Genbank Accession #AF012125 Salmo salar beta actin mRNA).

Materials and Methods

Primers:

Degenerate Primers

DSK-F3 and DSK-R4 primers are shown in Example 4.

| SalmoKCaR #1 | Specific Primers | SalmoKCaR #1 nts |
|---|---|---|
| AS1-F17 | 5'-CAA GCA TTA TCA AGA TCA AG-3' (SEQ ID NO:16) | nt 47–66 |
| AS2-R14 | 5'-CTC AGA GTG GCC TTG GC-3' (SEQ ID NO:17) | nt 2800–2784 |

Product from amplification=2754 nt. The SalmoKCaR #1 primer pair consists of a forward primer (AS1-F17) spanning the 5' UTR insertion in SalmoKCaR #2, and a reverse primer (AS2-R14) within the 158 bp deleted from SalmoKCaR #3.

| SalmoKCaR #2 | Specific Primers | SalmoKCaR #2 nts |
|---|---|---|
| AS2-F13 | 5'-CAG TTC TCT CTT TAA TGG AC-3' (SEQ ID NO:18) | nt 109–128 |
| A52-R14 | 5'-CTC AGA GTG GCC TTG GC -3' (SEQ ID NO:19) | nt 2890–2874 |

Product from amplification=2782 nt. The SalmoKCaR #2 primer pair is a forward primer (AS2-F13) in the 5' UTR insertion in SalmoKCaR #2 clone, and the same reverse primer as SalmoKCaR #1 primer (AS2-R14).

| SalmoKCaR #3 | Specific Primers | SalmoKCaR #3 nts |
|---|---|---|
| AS5-F11 | 5'-AGT CTA CAT CAT CCA TCA GCC-3' (SEQ ID NO:20) | nt 2700–2720 |
| A55-R12 | 5'-GAT TTT ATT GTC ATT GGA TGC-3' (SEQ ID NO:21) | nt 3810–3790 |

Product from amplification=1111 nt. The SalmoKCaR #3 primer pair consists of a forward primer (AS5-F11) which spans the 158 bp deletion, and a reverse primer (AS5-R12) located in the 36 bp insertion at the 3' end of the SalmoKCaR #3 clone.

| Salmon Actin Primers | | |
|---|---|---|
| SA-F1 | 5'-TGG AAG ATG AAA TCG CCG C-3' (SEQ ID NO:22) | nt 2–20 |
| SA-R2 | 5'-GTG GTG GTG AAA CTG TAA CCG C-3' (SEQ ID NO:23) | nt 608–587 |

Product from amplification=607 nt. This primer set is used to amplify salmon actin mRNA that serves as a control to quantify differences in mRNA content.

RNA Blotting Analysis and RT-PCR of Atlantic Salmon and Elasmobranch Tissues:

Total RNA was purified with Stat 60 reagent (Teltest B Friendswood, Tex.) DNAse (Introgen, Carlsbad, Calif.) treated and used for RT-PCR after cDNA production with cDNA Cycle Kit (Invitrogen, Carlsbad, Calif.). The cDNA was amplified (30 cycles of 1 min @ 94° C., 1 min @ 57° C., 3' @72° C.) using degenerate primers [forward primer dSK-F3 (SKCaR nts 2279–2306) and reverse primer dSK-R4 (SKCaR nts 2904–2934). Aliquots of PCR reactions were subjected to gel electrophoresis and ethidium bromide (EtBr) staining or blotted onto Magnagraph membranes (Osmonics, Westboro, Mass.) and probed with a $^{32}P$-atlantic salmon genomic PCR product (653 bp sequence identical to that shown in SEQ ID NO: 3 with added nt sequences, washed (0.1×SSC, 0.1% SDS @ 55° C.) and autoradiographed. Selected amplified PCR products from Atlantic salmon tissues were sequenced as described above. The following conditions were utilized for each of the SalmoKCaR specific primers and corresponding blots:

SalmoKCaR #1 amplification conditions and primer set: PCR: 1 min @ 94° C., 1 min @ 50° C., 3 min @72° C., 35 cycles. Amplification products attached to membrane were probed with full length SalmoKCaR #1 clone and washed (0.1×SSC, 0.1% SDS @ 55° C.) and autoradiographed for 48 hr.

SalmoKCaR #2 amplification conditions and primer set:

PCR: 1 min @94° C., 1 min @ 50° C., 3min @ 72° C., 35 cycles. Amplification products attached to membrane were probed with full length SalmoKCaR #2 clone and washed (0.1×SSC, 0.1% SDS @ 55° C.) and autoradiographed for 168 hr.

SalmoKCaR #3 amplification conditions and primer set: PCR: 1 min @94° C., 1 min @ 52° C., 3min @ 72° C., 35 cycles. Amplification products attached to membrane were probed with full length SalmoKCaR #3 clone and washed (0.1×SSC, 0.1% SDS @ 55° C.) and autoradiographed for 72 hr.

Results

Analysis of Atlantic Salmon Tissues from Freshwater vs. Seawater Adapted Fish Using Degenerate Primers:

FIG. 17 shows data obtained from 14 tissues of freshwater or seawater adapted Atlantic salmon using the degenerate primers described above. Samples were obtained from a single representative seawater adapted salmon (866 gm and 41 cm in length) from a group of 10 fish of average weight of 678 gm. Samples from nasal lamellae, urinary bladder, olfactory bulb and pituitary gland were all pooled samples from all 10 fish. The samples were from a representative single freshwater adapted fish (112 gm and 21.5 cm) selected from a group of 10 fish with an average weight of 142.8 gm. In contrast, samples from nasal lamellae, urinary bladder, olfactory bulb and pituitary gland were all pooled samples from all 10 fish. Note that the amplification products from these degenerate primers do not distinguish between SalmoKCaR #1, #2 or #3 since their nt sequences in the region amplified by the primers are all identical (lanes 7, 9 and 12 Lower gel—Panels A, B, C and D). Moreover, these degenerate primers also possess the capacity to amplify additional PVCRs (if any are present) in salmon tissues that could be distinct from either SalmoKCaR #1–3. Thus, amplified RT-PCR products are referred to as PVCR products since use of these degenerate primers do not distinguish between various PVCR species.

Analysis of panels A–D of FIG. 17 shows that the PVCR degenerate primers yield PCR products in various tissues of both seawater and freshwater adapted fish. These various bands are more visible in Southern blots (Panels C, D) of corresponding ethidium bromide gels (Panels A and B) because detection of PVCR amplified products via hybridization of a $^{32}$P-PVCR probe is more sensitive as compared to ethidium bromide staining. Prominent ethidium bromide stained bands are visible in urinary bladder (lane 4), kidney (lane 5) and muscle (lane 14) in seawater adapted fish (Panel A) while either faint or no bands are seen in other tissues. In contrast, ethidium bromide bands are also visible in nasal lamellae (lane 3), urinary bladder (lane 4) and kidney (lane 5) as well as olfactory bulb (lane 12) in freshwater fish (Panel B). In summary, these data show differential tissue expression of PVCRs FIG. 17 shows a RT-PCR analysis of freshwater (Panels B, D and F) and seawater (Panels A, C and E) adapted Atlantic salmon tissues using either degenerate PVCR or salmon actin PCR primers. Total RNA from 13 (seawater adapted) and 14 (freshwater adapted) tissues of Atlantic salmon was first treated with DNAase to remove any genomic DNA contamination then used to synthesize cDNA that was amplified using degenerate primers. (Panels A and B): Ethidium bromide stained agarose gel. DNA markers in lane 1 of both Panels A and B were used to indicate size of amplification products. (Panels C and D) Southern blot of gel in Top Panel using $^{32}$P-labeled Atlantic salmon genomic fragment. (Panels E and F) Ethidium bromide stained gels of RT-PCR amplification products using Atlantic salmon beta actin primers as described above. These reactions serve as controls to ensure that samples contain equal amounts of RNA.

Southern blots (Panels C and D) of the corresponding gels shown in Panels A and B reveal that amplified PVCR products are present in additional tissues not shown by simple ethidium bromide staining as described above. As shown in Panel C, PVCRs are present in tissues of seawater-adapted salmon including gill (lane 2), nasal lamellae (lane 3), urinary bladder (lane 4), kidney (lane 5), stomach (lane 6), pyloric caeca (lane 7), proximal (lane 8) and distal (lane 9) intestine, pituitary gland (11) and muscle (lane 14). Ovary tissue was not tested in seawater-adapted fish. In contrast, freshwater-adapted salmon possess amplified PVCR products in gill (lane 2), nasal lamellae (lane 3), urinary bladder (lane 4), kidney (lane 5), proximal intestine (lane 8), brain (lane 10), pituitary (lane 11), olfactory bulb (lane 12), liver (lane 13), muscle (lane 14) and ovary (lower lane 3). The intensity of individual actin bands shown in Panels E and F performed on identical aliquots of the RT-PCR reactions serve to quantify any differences in pools of cDNA from the individual RT reactions in each sample. Isolation and subcloning of the ethidium bromide stained bands from olfactory lamellae and urinary bladder show that nucleotide sequences of multiple subclones from these bands all are identical to the nucleotide sequence present in SalmoKCaR clones #1–3.

Close examination of the differences in Panel C (seawater adapted) vs. Panel D (freshwater adapted) reveal differences in the apparent abundance of PVCR mRNA in specific tissues. Apparent increases in tissue PVCR mRNA abundance in seawater-adapted salmon vs. freshwater-adapted salmon are present in gill, kidney, stomach, pyloric caeca, distal intestine, and muscle. The increased expression of PVCRs in Atlantic salmon exposed to seawater is consistent with other data that an increase in PVCR expression in at least one tissue occurs upon transfer of Atlantic salmon from freshwater to seawater. In contrast, the abundance of PVCR mRNA species in olfactory bulb tissue of seawater adapted salmon appears to be reduced as compared to olfactory bulbs of freshwater adapted counterparts (Lane 12 in Panels C vs. D). In other tissues such as nasal lamellae (Lane 3 in Panel C vs. D) there is little or no apparent change in the steady state PVCR MRNA content. In summary, these data demonstrate tissue specific changes in the steady state expression of PVCR mRNA species in seawater adapted vs. freshwater adapted Atlantic salmon. Depending on the tissue, steady state PVCR mRNA content is either increased, decreased or remains unchanged when freshwater adapted fish are compared to seawater adapted counterparts. Since these analyses shown in FIG. 17 use PVCR degenerate primers, it is not possible to determine from these experiments whether the alterations in steady state PVCR mRNA content are the result of changes in individual SalmoKCaRs #1–3.

RT-PCR Analysis Using Degenerate Primers Shows that Steady State Content of Kidney PVCRs is Increased by the SuperSmolt™ Process Similar to that Produced by Transfer of Atlantic Salmon to Seawater.

Figure 18A:
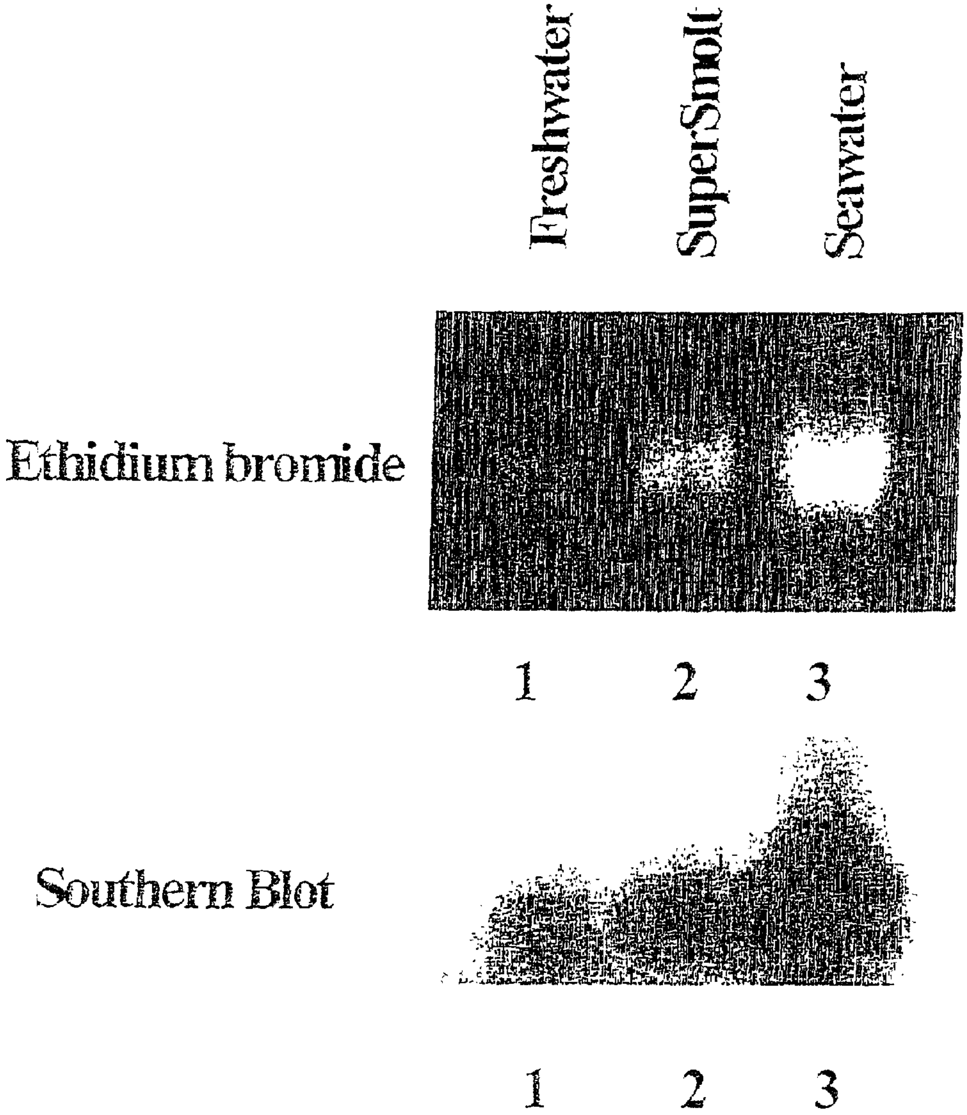
FIG. 18A is photograph of a RT-PCR analysis using degenerate primers of steady state SalmoKCaR mRNA transcripts from kidney tissue of Atlantic Salmon adapted to freshwater, after 9 weeks of Process II treatment or 26 days after transfer to seawater. Process II treatment is defined in the Exemplification.
Figure 18B:
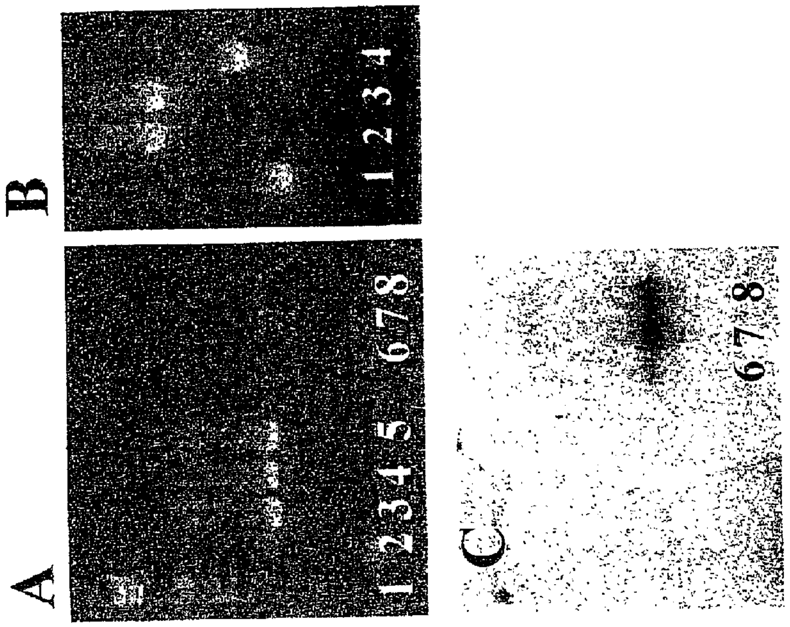
FIG. 18B is a photograph of a RT-PCR analysis showing increased steady state expression of SalmoKCaR transcripts in pyloric caeca of Process II treated and seawater fish as compared to freshwater Atlantic salmon smolt. Using degenerate (SEQ ID Nos 13 and 14) or actin (SEQ ID No 22 and 23) primers, samples of either freshwater (Panel A Lanes 3 and 6), Process II treated (Panel A Lanes 4 and 7) or seawater adapted (Panel A Lanes 5 and 8) Atlantic salmon smolt were analyzed by RT-PCR. To control for differences in sample loading, these identical samples were subjected to PCR analysis using actin specific primer (Panel A, Lanes 3–5). Note that both ethidium bromide stained gel (Panel A) and its corresponding Southern blot (Panel C) show increased amounts of SalmoKCaR transcripts in pyloric caeca from Process II and seawater adapted fish as compared to freshwater. As a control, Panel B demonstrates that these degenerate primers amplify SalmoKCaR #1 (Lane 1), SalmoKCaR #2 (Lane 2) and SalmoKCaR #3 (Lane 3) transcripts.
Figure 19:
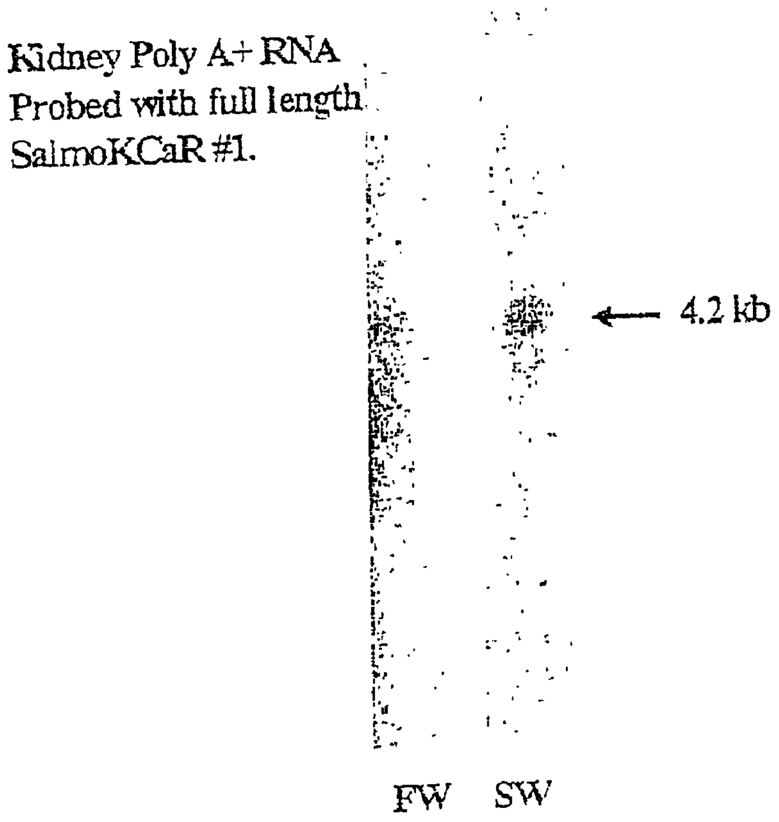
FIG. 19 is a photograph of a RNA blot containing 5 micrograms of poly $A^+$ RNA from kidney tissue dissected from either freshwater adapted (FW) or seawater adapted (SW) Atlantic salmon probed with full length SalmoKCaR #1 clone.

FIG. 18A shows RT-PCR analysis of a single representative experiment where kidney tissue was harvested from Atlantic salmon that had either been freshwater adapted (lane 1), exposed to 9 weeks of the SuperSmolt™ process in freshwater (lane 2) or transferred to seawater and maintained for 26 days. FIG. 18B shows RT-PCR analysis of a single representative experiment using pyloric caeca from the same fish shown in FIG. 18A. Note the significant increase in amplified PVCR product present in kidney (FIG. 18A) and pyloric caeca (FIG. 18B) for both SuperSmolt™ (lanes 2 and 7, respectively) and seawater adapted (lanes 3 and 8, respectively) fish as compared to freshwater (lanes 1 and 6, respectively). The increased expression of PVCRs in these 2 tissues of Atlantic salmon exposed to the SuperSmolt™ process where this increased PVCR expression mimics that produced after seawater transfer is consistent with earlier data that an increase in PVCR expression in at least one tissue occurs upon either treatment with the SuperSmolt™ process or transfer of Atlantic salmon to seawater.

Figure 18C:
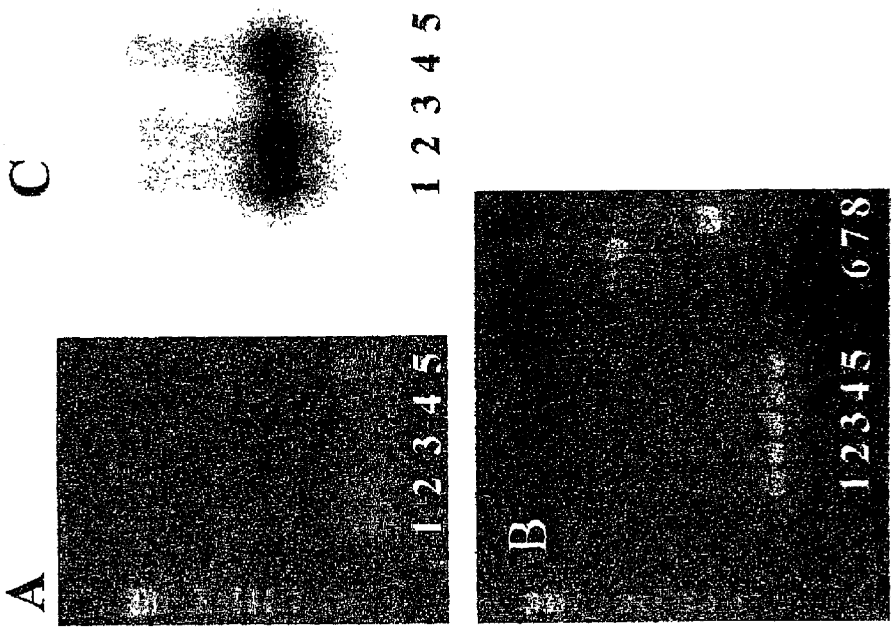
FIG. 18C is a photograph of RT-PCR analysis showing expression of SalmoKCaR transcripts in various stages of Atlantic salmon embryo development. Using degenerate (SEQ ID Nos. 13 and 14) or actin (SEQ ID No 22 and 23) primers, RNA obtained from samples of whole Atlantic salmon embryos at various stages of development were analyzed for expression of SalmoKCaRs using RT-PCR. Ethidium bromide staining of samples from dechorionated embryos (Lane 1), 50% hatched (Lane 2), 100% hatched (Lane 3), 2 weeks post hatched (Lane 4) and 4 weeks post hatched (Lane 5) shows that SalmoKCaR transcripts are present in Lanes 1–4). Southern blotting of the same gel (Panel C) confirms expression of SalmoKCaRs in embryos from very early stages up to 2 weeks after hatching. No expression of SalmoKCaR was observed in embryos 4 weeks after hatching. Panel B shows the series of controls where PCR amplification of actin content of each of the 5 samples shows they are approximately equal (lanes 1–5).

FIG. 18*c* shows RT-PCR analysis using the same degenerate primers to detect expression of SalmoKCaR transcripts in various stages of Atlantic salmon embryo development. Using degenerate (SEQ ID Nos 13 and 14) or actin (SEQ ID No 22 and 23) primers, RNA obtained from samples of whole Atlantic salmon embryos at various stages of development were analyzed for expression of SalmoKCaRs using RT-PCR. Ethidium bromide staining of samples from dechorionated embryos (Lane 1), 50% hatched (Lane 2), 100% hatched (Lane 3), 2 weeks post hatched (Lane 4) and 4 weeks post hatched (Lane 5) shows that SalmoKCaR transcripts are present in Lanes 1–4. Southern blotting of the same gel (Panel C) confirms expression of SalmoKCaRs in embryos from very early stages up to 2 weeks after hatching. No expression of SalmoKCaR was observed in embryos 4 weeks after hatching. Panel B shows the series of controls where PCR amplification of actin content of each of the 5 samples shows they are approximately equal.

Northern Blotting of Kidney Poly $A^+$ RNA with SalmoKCaR #1 Reveals an Increase in PVCR Expression in Seawater-Adapted vs. Freshwater-Adapted Atlantic Salmon.

To both confirm the size of SalmoKCaR transcripts and test for changes in SalmoKCaR expression in fish exposed to different salinities, poly $A^+$ RNA from kidney of either freshwater adapted (FW) or seawater adapted (SW) Atlantic salmon were probed with SalmoKCaR #1. As shown in FIG. 19, kidney RNA contains a 4.2 kb band that corresponds to the 3.9–4.0 kb sizes of SalmoKCaR #1–3 as determined by nucleotide sequence analysis. Because of the high degree of nucleotide identities between SalmoKCaR #1–3, the 4.2 kb band is actually derived from the combination of all 3 SalmoKCaR species and any additional PVCR species in salmon kidney due to crosshybridization of SalmoKCaR #1. However, these data show an increase in the intensity of the 4.2 kb SalmoKCaR band in SW adapted fish as compared to their FW adapted counterparts.

FIG. 19 shows a RNA blot containing 5 micrograms of poly $A^+$ RNA from kidney tissue dissected from either freshwater adapted (FW) or seawater adapted (SW) Atlantic salmon probed with full length SalmoKCaR #1 clone. Autoradiogram exposure after 7 days.

Use of RT-PCR with SalmoKCaR #3 Specific Primers Demonstrates that Tissue Specific Alterations in the Steady State Tissue Content of SalmoKCaR #3 mRNA in Freshwater vs. Seawater Adapted Atlantic Salmon.

To determine whether specific SalmoKCaRs #3 are modulated by exposure to different salinities, nucleotide primer sets that allows for the specific amplification of SalmoKCaR transcripts were designed. FIG. 20 shows RT-PCR analysis of freshwater (Panels B, D and F) and seawater (Panels A, C and E) adapted Atlantic salmon tissues using either SalmoKCaR #3 specific PCR primers or salmon actin PCR primers. Total RNA from 13 (seawater adapted) and 14 (freshwater adapted) tissues of Atlantic salmon identical to those shown in FIG. 17 were first treated with DNAase to remove any genomic DNA contamination, then used to synthesize cDNA that was amplified using SalmoKCaR #3 primers. All RNA samples were prepared from a single fish with the exception of olfactory bulb, pituitary, urinary bladder and nasal lamellae that are composed of RNA from pooled samples of fish. Selected reactions were subjected to primer amplification using SalmoKCaR#3 specific primers. DNA markers in lane 1 of both Panels A and B were used to indicate size of amplification products. (Panels C and D) Southern blot of gel in Top Panel using $^{32}P$-labeled Atlantic salmon genomic fragment. (Panels E and F) Ethidium bromide stained gel of RT-PCR amplification products using Atlantic salmon beta actin primers as described above. These reactions serve as controls to ensure that samples contain equal amounts of RNA. The specificity of these SalmoKCaR#3 primers is demonstrated in the bottom half of Panels A and B of FIG. 20. The specific SalmoKCaR #3 primers only amplify product from SalmoKCaR #3 clone (lane 14) and not SalmoKCaR #1 (lane 8) or SalmoKCaR #2 (lane 11). Note that in the tissue sample lanes, ethidium bromide stained bands are present in the kidney of seawater adapted salmon (lane 5 upper gel—Panel A) and only very faintly in urinary bladder of freshwater adapted salmon (lane 4 upper gel—Panel B). The corresponding Southern blots of freshwater adapted tissue samples (Panel D) reveal detectable SalmoKCaR #3 product only in urinary bladder (lane 4) and a small amount in kidney (lane 5). In contrast, in seawater-adapted salmon (Panel C) there are detectable increases in SalmoKCaR #3 product in both urinary bladder (lane 4) and kidney (lane 5) as well as the presence of SalmoKCaR #3 amplified product in gill (lane 2), nasal lamellae (lane 3), pyloric caeca (lane 7) and muscle (lane 14) of seawater adapted fish.

As described above, the increase in tissue expression of SalmoKCaR #3 serves to provide for a possible means to reduce the overall tissue sensitivity to PVCR-mediated sensing via an action where SalmoKCaR #3 would act as a dominant negative effector. In contrast to freshwater where the ambient water concentrations of both $Ca^{2+}$ and $Mg^{2+}$ are low and require a high degree of sensitivity from SalmoKCaRs to sense changes in concentration, the concentrations of $Ca^{2+}$ and $Mg^{2+}$ in seawater are 10 fold and 50 fold higher and thus may require reduction of the high sensitivity of SalmoKCaRs #1 and #2 by SalmoKCaR #3. It is of interest that many of these specific tissues exhibiting significant SalmoKCaR #3 expression are either exposed directly to the high $Ca^{2+}$ and $Mg^{2+}$ content of seawater (gill, nasal lamellae) or experience high $Ca^{2+}$ and $Mg^{2+}$ concentrations as the result of the excretion of these divalent cations (urinary bladder, kidney).

Use of RT-PCR with SalmoKCaR #1 Specific Primers Demonstrates Tissue Specific Alterations in the Steady State Tissue Content of SalmoKCaR #1 MRNA in Freshwater vs. Seawater Adapted Atlantic Salmon.

FIG. 21 shows RT-PCR analysis of freshwater (Panels B, D and F) and seawater (Panels A, C and E) adapted Atlantic salmon tissues using either SalmoKCaR #1 specific PCR primers or salmon actin PCR primers. Total RNA from 13 (seawater adapted) and 14 (freshwater adapted) tissues of Atlantic salmon identical to those shown in FIGS. 17 and 20 were used to synthesize cDNA that was amplified using SalmoKCaR #1 primers. All RNA samples were prepared from a single fish with the exception of olfactory bulb, pituitary, urinary bladder and nasal lamellae that are composed of RNA from pooled samples of fish. As controls to demonstrate primer specificity, selected reactions were subjected to primer amplification of portions of individual SalmoKCaR clones or water alone (Panels A and B): Ethidium bromide stained agarose gel. DNA markers in lane 1 of both Panels A and B were used to indicate size of amplification products. (Panels C and D) Southern blot of gel in Top Panel using $^{32}P$-labeled Atlantic salmon genomic fragment. (Panes E and F) Ethidium bromide stained gel of RT-PCR amplification products using Atlantic salmon beta actin primers as described above. These reactions serve as controls to ensure that samples contain equal amounts of RNA. As shown in lower halves of Panels A and B of FIG. 21, PCR amplification with these primers yields an ethidium bromide staining band (lane5) when SalmoKCaR #1 clone is used as a template but not either SalmoKCaR #2 (lane 6) or SalmoKCaR #3 (lane 7). Southern blotting analysis of the gels shown in Panels A and B reveals that the amplification product of the SalmoKCaR #3 is highly positive (lanes 5)—Panels C and D. In the various tissue samples, SalmoKCaR #1 product is amplified in selected tissues including urinary bladder (lane 4) and pyloric caeca (lane 7) in seawater-adapted salmon (Panel C) as compared to urinary bladder (lane 4) and kidney (lane 5) in freshwater-adapted salmon (Panel D). The exact nature of the smaller and larger than expected PCR amplification products present in gill (lane 2—Panels C, D) and nasal lamellae (lane 3—Panel D) are not known at present. These data show tissue specific expression of SalmoKCaR #1 in both freshwater and seawater adapted salmon.

Use of RT-PCR with SalmoKCaR #2 Specific Primers Demonstrates Tissue Specific Alterations in the Steady State Tissue Content of SalmoKCaR #2 mRNA in Freshwater vs. Seawater Adapted Atlantic Salmon.

FIG. 22 shows RT-PCR analysis of freshwater (Panels B, D and F) and seawater (Panels A, C and E) adapted Atlantic salmon tissues using either SalmoKCaR #2 specific PCR primers or salmon actin PCR primers. Total RNA from 13 (seawater adapted) and 14 (freshwater adapted) tissues of Atlantic salmon was used to synthesize cDNA that was amplified using SalmoKCaR #2 primers. All RNA samples were prepared from a single fish with the exception of olfactory bulb, pituitary, urinary bladder and nasal lamellae that are composed of RNA from pooled samples of fish. As controls to demonstrate primer specificity, selected reactions were subjected to primer amplification with samples of portions of individual SalmoKCaR clones or water alone (Panels A and B): Ethidium bromide stained agarose gel. DNA markers in lane 1 Panels A, B, E and F were used to indicate size of amplification products. (Panels C and D) Southern blot of gel in Top Panel using $^{32}P$-labeled Atlantic salmon genomic fragment. (Panes E and F) Ethidium bromide stained gel of RT-PCR amplification products using Atlantic salmon beta actin primers as described above. These reactions serve as controls to ensure that samples contain equal amounts of RNA. FIG. 22 shows data obtained using SalmoKCaR #2 specific primers and the identical tissue RT and plasmid samples as shown in FIGS. 17, 20, and 21. Corresponding Southern blots shown in Panels C and D reveal the presence of SalmoKCaR #2 PCR amplification product in urinary bladder of seawater-adapted salmon (lane 4) as well as urinary bladder (lane 4) and kidney (lane 5) of freshwater-adapted salmon. These data provide evidence of the tissue specific expression of SalmoKCaR #1 in both freshwater and seawater adapted salmon.

EXAMPLE 7

Survival and Growth of Pre-Adult Anadromous Fish by Modulating PVCRS

An important feature of current salmon farming is the placement of smolt from freshwater hatcheries to ocean netpens. Present day methods use smolt that have attained a critical size of approximately 70–110 grams body weight. The methods described herein to modulate one or more PVCRs of the anadromous fish including Atlantic Salmon, can either be utilized both to improve the ocean netpen transfer of standard 70–110 grams smolt as well as permit the successful ocean netpen transfer of smaller smolts weighing, for example, only 15 grams. As shown herein, one utility for the present invention is its use in conjunction with transferring Atlantic Salmon from freshwater to seawater. For standard 70–110 gram smolt, application of the invention eliminates the phenomenon known as “smolt window” and permits fish to be maintained and transferred into ocean water at 15° C. or higher. Use of these methods in 15 gram or larger smolt permits greater utilization of freshwater hatchery capacities followed by successful seawater transfer to ocean netpens. In both cases, fish that undergo the steps described herein feed vigorously within a short interval of time after transfer to ocean netpens and thus exhibit rapid growth rates upon transfer to seawater.

Figure 23:
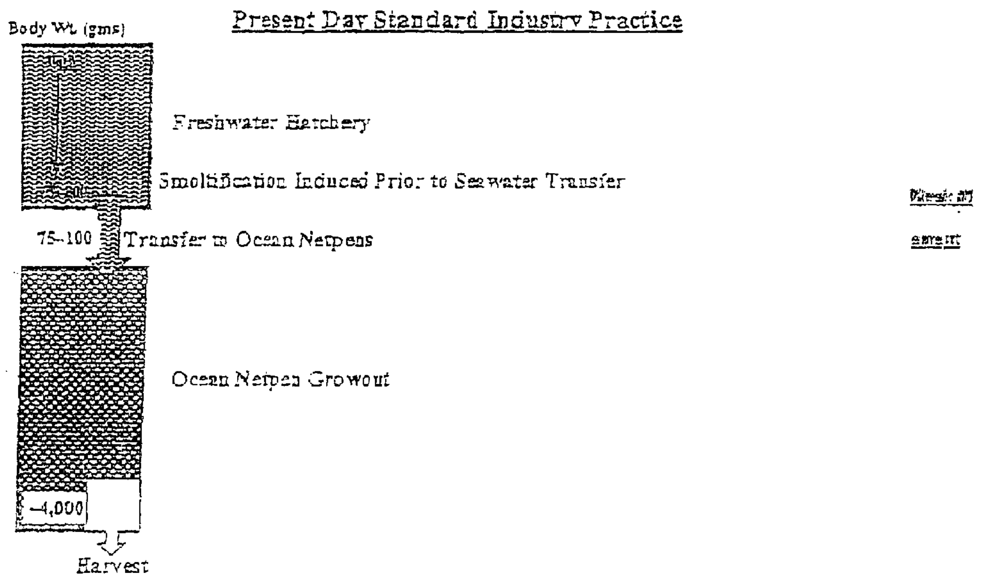
FIG. 23 is a schematic diagram illustrating industry practice for salmon aquaculture production, prior to the discovery of the present invention. The diagram depicts key steps in salmon production for S0 (75 gram) and S1 (100 gram) smolts. The wavy symbol indicates freshwater while the bubbles indicate seawater.

FIG. 23 shows in schematic form the key features of current aquaculture of Atlantic salmon in ocean temperatures present in Europe and Chile. Eggs are hatched in inland freshwater hatcheries and the resulting fry grow into fingerlings and parr. Faster growing parr are able to undergo smoltification and placement in ocean netpens as S0 smolt (70 gram) during year 01. In contrast, slower growing parr are smoltified in year 02 and placed in netpens as S1 smolt (100 gram). In both S0 and S1 transfers to seawater, the presence of cooler ocean and freshwater temperatures are desired to minimize the stress of osmotic shock to newly transferred smolt. This is particularly true for S1 smolt since freshwater hatcheries are often located at significant distances from ocean netpen growout sites and their water temperatures rise rapidly during early summer. Thus, the combination of rising water temperatures and the tendency of smolt to revert or die when held for prolonged intervals in freshwater produces a need to transfer smolt into seawater during the smolt window.

Standard smolts that are newly placed in ocean netpens are not able to grow optimally during their first 40–60 day interval in seawater because of the presence of osmotic stress that delays their feeding. This interval of osmotic adaptation prevents the smolts from taking advantage of the large number of degree days present immediately after either spring or fall placement. The combination of the presence of the smolt window together with delays in achieving optimal smolt growth prolong the growout interval to obtain market size fish. This is particularly problematic for S0's since the timing of their harvest is sometimes complicated by the occurrence of grilsing in maturing fish that are exposed to reductions in ambient photoperiod.

Methods

The smolt were subjected to the steps of Process I and II, as described herein.

Results and Discussion:

Section I: Demonstration of the Benefits of the Process I for Atlantic Salmon

Demonstration of the Benefits of the Process I for Atlantic Salmon:

Process I increases the survival of small Atlantic Salmon S2 like smolt after their transfer to seawater when compared to matched freshwater controls. Optimal survival is achieved by using the complete process consisting of both the magnesium and calcium water mixture as well as NaCl diet. In contrast, administration of calcium and magnesium either via the food only or without NaCl dietary supplementation does not produce results equivalent to Process I.

Table 3 shows data obtained from Atlantic salmon S2 like smolts less than 1 year old weighing approximately 25 gm. This single group of fish was apportioned into 4 specific groups as indicated below and each were maintained under identical laboratory conditions except for the variables tested. All fish were maintained at a water temperature of 9–13° C. and a continuous photoperiod for the duration of the experiment. The control freshwater group that remained in freshwater for the initial 45 day interval experienced a 33% mortality rate under these conditions such that only 67% were able to be transferred to seawater. After transfer to seawater, this group also experienced high mortality where only one half of these smolts survived. Inclusion of calcium (10 mM) and magnesium (5 mM) within the feed offered to smolt (Ca2+/Mg2+diet) reduced survival as compared to controls both in freshwater (51% vs 67%) as well after seawater transfer (1% vs 50%). In contrast, inclusion of 10 mM Ca2+ and 5 mM Mg2+ in the freshwater (Process I Water Only) improved smolt survival in Process I water as well as after transfer of smolt to seawater. However, optimal results were obtained (99% survival in both the Process I water mixture as well as after seawater transfer) when smolt were maintained in Process I water mixture and fed a diet supplemented with 7% sodium chloride.

TABLE 3

Comparison of the Survival of Atlantic Salmon S2 like Smolts After Various Treatments

| Parameter Sampled | Control Freshwater | Ca2 +/Mg2 + Diet | Process I Water Only | Process I Water + NaCl Diet |
|---|---|---|---|---|
| Starting # of fish | 66 | 70 | 74 | 130 |
| # of fish | 44 | 36 | 67 | 129 |
| % of fish surviving after 45 days in freshwater or Process I mixture | 67% | 51% | 91% | 99% |
| # of fish | 22 | 2 | 60 | 128 |
| % of fish surviving 5 days after transfer to seawater | 50% | 6% | 90% | 99% |

[1]Survival percentages expressed as rounded whole numbers

Application of the Process I to the Placement of 70–100 gm Smolts in Seawater.

These data show that use of the Process I eliminates the “smolt window” and provides for immediate smolt feeding and significant improvement in smolt growth rates.

Experimental Protocol:

Smolts derived from the St. John strain of Atlantic salmon produced by the Connors Brothers Deblois Hatchery located in Cherryfield, Me., U.S.A. were utilized for this large scale test. Smolts were produced using standard practices at this hatchery and were derived from a January 1999 egg hatching. All smolts were transferred with standard commercially available smolt trucks and transfer personnel. S1 smolt were purchased during Maine’s year 2000 smolt window and smolt deliveries were taken between the dates of Apr. 29, 2000–May 15, 2000. Smolts were either transferred directly to Polar Circle netpens (24 m diameter) located in Blue Hill Bay Maine (Controls) or delivered to the treatment facility where they were treated with Process I for a total of 45 days. After receiving the Process I treatment, the smolt were then transported to the identical Blue Hill Bay netpen site and placed in an adjacent rectangular steel cage (15 m×15 m×5 m) for growout. Both groups of fish received an identical mixture of moist (38% moisture) and dry (10% moisture) salmonid feed (Connors Bros). Each of the netpens were fed by hand or feed blower to satiation twice per day using camera visualization of feeding. Mort dives were performed on a regular basis and each netpen received identical standard care practices established on this salmon farm. Sampling of fish for growth analyses was performed at either 42 days (Process I) or 120 days or greater (Control) fish. In both cases, fish were removed from the netpens and multiple analyses performed as described below.

All calculations to obtain feed conversion ratio (FCR) or specific growth rate (SGR) and growth factor (GF3) were performed using standard accepted formulae (Willoughby, S. Manual of Salmonid Farming Blackwell Scientific, Oxford UK 1999) and established measurements of degree days for the Blue Hill Bay site as provided in Table 4 below. A degree day is calculated by multiplying the number of days in a month by the mean daily temperature in degrees Celsius.

TABLE 4

Degree days for Blue Hill Bay Salmon Aquaculture Site

| Month | Degree Days |
|---|---|
| Jan | 60 |
| Feb | 30 |
| Mar | 15 |
| April | 120 |
| May | 210 |
| June | 300 |
| July | 390 |
| Aug | 450 |
| Sept | 420 |
| Oct | 360 |
| Nov | 240 |
| Dec | 180 |

Table 5 displays data obtained after seawater transfer of Control S1 smolt. Smolt ranging from 75–125 gm were placed into 3 independent netpens and subjected to normal farm practices and demonstrated characteristics typical for present day salmon aquaculture in Maine. Significant mortalities (average 3.3%) were experienced after transfer into cool (10° C.) seawater and full feeding was achieved only after a significant interval (~56 days) in ocean netpens. As a result, the average SGR and GF3 values for these 3 netpens were 1.09 and 1.76 respectively for the 105–121 day interval measured.

In contrast to the immediate transfer of Control S1 smolt as described above to ocean netpens (Table 5), a total of 10,600 S1 smolt possessing an average size of 63.6 grams were transported on May 11, 2000 from the Deblois freshwater hatchery to the research facility. While being maintained in standard circular tanks, these fish were held for a total of 45 days at an average water temperature of 11° C. and were subjected to Process I. During this interval, smolt mortality was only 64 fish (0.6%). As a matched control for the Process I fish, a smaller group of control fish (n=220) were held under identical conditions but did not receive the Process I treatment. The mortalities of these control fish were minimized by the holding temperature of 10° C. and were equivalent to treated smolts prior to transfer to seawater.

TABLE 5

Characteristics of St. John S1 smolt subjected to immediate placement in ocean netpens after transport form the freshwater hatchery without Process I or Process II technology (the Control fish)

| | Netpen Number | | |
|---|---|---|---|
| | #17 | #18 | #10 |
| Total Fish | 51,363 | 43,644 | 55,570 |
| Mean Date of Seawater Transfer | May 1, 2000 | May 5, 2000 | May 14, 2000 |
| Average Size at Transfer (grams) | (117.6) 100–125 | 75–100 | 75–100 |
| Mortalities after 30 days (# and % total) | 1,785; 3.5% | 728; 1.7% | 2503; 4.5% |
| Time to achieve full feeding after transfer | 68 days | 48 days | 50 days |
| Interval between netpen placement and analysis | 121 | 120 | 105 |
| Average size at Analysis | | | |
| Weight (gram) | 376.8 ± 74 | 305.80 ± 64 | 298.90 ± 37.40 |
| Length (cm) | 33.4 ± 1.9 | 28.30 ± 9.0 | 30.40 ± 1.17 |
| Condition Factor (k) | 1.02 | 1.34 | 1.06 |
| SGR during initial 120 days | 0.96 | 1.10 | 1.17 |

During the 45 day interval when S1 smolts were receiving Process I, fish grew an average of 10 grams and thus possessed an average weight of 76.6 gm when transferred to an ocean netpen. The actual smolt transfer to seawater occurring on Jun. 26, 2000 was notable for the unusual vigor of the smolt that would have normally been problematic since this time is well past the normal window for ocean placement of smolt. The ocean temperature at the time of Process I smolt netpen placement was 15.1° C. In contrast to the counterpart S1 smolts subjected to standard industry practices described above, Process I smolts fed vigorously within 48 hours of ocean placement and continued to increase their consumption of food during the immediate post-transfer period. The mortality of Process I smolts was comparable to that of smolts placed earlier in the summer (6.1%) during initial 50 days after ocean netpen placement and two thirds of those mortalities were directly attributable to scale loss and other physical damage incurred during the transfer process itself.

In contrast, corresponding control fish (held under identical conditions without Process I treatment) did not fare well during transfer to the netpen (17% transfer mortality) and did not feed vigorously at any time during the first 20 days after ocean netpen placement. This smaller number of control fish (176) were held in a smaller (1.5 m×1.5 m×1.5 m) netpen floating within the larger netpen containing Process I smolts. Their mortality post-ocean netpen placement was very high at 63% within the 51 day interval.

Both Process I and control smolts were fed on a daily basis in a manner identical to that experienced by the Industry Standard Fish shown on Table 5. Process I fish were sampled 51 days after their seawater placement and compared to the Industry Standard smolts from Table 5. As shown in Table 6, comparison of their characteristics reveals dramatic differences between Industry Standard smolts vs Process I.

TABLE 6

Comparison of the characteristics of St. John S1 Process I Smolts subjected to Process I treatment and then placed in ocean netpens vs corresponding industry standard smolts.

| | Process I Smolts | Averaged Industry Standard Data from Table 5 in this Example |
|---|---|---|
| Total Fish | 10,600 | 150,577 |
| Mean Date of Seawater Transfer | Jun. 26, 2000 | May 7, 2000 |
| Average Size at Transfer (grams) | 76.6 | 95.8 |
| Mortalities after 30 days (# and %) | 648; 6.1% | 5,016; 3.3% |
| Time to achieve full Feeding after transfer | 2 days | 56 days |
| Interval between netpen placement and analysis | 51 | 115 |
| Average size at Analysis | | |
| Weight (gram) | 175.48 ± 50 | 327.2 ± 97 |
| Length (cm) | 26.2 ± 32 | 30.7 |
| Condition Factor (k) | 0.95 ± 0.9 | 1.14 |
| SGR | 1.80 | 1.09 |

In summary, notable differences between Process I, Control smolt and Industry Standard smolt include:

1. The mortalities observed after ocean netpen placement were low in Process I (6.1 %) vs Control (63%) despite the that fact these fish were transferred to seawater 1.5 months after the smolt window and into a very high (15.1° C.) ocean water temperature. The mortality of Process I was comparable to that of the accepted Industry Standard smolt (3–10%) transferred to cooler (10° C.) seawater during the smolt window. This characteristic of Process I provides for a greater flexibility in freshwater hatchery operations since placement of Process I smolts are not rigidly confined the conventional “smolt window” currently used in industry practice.

2. The Process I fish were in peak condition during and immediately after seawater transfer. Unlike industry standard smolt that required 56 days to reach full feeding, the Process I smolts fed vigorously within 2 days. Moreover, the initial growth rate (SGR 1.8) demonstrated by Process I smolts are significantly greater than published data for standard smolt during their initial 50 days after seawater placement (published values (Stradmeyer, L. Is feeding nonstarters a waste of time. Fish Farmer 3:12–13, 1991; Usher, M L, C Talbot and F B Eddy. Effects of transfer to seawater on growth and feeding in Atlantic salmon smolts (Salmo salar L.) Aquaculture 94:309–326, 1991) for SGR's range between 0.2–0.8). In fact, the growth rates of Process I smolts are significantly larger as compared to Industry standard smolts placed into seawater on the same site despite that industry standard smolt were both larger at the time of seawater placement as well as that their growth was measured 120 days after seawater placement. These data provide evidence that the Process I smolts were not subjected to significant osmoregulatory stress which would prevent them from feeding immediately.

3. The rapid growth of Process I smolts immediately upon ocean netpen placement provides for compounding increases in the size of salmon as seawater growout proceeds. Thus, it is anticipated that if Industry Standard Smolts weighing 112.5 gram (gm) were subjected to Process I treatment, placed in ocean netpens and examined at 120 days after ocean netpen placement their size would be average 782 gram instead of 377 gram as observed. This provides for more than a doubling in size of fish in the early stages of growout. Such fish would reach market size more rapidly as compared to industry standard fish.

Figure 24A:
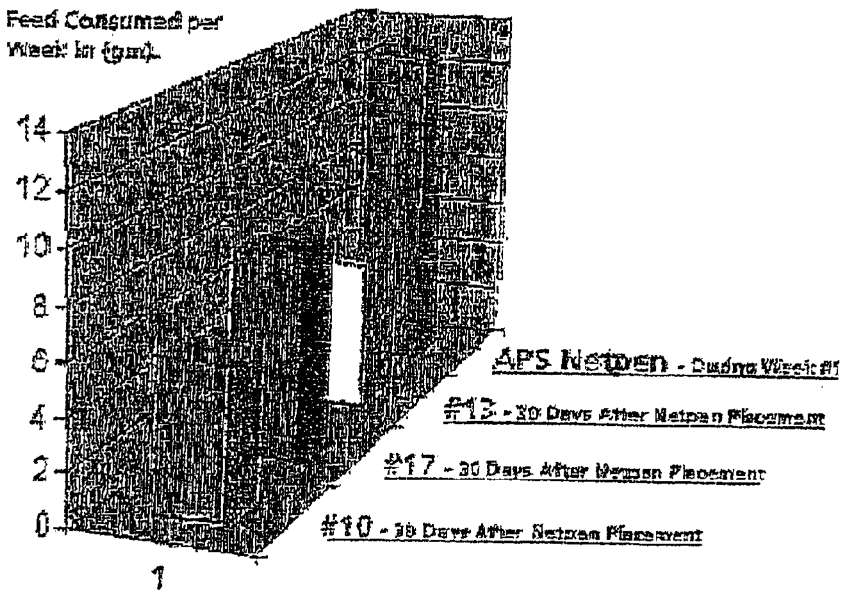
FIG. 24A is a graphical representation comparing the weekly feed consumption on a per fish basis between Process I treated smolts weighing approximately 76.6 gm vs industry standard smolt weighing approximately 95.8 gm. These data are derived from individual netpens of fish containing about 10,000–50,000 fish per pen. As shown, fish treated with Process I consumed approximately twice as much feed per fish during their first week after seawater transfer as compared to the large industry standard smolts weekly food consumption after 30 days. Process I treatment is defined in the Exemplification.

In contrast to the counterpart S1 smolts subjected to standard industry practices, smolt treated with Process I fed vigorously within 48 hours of ocean placement and continued to increase their consumption of food during the immediate post-transfer period. By comparison, the industry standard smolts consumed little or no feed within the first week after transfer. FIG. 24A compares the weekly feed consumption on a per fish basis between Process I treated smolts and industry standard smolts. As shown, Process I treated smolts consumed approximately twice as much feed per fish during their FIRST WEEK as compared to the industry standard smolts after 30 days. Since smolts treated with Process I fed significantly more as compared to Industry standard smolts, the Process I treated smolts grew faster.

Figure 24B:
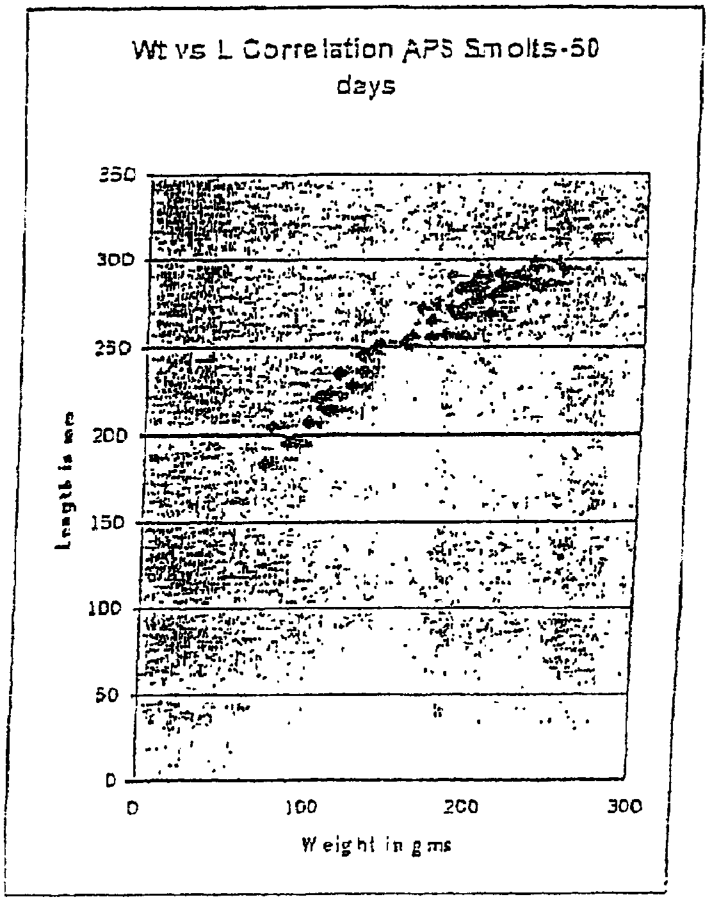
FIG. 24B is a graphical representation illustrating length (cm) and weight (gm) of Process I Smolts 50 days after ocean netpen placement. Process I smolts had an average weight of 76.6 gram when placed in seawater and were sampled after 50 days.

FIG. 24B provides data on the characteristics of Process I smolts after seawater transfer. These experiments were carried out for over 185 days.

Application of the Process I to Atlantic Salmon Pre-Adult Fish that are Smaller than the Industry Standard "Critical Size" Smolt.

A total of 1,400 Landcatch/St John strain fingerlings possessing an average weight of 20.5 gram were purchased from Atlantic Salmon of Maine Inc., Quossic Hatchery, Quossic, Me., U.S.A. on 1 Aug. 2000. These fingerlings were derived from an egg hatching in January 2000 and considered rapidly growing fish. They were transported to the treatment facility using standard conventional truck transport. After their arrival, these fingerlings were first placed in typical freshwater growout conditions for 14 days. These fingerlings were then subjected to Process I for a total of 29 days while being exposed to a continuous photoperiod. The Process I were then vaccinated with the Lipogen Forte product (Aquahealth LTD.) and transported to ocean netpens by conventional truck transport and placed into seawater (15.6° C.) in either a research ocean netpen possessing both a predator net as well as net openings small enough (0.25 inch) to prevent loss of these smaller Process I smolts. Alternatively, Process I smolts were placed in circular tanks within the laboratory. Forty eight hours after sea water transfer, Process I smolts were begun on standard moist (38% moisture) smolt feed (Connors Bros.) that had been re-pelletized due to the necessity to provide for smaller size feed for smaller Process I smolts, as compared to normal industry salmon. In a manner identical to that described for 70 gram smolts above, the mortality, feed consumption, growth and overall health of these 30 gram Process I smolts were monitored closely.

Figure 25:
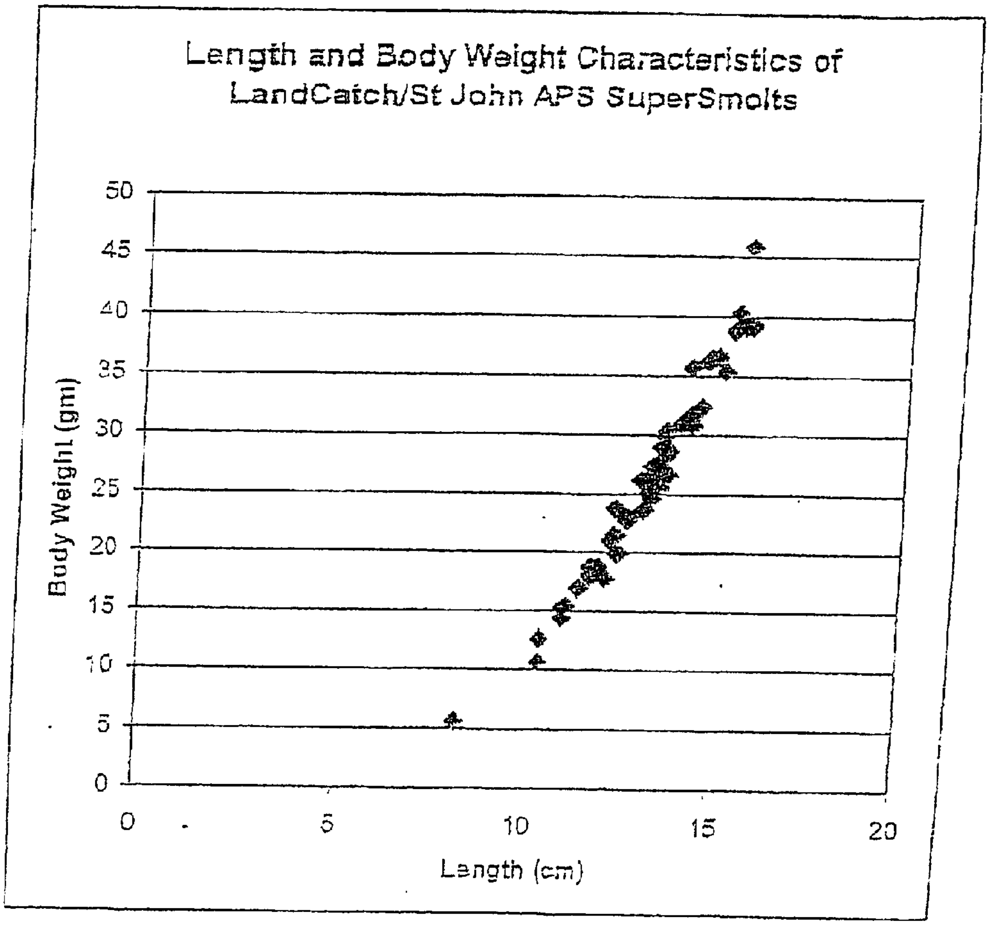
FIG. 25 is a graphical representation illustrating length (cm) and weight (gm) of representative Process I smolts prior to transfer to seawater.

FIG. 25 displays the characteristics of a representative sample of a larger group of 1,209 Process I smolts immediately prior to their transfer to seawater. These parameters included an average weight of 26.6+8.6 gram, length of 13.1+1.54 cm and condition factor of 1.12+0.06. After seawater transfer, Process I smolts exhibited a low initial mortality despite the fact that their average body weight is 26–38% of industry standard 70–100 gram S0–S1 smolts. As shown in Table 7, Process I smolts mortality within the initial 72 hr after seawater placement was 1/140or 0.07% for the laboratory tank. Ocean netpen mortalities after placement of Process I smolts were 143/1069 or 13.4%. FIG. 25 shows representative Landcatch/St John strain Process I smolts possessing a range of body sizes that were transferred to seawater either in ocean netpens or corresponding laboratory seawater tanks. Process I smolts possess a wide range of sizes (e.g., from about 5.6 grams to about 46.8 grams body weight) with an average body weight of 26.6 gram. Experiments with these data were carried out for 84 days after the transfer of fish to seawater tanks, and the data from these experiments are described in co-pending application Ser. No.: 09/975,553.

TABLE 7

Characteristics and survival of Landcatch/St. John Process I fish after their placement into seawater in either a laboratory tank or ocean netpen.

| | Laboratory Tank | Ocean Netpen |
|---|---|---|
| Total Fish | 140 | 1,069 |
| Date of Seawater Transfer | Sep. 5, 2000 (40); Sep. 12, 2000 (100) | Sep. 12, 2000 |
| Average Size at Transfer (gram) | 26.6 | 26.6 |
| Total mortalities after 4 days (# and % total) | 1; 0.7% | 143; 13.4% |
| % mortality of fish weighing 25 gm and above | 0; 0.0% | 4; 0.4% |
| Time to achieve feeding | 48 hrs | 72 hrs |

Figure 26:
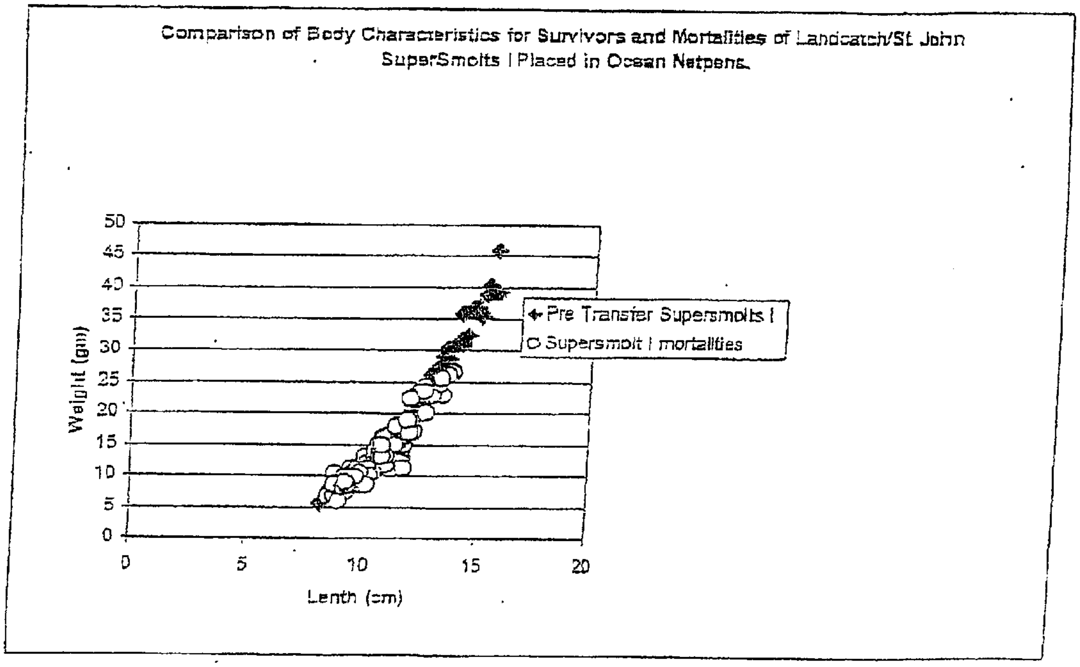
FIG. 26 is a graphical representation illustrating length (cm) and weight (gm) of Process I smolts before transfer, and mortalities after transfer to ocean netpens.

FIG. 26 shows a comparison of the distributions of body characteristics for total group of Landcatch/St John Process I smolts vs. mortalities 72 hr after seawater ocean netpen placement. Length and body weight data obtained from the 143 mortalities occurring after seawater placement of 1,069 Process I smolts were plotted on data obtained from a 100 fish sampling as shown previously in FIG. 25. Note that the mortalities are exclusively distributed among the smaller fish within the larger Process I netpen population.

Length and weight measurements for all mortalities collected from the bottom of the ocean netpen were compared to the distribution of Process I smolt body characteristics obtained from analysis of a representative sample prior shown in FIG. 26. The data show that the mortalities occurred selectively amongst Process I smolts possessing small body sizes such that the mean body weight of mortalities was 54% of the mean body weight of the total transfer population (14.7/27 gram or 54%). Thus, the actual mortality rates of Process I smolts weighing 25–30 gram is 0.4% (4/1069) and those weighing 18–30 gram is 2.9% (31/1069).

Application of Process I to Trout Pre-Adult Fish that are Smaller than the Industry Standard "Critical Size" Smolt.

Table 8 displays data on the use of the Process I on small (3–5 gram) rainbow trout. Juvenile trout are much less tolerant of abrupt transfers from freshwater to seawater as compared to juvenile Atlantic salmon. As a result, many commercial seawater trout producers transfer their fish to brackish water sites located in estuaries or fresh water lenses or construct "drinking water" systems to provide fresh water for trout instead of the full strength seawater present in standard ocean netpens. After a prolonged interval of osmotic adaptation, trout are then transferred to more standard ocean netpen sites to complete their growout cycle. In general, trout are transferred to these ocean sites for growout at body weights of approximately 70–90 or 90–120 gram.

TABLE 8

Comparison of the Survival of Rainbow Trout (3–5 gram) in Seawater After Various Treatments.
Percent Survival of Fish[1]

| Hours Post Seawater Transfer | Control Freshwater | Constant 14 day Photoperiod | Constant 14 day Photoperiod Process I | Constant 23 day Photoperiod + Process I |
|---|---|---|---|---|
| 0 | 100 | 100 | 100 | 100 |
| 24 | 0 | 25 | 80 | 99 |
| 48 | | 0 | 70 | 81 |
| 72 | | | 40 | 68 |
| 96 | | | 30 | 58 |
| 120 | | | 30 | 46 |
| Number of Fish Per Experiment | 10 | 20 | 30 | 80 |

[1]Survival percentages expressed as rounded whole numbers

A total of 140 trout from a single pool of fish less than 1 year old were divided into groups and maintained at a water temperature of 9–13° C. and pH 7.8–8.3 for the duration of the experiment described below. When control freshwater rainbow trout are transferred directly into seawater, there is 100% mortality within 24 hr (Control Freshwater). Exposure of the trout to a constant photoperiod for 14 days results in a slight improvement in survival after their transfer to seawater. In contrast, exposure of trout to Process I for either 14 days or 23 days results in significant reductions in mortalties after transfer to seawater such that 30% and 46% of the fish respectively have survived after a 5 day interval in seawater. These data demonstrate that application of the Process I increases in the survival of pre-adult trout that are less than 7% of the size of standard "critical size" trout produced by present day industry standard techniques.

Application of the Process I to Arctic Char pre-adult Fish that are Smaller than the Industry Standard "Critical Size" Smolt.

Figure 27:
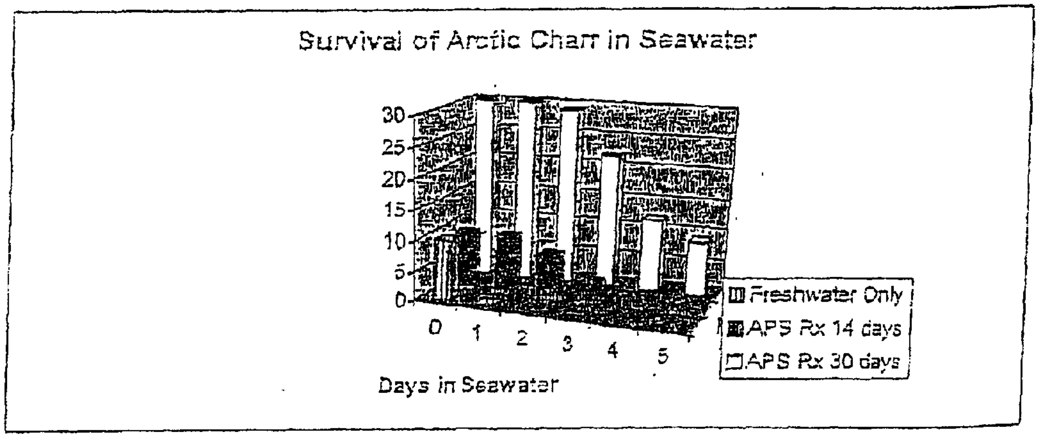
FIG. 27 is a three dimensional graph illustrating the survival over 5 days of Arctic Char in seawater after being maintained in freshwater, Process I for 14 days, and Process I for 30 days.

Although arctic char are salmonids and anadromous fish, their tolerance to seawater transfer is far less as compared to either salmon or trout. FIG. 27 shows the results of exposure of smaller char (3–5 gram) to the Process I for a total of 14 and 30 days. All fish shown in FIG. 27 were exposed to a continuous photoperiod. Transfer of char to seawater directly from freshwater results in the death of all fish within 24 hr. In contrast, treatment of char with the Process I for 14 and 30 days produces an increase in survival such that 33% (3/9) or 73% (22/30) respectively are still alive after a 3 day exposure. These data demonstrate that the enhancement of survival of arctic char that are less than 10% of the critical size as defined by industry standard methods after their exposure to the Process I followed by transfer to seawater.

FIG. 27 shows a comparison of survival of arctic char after various treatments. A single group of arctic char (3–5 gram were obtained from Pierce hatcheries (Buxton, Me.) and either maintained in freshwater or treated with the Process I prior to transfer to seawater.

Section II: The Use of the Process II to Permit Successful Transfer of 10–30 gram Smolt into Seawater Netpens and Tanks.

The Process II protocol is utilized to treat pre-adult anadromous fish for placement into seawater at an average size of 25–30 gram or less. This method differs from the Process I protocol by the inclusion of L-tryptophan in the diet of pre-adult anadromous fish prior to their transfer to seawater. Process II further improves the osmoregulatory capabilities of pre-adult anadromous fish and provides for still further reductions in the "critical size" for Atlantic salmon smolt transfers. In summary, Process II reduces the "critical size" for successful seawater transfer to less than one fifth the size of the present day industry standard S0 smolt.

Application of Process II to Atlantic Salmon Fingerlings:

St John/St John strain pre-adult fingerlings derived from a January 2000 egg hatching and possessing an average weight of 0.8 gram were purchased from Atlantic Salmon of Maine Inc. Kennebec Hatchery, Kennebec Me. on Apr. 27, 2000. These fish were transported to the treatment facility using standard conventional truck transport. After their arrival, these parr were first grown in conventional flow through freshwater growout conditions that included a water temperature of 9.6° C. and a standard freshwater parr diet (Moore-Clark Feeds). On 17 Jul. 2000, fingerlings were begun on Process II for a total of 49 days while being exposed to a continuous photoperiod. Process II smolts were then vaccinated with the Lipogen Forte product (Aquahealth LTD.) on Day 28 (14 Aug. 2000) of Process II treatment. Process II smolts were size graded prior to initiating Process II as well as immediately prior to transfer to seawater. St John/St John Process II smolts were transported to ocean netpens by conventional truck transport and placed into seawater (15.2° C.) in either a single ocean netpen identical to that described for placement of Process I smolts or into laboratory tanks (15.6° C.) within the research facility.

Figure 28:
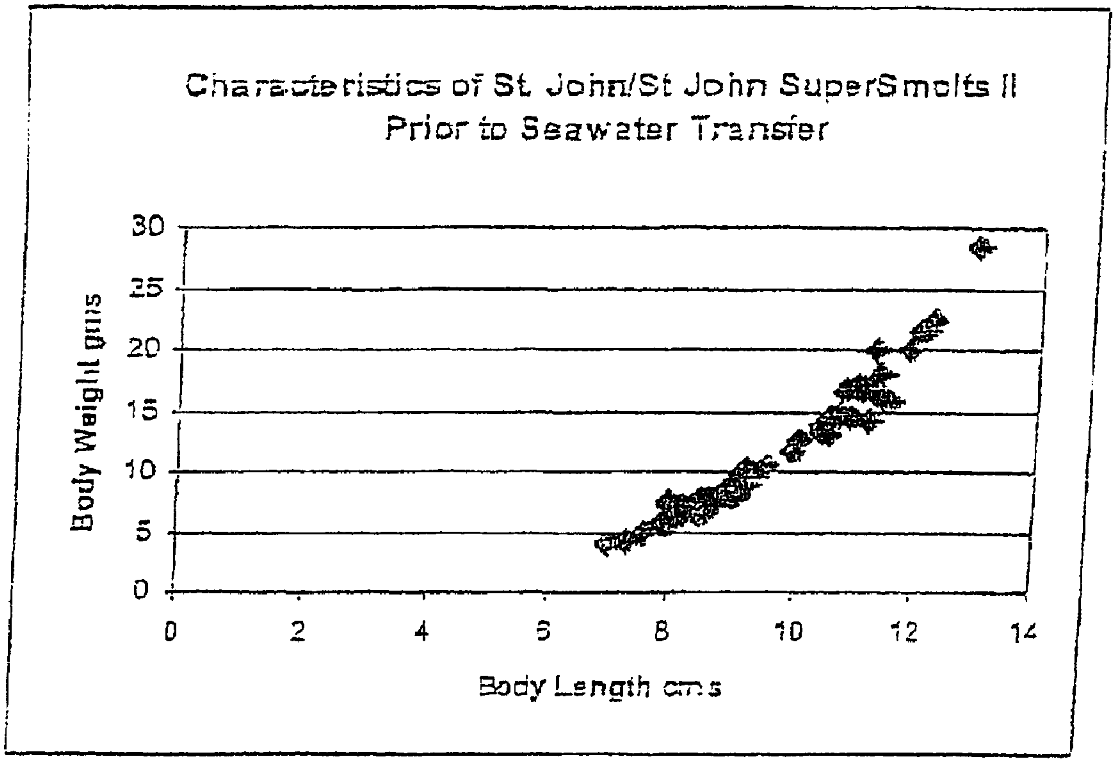
FIG. 28 is a graphical representation illustrating the length (cm) and weight (gm) of St. John/St. John Process II smolts prior to seawater transfer. Process II is defined in the Exemplification Section.

FIG. 28 shows representative St. John/St John strain Process II smolts possessing a range of body sizes were transferred to seawater either in ocean netpens or corresponding laboratory seawater tanks. Note that these Process II smolts possess a wide range of body weights (3.95–28 gram) that comprised an average body weight of 11.5 gram. FIG. 28 shows the characteristics of St. John/St John Process II smolts. The average measurements of these St. John/St. John Process II smolts included a body weight of 11.50+/−5.6 gram, length of 9.6+/−1.5 cm and condition factor of 1.19+/−0.09. The data displayed in Tables 9 and 10 show the outcomes for two groups of Process II smolts derived from a single production pool of fish after their seawater transfer into either laboratory tanks or ocean netpens. Although important variables such as the water temperatures and transportation of fish to the site of seawater transfer were identical, these 2 groups of Process II smolts experienced differential post seawater transfer mortalities after 5 days into laboratory tanks (10% mortality) and ocean netpens (37.7% mortality).

The probable explanation for this discrepancy in mortalities between seawater laboratory tanks (10% mortality) and ocean netpens (37.7% mortality) is exposure of these fish to different photoperiod regimens after seawater placement. Exposure of juvenile Atlantic salmon to a constant photoperiod after seawater placement reduced their post-seawater transfer mortality from approximately 34% to 6%. Fish transferred to ocean netpens experienced natural photoperiod that was not continuous and thus suffered an approximate 4-fold increase in mortality. As shown in Table 9, a separate seawater transfer of St John/St John juvenile Atlantic salmon possessing an average weight of 21 gms exhibited only 0.2% mortality after a six week treatment with Process and underwater lights. These fish were exposed to a continuous photoperiod by underwater halogen lights for an interval of 30 days.

TABLE 9

Characterization and survival of St. John/St. John Process II fish after their placement into seawater in ocean netpens containing underwater lights.

| | |
|---|---|
| Total Fish | 15,000 |
| Seawater Transfer Date | Aug. 9, 2001 |
| Water Temperature (° C.) | 12.6 |
| Size at Transfer (gram) | 21 +/− 4.5 |
| Total Mortalities after 30 days (# and % total) | 250 1.7% |
| % Mortalities weighing 15 grams or greater | 30 0.2% |
| Time to achieve feeding after transfer | 48 hr |

TABLE 10

Characteristics and survival of St. John/St. John Process II fish after their placement into seawater in either a laboratory tank or ocean netpen.

| | Laboratory Tank | Ocean Netpen |
|---|---|---|
| Total Fish | 100 | 1,316 |
| Seawater Transfer Date | Aug. 31, 2000 | Sep. 5, 2000 |
| Water Temperature (° C.) | 15.6 | 15.6 |
| Size at Transfer (gram) | 11.5 | 11.5 |
| Total Mortalities after 5 days (# and % total) | 10; 10% | 496; 37.7% |
| % mortalities weighing 13 grams or greater | 0; 0% | 1; 0.08% |
| Time to achieve feeding after transfer | 48 hrs | 48 hrs |

No apparent problems were observed with the smaller (10–30 gram) Process II smolts negotiating the conditions that exist within the confines of their ocean netpen. This included the lack of apparent problems including the ability to school freely as well as the ability to swim normally against the significant ocean currents that are continuously present in the commercial Blue Hill Bay salmon aquaculture site. While these observations are still ongoing, these data do not suggest that the placement and subsequent growth of Process II smolts in ocean netpens will be comprised because of lack of ability of these pre-adult anadromous fish to swim against existing ocean currents and therefore be unable to feed or develop properly.

Figure 29A:
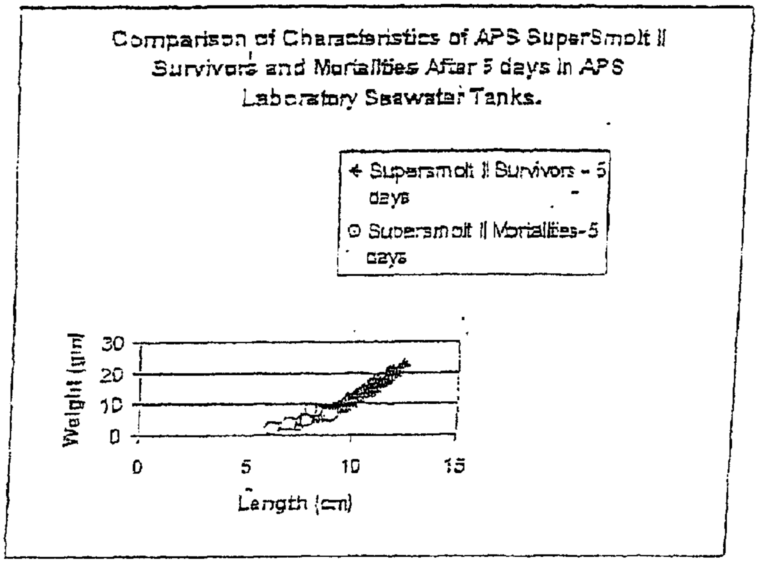
FIGS. 29A and 29B are graphical representations illustrating weight (gm) and length (cm) of Process II smolt survivors and mortalities 5 days after transfer to seawater tanks (A), and 96 hours after transfer to ocean netpens (B).
Figure 29B:
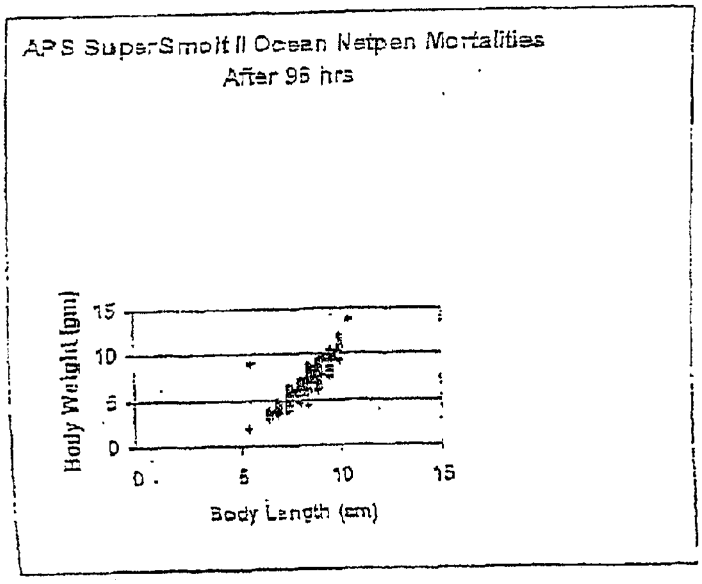

FIG. 29 compares characteristics of survivors and mortalities of Process II smolts after seawater transfer to either laboratory tanks (FIG. 29A) or ocean netpens (FIG. 29B). FIG. 29A data are derived from analyses of 100 Process II smolts transferred to seawater tank where all fish were killed and analyzed on Day 5. In contrast, FIG. 29B displays only mortality data from ocean netpen. In both cases, only smaller Process II smolts experienced mortality. Note differences in Y axis scales of FIGS. 29A–B. Comparison of the average body size of those Process II smolts that survived seawater transfer vs. those Process II smolts that died shows that unsuccessful Process II smolts possessed significantly smaller body weights as compared to average body size of whole Process II smolt transfer group. Thus, the average weight of mortalities in laboratory tank (5.10+/−2.2 gram) and ocean netpen (6.46+/−1.5 gram) are 44% and 56% respectively the value of the average body weight possessed by the entire transfer cohort (11.5 gram). In contrast, the mortalities of Process II smolts with body weights greater than 13 gram is 0/100 in the laboratory tank and 1/1316 or 0.076% for ocean netpens. Together, these data demonstrate that Process II is able to redefine the "critical size" of Atlantic salmon smolts from 70–100 gram to approximately 13 gram.

Quantitation of Feeding and Growth of Process I and II Smolts after Seawater Transfer:

Landcatch/St John Process I smolts were offered food beginning 48 hr after their seawater transfer to either laboratory tanks or ocean netpens. While these Process I smolts that were transferred to laboratory tanks began to feed after 48 hr, those fish transferred to ocean netpens were not observed to feed substantially until 7 days. To validate these observations, the inventors performed direct visual inspection of the gut contents from a representative sample of 49 Process I smolts 4 days after their seawater transfer to laboratory tanks. A total of 21/49 or 42.9% possessed food within their gut contents at that time.

The St John/St John Process II smolts fed vigorously when first offered food 48 hrs after their seawater transfer regardless of whether they were housed in laboratory tanks or ocean netpens. An identical direct analysis of Process II smolts gut contents performed as described above revealed that 61/83 or 73.5% of fish were feeding 4 days after transfer to seawater. The vigorous feeding activity of Process II smolts in an ocean netpen as well as laboratory tanks occurred. Taken together, these data suggest that Process I and II smolts do not suffer from a prolonged (20–40 day) interval of poor feeding after seawater transfer as is notable for the much larger industry standard Atlantic salmon smolts not treated with the process.

The growth rates of identical fish treated with either Process I or II within laboratory seawater tanks has been quantified. As shown in Table 12, both Atlantic salmon treated with Process I or II grow rapidly during the initial interval (21 days) after transfer to seawater. In contrast to industry standard smolt weighing 70–100 grams that eat poorly and thus have little or no growth during their first 20–30 days after transfer to seawater, pre-adult Atlantic salmon receiving Process I or II both exhibited substantial weight gains and growth despite the fact that they are only 27–38% (Process I) and 12–16% (Process II) of the critical size of industry standard smolts. Data that relates to mortalities, SGR, temperature corrected SGR (GF3), FCR, body weights, lengths and condition factors for these same fish were obtained a total of 4 additional intervals during an interval that now extends for 157 days.

TABLE 11

Comparison of Growth Rates of Pre-adult Atlantic Salmon Exposed to either Process I or Process II and Placed in Laboratory Tanks During Initial Interval After Seawater Transfer

| | Process I | Process II |
|---|---|---|
| Number of Fish | 140 | 437 |
| Weight at Placement into Seawater | 26.6 | 11.50 |
| Days in Seawater | 22 | 21 |
| Placement Weight Corrected for Mortalities | 26.6* | 13.15* |
| Weight after Interval in Seawater | 30.3 | 15.2 |
| Weight Gained in Seawater | 3.75 | 2.05 |
| SGR (% body weight/day) | 0.60 | 0.68 |
| FCR | 1.27 | 2.04 |

*Weight gain corrected for selective mortalities amongst smaller fish (4/140 or 2.9% Process I; 103/437 or 23.6% Process II)

EXAMPLE 8

Exposure of Salmon Smolts to CA2+ and MG2+ increases Expression of PVCR In Certain Tissues In smolts that were exposed to 10 mM $Ca^{2+}$ and 5.2 mM $Mg^{2+}$, the expression of PVCR was found to increase in a manner similar to that in smolts that are untreated, but are transferred directly to seawater.

Tissues were taken from either Atlantic salmon or rainbow trout, after anesthesitizing the animal with MS-222. Samples of tissues were then obtained by dissection, fixed by immersion in 3% paraformaldehyde, washing in Ringers then frozen in an embedding compound, e.g., O.C.T.™ (Miles, Inc., Elkahart, Ind., U.S.A.) using methylbutane cooled on dry ice. After cutting 8 micron thick tissue sections with a cryostat, individual sections were subjected to various staining protocols. Briefly, sections mounted on glass slides were: 1) blocked with goat serum or serum obtained from the same species of fish, 2) incubated with rabbit anti-CaR antiserum, and 3) washed and incubated with peroxidase-conjugated affinity-purified goat antirabbit antiserum. The locations of the bound peroxidase-conjugated goat anti-rabbit antiserum were visualized by development of a rose-colored aminoethylcarbazole reaction product. Individual sections were mounted, viewed and photographed by standard light microscopy techniques. The methods used to produce anti-PVCR antiserum are described below.

Figure 30A:
FIGS. 30A–G are photographs of immunocytochemistry of epithelia of the proximal intestine of Atlantic Salmon illustrating SalmoKCaR localization and expression.
Figure 30B:
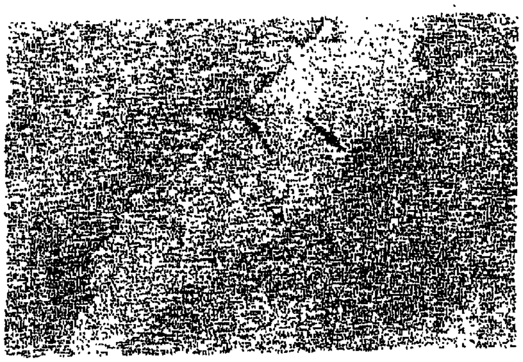
Figure 30C:
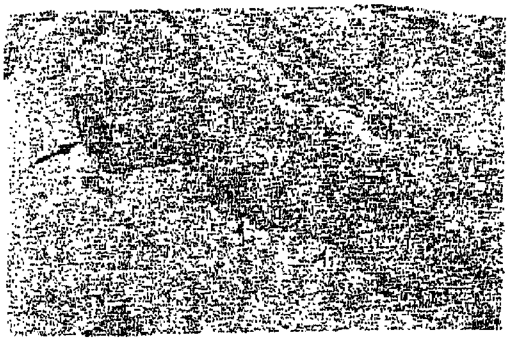
Figure 30D:
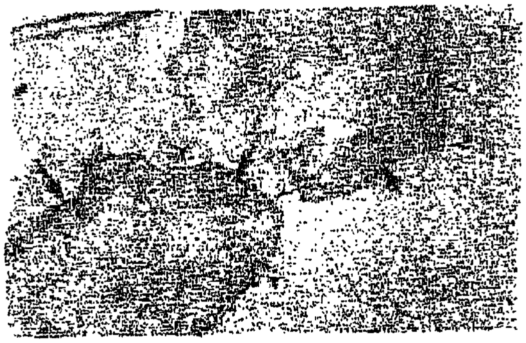
Figure 30E:
Figure 30F:
Figure 30G:
Figure 31:
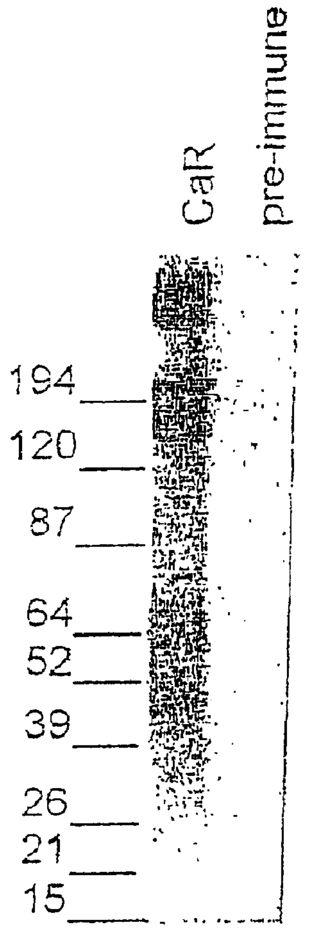
FIG. 31 is a photograph of a Western Blot of intestinal tissue from salmon subjected to Process I for immune (lane marked CaR, e.g., a SalmoKCaR) and preimmune (lane marked preimmune) illustrating SalmoKCaR expression.

The results are shown in FIGS. 30A–30G, which are a set of seven photomicrographs showing immunocytochemistry of epithelia of the proximal intestine of Atlantic salmon smolts using anti-PVCR antiserum, and in FIG. 31, which is a Western blot of intestine of a salmon smolt exposed to Ca2+- and Mg2+-treated freshwater, then transferred to seawater. The antiserum was prepared by immunization of rabbits with a 16-mer peptide containing the protein sequence encoded by the carboxyl terminal domain of the dogfish shark PVCR ("SKCaR") (Nearing, J. et al., 1997, J. Am. Soc. Nephrol. 8:40A). Specific binding of the anti-PVCR antibody is indicated by aminoethylcarbazole (AEC) reaction product.

FIGS. 30A and 30B show stained intestinal epithelia from smolts that were maintained in freshwater then transferred to seawater and held for an interval of 3 days. Abundant PVCR immunostaining is apparent in cells that line the luminal surface of the intestine. The higher magnification (1440×) shown in FIG. 30B displays PVCR protein localized to the apical (luminal-facing) membrane of intestinal epithelial cells. The pattern of PVCR staining is localized to the apical membrane of epithelial cells (small arrowheads) as well as membranes in globular round cells (arrows). FIG. 30C shows stained intestinal epithelia from a representative smolt that was exposed Process I and maintained in freshwater containing 10 mM Ca2+ and 5.2 mM Mg2+ for 50 days. Note that the pattern of PVCR staining resembles the pattern exhibited by epithelial cells displayed in FIGS. 30A and 30B including apical membrane staining (small arrowheads) as well as larger globular round cells (arrows). FIG. 30D shows a 1900× magnification of PVCR-stained intestinal epithelia from another representative fish that was exposed to the Process I and maintained in freshwater containing 10 mM Ca2+ and 5.2 mM Mg2+ for 50 days and fed 1% NaCl in the diet. Again, small arrowhead and arrows denote PVCR staining of the apical membrane and globular cells respectively. In contrast to the prominent PVCR staining shown in FIGS. 30A–D, FIGS. 30E (1440×) and 13F (1900×) show staining of intestinal epithelia from two representative smolt that were maintained in freshwater alone without supplementation of Ca2+ and Mg2+ or dietary NaCl. Both 13E and 13F display a marked lack of significant PVCR staining. FIG. 30G (1440×) shows the lack of any apparent PVCR staining upon the substitution of preimmune serum on a section corresponding to that shown in FIG. 30A where anti-PVCR antiserum identified the PVCR protein. The lack of any PVCR staining with preimmune antiserum is a control to demonstrate the specificity of the anti-PVCR antiserum under these immunocytochemistry conditions.

The relative amount of PVCR protein present in intestinal epithelial cells of freshwater smolts (FIGS. 30E and 30F) was negligible as shown by the faint staining of selected intestinal epithelial cells. In contrast, the PVCR protein content of the corresponding intestinal epithelial cells was significantly increased upon the transfer of these smolts to seawater (FIGS. 30A and 30B). Importantly, the PVCR protein content was also significantly increased in the intestinal epithelial cells of smolts maintained in freshwater supplemented with Ca2+ and Mg2+ (FIG. 30C and 30D). The AEC staining was specific for the presence of the anti-PVCR antiserum, since substitution of the immune antiserum by the preimmune eliminated all reaction product from intestinal epithelial cell sections (FIG. 30G).

Disclosure of Localization of PVCR Protein(s) in Additional Areas of Osmoregulatory Organs of Atlantic Salmon Using Paraffin Sections. Demonstration that PVCR Proteins are Localized to both the Apical and Basolateral Membranes of Intestinal Epithelial Cells.

Using the methods described herein, immunolocalization data from paraffin sections of various osmoregulatory organs of seawater-adapted juvenile Atlantic salmon smolt were obtained. PVCR proteins, as determined by the binding of a specific anti-PVCR antibody, were present in the following organs. These organs are important in various osmoregulatory functions. These organs include specific kidney tubules and urinary bladder responsible for processing of urine, and selected cells of the skin, nasal lamellae and gill each of which are bathed by the water surrounding the fish. The PVCR was also seen in various portions of the G.I. tract including stomach, pyloric caeca, proximal intestine and distal intestine that process seawater ingested by fish. These tissues were analyzed after treatment with Processes I and II, and after their transfer from freshwater to seawater. In addition, it is believed that the PVCR protein can also act as a nutrient receptor for various amino acids that are reported to be present in stomach, proximal intestine, pyloric caeca.

In particular, higher magnification views of PVCR immunolocalizations in selected cells of the stomach, proximal intestine and pyloric caeca were obtained. The PVCR protein is not only present on both the apical (luminally facing) and basolateral (blood-facing) membranes of stomach epithelial cells localized at the base of the crypts of the stomach, but also is present in neuroendocrine cells that are located in the submucosal area of the stomach. From its location on neuroendocrine cells of the G.I. tract, the PVCR protein is able to sense the local environment immediately adjacent to intestinal epithelial cells and modulate the secretion and synthesis of important G.I. tract hormones (e.g., 5-hydroxytryptamine (5-HT), serotonin, or cholecystokinin (CCK)). Importantly, it is believed that the constituents of Process II effect G.I. neuroendocrine cells by at least two means. The first way that constituents of Process II remodel the G.I. endocrine system is through alterations in the expression and/or sensitivity of PVCRs expressed by these cells. The second way is to supply large quantities of precursor compounds, for example, tryptophan that is converted into 5-HT and serotonin by G.I. metabolic enzymes.

In a similar manner, PVCR protein is localized to both the apical and basolateral membranes of epithelial cells lining the proximal intestine. From their respective locations, PVCR proteins can sense both the luminal and blood contents of divalent cations, NaCl and specific amino acids and thereby integrate the multiple nutrient and ion absorptive-secretory finctions of the intestinal epithelial cells. Epithelial cells of pyloric caeca also possess abundant apical PVCR protein.

To further demonstrate the specificity of the anti-CaR antiserum to recognize salmon smolt PVCRs, FIG. 31 shows a Western blot of intestinal protein from salmon smolt maintained in 10 mM Ca2+, 5 mM Mg2+ and fed 1% NaCl in the diet. Portions of the proximal and distal intestine were homogenized and dissolved in SDS-containing buffer, subjected to SDS-PAGE using standard techniques, transferred to nitrocellulose, and equal amounts of homogenate proteins as determined by both protein assay (Pierce Chem. Co, Rocford, Ill.) as well as Coomassie Blue staining were probed for presence of PVCR using standard western blotting techniques. The results are shown in the left lane, labeled "CaR", and shows a broad band of about 140–160 kDa and several higher molecular weight complexes. The pattern of PVCR bands is similar to that previously reported for shark kidney (Nearing, J. et al., 1997, J. Am. Soc. Nephrol. 8:40A) and rat kidney inner medullary collecting duct (Sands, J. M. et al., 1997, J. Clin. Invest. 99:1399–1405). The lane on the right was treated with the preimmune anti-PVCR serum used in FIG. 30G, and shows a complete lack of bands. Taken together with immunocytochemistry data shown in FIG. 30, this immunoblot demonstrates that the antiserum used is specific for detecting the PVCR protein in salmon.

EXAMPLE 9

Immunolocalization of Polyvalent Cation Receptor (PVCR) in Mucous Cells of Epidermis of Salmon The skin surface of sahnonids is extremely important as a barrier to prevent water gain or loss depending whether the fish is located in fresh or seawater. Thus, the presence of PVCR proteins in selected cells of the fish's epidermal layer would be able to "sense" the salinity of the surrounding water as it flowed past and provide for the opportunity for continuous remodeling of the salmonid's skin based on the composition of the water where it is located.

Methods: Samples of the skin from juvenile Atlantic Salmon resident in seawater for over 12 days were fixed in 3% paraformaldehyde dissolved in buffer (0.1M NaP04, 0.15M NaCl, 0.3M sucrose pH 7.4), manually descaled, rinsed in buffer and frozen at −80° C. for cryosectioning. Ten micron sections were either utilized for immunolocalization of PVCR using anti-shark PVCR antiserum or stained directly with 1% Alcian Blue dye to localize cells containing acidic glycoprotein components of mucous.

Figure 32A:
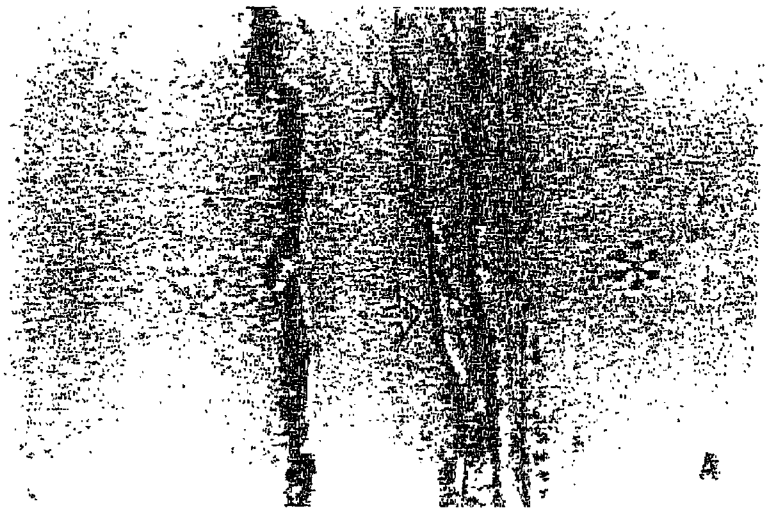
FIGS. 32A–C are photographs of immunolocalization of the SalmoKCaR in the epidermis of salmon illustrating SalmoKCaR localization and expression.
Figure 32B:
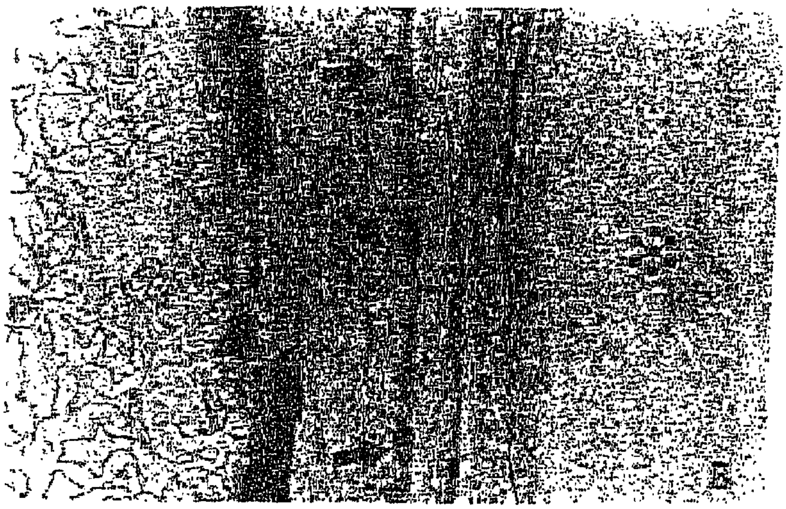
Figure 32C:
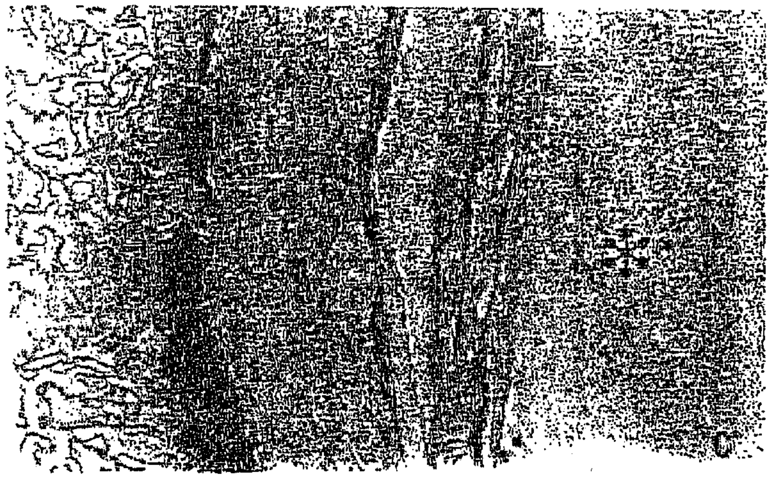

Results and Discussion: FIG. 32A shows that salmon epidermis contains multiple Alcian Blue staining cells present in the various skin layers. Note that only a portion of some larger cells (that containing acidic mucins) stains with Alcian Blue (denoted by the open arrowheads). For purposes of orientation, note that scales have been removed so asterisks denote surface that was previously bathed in seawater. FIG. 32B shows immunolocalization of salmon skin PVCR protein that is localized to multiple cells (indicated by arrowheads) within the epidermal layers of the skin. Note that anti-PVCR staining shows the whole cell body, which is larger than its corresponding apical portion that stains with Alcian Blue as shown in FIG. 32A. The presence of bound anti-CaR antibody was indicated by the rose color reaction product. Although formal quantitation has not yet been performed on these sections, it appears that the number of PVCR cells is less than the total number of Alcian Blue positive cells. These data indicate that only a subset of Alcian Blue positive cells contain abundant PVCR protein. FIG. 32C shows the Control Preimmune section where the primary anti-PVCR antiserum was omitted from the staining reaction. Note the absence of rose colored reaction product in the absence of primary antibody.

These data demonstrate the presence of PVCR protein in discrete epithelial cells (probably mucocytes) localized in the epidermis ofjuvenile Atlantic salmon. From this location, the PVCR protein could "sense" the salinity of the surrounding water and modulate mucous production via changes in the secretion of mucous or proliferation of mucous cells within the skin itself. The PVCR agonists (Ca2+, Mg2+) present in the surrounding water activate these epidermal PVCR proteins during the interval when smolts are being exposed to the process of the present invention. This treatment of Atlantic salmon smolts by the process of the present invention is important to increased survival of smolts after their transfer to seawater.

EXAMPLE 10

Figure 33:
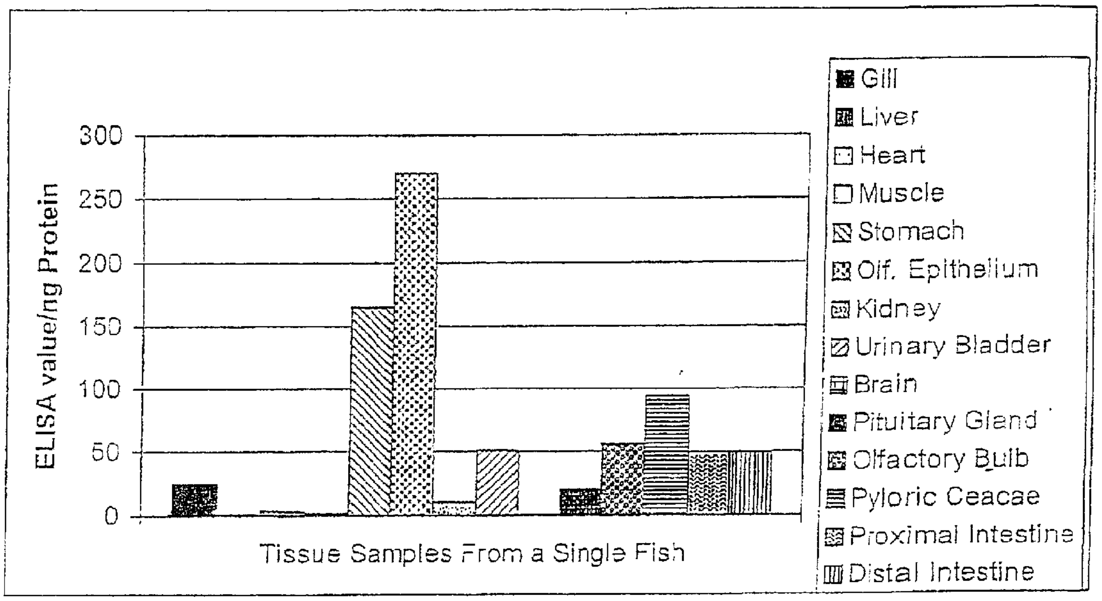
FIG. 33 is a graphical representation quantifying the Enzyme-Linked ImmunoSorbent Assay (ELISA) protein (ng) for various tissue samples (e.g., gill, liver, heart, muscle, stomach, olfactory epithelium, kidney, urinary bladder, brain, pituitary gland, olfactory bulb, pyloric ceacae, proximal intestine, and distal intestine) from a single fish.

Demonstration of the Use of Solid Phase Enzyme-Linked Assay for Detection of PVCRS In Various Tissues of Individual Atlantic Salmon Using Anti-PVCR Polyclonal Antiserum The PVCR content of various tissues of fish can be quantified using an ELISA 96 well plate assay system. The data, described herein, demonstrate the utility of a 96 well ELISA assay to quantify the tissue content of PVCR protein using a rabbit polyclonal anti-PVCR antibody utilized to perform immunocytochemistry and western blotting. These data form the basis for development of commercial assay kits that would monitor the expression levels of PVCR proteins in various tissues of juvenile anadromous fish undergoing the processes of the present invention, as described herein. The sensitivity of this ELISA is demonstrated by measurement of the relative PVCR content of 14 tissues from a single juvenile Atlantic salmon, as shown in FIG. 33.

Description of Experimental Protocol

Homogenates were prepared by placing various tissues of juvenile Atlantic salmon (St. John/St. John strain average weight 15–20 gm) into a buffer (10 mM HEPES, 1.5 mM MgC12, 10 mM KCl, 1 mM Phenylmethylsulfonyl fluoride (PMSF), 0.5 dithiothreitol (DTT) and I mM benzamidine pH 8.8) and using a standard glass Potter-Elvenhiem homogenizer with a rotary pestle. After centrifugation at 2,550×g for 20 min. at 4° C. to remove larger debris, the supernatant was either used directly or frozen at −80° C. until further use. Homogenate protein concentrations were determined using the BCA assay kit (Pierce Chem. Co.). Aliquots of individual tissue homogenates were diluted into a constant aliquot size of 100 microliters and each was transferred to a 96 well plate (Costar Plastic Plates) and allowed to dry in room air for 15 hr. After blocking of nonspecific binding with a solution of 5% nonfat milk powder +0.5% Tween 20 in TBS (25 mM Tris 137 mM sodium chloride, 2.7 mM KCl pH 8.0), primary antiserum (either rabbit anti-PVCR immune or corresponding rabbit pre-immune antiserum) at a 1:1500 dilution was added. After a 1 hr incubation, individual wells were rinsed 3 times with 500 microliters of TBS, an 1:3000 horseradish peroxidase conjugated goat anti-rabbit (Gibco-BRL ) were added and allowed to incubate for 1 hr. Individual wells were then rinsed and bound complex of primary-secondary antibody detected with Sigma A3219 2,2' Azino-bis(3-ethylbenzthiazidine-6-sulfonic acid) color reagent after 15 min of incubation using a Molecular Devices 96 well plate reader (Molecular Devices, VMAX) at 405 nm. Relative amounts of tissue PVCR content were determined after corrections for minimal background and nonspecific antibody binding as measured by binding of preimmune antiserum.

Results and Data Interpretation

FIG. 33 shows the data obtained from a representative single ELISA determination of PVCR protein content of 14 tissues of a single juvenile Atlantic salmon. Under the conditions specified in the Experimental Protocol as outlined above, nonspecific binding of both primary and secondary antibodies were minimized. While these quantitative values are measured relative to each other and not in absolute amounts, they provide data that parallels extensive immunocytochemistry examination of each of the tissues. Note that the PVCR content of various organs reflects their importance in osmoregulation of Atlantic salmon. Immunocytochemistry data described herein shows that tissues such as intestine (proximal and distal segments), gill, urinary bladder and kidney contained PVCR protein. In each case, epithelial cells that contact fluids that bathe the surfaces of these tissues express PVCR. In contrast, other organs including liver, heart and muscle contain minimal PVCR protein. Note that the highest PVCR content of any tissue tested is the olfactory lamellae where salmon possess the ability to "smell" alterations in calcium concentration in water. The olfactory bulb containing neurons that innervate the olfactory lamellae also possess abundant PVCR. Taken together, these data demonstrate the utility of ELISA kits to measure tissue content of PVCR proteins and form the basis for development of commercial assay kits that would monitor the expression levels of PVCR proteins in various tissues of juvenile anadromous fish undergoing the processes of the present invention. Alterations in PVCR tissue content measured in either relative changes in tissue PVCR content or absolute quantity of PVCR per tissue mass could, in turn, be utilized as correlative assays to determine the readiness of juvenile anadromous fish for sea water transfer or initiation of feeding. These data demonstrate the ability to perform such assays on individual juvenile Atlantic salmon in the range of body sizes that would be utilized to transfer fish from fresh to seawater after treatment with the methods of the present invention.

EXAMPLE 11

Antibodies Made from the Carboxyl Terminal Portion of an Atlantic Salmon PVCR Protein are Effective in Immunocytochemistry and Immunoblotting Assays to Determine the Presence, Absence or Amount of the PVCR Protein Degenerate primers, dSK-F3 (SEQ ID NO: 13) and dSK-R4 (SEQ ID NO: 14), described herein were constructed specifically from the SKCaR DNA sequence. These primers have proved to be useful reagents for amplification of portions of PVCR sequences from both genomic DNA as well as cDNA.

To obtain more cDNA sequence from anadromous fish PVCRs, in particular the putative amino acid sequence of the carboxyl terminal domain of PVCRs that are targets for generation of specific peptides and, as a result, specific anti-Atlantic Salmon PVCR antisera, an unamplified cDNA library from Atlantic salmon intestine was constructed. Phage plaques originating from this cDNA library were screened under high stringency using $^{32}$P-labeled 653 bp genomic Atlantic Salmon PCR product. From this cDNA library screening effort, a 2,021 bp cDNA clone was isolated and contained a single open reading frame for a putative amino acid sequence corresponding to approximately one half of a complete cDNA sequence from an intestinal PVCR protein. This putative amino acid sequence corresponds exactly to the sequence encoded by the corresponding genomic probe as well as the putative amino acid sequence corresponding to the carboxyl terminal domain of the PVCR.

On the basis of the knowledge of this putative amino acid sequence, a peptide, shown below, was synthesized and corresponded to a separate region of the putative carboxyl terminal PVCR amino acid sequence:

The peptide sequence for antibody production is as follows:
Peptide #1: Ac-CTNDNDSPSGQQRIHK-Amide (SEQ ID NO.:15) Producing Rabbit Antiserum SAL-1

The peptide was derivatized to carrier proteins and utilized to raise peptide specific antiserum in two rabbits using methods for making a polyclonal antibody.

The resulting peptide specific antiserum was then tested using both immunoblotting and immunocytochemistry techniques to determine whether the antibody bound to protein bands corresponding to PVCR proteins or yielded staining patterns similar to those produced using other anti-PVCR antiserum. A photograph of an immunoblot was taken showing protein bands that were recognized by antisera raised against peptides containing either SAL-1 (SEQ ID NO.: 15) or SKCaR (SEQ ID NO:2). As expected, antiserum raised to the peptide identified protein bands that co-electrophorese with PVCR proteins that are recognized by antisera raised to SKCaR (SEQ ID NO:2). Immunostaining of juvenile Atlantic salmon kidney sections with 3 different anti-PVCR antisera (anti-SalI, anti-4641, and anti-SKCaR) produces similar localizations of PVCR protein within the tubules of salmon kidney. Staining produced by anti-SKCaR antiserum is identical to that produced by anti-4641 antiserum, an anti-peptide antisera corresponding to extracellular domain of mammalian PVCRs that is very similar to SKCaR (SEQ ID NO: 2). These PVCR protein patterns stained identically to that produced by SAL-1 antiserum. Anti-Sal-1 antiserum also exhibits a similar staining pattern for the distribution of intestinal PVCR protein, as compared to anti-SKCaR. Thus, this new antiserum is specific for a PVCR in Atlantic Salmon tissues. This antiserum can be used to determine the presence, absence or amount of PVCR in various tissues of fish, using the methods described herein.

Figure 37B:
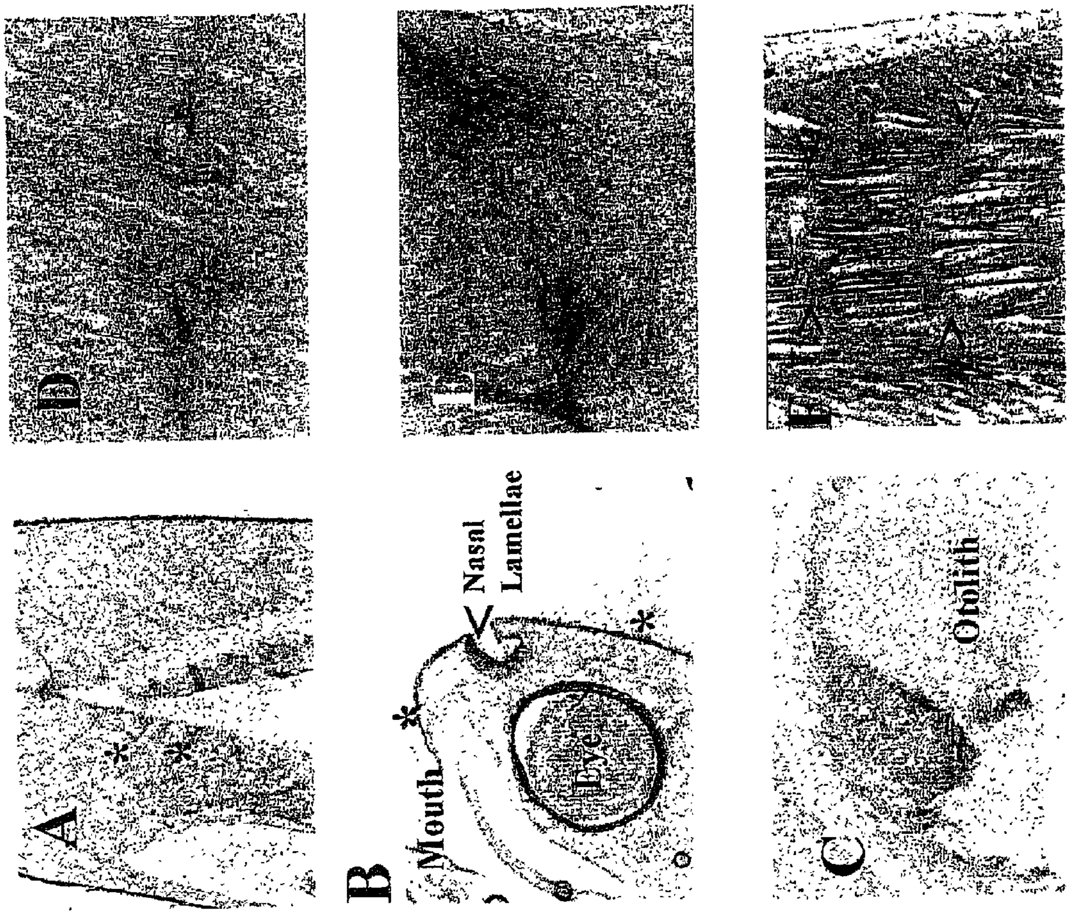
FIG. 37B is a photograph of immunocytochemistry of Atlantic salmon or trout larval fish using Sal-I antiserum shows abundant PVCR protein expression by selected cells. Specific binding of Sal-I antiserum denoting the presence of PVCR protein is shown by the dark reaction product. Staining of myosepta between various muscle bundles of larval fish is shown by asterisks (panel A). Panel B shows the head of a trout larvae in cross section where abundant PVCR protein is present in the skin (asterisks) and developing nasal lamellae (open arrowhead). Panel C shows PVCR expression in the developing otolith as well as localized PVCR protein in epithelial cells immediately adjacent to it. Panels D and E show high magnification views of myosepta shown in Panel A. Note the pattern of localized expression of PVCR protein where some cells contain large amounts of PVCR protein while those immediately adjacent to them have little or no expression. Panel F shows a corresponding H+E section where myosepta (open arrowheads) can be clearly distinguished from intervening muscle bundles.

The Sal I antiserum is also useful in localization of SalmoKCaR proteins in larval Atlantic salmon (See FIG. 37B). The Sal I antiserum localizes SalmoKCaR proteins in the developing nasal lamellae of anadromous fish, including Atlantic salmon and trout, skin, myosepta, otolith and sensory epithelium. The myoseptae are collagenous sheets that separate the various muscle bundles in the fish. Myosepta are important in both the development of muscle in larval fish as well as its function for muscle force generation in adult fish. Myosepta are also of significant commercial importance since they are one of the principal determinants of texture of smoked Atlantic salmon fillets.

The otolith is also of considerable importance to Atlantic salmon. It is a calcified structure located in the inner ear of salmon where it is closely associated with epithelial cells responsible for sensing sound and direction. It is likely that the SalmoKCaRs associated with the otolith participate in the calcification of the otolith structure that consists of proteins and calcium precipitate.

A second peptide sequence was used for antibody production:

Peptide #2: CSDDEYGRPGIEKFEKEM (SEQ ID NO: 27).

Figure 37C:
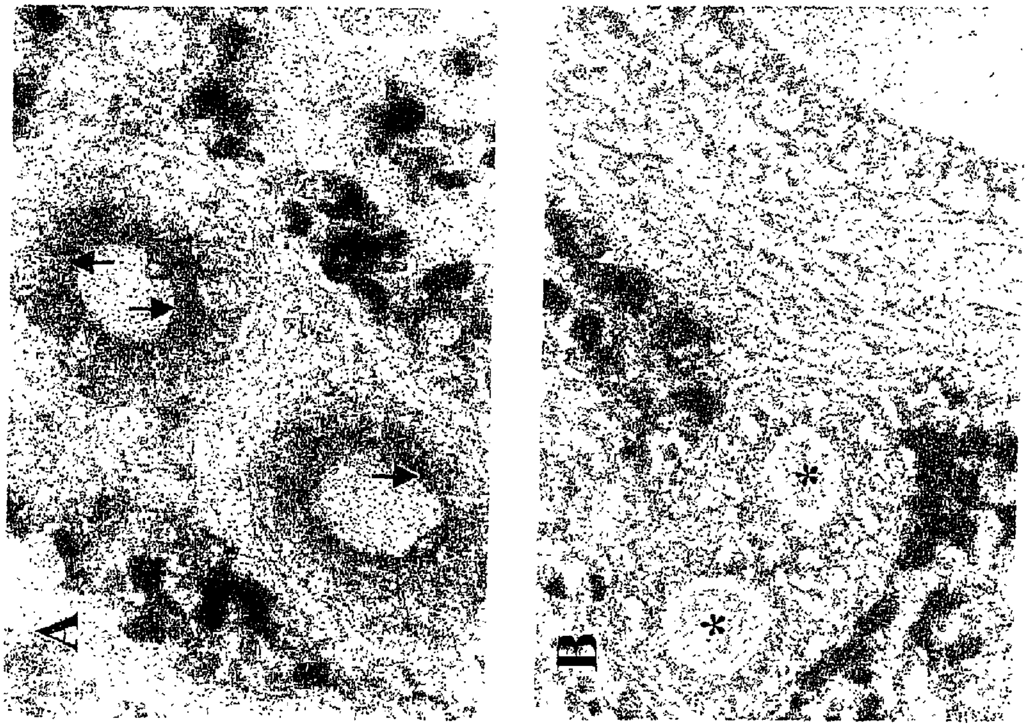
FIG. 37C is a photograph showing localization of Sal ADD antiserum by immunocytochemistry. Panel A shows the pattern of immunostaining of immune anti-Sal ADD serum as compared to lack of reactivity displayed by preimmune anti-Sal ADD serum when exposed to identical kidney tissue sections (Panel B). Note that anti-Sal ADD reactivity (denoted by arrows) is similar if not identical to that displayed by Sal-I antiserum. Corresponding kidney tubules exposed to preimmune antiserum show no reactivity (denoted by asterisks).

This peptide was synthesized, derivatized in a manner identical to that described for Peptide #1 and antiserum was raised in rabbits as described above. As expected, this antiserum (Salmo ADD) produced a pattern of immonostaining on sections of juvenile Atlantic salmon that is identical to that exhibited by Sal I. (See FIG. 37C). Since both SalmoKCaR #1 and #2 but not SalmoKCaR #3 possess the carboxyl terminal sequence recognized by the Sal I antibody, the antibody-staining pattern displayed by Sal I show the distribution of SalmoKCaR proteins #1 and #2 but not #3 within the kidney of Atlantic salmon.

In contrast, the Salmo ADD antibody binds to a peptide sequence present in the extracellular domain of all 3 SahnoKCaR proteins. Thus, any cells that possess no staining of Sal I but staining with Salmo ADD likely express either SalmoKCaR #3 or some similar SalmoKCaR protein.

EXAMPLE 12

Use of Reverse Transcriptase Polymerase Chain Reaction (TR-PCR) to Detect Expression of PVCRS in Various Tissues In Example 4, 2 degenerate primers, dSK-F3 (SEQ ID NO: 13) and dSK-R4 (SEQ ID NO: 14), are disclosed. These two primers were used to amplify genomic DNA and obtain the sequence of a portion of the genomic DNA sequences of PVCRs from various anadromous fish. These same primers can also be used to amplify a portion of corresponding PVCR mRNA transcripts in various tissues. DNA sequence analyses of amplified cDNAs from specific Atlantic salmon tissues (olfactory lamellae, kidney, urinary bladder) verifies these are all identical to certain genomic PVCR sequences described herein. These data show that:

1. PVCR mRNA transcripts are actually expressed in specific tissues of anadromous fish. These data reinforce the data regarding PVCR protein expression as detected by anti-PVCR antisera.
2. RT-PCR methods can be used to detect and quantify the degree of PVCR expression in various tissues, as a means to predict the readiness of anadromous fish for transfer to seawater.
3. cDNA probes can be generated from specific tissues of anadromous fish for use as specific DNA probes to either detect PVCR expression using solution or solid phase DNA-DNA or DNA-RNA nucleic acid hybridization or obtain putative PVCR protein sequences used for generation of specific anti-PVCR antisera.

RT-PCR Method

Total RNA was purified from selected tissues using Teltest B reagent (Friendswood, Tex.) and accompanying standard protocol. A total of 5 micrograms of total RNA was reverse transcribed with oligo dT primers using Invitrogen's cDNA Cycle Kit (Invitrogen Inc, Madison, Wis.). The resulting cDNA product was denatured and a second round of purification was performed. Two microliters of the resulting reaction mixture was amplified in a PCR reaction (30 cycles of 1 min. @94° C., 2 min. @ 57° C., 3 min. @72° C.) using degenerate primers dSK-F3 (SEQ ID NO: 13) and dSK-R4 (SEQ ID NO: 14). The resulting products were electrophoresed on a 2% (w/v) agarose gel using TAE buffer containing ethidium bromide for detection of amplified cDNA products. Gels were photographed using standard laboratory methods.

DNA Sequencing of RT-PCR Products were Performed as Follows:

A total of 15 microliters of Atlantic Salmon urinary bladder, kidney and nasal lamellae RT-PCR reactions were diluted in 40 microliters of water and purified by size exclusion on Amersham's MicroSpin S-400 HR spin columns (Amersham Inc, Piscataway, N.J.). Purified DNA was sequenced using degenerate PVCR primers (SEQ ID NO.: 13 and 14) as sequencing primers. Automated sequencing was performed using an Applied Biosystems Inc. Model 373A Automated DNA Sequencer (University of Maine, Orono, Me.). The resulting DNA sequences were aligned using MacVector (GCG) and LaserGene (DNA STAR) sequence analysis software.

Detection of Amplified RT-PCR cDNA Products by Southern Blotting:

Alternatively, the presence of amplified PVCR products was detected by Southern blotting analyses of gel fractionated RT-PCR products using a $^{32}P$-labeled 653 bp Atlantic salmon amplified genomic PCR product. A total of 10 microliters of each PCR reaction was electrophoresed on a 2% agarose gel using TAE buffer then blotted onto Magnagraph membrane (Osmonics, Westboro, Mass.). After crosslinking of the DNA, blots were prehybridized and then probed overnight (68° C. in 6×SSC, 5× Denhardt's Reagent, 0.5% SDS, 100 $\mu$g/ml calf thymus DNA) with the 653 bp Atlantic salmon PCR product (labeled with RadPrime DNA Labeling System, Gibco Life Sciences). Blots were then washed with 0.1×SSC, 0.1% SDS @55° C. and subjected to autoradiography under standard conditions.

FIG. 34 shows the results of RT-PCR amplification of a partial PVCR mRNA transcript from various tissues ofjuvenile Atlantic salmon. RT-PCR reactions were separated by gel electrophoresis and either stained in ethidium bromide (EtBr) or transferred to a membrane and Southern blotted using a $^{32}P$-labeled 653 bp genomic DNA fragment from the Atlantic salmon PVCR gene. FIG. 34 shows the detection of the PVCR in several tissue types of Atlantic Salmon using the RT-PCR method, as described herein. The types of tissue are gill, nasal lamellae, urinary bladder, kidney, intestine, stomach, liver, and brain.

EXAMPLE 13

Presence and Function of PVCR Protein in Nasal Lamellae and Olfactory Bulb as Well as GI Tract of Fish The data described herein described the roles of PVCR proteins in the olfactory organs (nasal lamellae and olfactory bulb) of fish as it relates to the ability of fish to sense or "smell" both alterations in the water salinity and/or ionic composition as well as specific amino acids. These data are particularly applicable to anadromous fish (salmon, trout and char) that are either transferred from freshwater directly to seawater or exposed to Process I or Process II in freshwater and then transferred to seawater.

These data described herein were derived from a combination of sources including immunocytochemistry using anti-PVCR antisera, RT-PCR amplification of PVCRs from nasal lamellae tissue, studies of the function of recombinant aquatic PVCR proteins expressed in cultured cells where these proteins "sense" specific ions or amino acids as well as electrophysiological recordings of nerve cell electrical activity from olfactory nerves or bulb of freshwater salmon.

The combination of immunocytochemistry and RT-PCR data, described herein, reveal the presence of PVCR proteins in both major families of fish (elasmobranch-shark; teleost-salmon) in both larval, juvenile and adult life stages. Immunocytochemistry analyses reveal that one or more PVCR proteins are present both on portions of olfactory receptor cells located in the nasal lamellae of fish (where they are bathed in water from the surrounding environment) as well as on nerve cells that compose olfactory glomeruli present in the olfactory bulb of fish brain (where these cells are exposed to the internal ionic environment of the fish's body).

Thus, from these locations fish are able to compare the ionic composition of the surrounding water with reference to their own internal ionic composition. Alterations in the expression and/or sensitivity of PVCR proteins provides the means to enable fish to determine on a continuous basis whether the water composition they encounter is different from that they have been adapted to or exposed to previously. This system is likely to be integral to both the control of the homing of salmon from freshwater to seawater as smolt and their return to freshwater from seawater as adults. Thus, fish have the ability to "smell" changes in water salinity directly via PVCR proteins and respond appropriately to regulate remain in environments that are best for their survival in nature.

One feature of this biological system is alteration in the sensitivity of the PVCR protein for divalent cations such as $Ca^{2+}$ and $Mg^{2+}$ by changes in the NaCl concentration of the water. Thus, PVCRs in fish olfactory organs have different apparent sensitivity to $Ca^{2+}$ in either the presence or absence of NaCl. These data presented here are the first direct evidence for these functions via PVCR proteins present in the olfactory apparatus of fish.

Another feature of PVCR protein function in the olfactory apparatus of fish is to modulate responses of olfactory cells to specific odorants (attractants or repellants). Transduction of cellular signals resulting from the binding of specific odorants to olfactory cells occurs via changes in standing ionic gradients across the plasma membranes of these cells. The binding of specific odorants to olfactory cells results in electrical nerve conduction signals that can be recorded using standardized electrophysiological electrodes and equipment. Using this apparatus, the olfactory apparatus of freshwater adapted salmon:

1. responded to PVCR agonists in a concentration-dependent manner similar to that shown previously for other fish tissues including that shown for winter flounder urinary bladder. These data provide the functional evidence of the presence of a PVCR protein; and
2. that the presence of a PVCR agonist reduces or ablates the signal resulting from odorants including both attractants or repellants. Thus, PVCRs in the olfactory apparatus of salmon possess the capacity of modulating responses to various odorants.

Another feature of PVCR proteins is their ability to "sense" specific amino acids present in surrounding environment. Using the full-length recombinant SKCaR cDNA, functional SKCaR protein was expressed in HEK cells and shown to respond in a concentration-dependent manner to both single and mixtures of L-amino acids. Since PVCR agonists including amino acids as well as polyamines (putrescine, spermine and spermidine) are attractants to marine organisms including fish and crustaceans, these data provide for another means by which PVCR proteins would serve not only as modulators of olfaction in fish but also as sensors of amino acids and polyamines themselves. PVCR proteins in other organs of fish including G.I. tract and endocrine organs of fish also function to sense specific concentrations of amino acids providing for integration of a wide variety of cellular processes in epithelial cells (amino acid transport, growth, ion transport, motility and growth) with digestion and utilization of nutrients in fish.

Description of Experimental Results And Data Interpretation

PVCR protein and mRNA are localized to the olfactory lamellae, olfactory nerve and olfactory bulb of freshwater adapted larval, juvenile and adult Atlantic salmon as well as the olfactory lamellae of dogfish shark:

FIG. 35 show representative immunocytochemistry photographs of PVCR protein localization in olfactory bulb and nerve as well as olfactory lamellae in juvenile Atlantic salmon. The specificity of staining for PVCR protein is verified by the use of 2 distinct antisera each directed to a different region of the PVCR protein. Thus, antiserum anti-4641 (recognizing an extracellular domain PVCR region) and antiserum anti-SKCaR (recognizing an intracellular domain PVCR region) exhibit similar staining patterns that include various glomeruli on serial sections of olfactory bulb. Using anti-SKCaR antiserum, specific staining of PVCR proteins is observed in discrete regions of the olfactory nerve as well as epithelial cells in the nasal lamellae that are exposed to the external ionic environment.

The presence of PVCR protein in both nasal lamellae cells as well as olfactory bulb and nerve shows that these respective PVCR proteins would be able to sense both the internal and external ionic environments of the salmon. For this purpose, cells containing internally-exposed PVCRs are connected to externally-exposed PVCRs via electrical connections within the nervous system. As shown schematically in FIG. 36, these data suggest that externally and internally-exposed PVCRs function together to provide for the ability to sense the ionic concentrations of the surrounding ionic environment using as a reference the ionic concentration of the salmon's body fluids. Changes in the expression and/or sensitivity of the external set of PVCRs vs internal PVCRs would then provide a long term "memory" of the adaptational state of the fish as it travels through ionic environments of different composition. FIG. 37 shows immunocytochemistry using anti-SKCaR antiserum that reveals the presence of PVCR protein in both the developing nasal lamellae cells and olfactory bulb of larval Atlantic salmon only days after hatching (yolk sac stage). As described herein, imprinting of salmon early in development as well as during smoltification have been shown to be key intervals in the successful return of wild salmon to their natal stream. The Sal I antiserum also localizes SalmoKCaR proteins in a variety of tissues in larval Atlantic salmon (FIG. 37B). These tissues include the developing nasal lamellae of salmon and trout, their skin, myosepta, otolith and sensory epithelium. Myosepta are important in both the development of muscle in larval fish since they separate and define the muscle bundles of the salmon. Myosepta are also of significant commercial importance since they are one of the principal determinants of texture for smoked Atlantic salmon fillets. SalmoKCaR proteins are also present in the otolith which is a calcified structure located in the inner ear of the salmon where it is closely associated with epithelial cells responsible for sensing sound and direction. The presence of PVCR proteins at these developmental stages of salmon lifecycle indicate that PVCRs participate in this process.

Data obtained from using anti-SKCaR antiserum from other fish species including elasmobranchs display similar staining of PVCR protein in cells (marked A) their nasal lamellae (FIG. 38). Use of other methodology including RT-PCR using specific degenerate primers (FIG. 39) and ELISA methods (FIG. 40) detects the presence of PVCR proteins and mRNA in nasal lamellae of fish. While neither of these 2 techniques provide quantitative measurements as described, both sets of data are consistent and show abundant PVCR protein present in this tissue.

Measurement of Extracellular Electrical Potentials (EEG's) from Olfactory Nerve from Freshwater Adapted Atlantic Salmon Reveals the Presence of Functional PVCR Proteins:

FIG. 41 displays representative recordings obtained from 6 freshwater adapted juvenile Atlantic salmon (approximately 300–400 gm) using methods similar to those described in *Bodznick, D. J.* Calcium ion: an odorant for natural water discriminations and the migratory behavior of sockeye salmon, *Comp. Physiol. A* 127:157–166 (1975), and *Hubbard, P C*, et al., Olfactory sensitivity to changes in environmental Ca2+ in the marine teleost Sparus Aurata, *J. Exp. Biol.* 203:3821–3829 (2000). After anaesthetizing the fish, it was placed in V-clamp apparatus where its gills were irrigated continuously with aerated seawater and its nasal lamellae bathed continuously by a stream of distilled water via a tube held in position in the inhalant olfactory opening. The olfactory nerves of the fish were exposed by removal of overlying bony structures. Stimuli were delivered as boluses to the olfactory epithelium via a 3 way valve where 1 cc of water containing the stimulus was rapidly injected into the tube containing a continuously stream of distilled water. Extracellular recordings were obtained using high resistance tungsten electrodes where the resultant amplified analog signals (Grass Amplifier Apparatus) were digitized, displayed and analyzed by computer using MacScope software. Using this experimental approach, stable and reproducible recordings could be obtained for up to 6 hr after the initial surgery on the fish.

Figure 42:
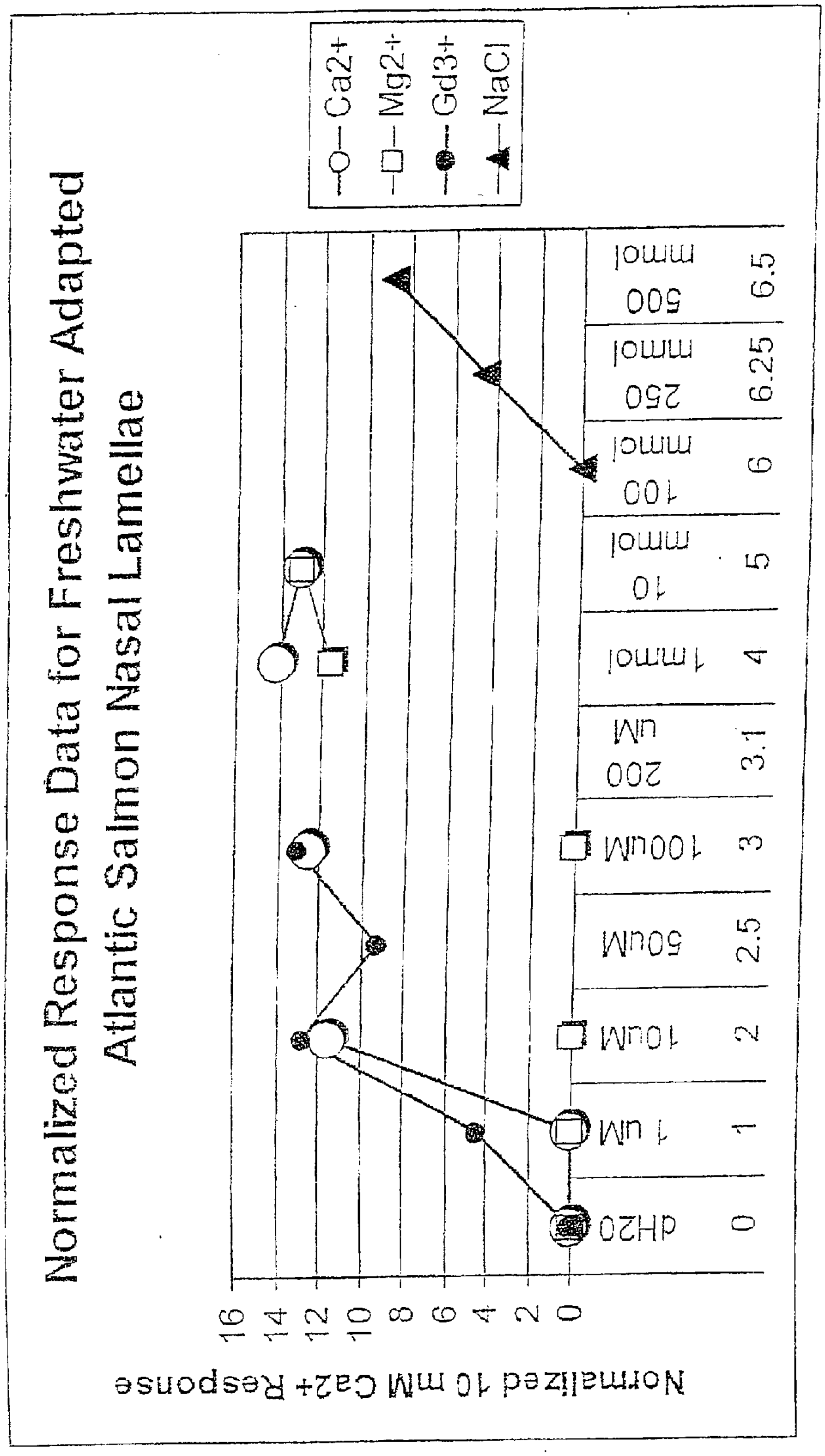
FIG. 42 is a graph showing the response data for freshwater adapted Atlantic salmon nasal lamellae for calcium, magnesium, gadolinium, and sodium chloride normalized to the signal obtained with 10 mM Calcium.

As shown in FIG. 41, irrigation of salmon olfactory epithelium with distilled water produces minimal generation of large signals in olfactory nerve. The data in FIG. 41 are displayed as both raw recordings (left column) and the corresponding integrated signals for each raw recording shown in the right column. Exposure of the olfactory epithelium to 500 micromolar L-alanine (a well known amino acid attractant for fish) produces large increases in both the firing frequency and amplitude in the olfactory nerve lasting approximately 2 seconds in duration. Similarly, application of either 1 mM $Ca^{2+}$ or 250 mM NaCl also produce responses in EEG activity. To test for the presence of functional PVCR protein, the olfactory epithelium was exposed to 50 micromolar gadolinium ($Gd^{3+}$-a PVCR agonist) and also obtained a response. FIG. 42 shows dose response data from multiple fish to various PVCR agonists or modulators where the relative magnitudes of individual olfactory nerve response were normalized relative to the response produced by the exposure of the olfactory epithelium to 10 mM $Ca^{2+}$. As shown in FIG. 42, the olfactory epithelium of freshwater adapted juvenile salmon is very sensitive to $Ca^{2+}$ where the half maximal excitatory response ($EC_{50}$) is approximately 1–10 micromolar. Similarly, exposure of olfactory epithelium to the PVCR agonist $Gd^{3+}$ produces responses of a similar magnitude to those evoked by $Ca^{2+}$ in a concentration range of 1–10 micromolar. In contrast, olfactory epithelium responses to $Mg^{2+}$ do not occur until 10–100 micromolar solutions are applied. These dose response curves ($EC_{50}$ $Gd^{+3} \leqq Ca^{2+} < Mg^{2+}$) are similar to those obtained for PVCR modulated responses in other fish epithelium (flounder urinary bladder NaCl-mediated water transport-see SKCaR application).

In contrast, analysis of the olfactory epithelium responses to NaCl exposure shows that it is unresponsive until a concentration of 250 millimolar NaCl is applied. Since NaCl does not directly activate PVCRs in a manner such as $Gd^{+3}$ $Ca^{2+}$ or $Mg^{2+}$ but rather reduces the sensitivity of PVCRs to these agonists, these data are also consistent with the presence of an olfactory epithelium PVCR. The response evoked by exposure of the epithelium to significant concentrations of NaCl likely occurs via other PVCR independent mechanisms.

These data suggest that PVCR proteins present in olfactory epithelium are capable of sensing and generating corresponding olfactory nerve signals in response to PVCR agonists at appropriate concentrations in distilled water.

Figure 43:
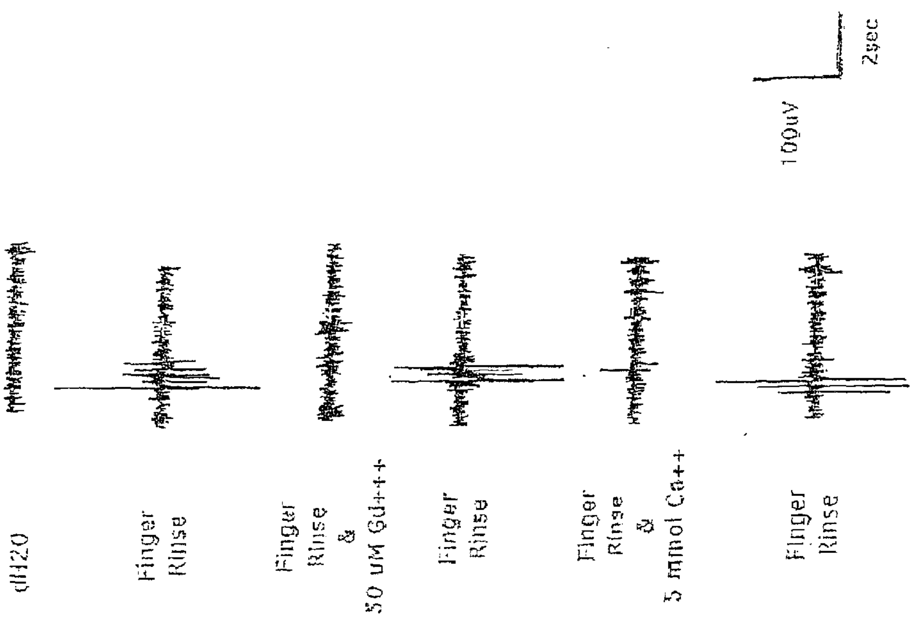
FIG. 43 shows raw recording from high resistance electrodes of olfactory nerve impulse in the presence of a repellant (finger rinse) and in the presence of a SalmoKCaR agonist (gadolinium) and a repellant (finger rinse). The figure shows that the olfactory nerve impulse to the repellant is reversibly altered in the presence of a SalmoKCaR agonist.

Addition of PVCR Agonists such as Ca2+ or Gd3+ to Distilled Water Containing Well Known Salmon Repellants Reversibly Ablates the Response of the Olfactory Epithelium to these Stimuli:

FIG. 43 shows representative data obtained from a single continuous recording where the olfactory epithelium was first exposed to a well-known repellant, mammalian finger rinse. Finger rinse is obtained by simply rinsing human fingers of adherent oils and fatty acids using distilled water and has been shown previously to be a powerful repellant stimulus both in EEG recordings as well as behavioral avoidance assays (Royce-Malmgren and W. H. Watson *J. Chem. Ecology* 13:533–546 (1987)). Note however that inclusion of the PVCR agonists 5 mM $Ca^{2+}$ or 50 micromolar $Gd^{3+}$ reversibly ablated the response by the olfactory epithelium to mammalian finger rinse. These data show that PVCR agonists modulated the response of the olfactory epithelium to an odorant such as mammalian finger rinse. The ablation of responses to both the PVCR agonists as shown in FIG. 42 as well as mammalian finger rinse indicate that there are some complex interactions between PVCR proteins and other odorant receptors. It is also extremely unlikely that inclusion of PVCR agonists removed all the stimulatory components of mammalian finger rinse from solution such that they were not able to stimulate the epithelium.

Figure 44:
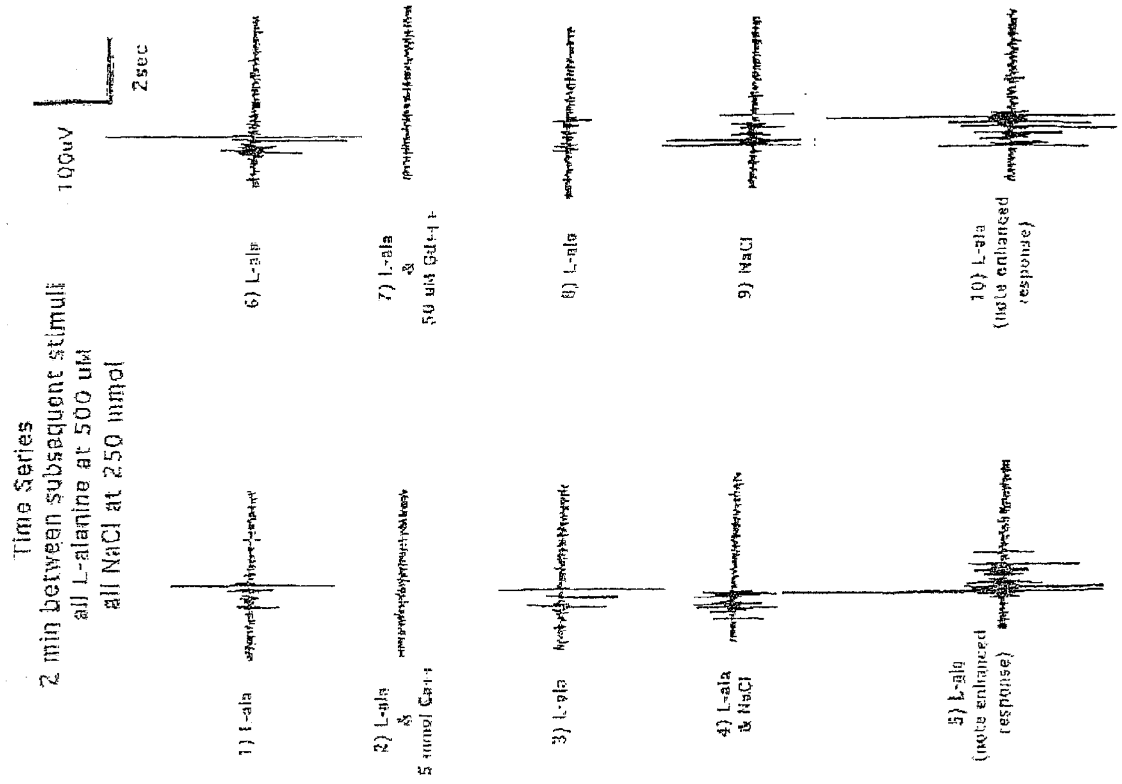
FIG. 44 shows the raw recordings from high resistance electrodes of freshwater adapted Atlantic Salmon in response to a series of repeated stimuli (L-alanine or NaCl) in 2 minute intervals. The figure shows that the olfactory nerve impulse to the attractant is reversibly altered in the presence of a SalmoKCaR agonist

Addition of PVCR agonists such as Ca2+ or Gd3+ but not NaCl to distilled water containing the well known salmon attractant L-alanine reversibly ablates the response of the olfactory epithelium to these stimuli:

FIG. 44 shows a time series of stimuli (2 min between each stimulus in a single fish) similar to that displayed on FIG. 43 except that 500 micromolar L-Alanine (a salmon attractant) was used to produce a signal in the olfactory nerve. Note that the addition of either 5 mM $Ca^{2+}$ (recording #2) or 50 micromolar $Gd^{3+}$ (recording #7) to 500 micromolar L-alanine resulted in the complete loss of the corresponding response from the olfactory nerve after injection of this mixture. In both cases, this was not due to a permanent alteration of the olfactory epithelium by either of these PVCR agonists because a subsequent identical stimulus without the PVCR agonist (recordings #3 and #8) caused a return of the signal. It is noteworthy that in the case of $Gd^{3+}$ addition, the magnitude of the subsequent L-alanine signal was decreased as compared to control (compare recordings #6 vs #8) indicating that the olfactory epithelium prefers an interval of recovery from its exposure to this potent PVCR agonist. However, the alteration of response to the L-Alanine stimulus is not permanent or nonspecific since combining the same dose of L-Alanine with 250 mM NaCl resulted initially in a similar response (recordings #4 and #9) followed by an enhanced response to L-Alanine alone (recordings #5 and #10).

In summary, the data displayed in FIGS. 43 and 44 show that inclusion of a PVCR agonist in solutions containing either a repellant (finger rinse) or attractant (L-alanine) causes a dramatic reduction in the response of the olfactory epithelium to those odorants. For both repellants and attractants, some form of complex interactions occur within olfactory epithelial cells since mixing of PVCR agonists and odorants renders the epithelia temporary unresponsive to either stimulus. While the nature of such interactions are not known at the present time, such interactions do not occur at the level of the PVCR molecule itself as shown by data from experiments using recombinant PVCR protein SKCaR. As further described herein, inclusion of amino acids in the presence of $Ca^{2+}$ enhances the response of SKCaR to ambient $Ca^{2+}$ concentrations. Regardless of their nature, these negative modulatory effects of PVCR agonists including $Ca^{2+}$ is likely to produce major effects on how freshwater salmon smell objects in their environment after transfer from a low calcium to a high calcium environment. Use of this assay system would permit the identification and analyses of both specific classes of PVCR agonists and antagonists as well as the specific effects of each PVCR modulator on specific odorants including both repellants and attractants.

Recombinant PVCR Protein SKCaR Possesses the Capability to Sense Concentrations of Amino Acids after its Expression in Human Embryonic Kidney (HEK) Cells:

Full length recombinant dogfish (*Squalus acanthias*) shark kidney calcium receptor (SKCaR) was expressed in human embryonic kidney cells using methods described herein. The ability of SKCaR to respond to individual amino acids as well as various mixtures was quantified using FURA-2 ratio imaging fluorescence.

Figure 45:
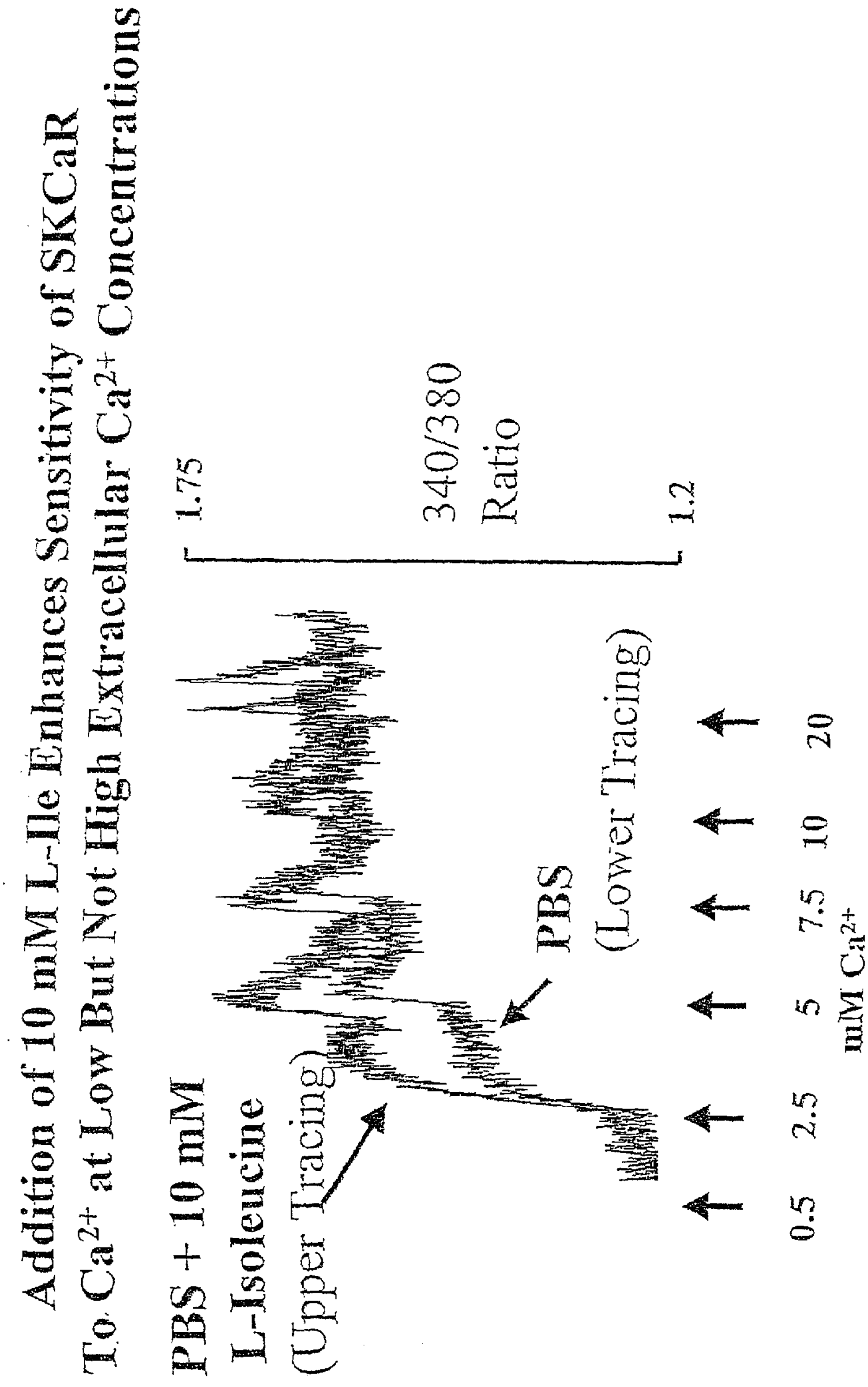
FIG. 45 is a graphical representation of the ratio from FURA-2 cells expressing a PVCR in the presence or absence of 10 mM L-Isoleucine in various concentrations (0.5, 2.5, 5.0, 7.5, 10.0 and 20.0 mM) of extracellular calcium ($Ca^{2+}$).

FIG. 45 shows a comparison of fluorescence tracings of FURA2-loaded cells stably expressing SKCaR that were bathed in physiological saline (125 mM NaCl, 4 mM KCl, 0.5 mM $CaCl_2$, 0.5 $MgCl_2$, 20 mM HEPES (NaOH), 0.1% D-glucose pH 7.4) in the presence or absence of 10 mM L-Isoleucine (L-Ile) before being placed into the fluorimeter. Baseline extracellular $Ca^{2+}$ concentration was 0.5 mM. Aliquots of $Ca^{2+}$ were added to produce final extracellular concentrations of 2.5 mM, 5 mM, 7.5 mM, 10 mM and 20 mM $Ca^{2+}$ with changes in the fluorescence recorded. Note that increases in cell fluorescence were greater in the presence of 10 mM Phe for extracellular $Ca^{2+}$ concentrations less than 10 mM.

Figure 46:
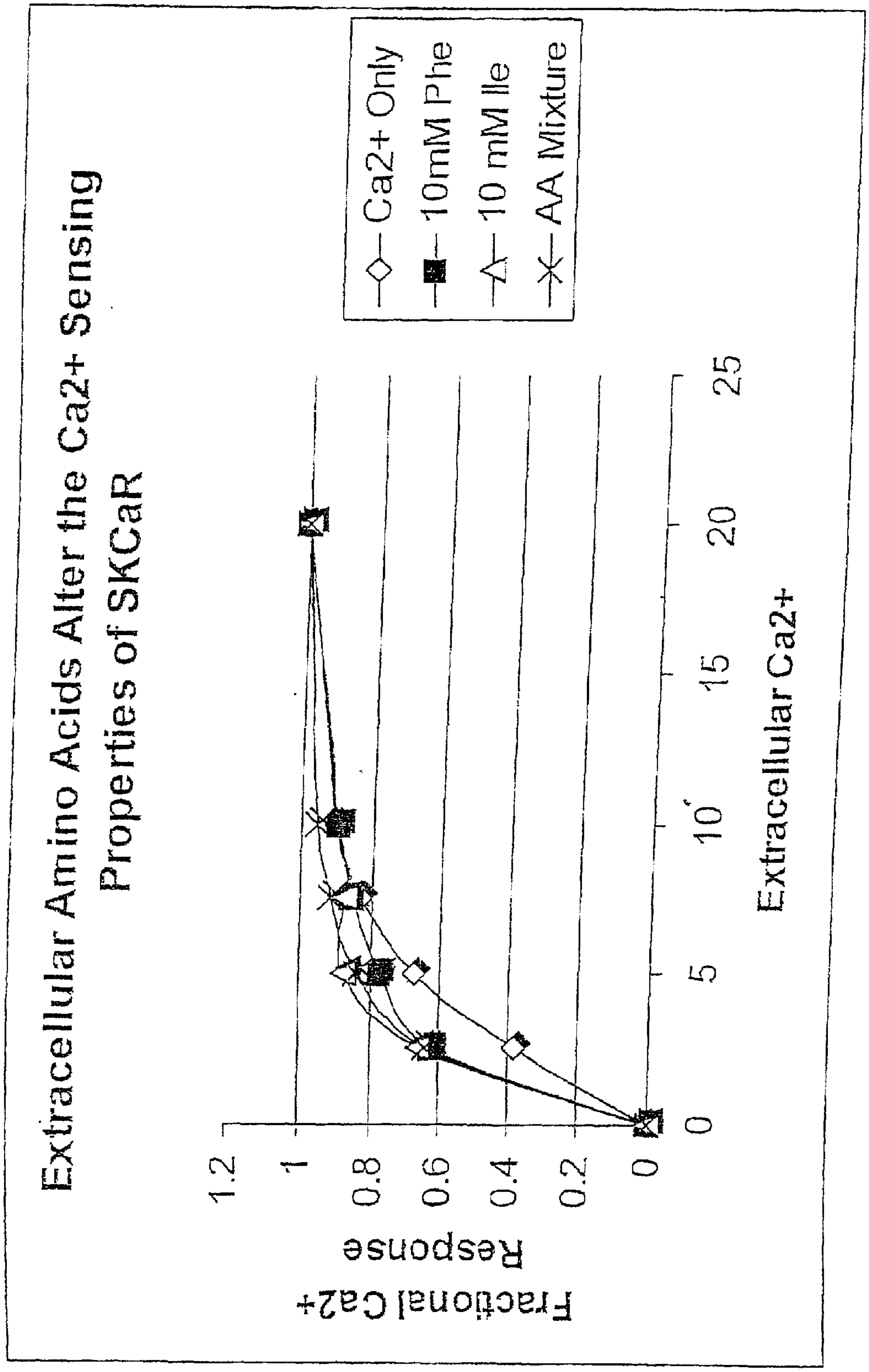
FIG. 46 is a graphical representation of the fractional $Ca^{2+}$ response, as compared to the extracelluar $Ca^{2+}$ (mM) for the PVCR in $Ca^{2+}$ only, Phenylalanine, Isoleucine, or AA Mixture (a variety of L-isomers in various concentrations).

FIG. 46 shows data plotted from multiple experiments as described in FIG. 45 where the effects of 10 mM Phe, 10 mM Ile or an amino acid mixture (AA Mixture) containing all L-isomers in the following concentrations in micromoles/liter: 50 Phe, 50 Trp, 80 His, 60 Tyr, 30 Cys, 300 Ala, 200 Thr, 50 Asn, 600 Gln, 125 Ser, 30 Glu, 250 Gly, 180 Pro, 250 Val, 30 Met, 10 Asp, 200 Lys, 100 Arg, 75 Ile, 150 Leu. Note that both 10 mM Phe and 10 mM Ile as well as the mixture of amino acids increase SKCaR's response to a given $Ca^{2+}$ concentration. Thus, these data show that presence of amino acids either alone or in combination increase the apparent sensitivity to $Ca^{2+}$ permitting SKCaR to "sense" amino acids in the presence of physiological concentrations of $Ca^{2+}$. These data obtained for SKCaR are comparable to those obtained for the human CaR.

The significance of these data for aquatic organisms stand in marked contrast to the roles of human CaRs amino acid sensing capabilities. FIG. 45 shows that SKCaR's maximal capability to sense amino acids is confined to a range of $Ca^{2+}$ that is present both in aquatic external environments as well as the body fluids of various fish. The following physiological processes occur: 1) Sensing of amino acids in the proximal intestine and pyloric caeca of fish: The PVCR present on the apical surface of intestinal epithelial cells is capable of responding to amino acids such as tryptophan as part of the Process II. Inclusion of tryptophan in the feed of fish interacts with the intestinal PVCR to improve the development of juvenile anadromous fish to tolerate seawater transfer. 2) In both adult, juvenile and larval fish, PVCR localized to the apical membrane of stomach and intestinal epithelial cells could "sense" the presence of amino acids produced by the proteolysis of proteins into amino acids. This mechanism could be used to inform both epithelial and neuroendocrine cells of the intestine of the presence of nutrients (proteins) and trigger a multitude of responses including growth and differentiation of intestinal epithelia as well as their accompanying transport proteins, secretion or reabsorption of ions such as gastric acid. The apical PVCR also regulates the secretion of intestinal hormones such as cholecystokin (CCK) and others. 3) PVCR proteins present in cells of the nasal lamellae of fish "smell" both water salinity (via $Ca^{2+}$, Mg2+ and NaCl) and amino acids which is an example of an attractant. At the present time, it is unclear whether the amino acid sensing capabilities of PVCRs are utilized by the olfactory epithelium to enable fish to smell various amino acid attractants.

These data show that PVCR sensing of amino acids occurs in a range of extracellular calcium that is present in various concentrations of seawater present in estuaries and fish migration routes as well as various compartments of a fish's body including serum and body cavities including intestine, pyloric caeca and kidney where transepithelial amino acid absorption occurs. These data constitute the first report showing the amino acid sensitivity of a PVCR in fish.

Companion Patent Application Ser. Nos.10/125,778 and 10/125,772 both entitled "Polyvalent Cation-sensing Receptor in Atlantic Salmon," filed on Apr. 18, 2002; patent application Ser. No. 09/687,373, entitled "Growing Marine Fish in Fresh Water," filed on Oct. 12, 2000; PCT Application No.: PCT/US01/31625, entitled "Growing Marine Fish in Fresh Water," filed Oct. 11, 2001; patent application Ser. No. 09/687,476, entitled "Methods for Raising Pre-adult Anadromous Fish," filed on Oct. 12, 2000; patent application Ser. No. 09/687,372, entitled "Methods for Raising Pre-adult Anadromous Fish," filed on Oct. 12, 2000; patent application Ser. No. 09/687,477, entitled "Methods for Raising Pre-adult Anadromous Fish," filed on Oct. 12, 2000; patent application Ser. No. 09/975,553, entitled "Methods for Raising Pre-adult Anadromous Fish," filed on Oct. 11, 2001; International PCT Application No. PCT/US01/31562, entitled, "Methods for Raising Pre-adult Anadromous Fish," filed on Oct. 11, 2001; Provisional Patent Application No. 60/382,464, "Methods for Growing and Imprinting Fish Using an Odorant," filed Oct. 11, 2001; are all hereby incorporated by reference in their entirety.

Additionally, U.S. Pat. No. 6,334,391, issued on Jan. 8, 2002, International PCT application No. PCT/US97/05031, filed on Mar. 27, 1997, and application Ser. No. 08/622,738 filed Mar. 27, 1996, all entitled, "Polycation Sensing Receptor in Aquatic Species and Methods of Use Thereof" are all hereby incorporated by reference in their entirety.

All relevant portions of literature articles, references, patent applications, patent publications, and patents cited herein are hereby incorporated by referenced in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated nucleic acid molecule that comprises:

a) SEQ ID NO: 11; or b) the complementary strand of a).

2. An isolated nucleic acid molecule that comprises a nucleic acid sequence that has at least about 70% identity with SEQ ID NO: 11, or the coding region of SEQ ID NO: 11; and that encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

3. An isolated nucleic acid molecule that comprises a nucleic acid sequence that has at least about 80% identity with SEQ ID NO: 11, or the coding region of SEQ ID NO: 11; and that encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

4. An isolated nucleic acid molecule that comprises a nucleic acid sequence that has at least about 90% identity with SEQ ID NO: 11, or the coding region of SEQ ID NO: 11; and that encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

5. An isolated nucleic acid molecule that comprises a nucleic acid sequence comprising the coding region of SEQ ID NO: 11; or the complementary strand of the coding region of SEQ ID NO: 11.

6. An isolated nucleic acid molecule that comprises a nucleic acid sequence that encodes a polypeptide comprising an amino acid sequence of SEQ ID NO: 12.

7. An isolated nucleic acid molecule that comprises a nucleic acid sequence that hybridizes under high stringent conditions to SEQ ID NO: 11; but not SEQ ID NO: 1 under said conditions, wherein said conditions are 1×SSC, 1% SDS, and 0.1–2 mg/ml denatured calf thymus DNA at 65° C. and wherein said nucleic acid molecule encodes a polypeptide that allows for or assists in one or more of the following functions: sensing at least one SalmoKCaR modulator in serum or in the surrounding environment, adapting to at least one SalmoKCaR modulator present in the serum or surrounding environment; imprinting Atlantic Salmon with an odorant; or altering water intake, altering water absorption, or altering urine output in Atlantic salmon.

8. An isolated nucleic acid molecule that comprises a nucleic acid sequence that hybridizes under high stringent conditions to the coding region of SEQ ID NO: 11; but not the coding region of SEQ ID NO: 1 under said conditions, wherein said conditions are 1×SSC, 1% SDS, and 0.1–2 mg/ml denatured calf thymus DNA at 65° C. and wherein said nucleic acid molecule encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

9. An isolated nucleic acid molecule that comprises a nucleic acid sequence that encodes SEQ ID NO: 12, wherein the nucleic acid molecule is an RNA molecule.

10. A vector or plasmid that comprises an isolated nucleic acid sequence comprising SEQ ID NO: 11; or the coding region of SEQ ID NO: 11.

11. A vector or plasmid that comprises an isolated nucleic acid sequence that encodes a polypeptide comprising the amino acid sequence of SEQ ID NO: 12.

12. A vector or plasmid that comprises a nucleic acid sequence that hybridizes under high stringency conditions to SEQ ID NO: 11; or to the coding region of SEQ ID NO: 11; but not to SEQ ID NO: 1 or the coding region of SEQ ID NO: 1 under said conditions, wherein said conditions are 1×SSC, 1% SDS, and 0.1–2 mg/ml denatured calf thymus DNA at 65° C. and wherein said nucleic acid molecule encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

13. An isolated host cell transformed with a nucleic acid molecule that comprises a nucleic acid sequence comprising SEQ ID NO: 11; or the coding region of SEQ ID NO: 11.

14. An isolated host cell transformed with a nucleic acid molecule that comprises an isolated nucleic acid sequence that encodes a polypeptide comprising an amino acid sequence of SEQ ID NO: 12.

15. An isolated host cell transformed with a nucleic acid molecule that comprises a nucleic acid sequence that hybridizes under high stringency conditions to SEQ ID NO: 11 or to the coding region of SEQ ID NO: 11, wherein said conditions are 1×SSC, 1% SDS, and 0.1–2 mg/ml denatured calf thymus DNA at 65° C. and wherein said nucleic acid molecule encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

16. A nucleic acid purified from a clone deposited under ATCC NO: PTA-4190.

17. An isolated nucleic acid molecule that comprises a nucleic acid sequence that encodes a polypeptide comprising at least about 70% identity with SEQ ID NO: 12, and wherein the polypeptide allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

18. An isolated nucleic acid molecule that comprises a nucleic acid sequence that encodes a polypeptide comprising at least about 80% identity with SEQ ID NO: 12, and wherein the polypeptide allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

19. An isolated nucleic acid molecule that comprises a nucleic acid sequence that encodes a polypeptide comprising at least about 90% identity with SEQ ID NO: 12, and wherein the polypeptide allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic salmon.

20. A method of producing a recombinant SalmoKCaR protein comprising maintaining the host cell of claim 13 under suitable conditions for expression and recovery of said SalmoKCaR protein.

21. A method of producing a recombinant SalmoKCaR protein comprising maintaining the host cell of claim 14 under suitable conditions for expression and recovery of said SalmoKCaR protein.

22. A method of producing a recombinant SalmoKCaR protein comprising maintaining the host cell of claim 15 under suitable conditions for expression and recovery of said SalmoKCaR protein.

* * * * *

UNITED STATES PATENT AND TRADEMARK OFFICE

CERTIFICATE OF CORRECTION

PATENT NO. : 6,979,559 B2

DATED : December 27, 2005

INVENTOR(S) : H. William Harris, Jr., Jacqueline Nearing and Marlies Betka

It is certified that error appears in the above-identified patent and that said Letters Patent is hereby corrected as shown below:

Column 60,
Line 25, delete "Table 12" and insert -- Table 11 --.

Column 125,
Line 26, delete "environment, adapting" and insert -- environment; adapting --.

Column 126,
Line 23, delete "PTA-4190" and insert -- PTA-4192 --.

Signed and Sealed this

Sixteenth Day of May, 2006

JON W. DUDAS

*Director of the United States Patent and Trademark Office*